(12) United States Patent
Dietrich et al.

(10) Patent No.: US 9,939,441 B2
(45) Date of Patent: *Apr. 10, 2018

(54) METHODS AND NUCLEIC ACIDS FOR ANALYSES FOR CELLULAR PROLIFERATIVE DISORDERS

(75) Inventors: Dimo Dietrich, Berlin (DE); Catherine E. Lofton-Day, Seattle, WA (US); Shannon Payne, Seattle, WA (US)

(73) Assignee: EPIGENOMICS AG, Berlin (DE)

( * ) Notice: Subject to any disclaimer, the term of this patent is extended or adjusted under 35 U.S.C. 154(b) by 1139 days.

This patent is subject to a terminal disclaimer.

(21) Appl. No.: 12/374,651

(22) PCT Filed: Jul. 23, 2007

(86) PCT No.: PCT/EP2007/006539
§ 371 (c)(1),
(2), (4) Date: Dec. 4, 2009

(87) PCT Pub. No.: WO2008/009479
PCT Pub. Date: Jan. 24, 2008

(65) Prior Publication Data
US 2010/0092953 A1    Apr. 15, 2010

Related U.S. Application Data

(60) Provisional application No. 60/832,509, filed on Jul. 21, 2006, provisional application No. 60/853,097, filed on Oct. 20, 2006.

(30) Foreign Application Priority Data

Nov. 14, 2006  (EP) .................................... 06123989
Dec. 1, 2006   (EP) .................................... 06125256

(51) Int. Cl.
    *C12Q 1/68*      (2006.01)
    *G01N 33/574*    (2006.01)

(52) U.S. Cl.
    CPC ..... *G01N 33/57434* (2013.01); *C12Q 1/6844* (2013.01); *C12Q 1/6886* (2013.01); *C12Q 2600/112* (2013.01); *C12Q 2600/154* (2013.01); *C12Q 2600/158* (2013.01)

(58) Field of Classification Search
    None
    See application file for complete search history.

(56) References Cited

U.S. PATENT DOCUMENTS

| 2002/0182586 A1* | 12/2002 | Morris et al. .................. 435/4 |
| 2008/0241842 A1* | 10/2008 | Belinsky ........................ 435/6 |
| 2009/0005268 A1* | 1/2009  | Berlin ........................... 506/26 |
| 2010/0092981 A1* | 4/2010  | Shuber .......................... 435/6 |

FOREIGN PATENT DOCUMENTS

| WO | WO 2005054517 A2 * | 6/2005 | .......... C12Q 1/6886 |
| WO | WO 2006008128 A2 * | 1/2006 | .......... C12Q 1/6886 |
| WO | 2007/008693 A2 | 1/2007 | |
| WO | WO 2008/011620 A2 | 1/2008 | |

OTHER PUBLICATIONS

Hesson, L.B. et al. CpG island promoter hypermethylation of a novel Ras-effector gene RASSF2A is an early event in colon carcinogenesis and correlates inversely with K-ras mutations. Oncogene, vol. 24, p. 3987-3994, Apr. 2005.*
Endoh, M. et al. RaSSF2, a potential tumour suppressor, is silenced by CpG island hypermethylation in gastric cancer. Brithish Journal of Cancer, vol. 93, p. 1395-1399, 2005.*
Akino, K. et al. The Ras effector RASSF2 is a novel tumor-suppressor gene in human colorectal cancer. Gastroenterology, vol. 12, p. 156-169, May 2005.*
Lecomte et al., "Detection of Free-Circulating Tumor-Associated DNA in Plasma of Colorectal Cancer Patients and its Association with Prognosis", *Int. J. Cancer*. 100:542-548, 2002.
Kaira et al. (2007) "Epigenetic inactivation of the RAS-effector gene RASSF2 in lung cancers," Int. J. Oncol. 31(1):169-173.
Nosho et al. (2007) "Genetic and epigenetic profiling in early colorectal tumors and prediction of invasive potential in oT1 (early invasive) colorectal cancers," Carcinogenesis. 28(6):1364-1370.
Zhang et al. (2007) "Inactivation of RASSF2A by promoter methylation correlates with lymph node metastasis in nasopharyngeal carcinoma," Int. J. Cancer. 120(1):32-38.
International Search Report with Written Opinion corresponding to International Patent Application No. PCT/EP2007/006539, dated Dec. 3, 2007.

* cited by examiner

*Primary Examiner* — Suryaprabha Chunduru
(74) *Attorney, Agent, or Firm* — Lathrop Gage LLP; James H. Velema, Esq.; Sean M. Coughlin, Esq.

(57) ABSTRACT

Provided herein are methods, nucleic acids and kits for detecting a cell proliferative disorder. Also provided herein are genomic sequences of RASSF'-2, the methylation patterns of which have utility for the improved detection of cell proliferative disorders, thereby enabling the improved diagnosis and treatment of patients.

12 Claims, 31 Drawing Sheets

Figure 1:
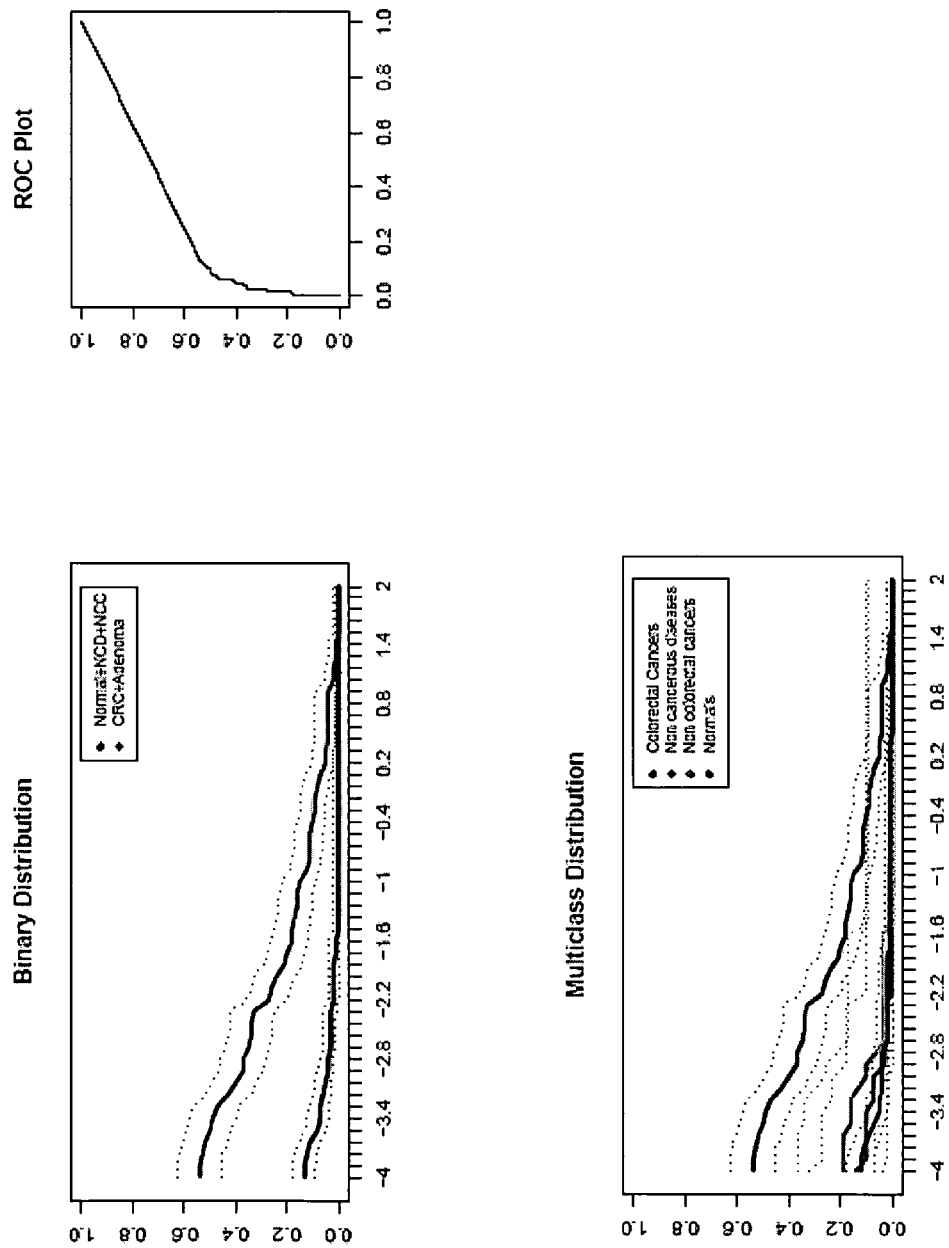

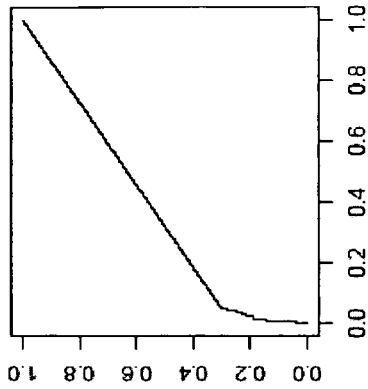
FIGURE 14
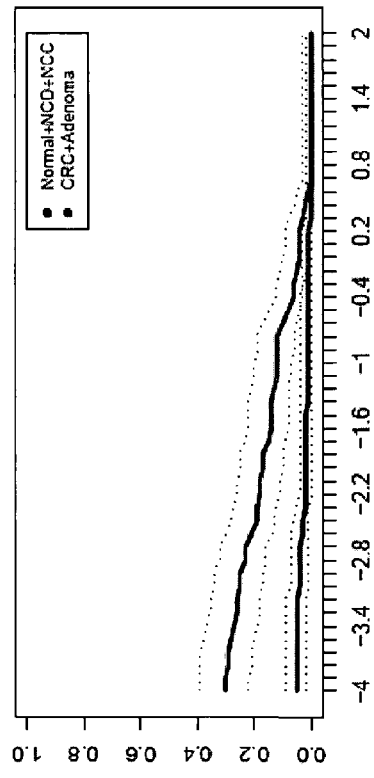
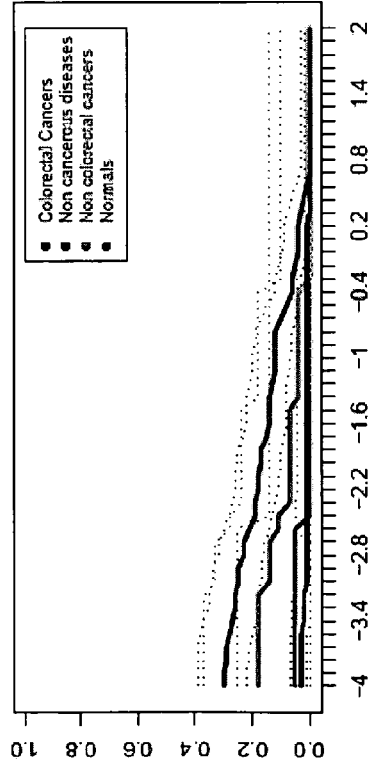

RASSF2A

TFAP2E

GSTP1

HIST1H4J

METHODS AND NUCLEIC ACIDS FOR ANALYSES FOR CELLULAR PROLIFERATIVE DISORDERS

CROSS-REFERENCE TO RELATED APPLICATIONS

This application is the United States nationalization, under 35 U.S.C. § 371, of International Application No. PCT/EP2007/006539, filed 23 Jul. 2007, which claims the benefit of priority to U.S. Provisional Patent Application Ser. Nos. 60/832,509 filed Jul. 21, 2006, 60/853,097 filed 20 Oct. 2006, EP06123989.3 filed Nov. 14, 2006, and EP06125256.5 filed Dec. 1, 2006, all of which are incorporated by reference herein in their entirety.

FIELD OF THE INVENTION

The present invention relates to genomic DNA sequences that exhibit altered expression patterns in disease states relative to normal. Particular embodiments provide methods, nucleic acids, nucleic acid arrays and kits useful for detecting, or for diagnosing carcinoma.

BACKGROUND

Incidence and Diagnosis of Cancer.

Cancer is the second leading cause of death of the United States. Mortality rates could be significantly improved if current screening methods would be improved in terms of patient compliance, sensitivity and ease of screening. Current recommended methods for diagnosis of cancer are often invasive, expensive or are otherwise not suitable for application as population wide screening tests.

Incidence and diagnosis of prostate cancer. Prostate cancer is the most common malignancy among men in the United States (~200,000 new cases per year), and the sixth leading cause of male cancer-related deaths worldwide (~204,000 per year). Prostate cancer is primarily a disease of the elderly, with approximately 16% of men between the ages of 60 and 79 having the disease. According to some estimates at autopsy, 80% of all men over 80 years of age have some form of prostate disease (e.g. cancer, BPH, prostatitis, etc). Benign prostate hypertrophy is present in about 50% of men aged 50 or above, and in 95% of men aged 75 or above. It is obvious from these reports that prostate cancer is often not a disease that men die from, but with. Recent evidence suggests that the incidence of prostate cancer may in fact be declining, likely as result of better treatment, better surgery, and earlier detection.

Current guidelines for prostate cancer screening have been suggested by the American Cancer Society and are as follows: At 50 years of age, health care professionals should offer a blood test for prostate specific antigen (PSA) and perform a digital rectal exam (DRE). It is recommended that high risk populations, such as African Americans and those with a family history of prostate disease, should begin screening at 45 years of age. Men without abnormal prostate pathology generally have a PSA level in blood below 4 ng/ml. PSA levels between 4 ng/ml and 10 ng/ml (called the "Grey Zone") have a 25% chance of having prostate cancer. The result is that 75% of the time, men with an abnormal DRE and a PSA in this grey zone have a negative, or a seemingly unnecessary biopsy. Above the grey zone, the likelihood of having prostate cancer is significant (>67%) and increases even further as PSA levels go up. Numerous methods exist for measuring PSA (percent-free PSA, PSA velocity, PSA density, etc.), and each has an associated accuracy for detecting the presence of cancer. Yet, even with the minor improvements in detection, and the reported drops in mortality associated with screening, the frequency of false positives remains high. Reduced specificity results in part from increased blood PSA associated with BPH, and prostatitis. It has also been estimated that up to 45% of prostate biopsies under current guidelines are falsely negative, resulting in decreased sensitivity even with biopsy.

TRUS guided biopsy is considered the gold standard for diagnosing prostate cancer. Recommendations for biopsy are based upon abnormal PSA levels and or an abnormal DREs. For PSA there is a grey zone where a high percentage of biopsies are perhaps not necessary. Yet the ability to detect cancer in this grey zone (PSA levels of 4.0 to 10 ng/ml) is difficult without biopsy. Due to this lack of specificity, 75% of men undergoing a biopsy do not have cancer. Yet without biopsy, those with cancer would be missed, resulting in increased morbidity and mortality. However the risks associated with an unnecessary biopsy are also high.

It is clear that there is a need for an early, specific prostate cancer test for more accurate detection and treatment monitoring, to improve morbidity and mortality rates. However, using routine histological examination, it is often difficult to distinguish benign hyperplasia of the prostate from early stages of prostate carcinoma, even if an adequate biopsy is obtained (McNeal J. E. et al., *Hum. Pathol.* 2001, 32:441-6). Furthermore, small or otherwise insufficient biopsy samples often impede the analysis.

Incidence and diagnosis of colon cancer. In the United States the annual incidence of colorectal cancer is approximately 150,000, with 56,600 individuals dying form colorectal cancer each year. The lifetime risk of colorectal cancer in the general population is about 5 to 6 percent. Despite intensive efforts in recent years in screening and early detection of colon cancer, until today most cases are diagnosed in an advanced stage with regional or distant metastasis. While the therapeutic options include surgery and adjuvant or palliative chemotherapy, most patients die from progression of their cancer within a few months. Identifying the molecular changes that underlie the development of colon cancer may help to develop new monitoring, screening, diagnostic and therapeutic options that could improve the overall poor prognosis of these patients.

The current guidelines for colorectal screening according to the American Cancer Society utilizes one of five different options for screening in average risk individuals 50 years of age or older. These options include 1) fecal occult blood test (FOBT) annually, 2) flexible sigmoidoscopy every five years, 3) annual FPBT plus flexible sigmoidoscopy every five years, 4) double contrast barium enema (DCBE) every five years or 5) colonoscopy every ten years. Even though these testing procedures are well accepted by the medical community, the implementation of widespread screening for colorectal cancer has not been realized. Patient compliance is a major factor for limited use due to the discomfort or inconvenience associated with the procedures. FOBT testing, although a non-invasive procedure, requires dietary and other restrictions 3-5 days prior to testing. Sensitivity levels for this test are also very low for colorectal adenocarcinoma with wide variability depending on the trial. Sensitivity measurements for detection of adenomas is even less since most adenomas do not bleed. In contrast, sensitivity for more invasive procedures such as sigmoidoscopy and colonoscopy are quite high because of direct visualization of the lumen of the colon. No randomized trials have evaluated the efficacy of these techniques, however, using data from case-control studies and data from the National Polyp Study (U.S.) it has been shown that removal of adenomatous polyps results in a 76-90% reduction in CRC incidence. Sigmoidoscopy has the limitation of only visualizing the left side of the colon leaving lesions in the right colon undetected. Both scoping procedures are expensive, require cathartic preparation and have increased risk of morbidity and mortality. Improved tests with increased sensitivity, specificity, ease of use and decreased costs are clearly needed before general widespread screening for colorectal cancer becomes routine.

Early colorectal cancer detection is generally based on the fecal occult blood test (FOBT) performed annually on asymptomatic individuals. Current recommendations adapted by several healthcare organizations, including the American Cancer Society, call for fecal occult blood testing beginning at age 50, repeated annually until such time as the patient would no longer benefit from screening. A positive FOBT leads to colonoscopic examination of the bowel; an expensive and invasive procedure, with a serious complication rate of one per 5,000 examinations. Only 12% of patients with heme-positive stool are diagnosed with cancer or large polyps at the time of colonoscopy. A number of studies show that FOBT screening does not improve cancer-related mortality or overall survival. Compliance with occult blood testing has been poor; less than 20 percent of the population is offered or completes FOBT as recommended. If FOBT is properly done, the patient collects a fecal sample from three consecutive bowel movements. Samples are obtained while the patient adheres to dietary guidelines and avoids medications known to induce occult gastrointestinal bleeding. In reality, physicians frequently fail to instruct patients properly, patients frequently fail to adhere to protocol, and some patients find the task of collecting fecal samples difficult or unpleasant, hence compliance with annual occult blood testing is poor. If testing sensitivity and specificity can be improved over current methods, the frequency of testing could be reduced, collection of consecutive samples would be eliminated, dietary and medication schedule modifications would be eliminated, and patient compliance would be enhanced. Compounding the problem of compliance, the sensitivity and specificity of FOBT to detect colon cancer is poor. Poor test specificity leads to unnecessary colonoscopy, adding considerable expense to colon cancer screening.

Specificity of the FOBT has been calculated at best to be 96%, with a sensitivity of 43% (adenomas) and 50% (colorectal carcinoma). Sensitivity can be improved using an immunoassay FOBT such as that produced under the trade name 'InSure™', with an improved sensitivity of 77% (adenomas) and 88.9% (colorectal carcinoma.

Molecular disease markers. Molecular disease markers offer several advantages over other types of markers, one advantage being that even samples of very small sizes and/or samples whose tissue architecture has not been maintained can be analyzed quite efficiently. Within the last decade a number of genes have been shown to be differentially expressed between normal and colon carcinomas. However, no single or combination of marker has been shown to be sufficient for the diagnosis of colon carcinomas. High-dimensional mRNA based approaches have recently been shown to be able to provide a better means to distinguish between different tumor types and benign and malignant lesions. However its application as a routine diagnostic tool in a clinical environment is impeded by the extreme instability of mRNA, the rapidly occurring expression changes following certain triggers (e.g., sample collection), and, most importantly, the large amount of mRNA needed for analysis (Lipshutz, R. J. et al., Nature Genetics 21:20-24, 1999; Bowtell, D. D. L. Nature genetics suppl. 21:25-32, 1999), which often cannot be obtained from a routine biopsy.

The use of biological markers to further improve sensitivity and specificity of FOBT has been suggested, examples of such tests include the PreGen-Plus™ stool analysis assay available from EXACT Sciences which has a sensitivity of 20% (adenoma) and 52% (colorectal carcinoma) and a specificity of 95% in both cases. This test assays for the presence of 23 DNA mutations associated with the development of colon neoplasms.

CpG island methylation. Apart from mutations aberrant methylation of CpG islands has been shown to lead to the transcriptional silencing of certain genes that have been previously linked to the pathogenesis of various cancers. CpG islands are short sequences which are rich in CpG dinucleotides and can usually be found in the 5' region of approximately 50% of all human genes. Methylation of the cytosines in these islands leads to the loss of gene expression and has been reported in the inactivation of the X chromosome and genomic imprinting.

The RASSF2 gene is located at chromosomal location 20p13, and encodes multiple mRNA transcript isoforms. Members of the Ras protein family are associated with cancer, RASSF2 binds to K-Ras, and expression of RASSF2 is associated with controlled cell growth. Loss of expression results in uninhibited cell proliferation, and accordingly RASSF2 is a tumour suppressor gene (Vos et. al. J. Biol. Chem., Vol. 278, Issue 30, 28045-28051, Jul. 25, 2003).

Multifactorial approach. Cancer diagnostics has traditionally relied upon the detection of single molecular markers (e.g., gene mutations, elevated PSA levels). Unfortunately, cancer is a disease state in which single markers have typically failed to detect or differentiate many forms of the disease. Thus, assays that recognize only a single marker have been shown to be of limited predictive value. A fundamental aspect of this invention is that methylation-based cancer diagnostics and the screening, diagnosis, and therapeutic monitoring of such diseases will provide significant improvements over the state-of-the-art that uses single marker analyses by the use of a selection of multiple markers. The multiplexed analytical approach is particularly well suited for cancer diagnostics since cancer is not a simple disease, this multi-factorial "panel" approach is consistent with the heterogeneous nature of cancer, both cytologically and clinically.

Key to the successful implementation of a panel approach to methylation based diagnostic tests is the design and development of optimized panels of markers that can characterize and distinguish disease states. The present invention describes a plurality of particularly efficient and unique panels of genes, the methylation analysis of one or a combination of the members of the panel enabling the detection of colon cell proliferative disorders with a particularly high sensitivity, specificity and/or predictive value.

Development of medical tests. Two key evaluative measures of any medical screening or diagnostic test are its sensitivity and specificity, which measure how well the test performs to accurately detect all affected individuals without exception, and without falsely including individuals who do not have the target disease (predictive value). Historically, many diagnostic tests have been criticized due to poor sensitivity and specificity.

A true positive (TP) result is where the test is positive and the condition is present. A false positive (FP) result is where the test is positive but the condition is not present. A true negative (TN) result is where the test is negative and the condition is not present. A false negative (FN) result is where the test is negative but the condition is not present. In this context: Sensitivity=TP/(TP+FN); Specificity=TN/(FP+TN); and Predictive value=TP/(TP+FP).

Sensitivity is a measure of a test's ability to correctly detect the target disease in an individual being tested. A test having poor sensitivity produces a high rate of false negatives, i.e., individuals who have the disease but are falsely identified as being free of that particular disease. The potential danger of a false negative is that the diseased individual will remain undiagnosed and untreated for some period of time, during which the disease may progress to a later stage wherein treatments, if any, may be less effective. An example of a test that has low sensitivity is a protein-based blood test for HIV. This type of test exhibits poor sensitivity because it fails to detect the presence of the virus until the disease is well established and the virus has invaded the bloodstream in substantial numbers. In contrast, an example of a test that has high sensitivity is viral-load detection using the polymerase chain reaction (PCR). High sensitivity is achieved because this type of test can detect very small quantities of the virus. High sensitivity is particularly important when the consequences of missing a diagnosis are high.

Specificity, on the other hand, is a measure of a test's ability to identify accurately patients who are free of the disease state. A test having poor specificity produces a high rate of false positives, i.e., individuals who are falsely identified as having the disease. A drawback of false positives is that they force patients to undergo unnecessary medical procedures treatments with their attendant risks, emotional and financial stresses, and which could have adverse effects on the patient's health. A feature of diseases which makes it difficult to develop diagnostic tests with high specificity is that disease mechanisms, particularly in cancer, often involve a plurality of genes and proteins. Additionally, certain proteins may be elevated for reasons unrelated to a disease state. Specificity is important when the cost or risk associated with further diagnostic procedures or further medical intervention are very high.

Background of the RASSF2 gene. The RASSF2 gene comprises a CpG dense region in the gene promoter, spanning the first 2 non-coding exons. This region has been characterised as being co-methylated, and furthermore, methylation thereof has been associated with the development of gastric and colon carcinomas. Hesson et al. (Oncogene. 2005 Jun. 2; 24(24):3987-94.) characterised the CpG island as being co-methylated, by means of COBRA analysis and bisulfite sequencing of colon cancer cell lines. Furthermore, they confirmed by MSP analysis that 21/30 (70%) of analysed colon cancer cell lines were methylated within the RASSF2 promoter region. Further research has indicated that RASSF2 methylation may be associated with gastric cancer (Endoh et. al Br J. Cancer. 2005 Dec. 12; 93(12):1395-9) and nasopharyngeal cancer (Zhang et. al Int J. Cancer. 2007 Jan. 1; 120(1):32-8).

The subject matter of the present invention differs from the state of the art in that the present invention demonstrates for the first time the RASSF2 methylation is a hallmark of multiple cancer types e.g. colon and prostate and that it can be detected in a wide variety of body fluids.

The technical effect of analysing body fluids as opposed to tissue is to enable the diagnosis of cancer without the need for biopsy, or other invasive procedures. There are currently no body fluid based tests that are suitable for the routine diagnosis of cancer. Body fluid tests such as the PSA (prostate cancer) and FOBT (colon cancer) are routinely carried out, but are considered as indicators of cancer to be followed with e.g. invasive or imaging tests upon whose results the clinicians will provide a diagnosis.

The development of a body fluid based cancer diagnostic test would increase patient compliance to the level where it would be possible to screen asymptomatic populations, i.e. would enable general screening for colon cancer. This would greatly increase the early detection of cancer, and accordingly improve patient survival rates. Thus there is a need in the art for a body fluid based colon cancer screening/diagnostic test.

Accordingly the problem to be solved is how to non-invasively diagnose cancer. From the teachings cited above the person skilled in the art would have been aware that RASSF2 is a suitable methylation marker for differentiating between colon neoplastic and colon healthy tissue, and may thus have been minded to further investigate it as a diagnostic marker. However there is no teaching in the art that would motivate said person to investigate said marker as a body fluid cancer marker as opposed to a more traditional biopsy analysis test, as he would not have had a reasonable expectation of success.

Markers that are methylated in a specific cancer type are rarely detectable in body fluids, due to the presence of a general background methylation resultant from the many different tissue types that may be present, and also due to the tiny amounts of tumour DNA present in body fluids. For example, although the gene RASSF2 is not methylated in healthy colon tissues it may be methylated in other tissues which could be present in body fluids. There is no teaching in the art that RASSF2 is not methylated in body fluids. Accordingly the person skilled in the art would not have had any motivation to investigate its performance in body fluids.

FIGS. 1 to 10 provide an overview of the log mean methylation measured by means of the HM assay according to Example 2. Each figures consists of three plots, the upper and lower left hand side plots provide the binary and multi-class analysis respectively, sensitivity is shown on the Y-axis, DNA methylation measured in (log 10 ng/mL) is shown on the X-axis. In each figure the right hand plot provides an ROC wherein sensitivity is shown on the Y-axis and 1-specificity is shown on the X-axis.

FIG. 1 provides an overview of the performance of the RASSF2 HM assay according to Example 2, in all samples.

Figure 2:
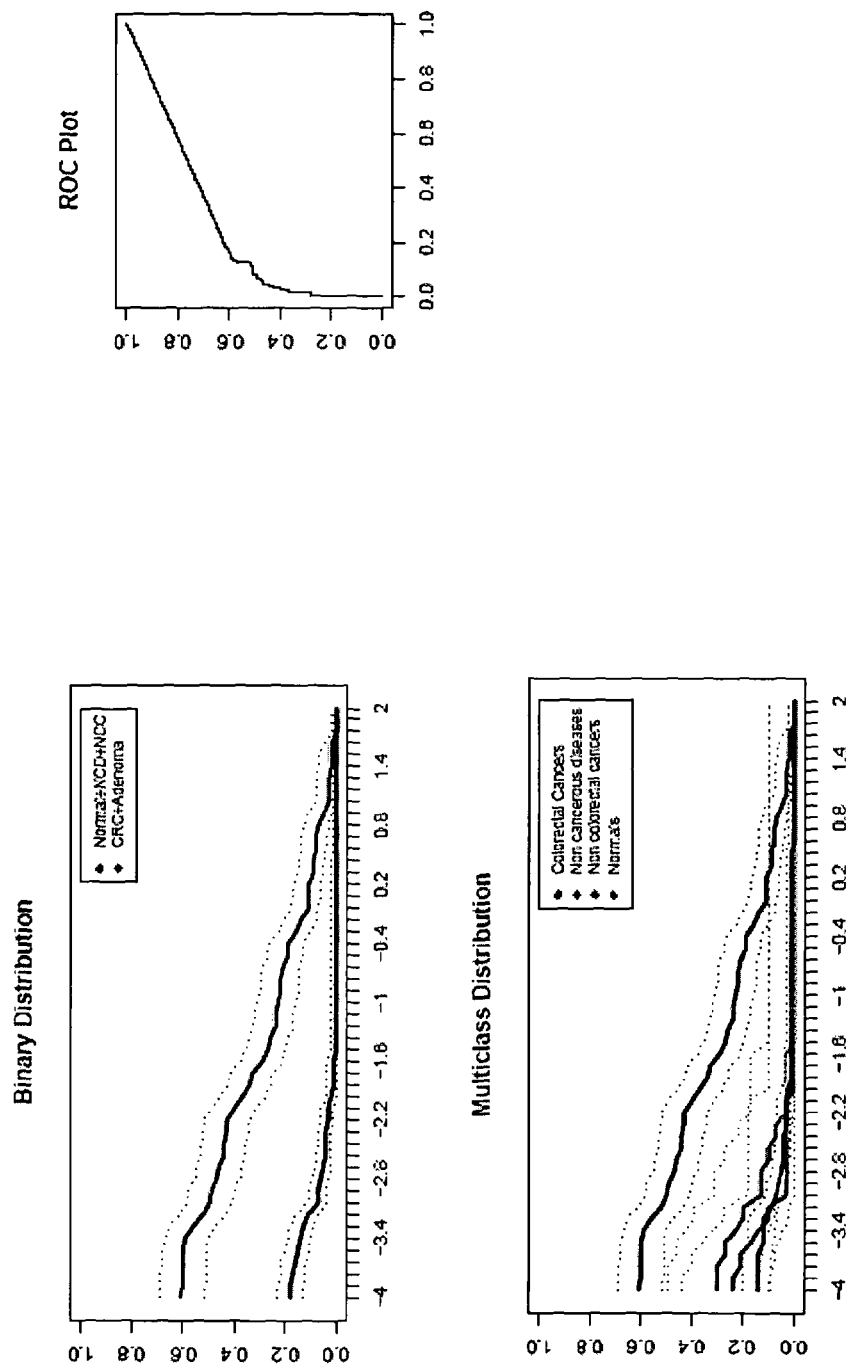

FIG. 2 provides an overview of the performance of the Septin 9 HM assay according to Example 2, in all samples.

Figure 3:
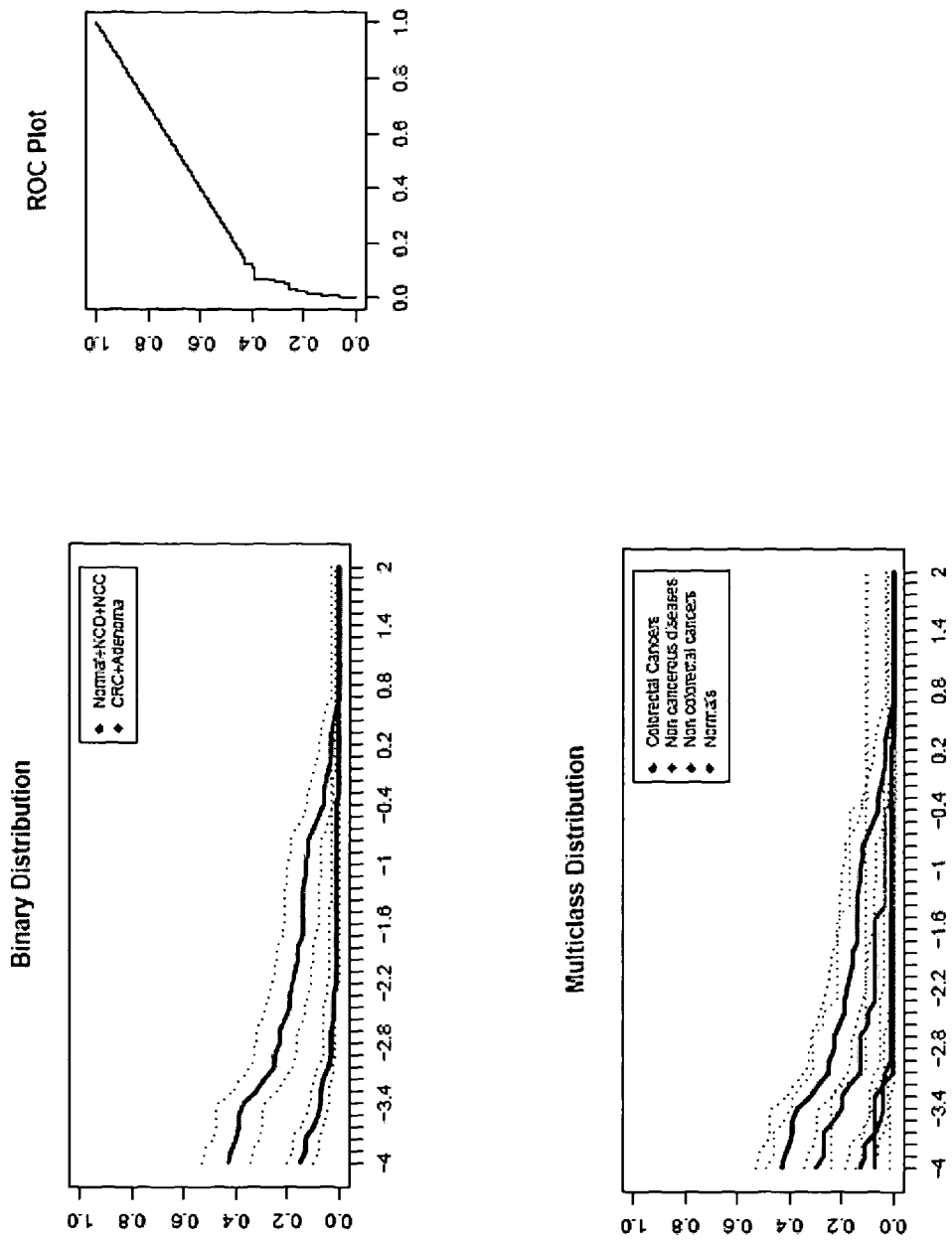

FIG. 3 provides an overview of the performance of the SND1 HM assay according to Example 2, in all samples.

Figure 4:
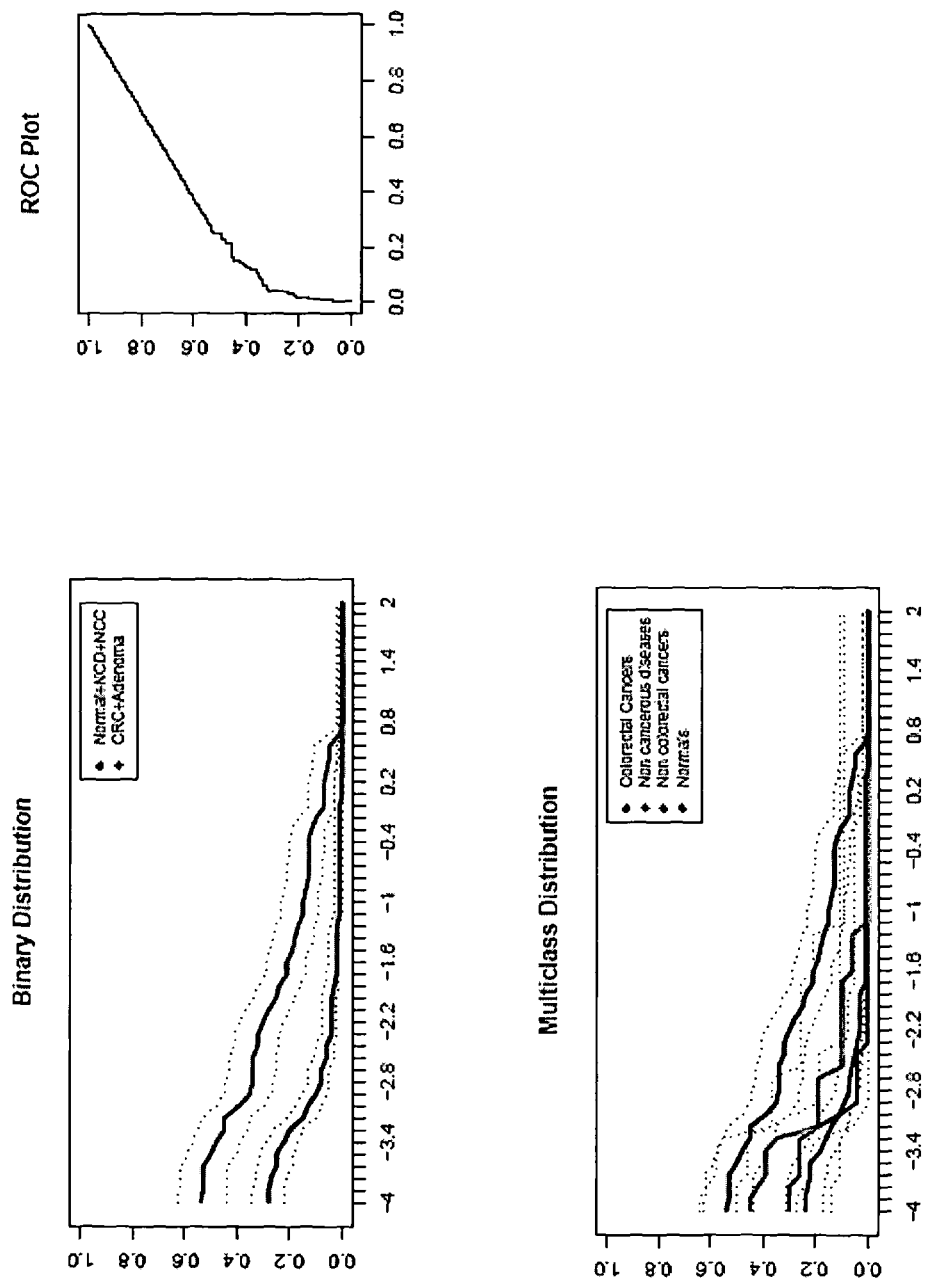

FIG. 4 provides an overview of the performance of the PCDHGC3 HM assay according to Example 2, in all samples.

Figure 5:
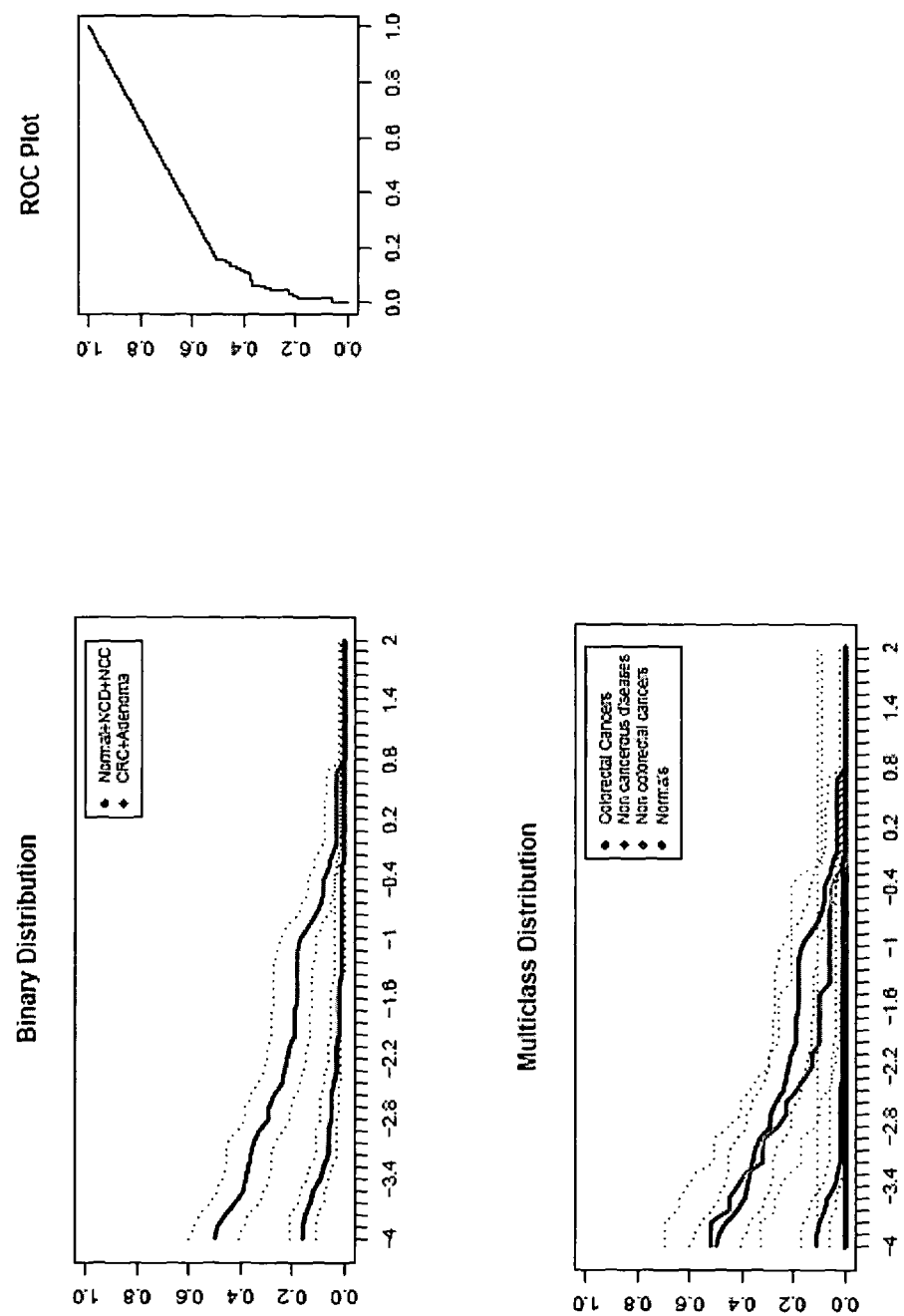

FIG. 5 provides an overview of the performance of the TFAP2E HM assay according to Example 2, in all samples.

Figure 6:
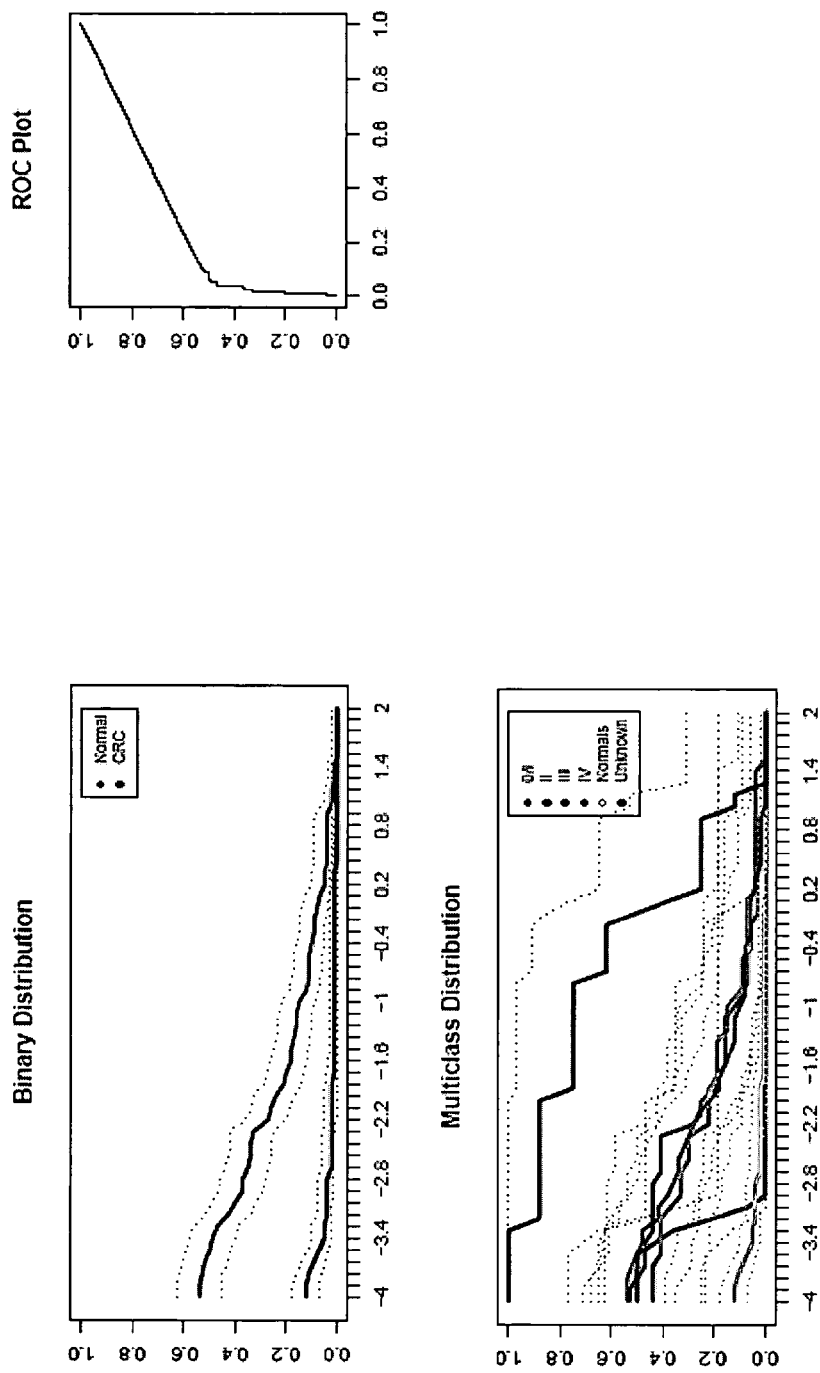

FIG. 6 provides an overview of the performance of the RASSF2 HM assay according to Example 2, in all colorectal carcinoma and normal colorectal tissue samples.

Figure 7:
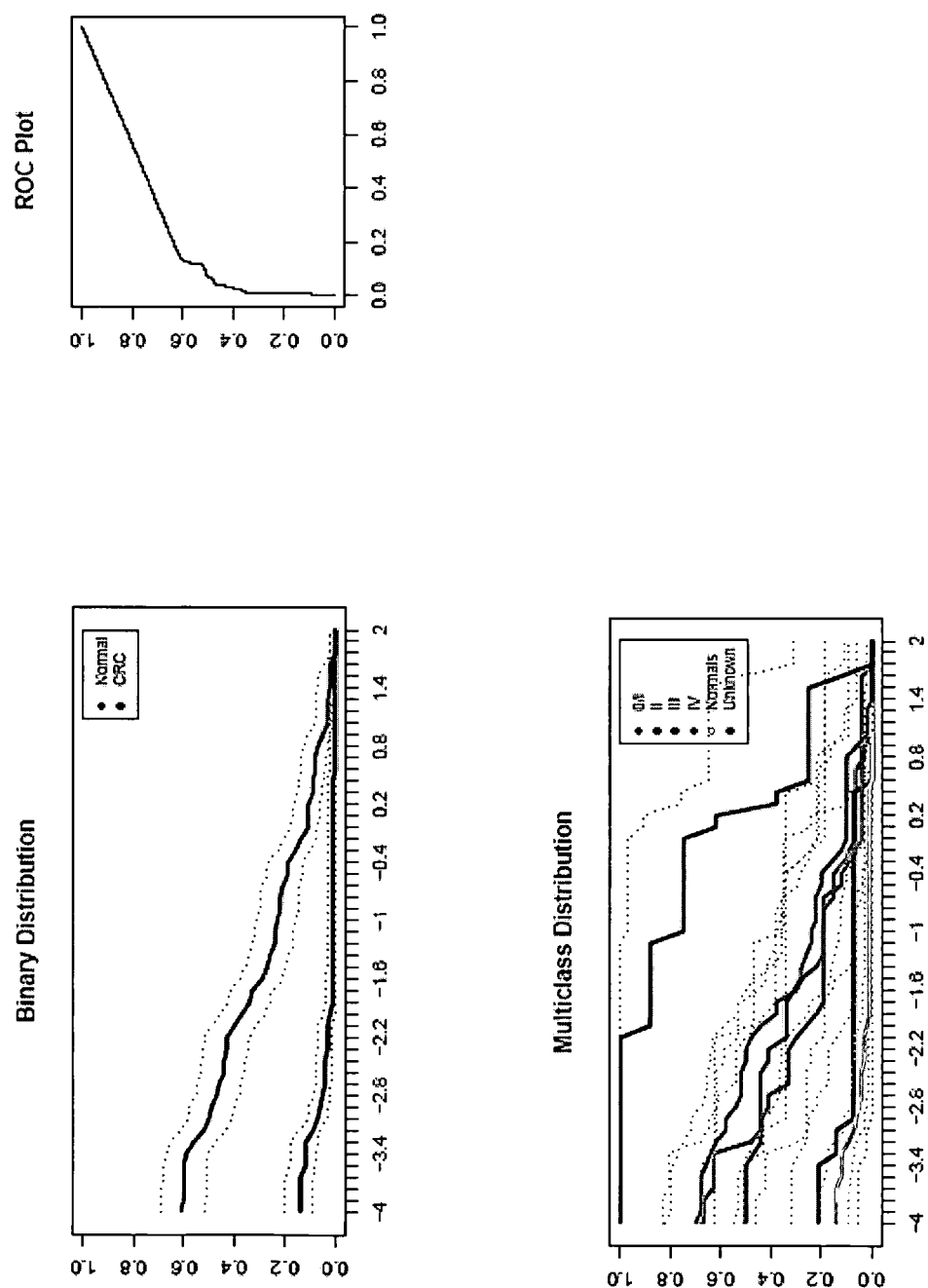

FIG. 7 provides an overview of the performance of the Septin 9 HM assay according to Example 2, in all colorectal carcinoma and normal colorectal tissue samples.

Figure 8:
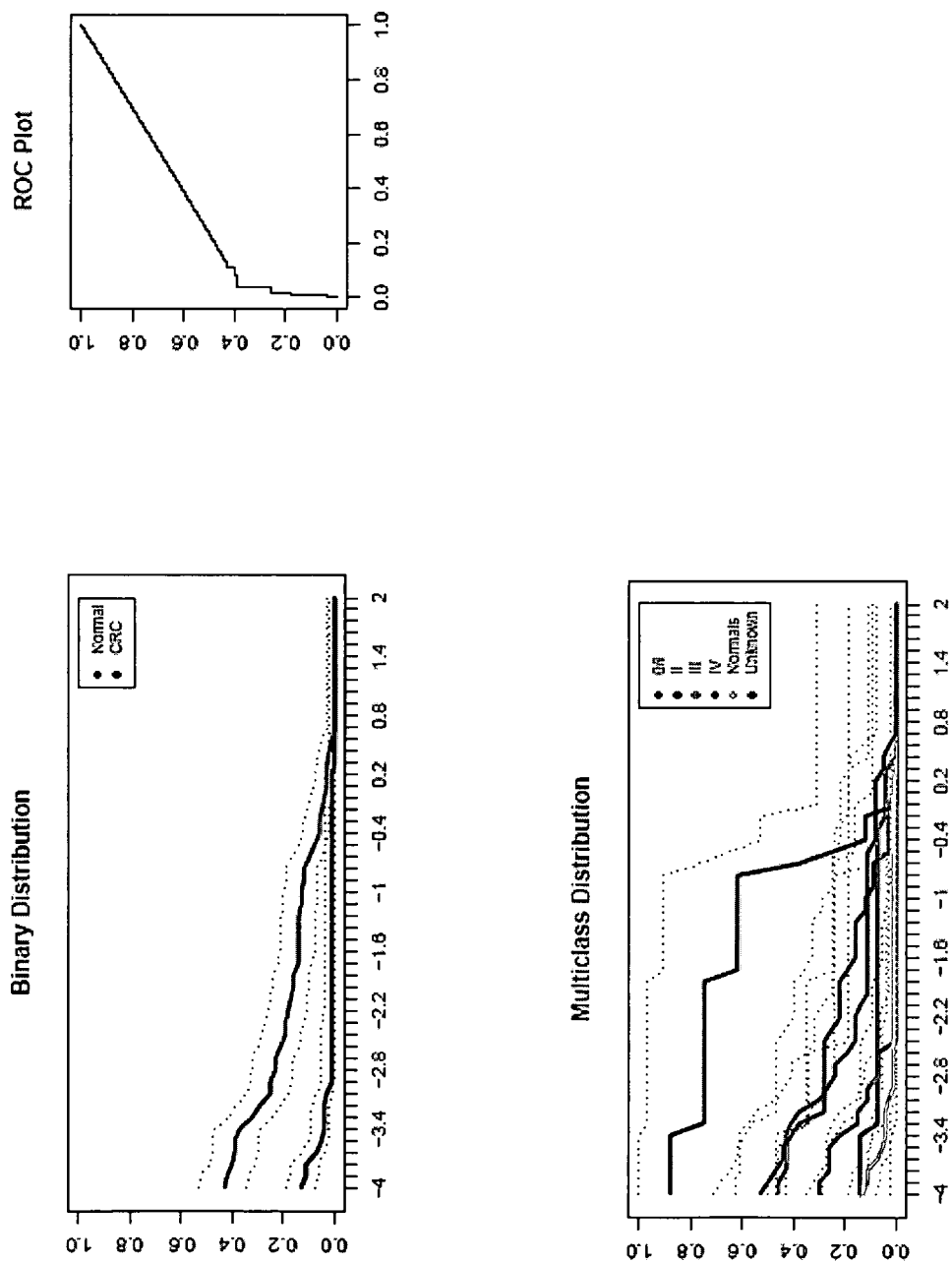

FIG. 8 provides an overview of the performance of the SND1 HM assay according to Example 2, in all colorectal carcinoma and normal colorectal tissue samples.

Figure 9:
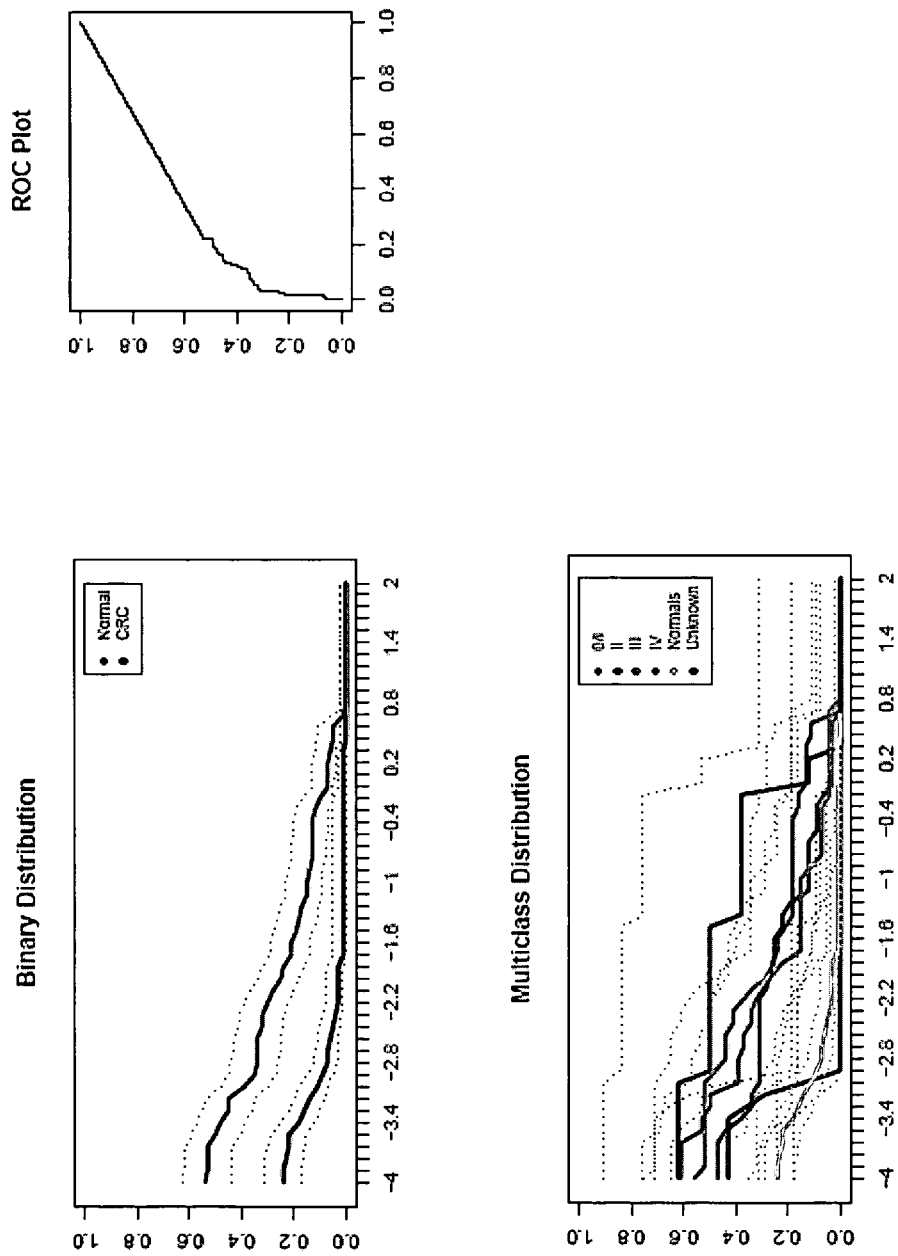

FIG. 9 provides an overview of the performance of the PCDHGC3 HM assay according to Example 2, in all colorectal carcinoma and normal colorectal tissue samples.

Figure 10:
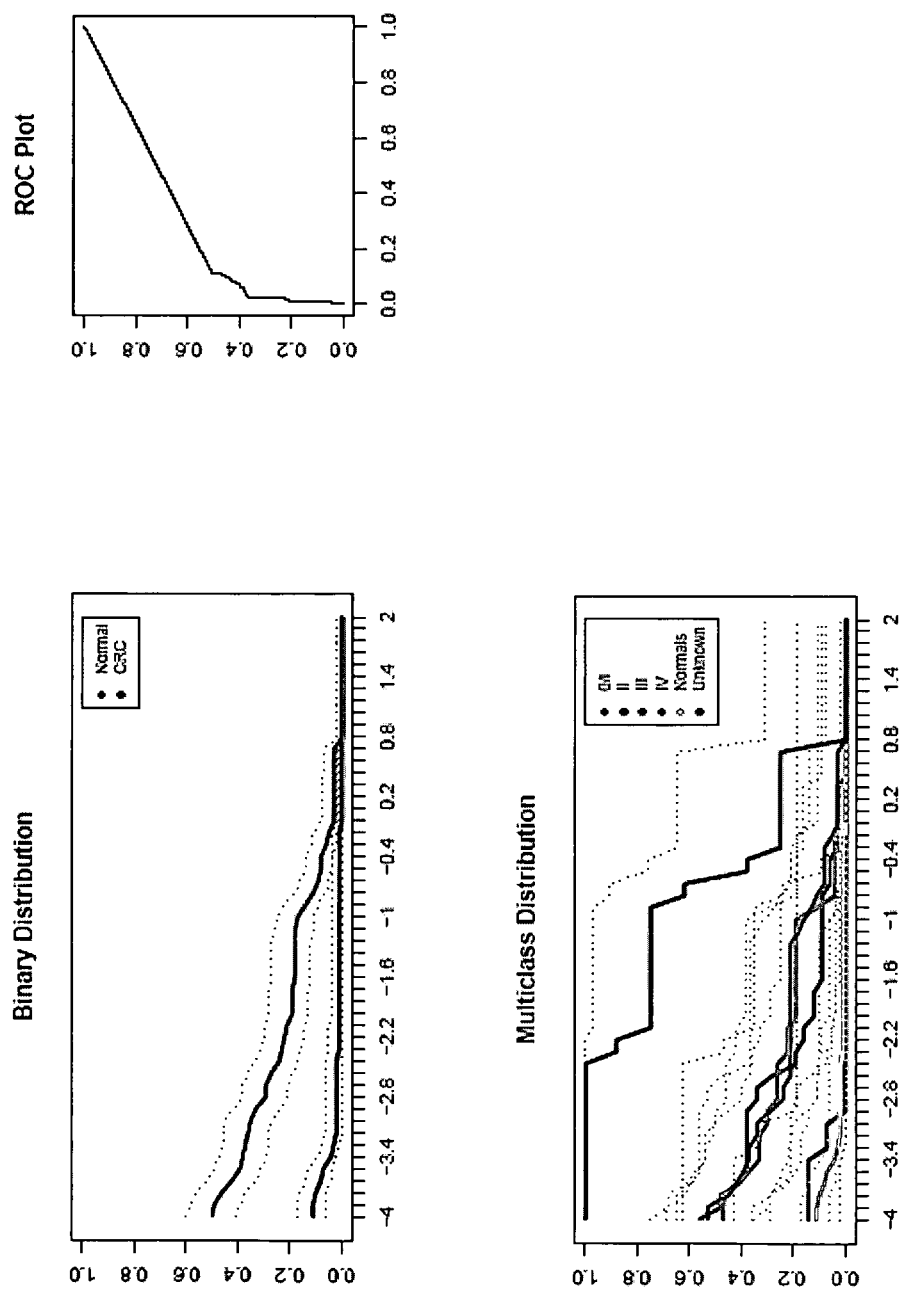

FIG. 10 provides an overview of the performance of the TFAP2E HM assay according to Example 2, in all colorectal carcinoma and normal colorectal tissue samples.

Figure 11:
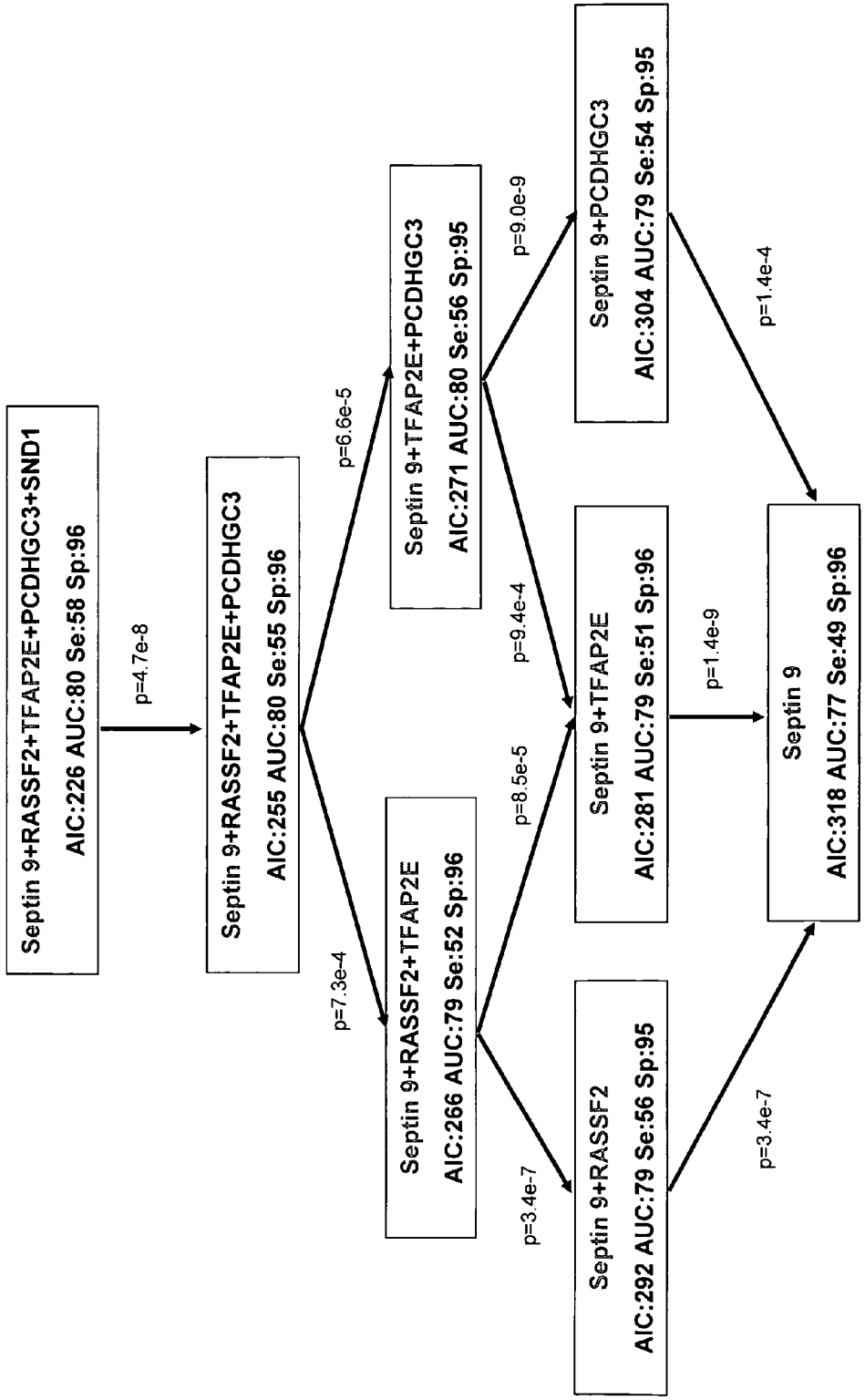

FIG. 11 provides an overview of the predictive power of the logistic regression model of combinations of markers. Se is sensitivity, sp is specificity, AUC is area under the curve.

FIGS. 12 to 21 provide an overview of the log majority mean methylation measured by means of the HM assay according to Example 2. Each figures consists of three plots, the upper and lower left hand side plots provide the binary and multi-class analysis respectively, sensitivity is shown on the Y-axis, DNA methylation measured in (log 10 ng/ml) is shown on the X-axis. In each figure the right hand plot provides an ROC wherein sensitivity is shown on the Y-axis and 1-specificity is shown on the X-axis.

Figure 12:
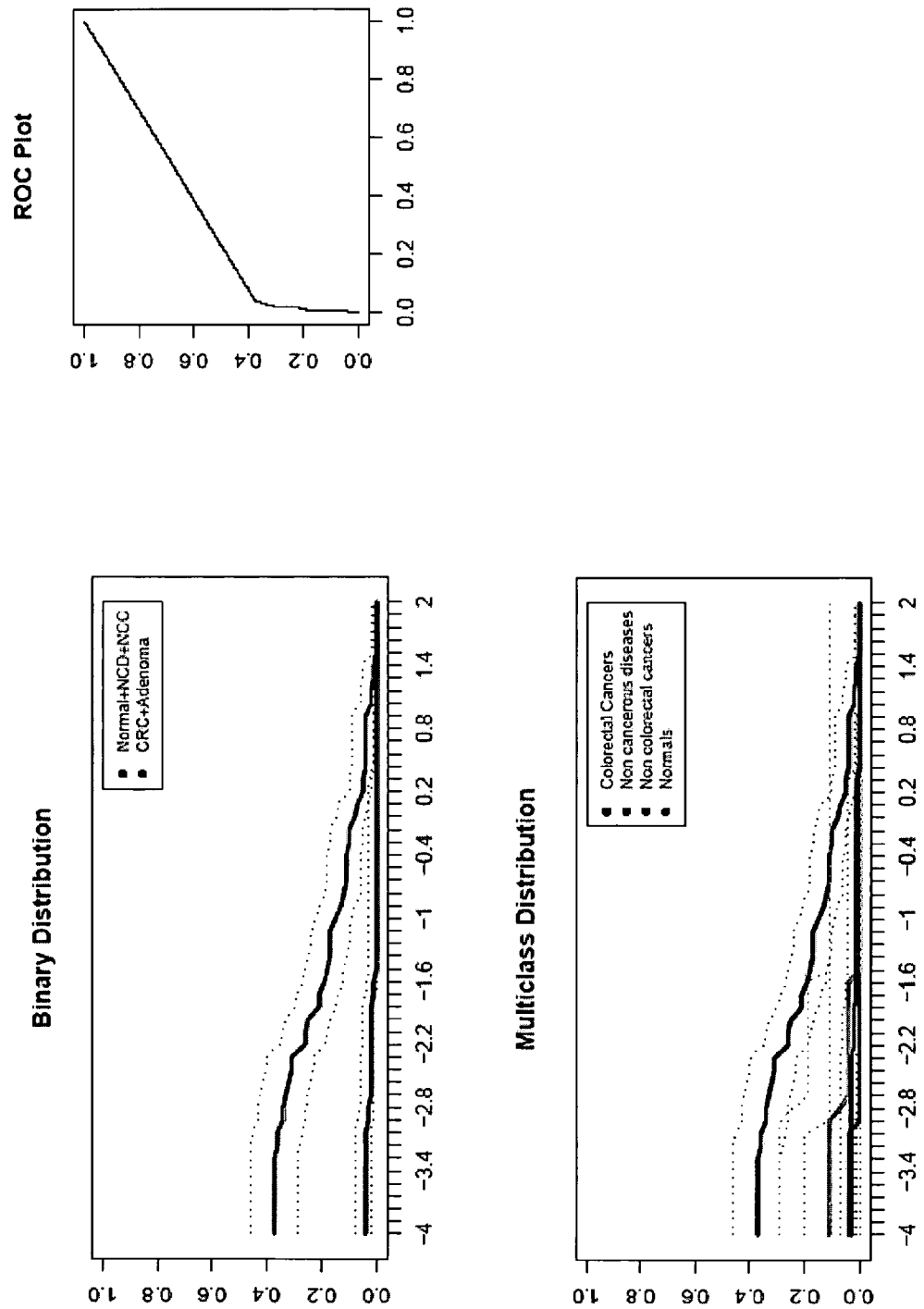

FIG. 12 provides an overview of the performance of the RASSF2 HM assay according to Example 2, in all samples.

Figure 13:
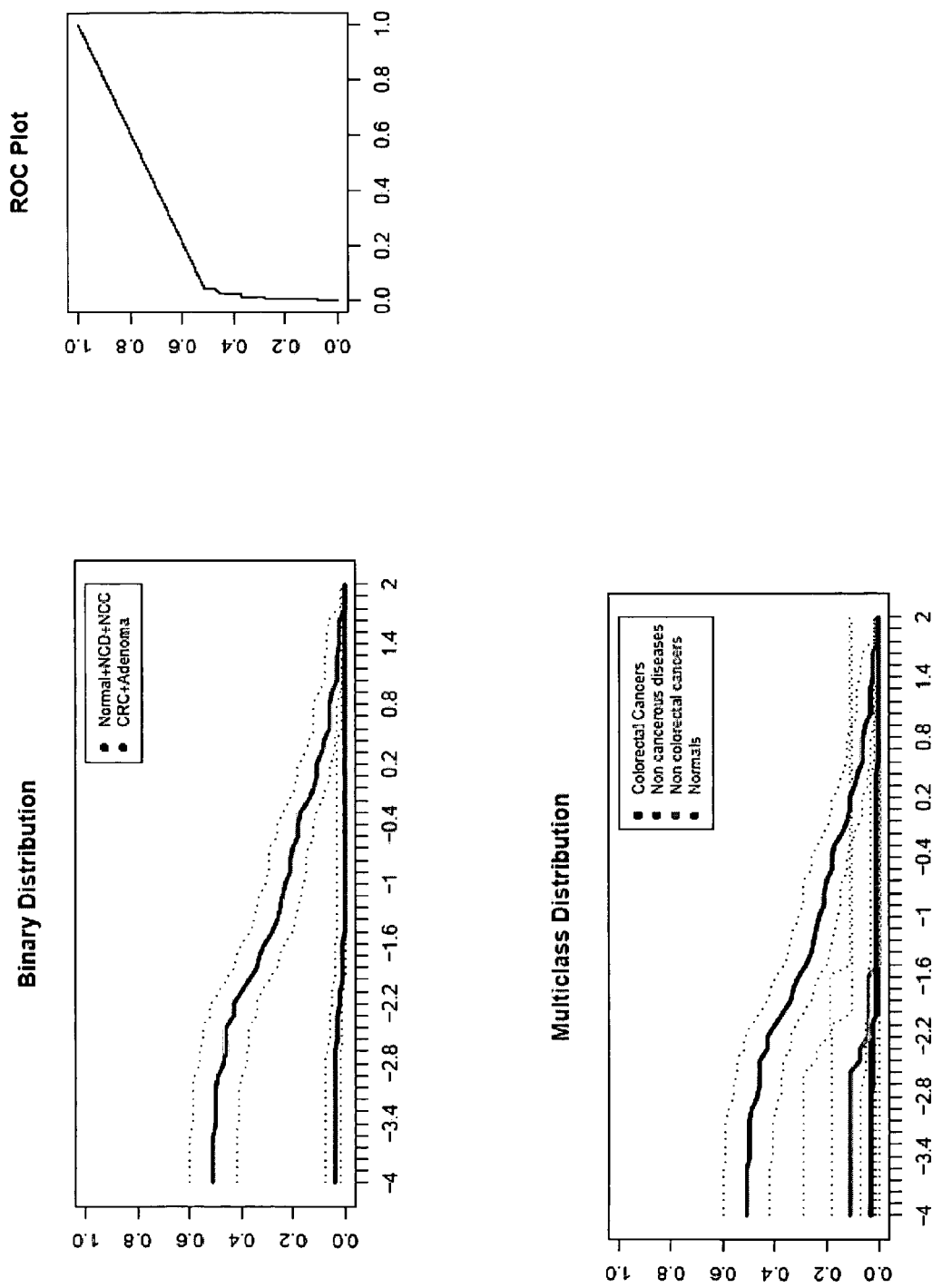

FIG. 13 provides an overview of the performance of the Septin 9 HM assay according to Example 2, in all samples.

FIG. 14 provides an overview of the performance of the SND1 HM assay according to Example 2, in all samples.

Figure 15:
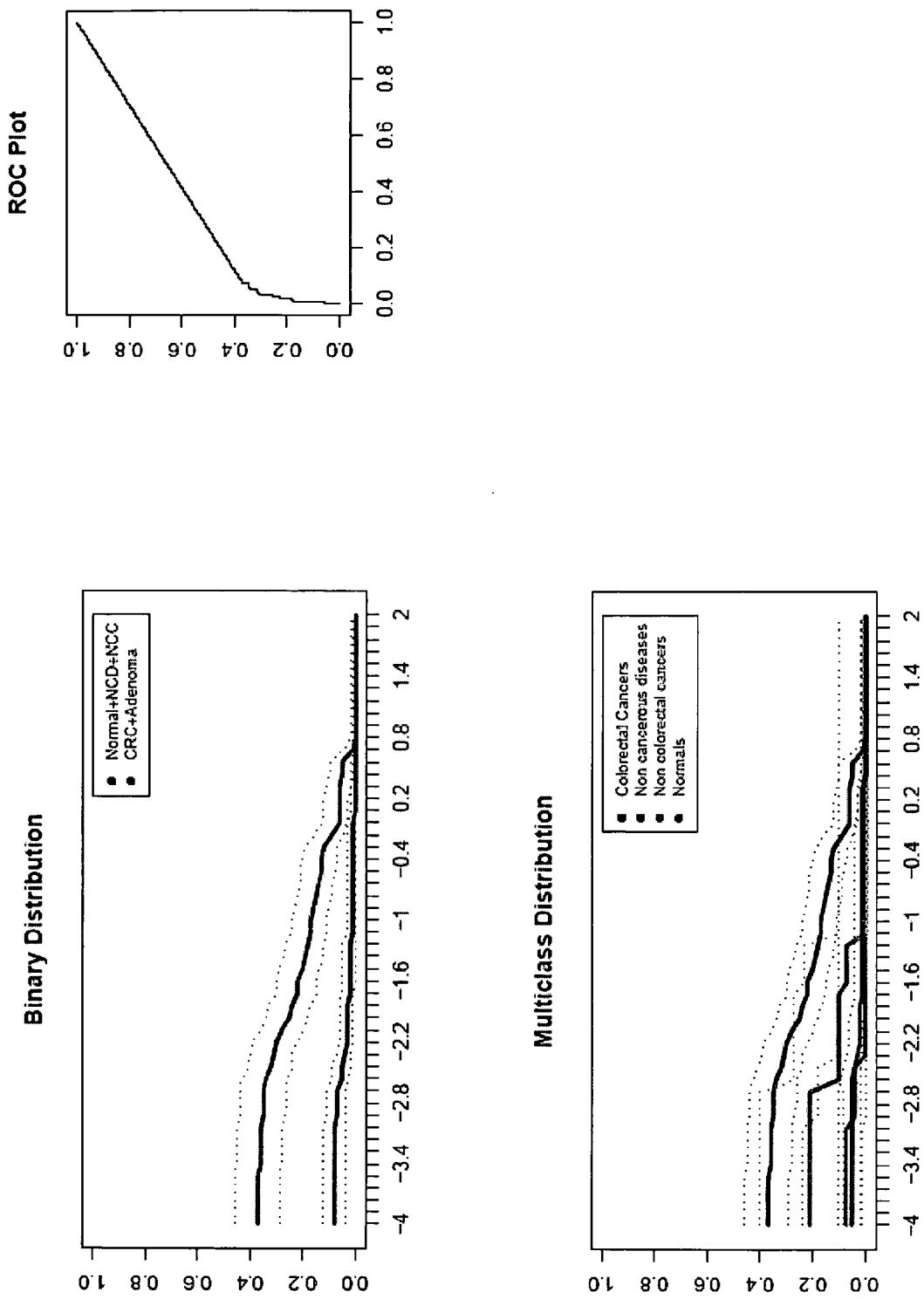

FIG. 15 provides an overview of the performance of the PCDHGC3 HM assay according to Example 2, in all samples.

Figure 16:
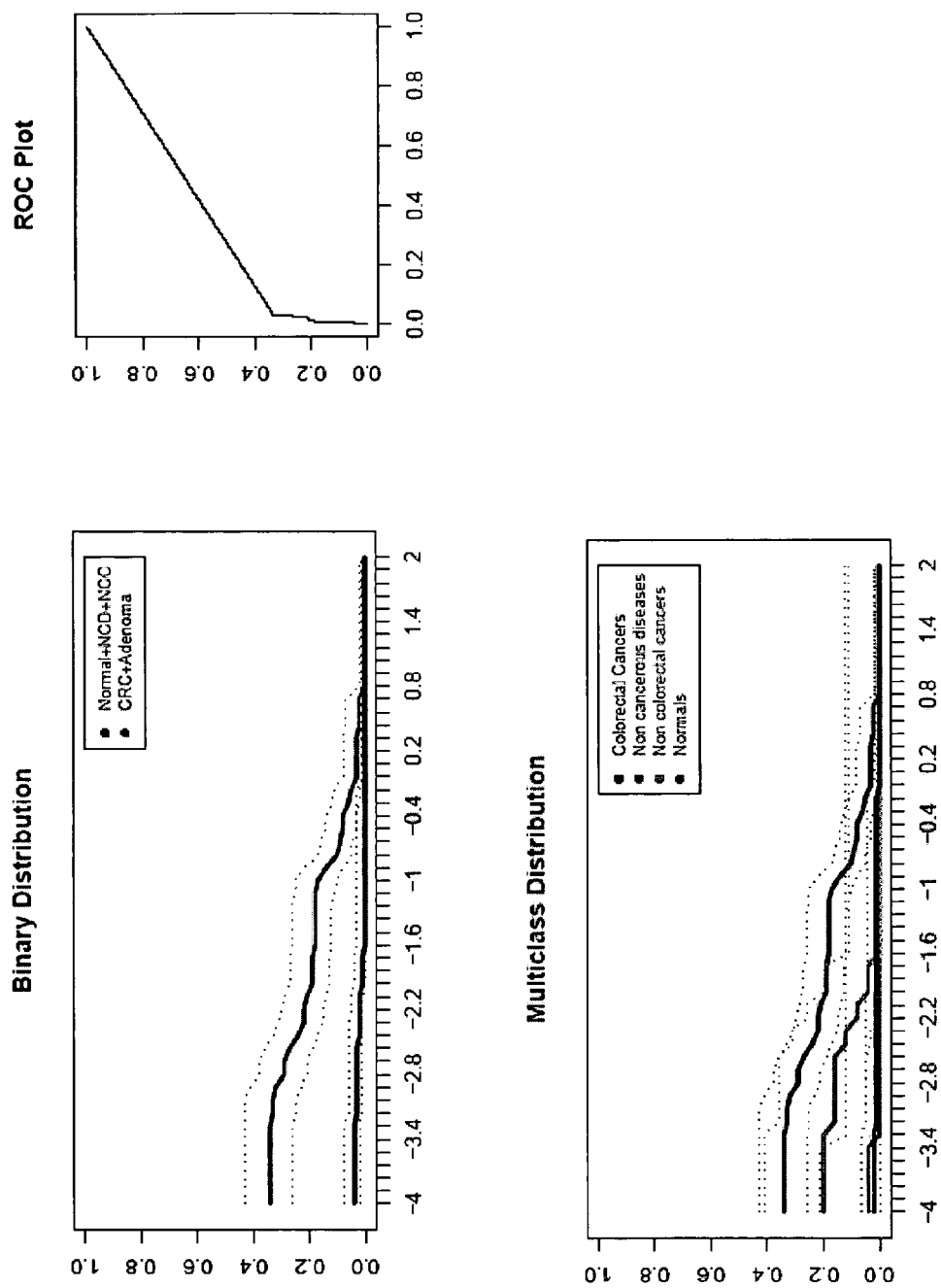

FIG. 16 provides an overview of the performance of the TFAP2E HM assay according to Example 2, in all samples.

Figure 17:
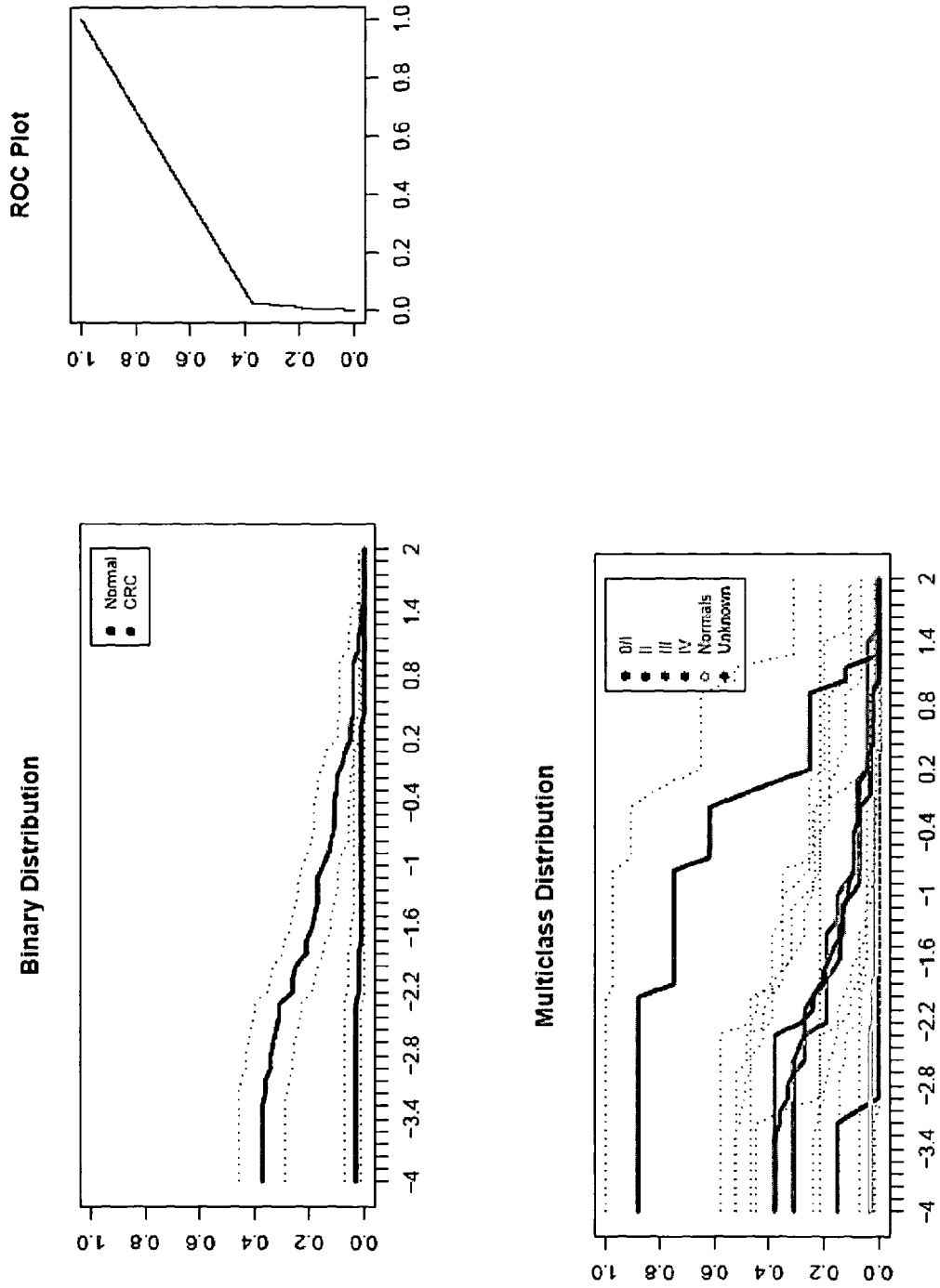

FIG. 17 provides an overview of the performance of the RASSF2 HM assay according to Example 2, in all colorectal carcinoma and normal colorectal tissue samples.

Figure 18:
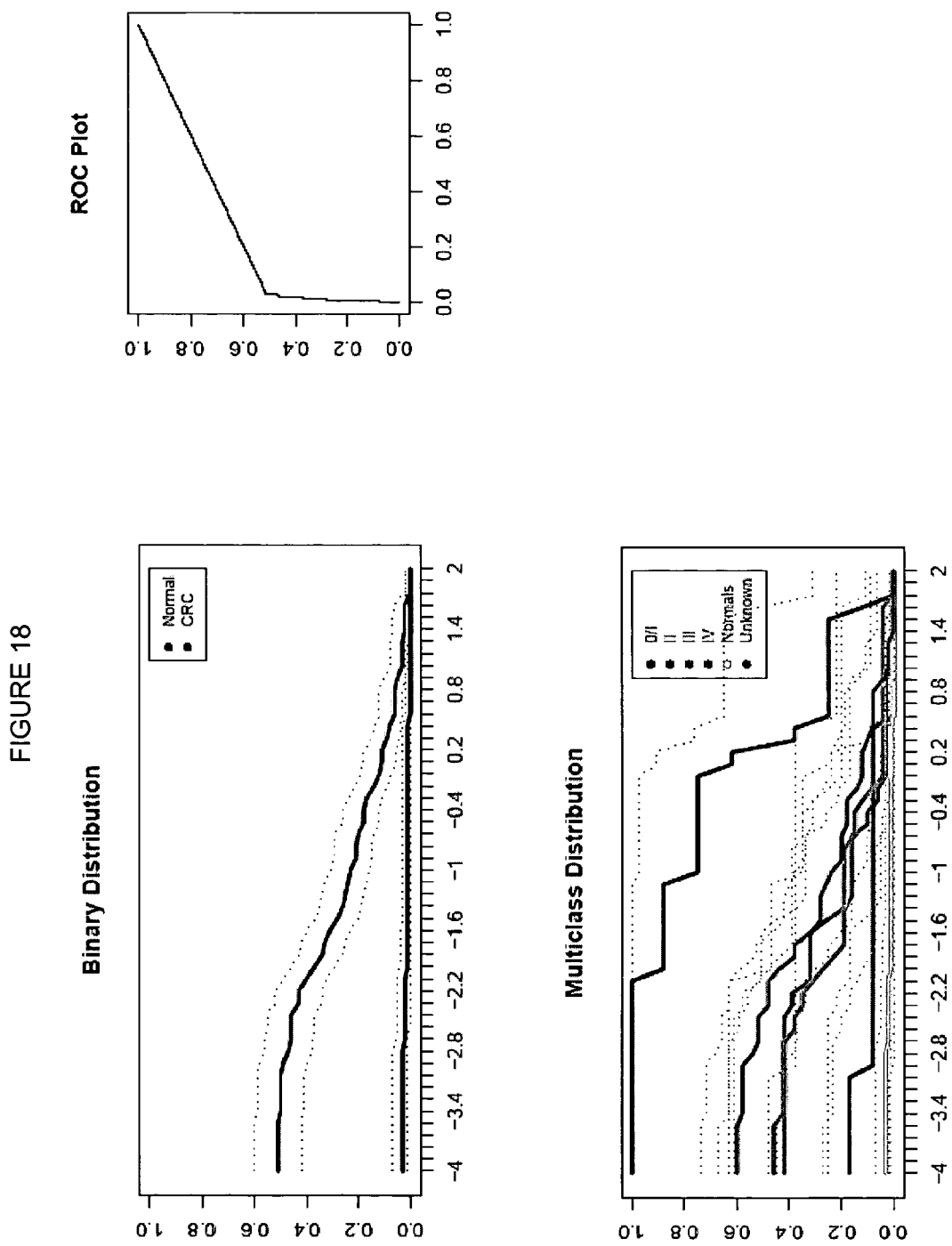

FIG. 18 provides an overview of the performance of the Septin 9 HM assay according to Example 2, in all colorectal carcinoma and normal colorectal tissue samples.

Figure 19:
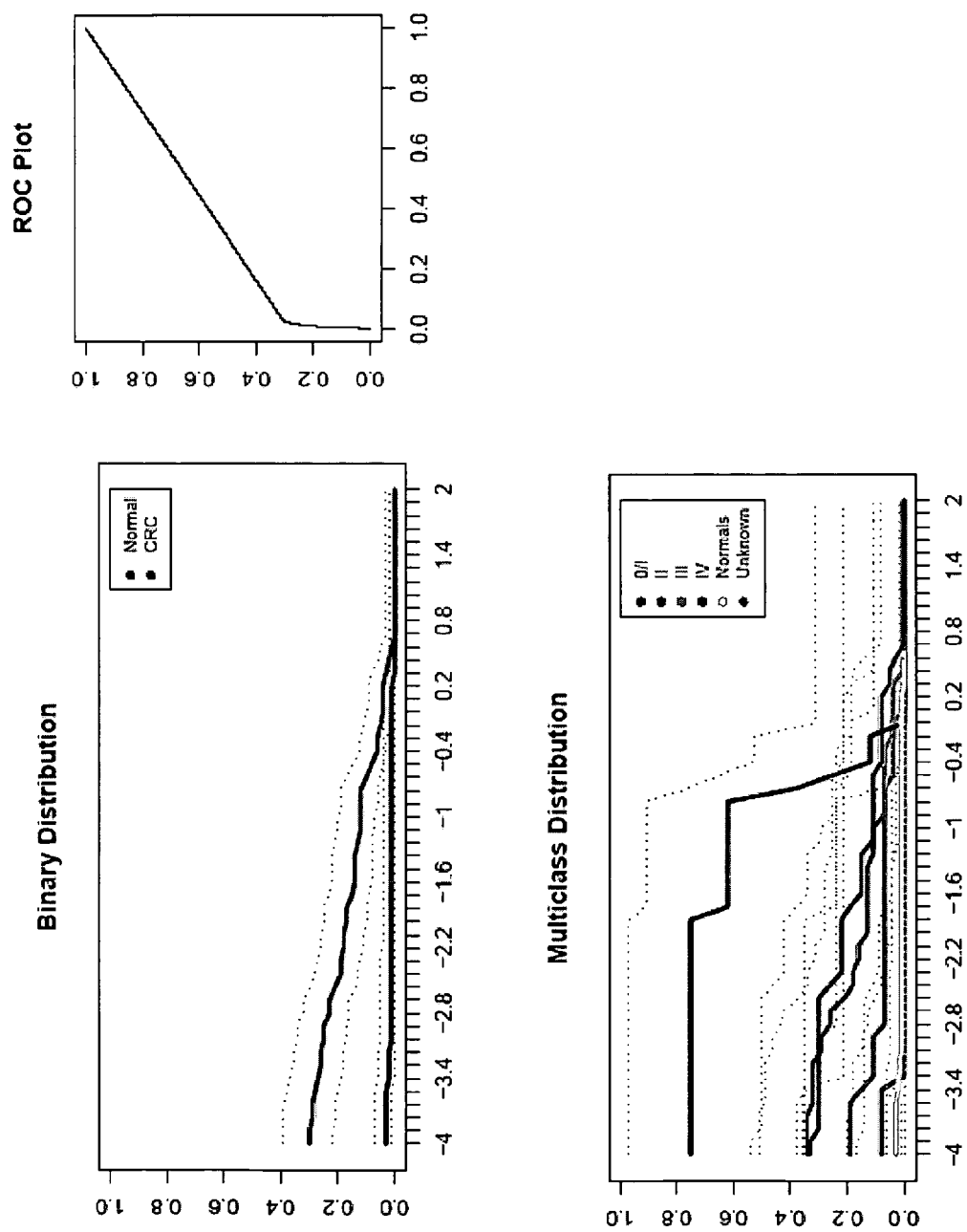

FIG. 19 provides an overview of the performance of the SND1 HM assay according to Example 2, in all colorectal carcinoma and normal colorectal tissue samples.

Figure 20:
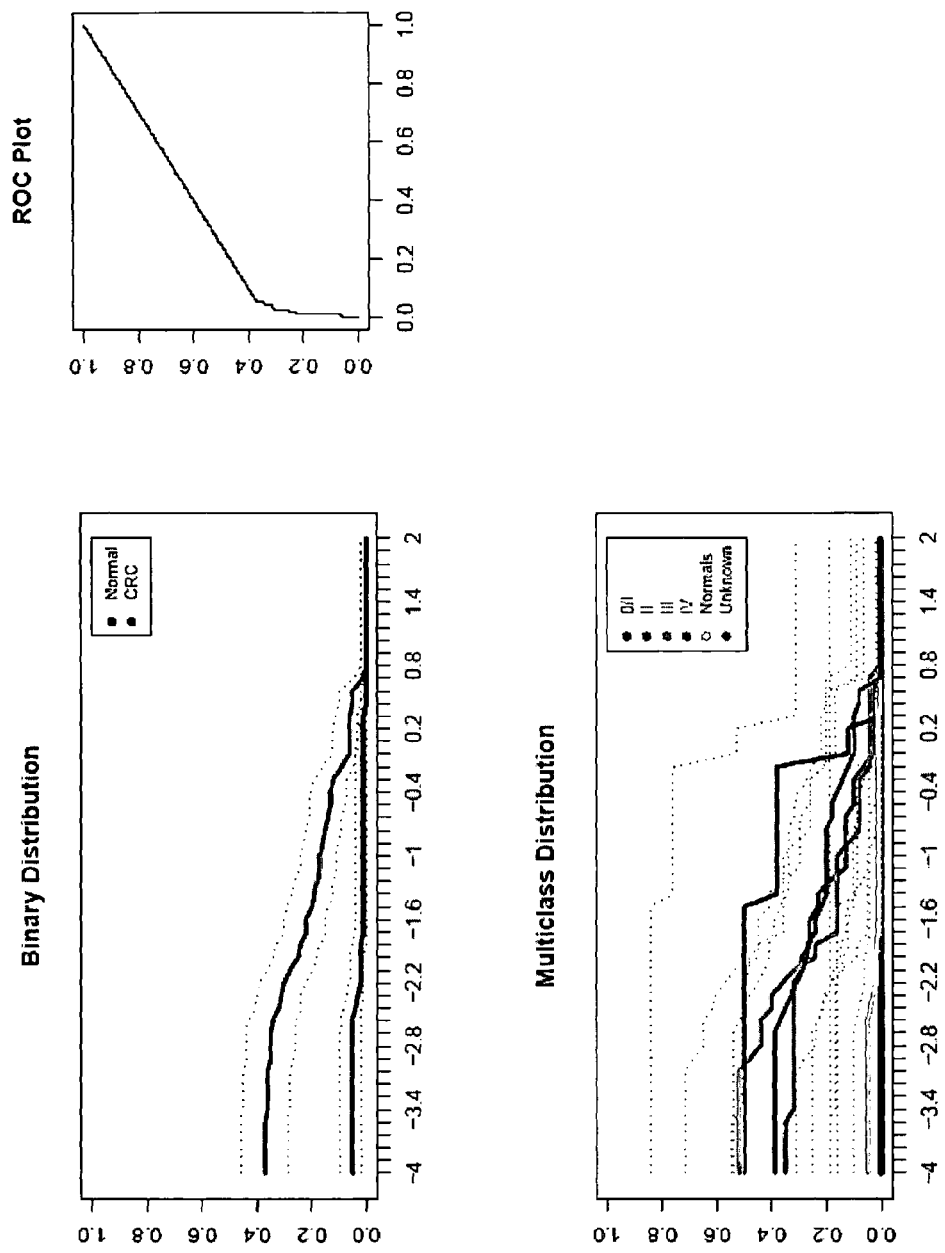

FIG. 20 provides an overview of the performance of the PCDHGC3 HM assay according to Example 2, in all colorectal carcinoma and normal colorectal tissue samples.

Figure 21:
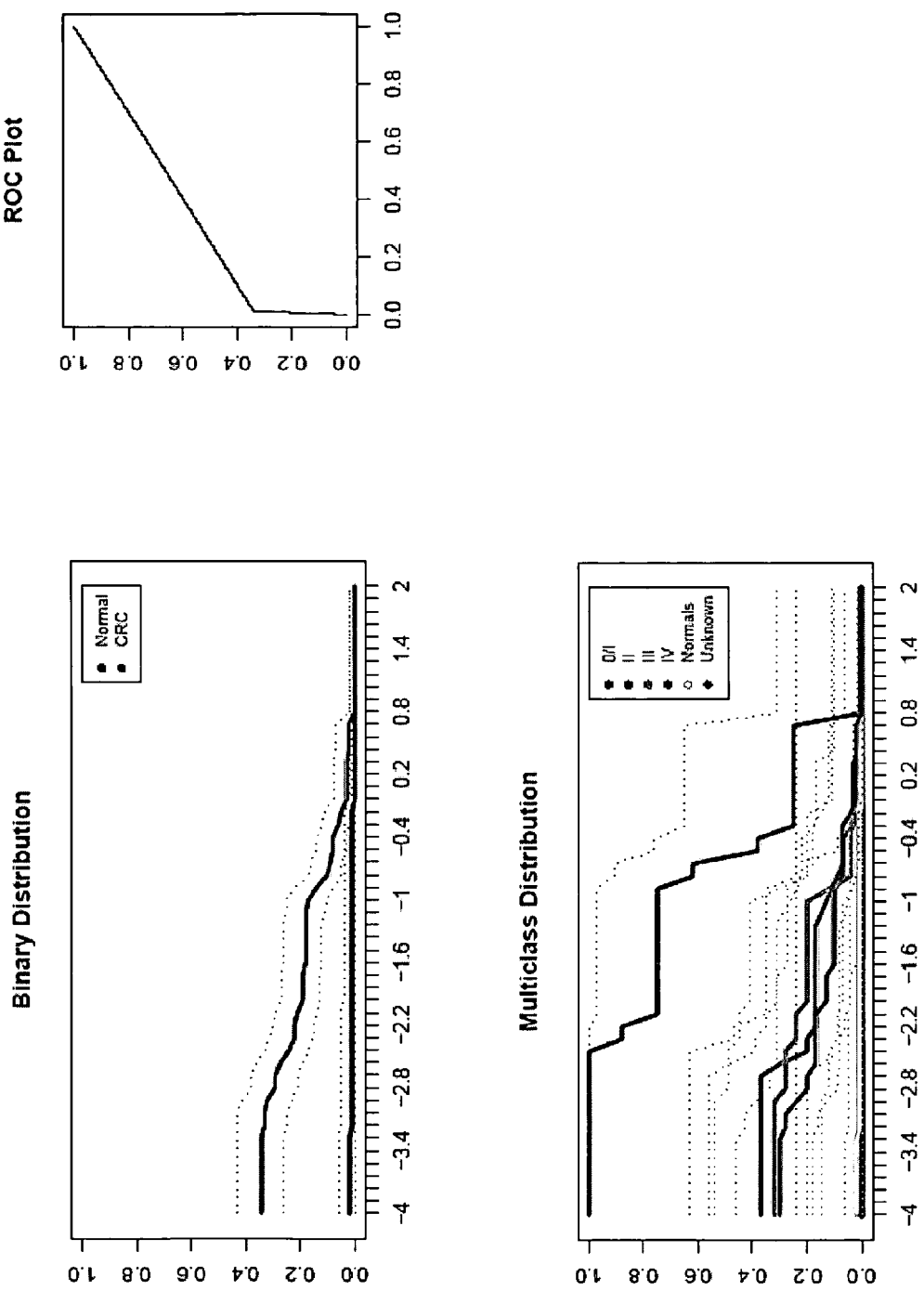

FIG. 21 provides an overview of the performance of the TFAP2E HM assay according to Example 2, in all colorectal carcinoma and normal colorectal tissue samples.

FIGS. 22 to 26 provide an overview of the log mean methylation measured by means of combinations HM assays (gene panels) according to Example 2. Each figures consists of two plots, The upper plot shows all samples (Normals, Non Colorectal Disease, Non-Coloretal Cancers and all CRC stages), the lower plot shows only Normaland CRC samples. Sensitivity is shown on the Y-axis, DNA methylation measured in (log 10 ng/mL) is shown on the X-axis.

Figure 22:
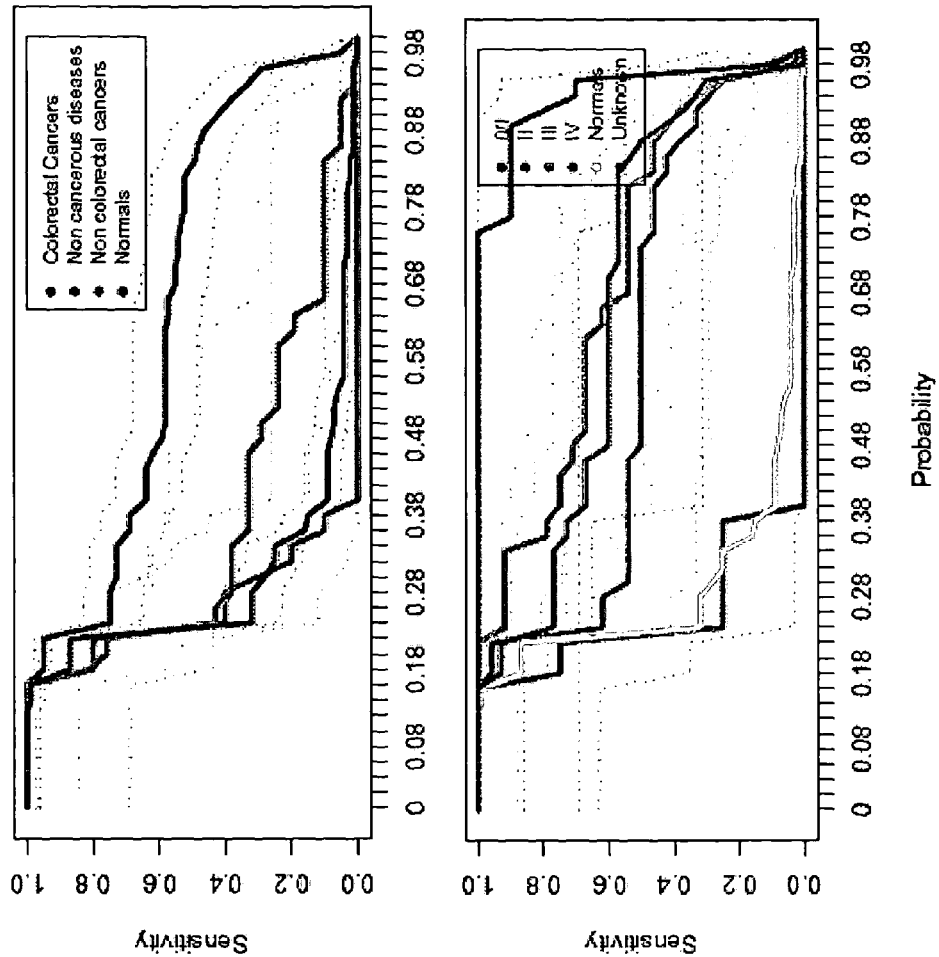

FIG. 22 provides an overview of the performance of the Septin 9+TFAP2E+RASSF2+PCDHGC3+SND1 assays.

Figure 23:
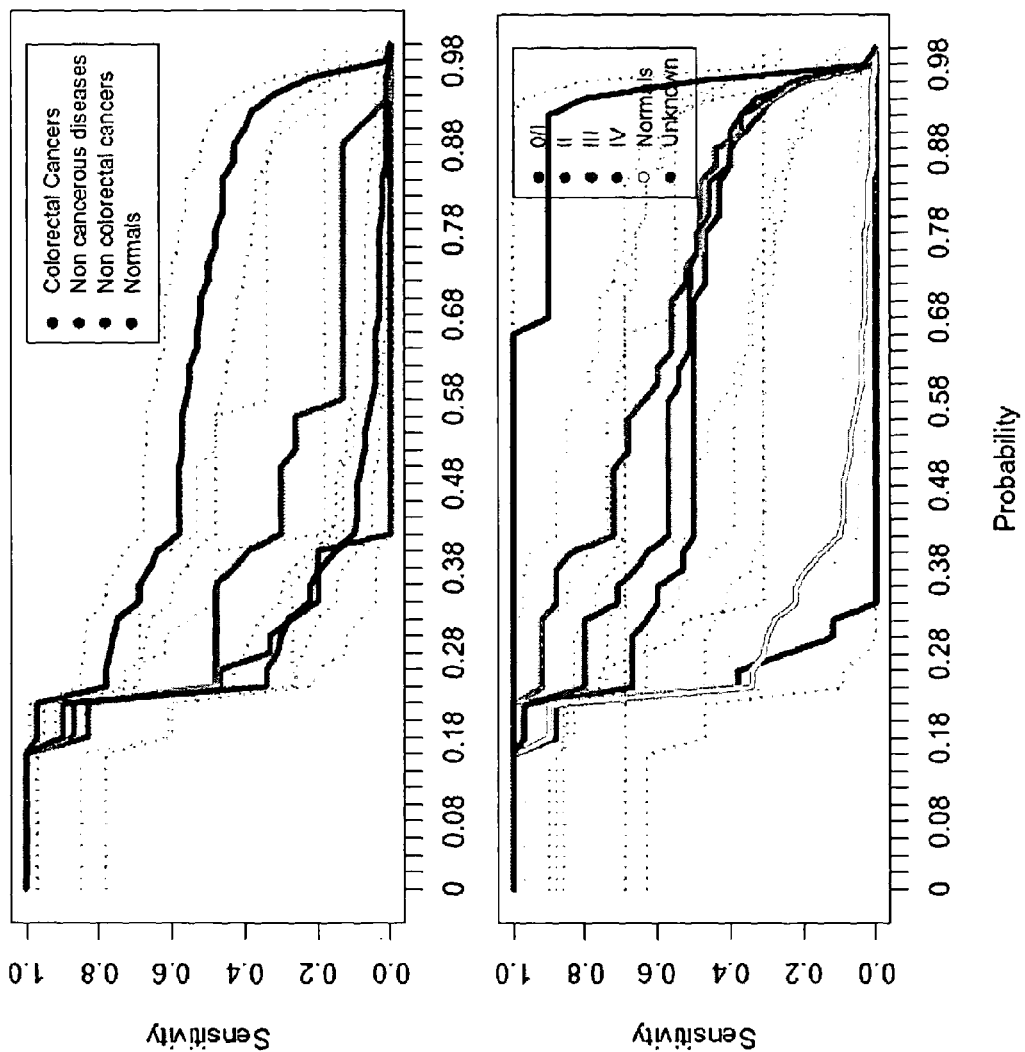

FIG. 23 provides an overview of the performance of the Septin 9+TFAP2E+RASSF2+PCDHGC3 assays.

Figure 24:
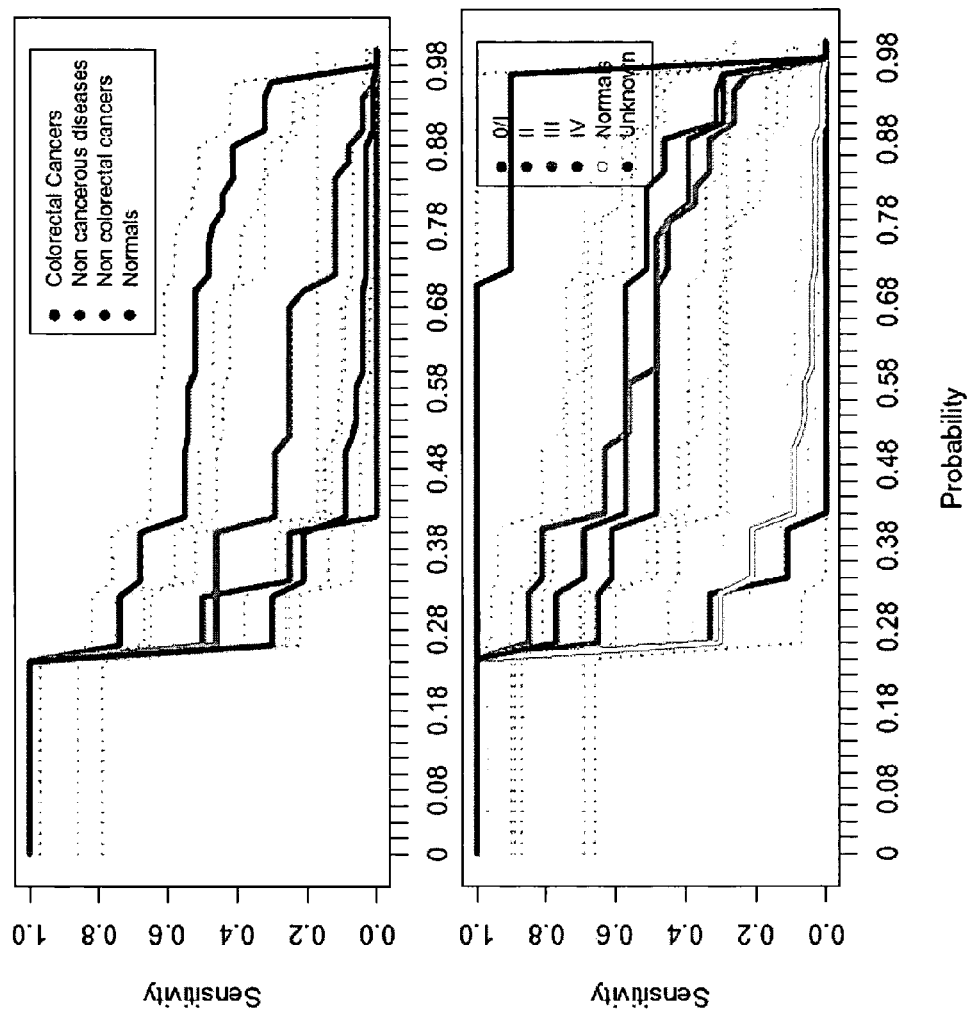

FIG. 24 provides an overview of the performance of the Septin 9+TFAP2E+RASSF2 assays.

Figure 25:
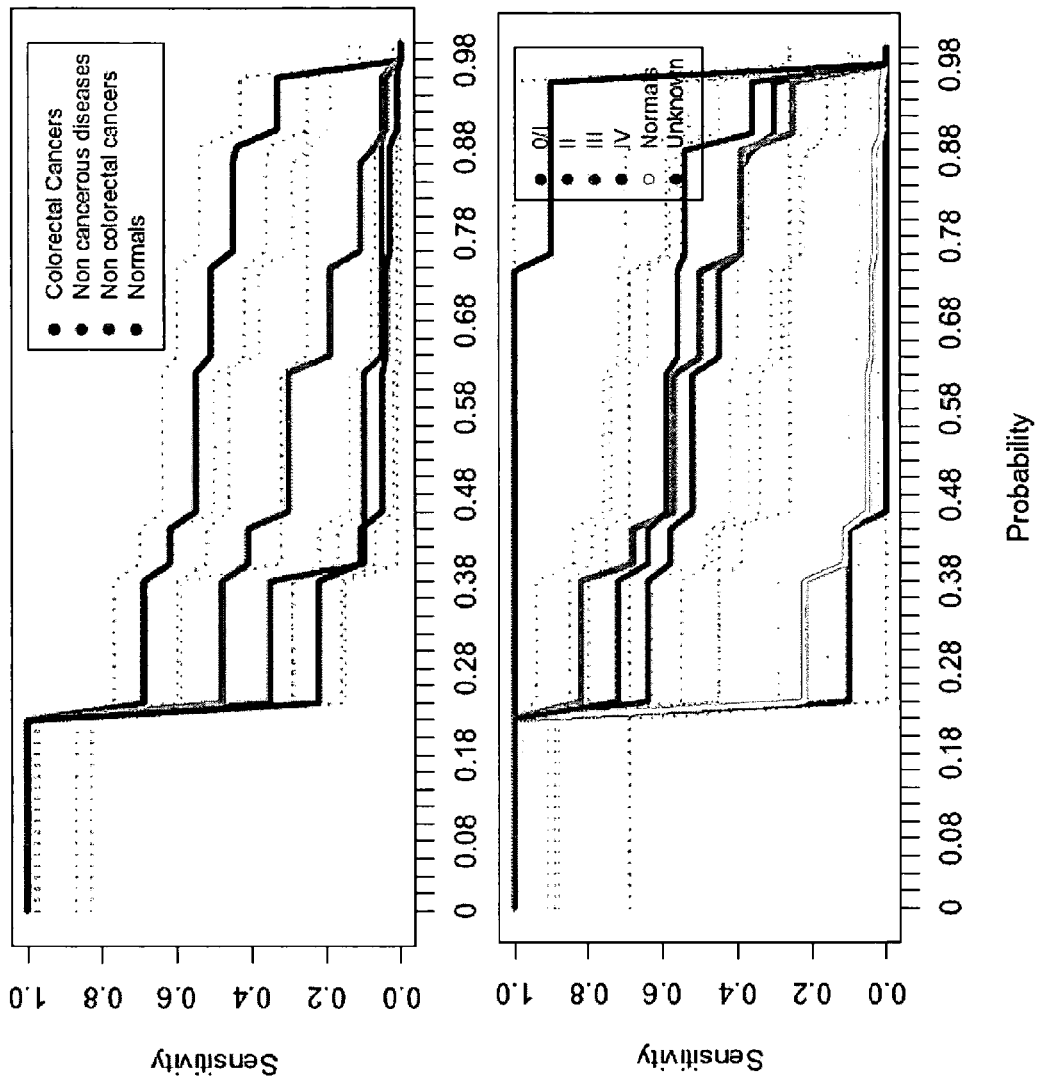

FIG. 25 provides an overview of the performance of the Septin 9+TFAP2E assays.

Figure 26:
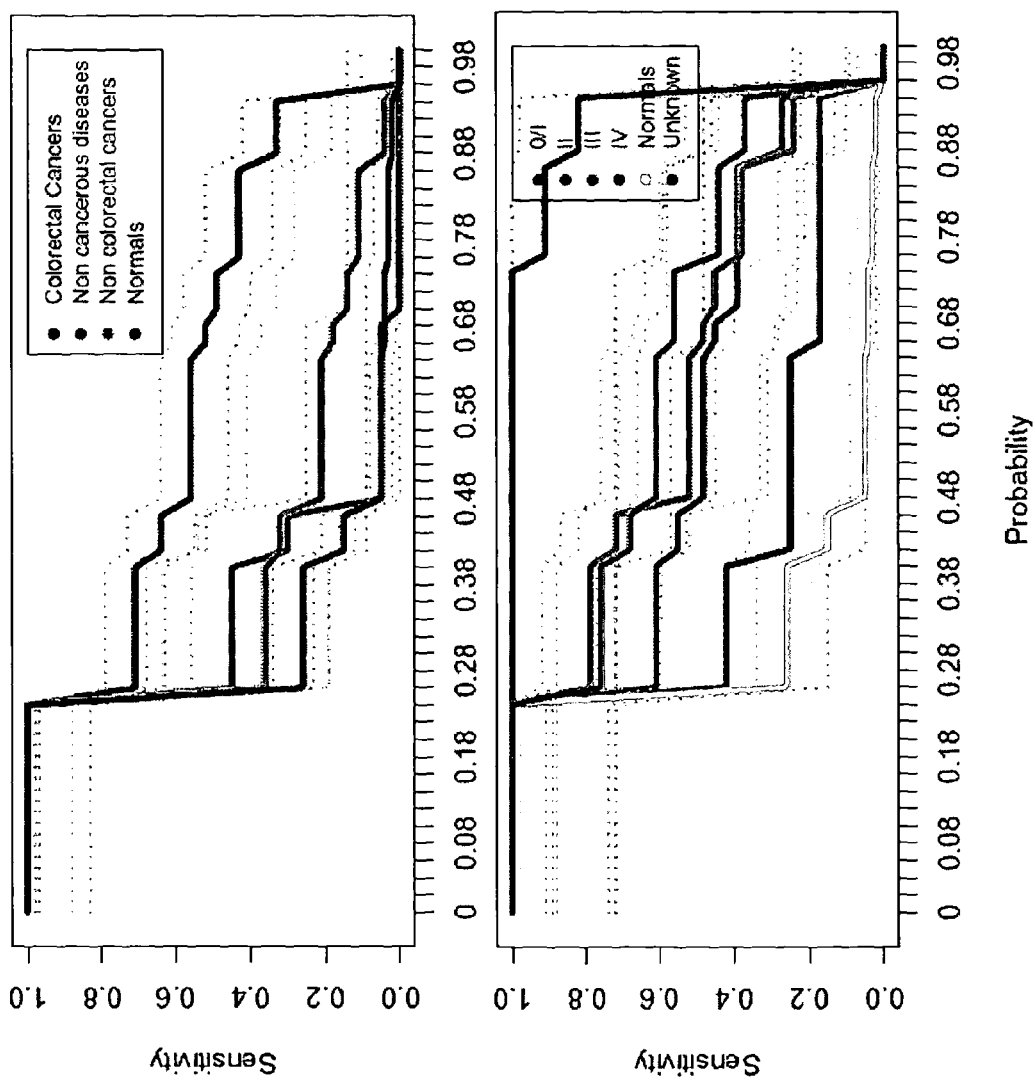

FIG. 26 provides an overview of the performance of the Septin 9+RASSF2 assays.

FIGS. 27 to 31 each provide an overview of the performance of assays according to Example 3 in various patient populations. Each figures consists of four plots, one for each assay), wherein the Y axis provides sensitivity and the X axis DNA concentration in log 10 ng/ml.

SUMMARY OF THE INVENTION

The present invention provides a method for detecting cell proliferative disorders, preferably cancerous or pre-cancerous disorders, in a subject comprising determining the expression levels of RASSF2 in a biological sample isolated from said subject wherein underexpression and/or CpG methylation is indicative of the presence of said disorder. Said method is particularly suited to the detection and/or diagnosis of prostate carcinoma, colorectal carcinoma and pre-cancerous colorectal conditions. Various aspects of the present invention provide an efficient and unique genetic marker, whereby expression analysis of said marker enables the detection of cancer with a particularly high sensitivity, specificity and/or predictive value.

In one embodiment the invention provides a method for detecting cell proliferative disorders, preferably cancerous or pre-cancerous disorders, in a subject comprising determining the expression levels of RASSF2 in a biological sample isolated from said subject wherein under-expression and/or CpG methylation is indicative of the presence of said disorder. Said method is particularly suited to the detection and/or diagnosis of prostate carcinoma, colorectal carcinoma and pre-cancerous colorectal conditions. In one embodiment said expression level is determined by detecting the presence, absence or level of mRNA transcribed from said gene. In a further embodiment said expression level is determined by detecting the presence, absence or level of a polypeptide encoded by said gene or sequence thereof.

In a further preferred embodiment said expression is determined by detecting the presence or absence of CpG methylation within said gene, wherein the presence of methylation indicates the presence of cell proliferative disorders, preferably cancerous or pre-cancerous disorders and more preferably prostate carcinoma, colorectal carcinoma and pre-cancerous colorectal conditions.

Said method comprises the following steps: i) contacting genomic DNA isolated from a biological sample (preferably selected from the group consisting of ejaculate, blood plasma, blood serum, whole blood, isolated blood cells, cells isolated from the blood) obtained from the subject with at least one reagent, or series of reagents that distinguishes between methylated and non-methylated CpG dinucleotides within at least one target region of the genomic DNA, wherein the nucleotide sequence of said target region comprises at least one CpG dinucleotide sequence of the gene RASSF2; and ii) detecting carcinoma, at least in part. Preferably the target region comprises, or hybridizes under stringent conditions to a sequence of at least 16 contiguous nucleotides of SEQ ID NO: 1.

Preferably, the sensitivity of said detection is from about 75% to about 96%, or from about 80% to about 90%, or from about 80% to about 85%. Preferably, the specificity is from about 75% to about 96%, or from about 80% to about 90%, or from about 80% to about 85%.

Said use of the gene may be enabled by means of any analysis of the expression of the gene, by means of mRNA expression analysis or protein expression analysis. However, in the most preferred embodiment of the invention the detection of cell proliferative disorders, (preferably cancerous or pre-cancerous disorders, and even more preferably a disorder selected from the group consisting of prostate cancer, colorectal cancer and pre-cancerous colorectal conditions), is enabled by means of analysis of the methylation status of the gene RASSF2, and/or its promoter or regulatory elements.

The invention provides a method for the analysis of biological samples for features associated with the development of cancer, the method characterized in that the nucleic acid, or a fragment thereof of SEQ ID NO: 1 is contacted with a reagent or series of reagents capable of distinguishing between methylated and non methylated CpG dinucleotides within the genomic sequence.

The present invention provides a method for ascertaining epigenetic parameters of genomic DNA associated with the development of prostate cancer. The method has utility for the improved detection and diagnosis of said disease.

Preferably, the source of the test sample is selected from the group consisting of cells or cell lines, histological slides, biopsies, paraffin-embedded tissue, body fluids, ejaculate, ejaculate, urine, blood, and combinations thereof. More preferably, the source is selected from the group consisting of ejaculate, urine, blood plasma, blood serum, whole blood, isolated blood cells, cells isolated from the blood obtained from the subject.

Specifically, the present invention provides a method for detecting prostate cancer suitable for use in a diagnostic tool, comprising: obtaining a biological sample comprising genomic nucleic acid(s); contacting the nucleic acid(s), or a fragment thereof, with a reagent or a plurality of reagents sufficient for distinguishing between methylated and non methylated CpG dinucleotide sequences within a target sequence of the subject nucleic acid, wherein the target sequence comprises, or hybridises under stringent conditions to, a sequence comprising at least 16 contiguous nucleotides of SEQ ID NO: 1 said contiguous nucleotides comprising at least one CpG dinucleotide sequence; and determining, based at least in part on said distinguishing, the methylation state of at least one target CpG dinucleotide sequence, or an average, or a value reflecting an average methylation state of a plurality of target CpG dinucleotide sequences.

Preferably, distinguishing between methylated and non methylated CpG dinucleotide sequences within the target sequence comprises methylation state-dependent conversion or non-conversion of at least one such CpG dinucleotide sequence to the corresponding converted or non-converted dinucleotide sequence within a sequence selected from the group consisting of SEQ ID Nos: 6, 7, 16 and 17, and contiguous regions thereof corresponding to the target sequence.

Additional embodiments provide a method for the detection of prostate cancer comprising: obtaining a biological sample having subject genomic DNA; extracting the genomic DNA; treating the genomic DNA, or a fragment thereof, with one or more reagents to convert 5-position unmethylated cytosine bases to uracil or to another base that is detectably dissimilar to cytosine in terms of hybridization properties; contacting the treated genomic DNA, or the treated fragment thereof, with an amplification enzyme and at least two primers comprising, in each case a contiguous sequence at least 9 nucleotides in length that is complementary to, or hybridizes under moderately stringent or stringent conditions to a sequence selected from the group consisting SEQ ID Nos: 6, 7, 16 and 17, and complements thereof, wherein the treated DNA or the fragment thereof is either amplified to produce an amplificate, or is not amplified; and determining, based on a presence or absence of, or on a property of said amplificate, the methylation state or an average, or a value reflecting an average of the methylation level of at least one, but more preferably a plurality of CpG dinucleotides of SEQ ID NO: 1.

Preferably, determining comprises use of at least one method selected from the group consisting of: i) hybridizing at least one nucleic acid molecule comprising a contiguous sequence at least 9 nucleotides in length that is complementary to, or hybridizes under moderately stringent or stringent conditions to a sequence selected from the group consisting of SEQ ID Nos: 6, 7, 16 and 17, and complements thereof; ii) hybridizing at least one nucleic acid molecule, bound to a solid phase, comprising a contiguous sequence at least 9 nucleotides in length that is complementary to, or hybridizes under moderately stringent or stringent conditions to a sequence selected from the group consisting of SEQ ID Nos: 6, 7, 16 and 17, and complements thereof; iii) hybridizing at least one nucleic acid molecule comprising a contiguous sequence at least 9 nucleotides in length that is complementary to, or hybridizes under moderately stringent or stringent conditions to a sequence selected from the group consisting of SEQ ID Nos: 6, 7, 16 and 17, and complements thereof, and extending at least one such hybridized nucleic acid molecule by at least one nucleotide base; and iv) sequencing of the amplificate.

Further embodiments provide a method for the analysis (i.e. detection of classification) of carcinoma, comprising: obtaining a biological sample having subject genomic DNA; extracting the genomic DNA; contacting the genomic DNA, or a fragment thereof, comprising one or more sequences selected from the group consisting of SEQ ID NO: 1 or a sequence that hybridizes under stringent conditions thereto, with one or more methylation-sensitive restriction enzymes, wherein the genomic DNA is either digested thereby to produce digestion fragments, or is not digested thereby; and determining, based on a presence or absence of, or on property of at least one such fragment, the methylation state of at least one CpG dinucleotide sequence of SEQ ID NO: 1 or an average, or a value reflecting an average methylation state of a plurality of CpG dinucleotide sequences thereof. Preferably, the digested or undigested genomic DNA is amplified prior to said determining.

Additional embodiments provide novel genomic and chemically modified nucleic acid sequences, as well as oligonucleotides and/or PNA-oligomers for analysis of cytosine methylation patterns within SEQ ID NO: 1.

DETAILED DESCRIPTION OF THE INVENTION

Definitions

The term "Observed/Expected Ratio" ("O/E Ratio") refers to the frequency of CpG dinucleotides within a particular DNA sequence, and corresponds to the [number of CpG sites/(number of C bases×number of G bases)]/band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 KB, or to about 2 kb in length.

The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two CpG dinucleotide sequences) within a DNA sequence include "unmethylated," "fully-methylated" and "hemi-methylated."

The term "hemi-methylation" or "hemimethylation" refers to the methylation state of a double stranded DNA wherein only one strand thereof is methylated.

The term 'AUC' as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylation. Further epigenetic parameters include, for example, the acetylation of histones which, however, cannot be directly analyzed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

The term "MethyLight™" refers to the art-recognized fluorescence-based real-time PCR technique described by Eads et al., *Cancer Res.* 59:2302-2306, 1999.

The term "HeavyMethyl™" assay, in the embodiment thereof implemented herein, refers to an assay, wherein methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo and Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong and Laird, *Nucleic Acids Res.* 25:2532-2534, 1997.

The term "MCA" (Methylated CpG Island Amplification) refers to the methylation assay described by Toyota et al., *Cancer Res.* 59:2307-12, 1999, and in WO 00/26401A1.

The term "hybridization" is to be understood as a bond of an oligonucleotide to a complementary sequence along the lines of the Watson-Crick base pairings in the sample DNA, forming a duplex structure.

"Stringent hybridization conditions," as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley and Sons, N.Y.) at Unit 2.10.

The terms "Methylation-specific restriction enzymes" or "methylation-sensitive restriction enzymes" shall be taken to mean an enzyme that selectively digests a nucleic acid dependant on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methylated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

In reference to composite array sequences, the phrase "contiguous nucleotides" refers to a contiguous sequence region of any individual contiguous sequence of the composite array, but does not include a region of the composite array sequence that includes a "node," as defined herein above.

The term "RASSF2" shall be taken to include all transcript variants thereof and all promoter and regulatory elements thereof. Furthermore as a plurality of SNPs are known within said gene the term shall be taken to include all sequence variants thereof.

The term "pre-cancerous" shall be taken to mean any cellular proliferative disorder which is undergoing malignant transformation.

The present invention provides a method for detecting carcinoma in a subject comprising determining the expression levels of RASSF2 in a biological sample isolated from said subject wherein underexpression and/or CpG methylation is indicative of the presence or class of said disorder. Said markers may be used for the diagnosis of cancers such as prostate or colon cancer including early detection during the pre-cancerous stages of the disease.

The markers of the present invention are particularly efficient in detecting malignant cell proliferative disorders, (preferably cancerous or pre-cancerous disorders and more preferably a disorder selected from the group consisting of prostate cancer, colorectal cancer and pre-cancerous colorectal conditions), thereby providing improved means for the early detection, classification and treatment of said disorders.

In addition to the embodiments above wherein the methylation analysis of the gene RASSF2 is analysed, the invention presents further panels of genes comprising RASSF2 with novel utility for the detection of cancers, in particular prostate and/or colorectal cancer.

In one embodiment of the method prostate cancer is detected and/or differentiated from benign prostate disorders by determining the expression of a plurality of genes comprising RASSF2A. In one embodiment said plurality of genes additionally consists of 1, 2 or 3 genes selected from the group consisting of GSTP1, HIST1H4J and TFAP2E. Particularly preferred is the combined analysis of RASSF2A and TFAP2E.

In a further embodiment of the method colorectal cancer (including pre-cancerous colorectal conditions) is detected by determining the expression of a plurality of genes comprising RASSF2A. In one embodiment said plurality of genes additionally consists of 1, 2 or 3 genes selected from the group consisting of Septin 9, PCDHGC3, SND1 and TFAP2E. Particularly preferred is the combined analysis of RASSF2A and Septin 9. Other preferred combinations include:

Septin 9+TFAP2E+RASSF2+PCDHGC3+SND1
Septin 9+TFAP2E+RASSF2+PCDHGC3
Septin 9+TFAP2E+RASSF2

It is particularly preferred that CpG positions of said genes comprised within the sequences according to Table 1 are analyzed.

Bisulfate modification of DNA is an art-recognized tool used to assess CpG methylation status. 5-methylcytosine is the most frequent covalent base modification in the DNA of eukaryotic cells. It plays a role, for example, in the regulation of the transcription, in genetic imprinting, and in tumourigenesis. Therefore, the identification of 5-methylcytosine as a component of genetic information is of considerable interest. However, 5-methylcytosine positions cannot be identified by sequencing, because 5-methylcytosine has the same base pairing behavior as cytosine. Moreover, the epigenetic information carried by 5-methylcytosine is completely lost during, e.g., PCR amplification.

The most frequently used method for analyzing DNA for the presence of 5-methylcytosine is based upon the specific reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

The prior art, in terms of sensitivity, is defined by a method comprising enclosing the DNA to be analyzed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996). It is thus possible to analyze individual cells for methylation status, illustrating the utility and sensitivity of the method. An overview of art-recognized methods for detecting 5-methylcytosine is provided by Rein, T., et al., *Nucleic Acids Res.*, 26:2255, 1998.

The bisulfite technique, barring few exceptions (e.g., Zeschnigk M, et al., *Eur J Hum Genet.* 5:94-98, 1997), is currently only used in research. In all instances, short, specific fragments of a known gene are amplified subsequent to a bisulfite treatment, and either completely sequenced (Olek and Walter, *Nat. Genet.* 1997 17:275-6, 1997), subjected to one or more primer extension reactions (Gonzalgo and Jones, *Nucleic Acids Res.*, 25:2529-31, 1997; WO 95/00669; U.S. Pat. No. 6,251,594) to analyze individual cytosine positions, or treated by enzymatic digestion (Xiong and Laird, *Nucleic Acids Res.*, 25:2532-4, 1997). Detection by hybridization has also been described in the art (Olek et al., WO 99/28498). Additionally, use of the bisulfite technique for methylation detection with respect to individual genes has been described (Grigg and Clark, *Bioessays*, 16:431-6, 1994; Zeschnigk M, et al., *Hum Mol. Genet.*, 6:387-95, 1997; Feil R, et al., *Nucleic Acids Res.*, 22:695-, 1994; Martin V, et al., *Gene*, 157:261-4, 1995; WO 97/46705 and WO 95/15373).

The present invention provides for the use of the bisulfite technique, in combination with one or more methylation assays, for determination of the methylation status of CpG dinucleotide sequences within SEQ ID NO: 1. Genomic CpG dinucleotides can be methylated or unmethylated (alternatively known as up- and down-methylated, respectively). However the methods of the present invention are suitable for the analysis of biological samples of a heterogeneous nature e.g. a low concentration of tumor cells within a background of blood or ejaculate. Accordingly, when analyzing the methylation status of a CpG position within such a sample the person skilled in the art may use a quantitative assay for determining the level (e.g. percent, fraction, ratio, proportion or degree) of methylation at a particular CpG position as opposed to a methylation state. Accordingly the term methylation status or methylation state should also be taken to mean a value reflecting the degree of methylation at a CpG position. Unless specifically stated the terms "hypermethylated" or "upmethylated" shall be taken to mean a methylation level above that of a specified cut-off point, wherein said cut-off may be a value representing the average or median methylation level for a given population, or is preferably an optimized cut-off level. The "cut-off" is also referred herein as a "threshold". In the context of the present invention the terms "methylated", "hypermethylated" or "upmethylated" shall be taken to include a methylation level above the cut-off be zero (0) % (or equivalents thereof) methylation for all CpG positions within and associated with (e.g. in promoter or regulatory regions) the RASSF2 gene.

According to the present invention, determination of the methylation status of CpG dinucleotide sequences within SEQ ID NO: 1 has utility in the diagnosis and detection of cancer.

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri and Hornsby (*Nucl. Acids Res.* 24:5058-5059, 1996), or COBRA (Combined Bisulfite Restriction Analysis) (Xiong and Laird, *Nucleic Acids Res.* 25:2532-2534, 1997).

COBRA. COBRA™ analysis is a quantitative methylation assay useful for determining DNA methylation levels at specific gene loci in small amounts of genomic DNA (Xiong and Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples.

Typical reagents (e.g., as might be found in a typical COBRA™-based kit) for COBRA™ analysis may include, but are not limited to: PCR primers for specific gene (or bisulfite treated DNA sequence or CpG island); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., *Cancer Res.* 59:2302-2306, 1999), Ms-SNuPE™ (Methylation-sensitive Single Nucleotide Primer Extension) reactions (Gonzalgo and Jones, *Nucleic Acids Res.* 25:2529-2531, 1997), methylation-specific PCR ("MSP"; Herman et al., *Proc. Natl. Acad. Sci. USA* 93:9821-9826, 1996; U.S. Pat. No. 5,786,146), and methylated CpG island amplification ("MCA"; Toyota et al., *Cancer Res.* 59:2307-12, 1999) are used alone or in combination with other of these methods.

The "HeavyMethyl™" assay, technique is a quantitative method for assessing methylation differences based on methylation specific amplification of bisulfite treated DNA. Methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific genes (or bisulfite treated DNA sequence or CpG island); blocking oligonucleotides; optimized PCR buffers and deoxynucleotides; and Taq polymerase.

MSP. MSP (methylation-specific PCR) allows for assessing the methylation status of virtually any group of CpG sites within a CpG island, independent of the use of methylation-sensitive restriction enzymes (Herman et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or bisulfite treated DNA sequence or CpG island), optimized PCR buffers and deoxynucleotides, and specific probes.

MethyLight. The MethyLight assay is a high-throughput quantitative methylation assay that utilizes fluorescence-based real-time PCR (TAQMAN®)technology that requires no further manipulations after the PCR step (Eads et al., *Cancer Res.* 59:2302-2306, 1999). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" (with PCR primers that overlap known CpG dinucleotides) reaction. Sequence discrimination can occur both at the level of the amplification process and at the level of the fluorescence detection process.

The MethyLight assay may be used as a quantitative test for methylation patterns in the genomic DNA sample, wherein sequence discrimination occurs at the level of probe hybridization. In this quantitative version, the PCR reaction provides for a methylation specific amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HEAVYMETHYL® and MSP techniques), or with oligonucleotides covering potential methylation sites.

The MethyLight process can be used with any suitable probes e.g., "TAQMAN®", "LIGHTCYCLER®", etc. For example, double-stranded genomic DNA is treated with sodium bisulfite and subjected to one of two sets of PCR reactions using TAQMAN® probes; e.g., with MSP primers and/or HEAVYMETHYL® blocker oligonucleotides and TAQMAN® probe. The TAQMAN® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TAQMAN® probe to remain fully hybridized during the PCR annealing/extension step. As the Taq polymerase enzymatically synthesizes a new strand during PCR, it will eventually reach the annealed TAQMAN® probe. The Taq polymerase 5' to 3' endonuclease activity will then displace the TAQMAN® probe by digesting it to release the fluorescent reporter molecule for quantitative detection of its now unquenched signal using a real-time fluorescent detection system.

Typical reagents (e.g., as might be found in a typical MethyLight-based kit) for MethyLight analysis may include, but are not limited to: PCR primers for specific gene (or bisulfite treated DNA sequence or CpG island); TAQMAN® or LIGHTCYCLER® probes; optimized PCR buffers and deoxynucleotides; and Taq polymerase.

The QM (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HEAVYMETHYL® and MSP techniques), or with oligonucleotides covering potential methylation sites.

The QM process can be used with any suitable probes e.g., "TAQMAN®", "LIGHTCYCLER®", etc. in the amplification process. For example, double-stranded genomic DNA is treated with sodium bisulfite and subjected to unbiased primers and the TAQMAN® probe. The TAQMAN® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TAQMAN® probe to remain fully hybridized during the PCR annealing/extension step. As the Taq polymerase enzymatically synthesizes a new strand during PCR, it will eventually reach the annealed TAQMAN® probe. The Taq polymerase 5' to 3' endonuclease activity will then displace the TaqMan™ probe by digesting it to release the fluorescent reporter molecule for quantitative detection of its now unquenched signal using a real-time fluorescent detection system.

Typical reagents (e.g., as might be found in a typical QM-based kit) for QM analysis may include, but are not limited to: PCR primers for specific gene (or bisulfite treated DNA sequence or CpG island); TAQMAN ® or LIGHTCYCLER® probes; optimized PCR buffers and deoxynucleotides; and Taq polymerase.

Ms-SNuPE. The Ms-SNuPE technique is a quantitative method for assessing methylation differences at specific CpG sites based on bisulfite treatment of DNA, followed by single-nucleotide primer extension (Gonzalgo & Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE based kit) for Ms-SNuPE analysis may include, but are not limited to: PCR primers for specific gene (or bisulfite treated DNA sequence or CpG island); optimized PCR buffers and deoxynucleotides; gel extraction kit; positive control primers; Ms-SNuPE primers for specific gene; reaction buffer (for the Ms-SNuPE reaction); and labeled nucleotides. Additionally, bisulfite conversion reagents may include DNA denaturation buffer; sulfonation buffer; DNA recovery regents or kit (e.g., precipitation, ultrafiltration, affinity column); desulfonation buffer; and DNA recovery components.

The genomic sequence according to SEQ ID NO: 1, and non-naturally occurring treated variants thereof according to SEQ ID NOS: 6, 7, 16, and 17, were determined to have novel utility for the early detection of cancer, in particular prostate cancer, colorectal cancer and pre-cancerous colorectal conditions.

In one embodiment the invention of the method comprises the following steps: i) contacting genomic DNA (preferably isolated from body fluids) obtained from the subject with at least one reagent, or series of reagents that distinguishes between methylated and non-methylated CpG dinucleotides within the gene RASSF2 (including its promoter and regulatory regions); and ii) detecting cell proliferative disorders, preferably cancerous or pre-cancerous disorders and more preferably a disorder selected from the group consisting of prostate cancer, colorectal cancer and pre-cancerous colorectal conditions, afforded with a sensitivity of greater than or equal to 80% and a specificity of greater than or equal to 80%.

Preferably, the sensitivity is from about 75% to about 96%, or from about 80% to about 90%, or from about 80% to about 85%. Preferably, the specificity is from about 75% to about 96%, or from about 80% to about 90%, or from about 80% to about 85%.

Genomic DNA may be isolated by any means standard in the art, including the use of commercially available kits. Briefly, wherein the DNA of interest is encapsulated in by a cellular membrane the biological sample must be disrupted and lyzed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic matter or pre-neoplastic matter are suitable for use in the present method, preferred are cell lines, histological slides, biopsies, paraffin-embedded tissue, body fluids, ejaculate, urine, blood plasma, blood serum, whole blood, isolated blood cells, cells isolated from the blood and combinations thereof. Body fluids are the preferred source of the DNA; particularly preferred are ejaculate, blood plasma, blood serum, whole blood, isolated blood cells and cells isolated from the blood.

The genomic DNA sample is then treated with at least one reagent, or series of reagents that distinguishes between methylated and non-methylated CpG dinucleotides within at least one target region of the genomic DNA, wherein the target region comprises, or hybridizes under stringent conditions to a sequence of at least 16 contiguous nucleotides of sequence according to SEQ ID NO: 1 respectively, wherein said contiguous nucleotides comprise at least one CpG dinucleotide sequence.

It is particularly preferred that said reagent converts cytosine bases which are unmethylated at the 5'-position to uracil, thymine, or another base which is dissimilar to cytosine in terms of hybridization behavior. However in an alternative embodiment said reagent may be a methylation sensitive restriction enzyme.

Wherein the genomic DNA sample is treated in such a manner that cytosine bases which are unmethylated at the 5'-position are converted to uracil, thymine, or another base which is dissimilar to cytosine in terms of hybridization behavior It is preferred that this treatment is carried out with bisulfite (hydrogen sulfite, disulfite) and subsequent alkaline hydrolysis. Such a treatment results in the conversion of SEQ ID NO: 1 to SEQ ID Nos: 6, and 7 (respectively) wherein said CpG dinucleotides are methylated or SEQ ID Nos: 16, and 17 wherein said CpG dinucleotides are unmethylated.

The treated DNA is then analyzed in order to determine the methylation state of RASSF2 prior to the treatment. It is particularly preferred that the target region comprises, or hybridizes under stringent conditions to at least 16 contiguous nucleotides of RASSF2. It is preferred that the sequence of said gene according to SEQ ID NO: 1 is analyzed. The method of analysis may be selected from those known in the art, including those listed herein. Particularly preferred are MethyLight™, MSP and the use of blocking oligonucleotides (HeavyMethyl™) as described herein. It is further preferred that any oligonucleotides used in such analysis (including primers, blocking oligonucleotides and detection probes) should be reverse complementary, identical, or hybridize under stringent or highly stringent conditions to an at least 16-base-pair long segment of the base sequences of one or more of SEQ ID Nos: 6, 7, 16, and 17 and sequences complementary thereto.

Aberrant methylation, more specifically hypermethylation of RASSF2 (as well as promoter and/or regulatory regions thereof) is associated with the presence of prostate cancer. Accordingly wherein a biological sample presents within any degree of methylation, said sample should be determined as neoplastic.

Analysis of the RASSF2 gene enables for the first time detecting cell proliferative disorders, preferably cancerous or pre-cancerous disorders and more preferably a disorder selected from the group consisting of prostate cancer, colorectal cancer and pre-cancerous colorectal conditions, afforded with a sensitivity of greater than or equal to 80% and a specificity of greater than or equal to 80%. Sensitivity is calculated as: {detected neoplasia/all neoplasia) e.g.: {detected prostate carcinoma/all prostate carcinoma); and specificity is calculated as (non-detected negatives/total negatives).

Preferably, the sensitivity is from about 75% to about 96%, or from about 80% to about 90%, or from about 80% to about 85%. Preferably, the specificity is from about 75% to about 96%, or from about 80% to about 90%, or from about 80% to about 85%.

Said method may be enabled by means of any analysis of the expression of an RNA transcribed therefrom or polypeptide or protein translated from said RNA, preferably by means of mRNA expression analysis or polypeptide expression analysis. Accordingly the present invention also provides diagnostic assays and methods, both quantitative and qualitative for detecting the expression of the gene RASSF2 in a subject and determining therefrom upon the presence or absence of cancer in said subject.

Aberrant expression of mRNA transcribed from the gene RASSF2 is associated with the presence of prostate and colorectal cancer in a subject. According to the present invention, under expression (and/or presence methylation) is associated with the presence of cancer, and vice versa over-expression (and/or absence of methylation) is associated with the absence of cancer.

To detect the presence of mRNA encoding a gene or genomic sequence, a sample is obtained from a patient. The sample may be any suitable sample comprising cellular matter of the tumor. Suitable sample types include cell lines, histological slides, biopsies, paraffin-embedded tissue, body fluids, ejaculate, urine, blood plasma, blood serum, whole blood, isolated blood cells, cells isolated from the blood and all possible combinations thereof. It is preferred that said sample types are ejaculate or body fluids selected from the group consisting ejaculate, urine, blood plasma, blood serum, whole blood, isolated blood cells, cells isolated from the blood.

The sample may be treated to extract the RNA contained therein. The resulting nucleic acid from the sample is then analyzed. Many techniques are known in the state of the art for determining absolute and relative levels of gene expression, commonly used techniques suitable for use in the present invention include in situ hybridization (e.g. FISH), Northern analysis, RNase protection assays (RPA), microarrays and PCR-based techniques, such as quantitative PCR and differential display PCR or any other nucleic acid detection method.

Particularly preferred is the use of the reverse transcription/polymerization chain reaction technique (RT-PCR). The method of RT-PCR is well known in the art (for example, see Watson and Fleming, supra).

The RT-PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end oligonucleotide dT primer and/or random hexamer primers. The cDNA thus produced is then amplified by means of PCR. (Belyaysky et al, Nucl Acid Res 17:2919-2932, 1989; Krug and Berger, Methods in Enzymology, Academic Press, N.Y., Vol. 152, pp. 316-325, 1987 which are incorporated by reference). Further preferred is the "Real-time" variant of RT-PCR, wherein the PCR product is detected by means of hybridization probes (e.g. TaqMan, Lightcycler, Molecular Beacons and Scorpion) or SYBR green. The detected signal from the probes or SYBR green is then quantitated either by reference to a standard curve or by comparing the Ct values to that of a calibration standard. Analysis of housekeeping genes is often used to normalize the results.

In Northern blot analysis total or poly(A)+ mRNA is run on a denaturing agarose gel and detected by hybridisation to a labelled probe in the dried gel itself or on a membrane. The resulting signal is proportional to the amount of target RNA in the RNA population.

Comparing the signals from two or more cell populations or tissues reveals relative differences in gene expression levels. Absolute quantitation can be performed by comparing the signal to a standard curve generated using known amounts of an in vitro transcript corresponding to the target RNA. Analysis of housekeeping genes, genes whose expression levels are expected to remain relatively constant regardless of conditions, is often used to normalize the results, eliminating any apparent differences caused by unequal transfer of RNA to the membrane or unequal loading of RNA on the gel.

The first step in Northern analysis is isolating pure, intact RNA from the cells or tissue of interest. Because Northern blots distinguish RNAs by size, sample integrity influences the degree to which a signal is localized in a single band. Partially degraded RNA samples will result in the signal being smeared or distributed over several bands with an overall loss in sensitivity and possibly an erroneous interpretation of the data. In Northern blot analysis, DNA, RNA and oligonucleotide probes can be used and these probes are preferably labelled (e.g. radioactive labels, mass labels or fluorescent labels). The size of the target RNA, not the probe, will determine the size of the detected band, so methods such as random-primed labelling, which generates probes of variable lengths, are suitable for probe synthesis. The specific activity of the probe will determine the level of sensitivity, so it is preferred that probes with high specific activities, are used.

In an RNase protection assay, the RNA target and an RNA probe of a defined length are hybridised in solution. Following hybridisation, the RNA is digested with RNases specific for single-stranded nucleic acids to remove any unhybridized, single-stranded target RNA and probe. The RNases are inactivated, and the RNA is separated e.g. by denaturing polyacrylamide gel electrophoresis. The amount of intact RNA probe is proportional to the amount of target RNA in the RNA population. RPA can be used for relative and absolute quantitation of gene expression and also for mapping RNA structure, such as intron/exon boundaries and transcription start sites. The RNase protection assay is preferable to Northern blot analysis as it generally has a lower limit of detection.

The antisense RNA probes used in RPA are generated by in vitro transcription of a DNA template with a defined endpoint and are typically in the range of 50-600 nucleotides. The use of RNA probes that include additional sequences not homologous to the target RNA allows the protected fragment to be distinguished from the full-length probe. RNA probes are typically used instead of DNA probes due to the ease of generating single-stranded RNA probes and the reproducibility and reliability of RNA:RNA duplex digestion with RNases (Ausubel et al. 2003), particularly preferred are probes with high specific activities.

Particularly preferred is the use of microarrays. The microarray analysis process can be divided into two main parts. First is the immobilization of known gene sequences onto glass slides or other solid support followed by hybridisation of the fluorescently labelled cDNA (comprising the sequences to be interrogated) to the known genes immobilized on the glass slide (or other solid phase). After hybridisation, arrays are scanned using a fluorescent microarray scanner. Analysing the relative fluorescent intensity of different genes provides a measure of the differences in gene expression.

DNA arrays can be generated by immobilizing pre-synthesized oligonucleotides onto prepared glass slides or other solid surfaces. In this case, representative gene sequences are manufactured and prepared using standard oligonucleotide synthesis and purification methods. These synthesized gene sequences are complementary to the RNA transcript(s) of the RASSF2 gene and tend to be shorter sequences in the range of 25-70 nucleotides. Alternatively, immobilized oligonucleotides can be chemically synthesized in situ on the surface of the slide. In situ oligonucleotide synthesis involves the consecutive addition of the appropriate nucleotides to the spots on the microarray; spots not receiving a nucleotide are protected during each stage of the process using physical or virtual masks. Preferably said synthesized nucleic acids are locked nucleic acids.

In expression profiling microarray experiments, the RNA templates used are representative of the transcription profile of the cells or tissues under study. RNA is first isolated from the cell populations or tissues to be compared. Each RNA sample is then used as a template to generate fluorescently labelled cDNA via a reverse transcription reaction. Fluorescent labelling of the cDNA can be accomplished by either direct labelling or indirect labelling methods. During direct labelling, fluorescently modified nucleotides (e.g., Cy®3- or Cy®5-dCTP) are incorporated directly into the cDNA during the reverse transcription. Alternatively, indirect labelling can be achieved by incorporating aminoallyl-modified nucleotides during cDNA synthesis and then conjugating an N-hydroxysuccinimide (NHS)-ester dye to the aminoallyl-modified cDNA after the reverse transcription reaction is complete. Alternatively, the probe may be unlabelled, but may be detectable by specific binding with a ligand which is labelled, either directly or indirectly. Suitable labels and methods for labelling ligands (and probes) are known in the art, and include, for example, radioactive labels which may be incorporated by known methods (e.g., nick translation or kinasing). Other suitable labels include but are not limited to biotin, fluorescent groups, chemiluminescent groups (e.g., dioxetanes, particularly triggered dioxetanes), enzymes, antibodies, and the like.

To perform differential gene expression analysis, cDNA generated from different RNA samples are labelled with Cy®3. The resulting labelled cDNA is purified to remove unincorporated nucleotides, free dye and residual RNA. Following purification, the labelled cDNA samples are hybridised to the microarray. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2nd ed., 1989). The microarray is scanned post-hybridisation using a fluorescent microarray scanner. The fluorescent intensity of each spot indicates the level of expression of the analysed gene; bright spots correspond to strongly expressed genes, while dim spots indicate weak expression.

Once the images are obtained, the raw data must be analysed. First, the background fluorescence must be subtracted from the fluorescence of each spot. The data is then normalized to a control sequence, such as exogenously added nucleic acids (preferably RNA or DNA), or a housekeeping gene panel to account for any non-specific hybridisation, array imperfections or variability in the array set-up, cDNA labelling, hybridisation or washing. Data normalization allows the results of multiple arrays to be compared.

Another aspect of the invention relates to a kit for use in diagnosis of prostate and/or colorectal cancer in a subject according to the methods of the present invention, said kit comprising: a means for measuring the level of transcription of the gene RASSF2. In a preferred embodiment the means for measuring the level of transcription comprise oligonucleotides or polynucleotides able to hybridise under stringent or moderately stringent conditions to the transcription products of RASSF2. In a most preferred embodiment the level of transcription is determined by techniques selected from the group of Northern Blot analysis, reverse transcriptase PCR, real-time PCR, RNAse protection, and microarray. In another embodiment of the invention the kit further comprises means for obtaining a biological sample of the patient. Preferred is a kit, which further comprises a container which is most preferably suitable for containing the means for measuring the level of transcription and the biological sample of the patient, and most preferably further comprises instructions for use and interpretation of the kit results.

In a preferred embodiment the kit comprises (a) a plurality of oligonucleotides or polynucleotides able to hybridise under stringent or moderately stringent conditions to the transcription products of the gene RASSF2; (b) a container, preferably suitable for containing the oligonucleotides or polynucleotides and a biological sample of the patient comprising the transcription products wherein the oligonucleotides or polynucleotides can hybridise under stringent or moderately stringent conditions to the transcription products, (c) means to detect the hybridisation of (b); and optionally, (d) instructions for use and interpretation of the kit results The kit may also contain other components such as hybridisation buffer (where the oligonucleotides are to be used as a probe) packaged in a separate container. Alternatively, where the oligonucleotides are to be used to amplify a target region, the kit may contain, packaged in separate containers, a polymerase and a reaction buffer optimised for primer extension mediated by the polymerase, such as PCR. Preferably said polymerase is a reverse transcriptase. It is further preferred that said kit further contains an RNAse reagent.

The present invention further provides for methods for the detection of the presence of the polypeptide encoded by said gene sequences in a sample obtained from a patient.

Aberrant levels of polypeptide expression of the polypeptides encoded by the gene RASSF2 are associated with the presence of cancer.

According to the present invention, under expression of said polypeptides is associated with the presence of prostate and/or colorectal cancer.

Any method known in the art for detecting polypeptides can be used. Such methods include, but are not limited to mass-spectrometry, immunodiffusion, immunoelectrophoresis, immunochemical methods, binder-ligand assays, immunohistochemical techniques, agglutination and complement assays (e.g., see Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labelled polypeptide or derivative thereof.

Certain embodiments of the present invention comprise the use of antibodies specific to the polypeptide(s) encoded by the RASSF2 gene.

Such antibodies are useful for cancer diagnosis. In certain embodiments production of monoclonal or polyclonal antibodies can be induced by the use of an epitope encoded by a polypeptide of the RASSF2 gene as an antigene. Such antibodies may in turn be used to detect expressed polypeptides as markers for cancer diagnosis. The levels of such polypeptides present may be quantified by conventional methods. Antibody-polypeptide binding may be detected and quantified by a variety of means known in the art, such as labelling with fluorescent or radioactive ligands. The invention further comprises kits for performing the above-mentioned procedures, wherein such kits contain antibodies specific for the investigated polypeptides.

Numerous competitive and non-competitive polypeptide binding immunoassays are well known in the art. Antibodies employed in such assays may be unlabelled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like. Preferred assays include but are not limited to radioimmunoassay (RIA), enzyme immunoassays, e.g., enzyme-linked immunosorbent assay (ELISA), fluorescent immunoassays and the like. Polyclonal or monoclonal antibodies or epitopes thereof can be made for use in immunoassays by any of a number of methods known in the art.

In an alternative embodiment of the method the proteins may be detected by means of western blot analysis. Said analysis is standard in the art, briefly proteins are separated by means of electrophoresis e.g. SDS-PAGE. The separated proteins are then transferred to a suitable membrane (or paper) e.g. nitrocellulose, retaining the spatial separation achieved by electrophoresis. The membrane is then incubated with a blocking agent to bind remaining sticky places on the membrane, commonly used agents include generic protein (e.g. milk protein). An antibody specific to the protein of interest is then added, said antibody being detectably labelled for example by dyes or enzymatic means (e.g. alkaline phosphatase or horseradish peroxidase). The location of the antibody on the membrane is then detected.

In an alternative embodiment of the method the proteins may be detected by means of immunohistochemistry (the use of antibodies to probe specific antigens in a sample). Said analysis is standard in the art, wherein detection of antigens in tissues is known as immunohistochemistry, while detection in cultured cells is generally termed immunocytochemistry. Briefly the primary antibody to be detected by binding to its specific antigen. The antibody-antigen complex is then bound by a secondary enzyme conjugated antibody. In the presence of the necessary substrate and chromogen the bound enzyme is detected according to coloured deposits at the antibody-antigen binding sites. There is a wide range of suitable sample types, antigen-antibody affinity, antibody types, and detection enhancement methods. Thus optimal conditions for immunohistochemical or immunocytochemical detection must be determined by the person skilled in the art for each individual case.

One approach for preparing antibodies to a polypeptide is the selection and preparation of an amino acid sequence of all or part of the polypeptide, chemically synthesising the amino acid sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference in its entirety). Methods for preparation of the polypeptides or epitopes thereof include, but are not limited to chemical synthesis, recombinant DNA techniques or isolation from biological samples.

In the final step of the method the diagnosis of the patient is determined, whereby under-expression (of RASSF2 mRNA or polypeptides) is indicative of the presence of cancer. The term under-expression shall be taken to mean expression at a detected level less than a pre-determined cut off which may be selected from the group consisting of the mean, median or an optimised threshold value.

Another aspect of the invention provides a kit for use in diagnosis of cancer in a subject according to the methods of the present invention, comprising: a means for detecting RASSF2 polypeptides. The means for detecting the polypeptides comprise preferably antibodies, antibody derivatives, or antibody fragments. The polypeptides are most preferably detected by means of Western Blotting utilizing a labelled antibody. In another embodiment of the invention the kit further comprising means for obtaining a biological sample of the patient. Preferred is a kit, which further comprises a container suitable for containing the means for detecting the polypeptides in the biological sample of the patient, and most preferably further comprises instructions for use and interpretation of the kit results. In a preferred embodiment the kit comprises: (a) a means for detecting RASSF2 polypeptides; (b) a container suitable for containing the said means and the biological sample of the patient comprising the polypeptides wherein the means can form complexes with the polypeptides; (c) a means to detect the complexes of (b); and optionally (d) instructions for use and interpretation of the kit results.

The kit may also contain other components such as buffers or solutions suitable for blocking, washing or coating, packaged in a separate container.

Particular embodiments of the present invention provide a novel application of the analysis of methylation levels and/or patterns within said sequences that enables a precise detection, characterisation and/or treatment of cancer. Early detection of cancer is directly linked with disease prognosis, and the disclosed method thereby enables the physician and patient to make better and more informed treatment decisions.

Further Improvements

The present invention provides novel uses for the genomic sequence SEQ ID NO: 1. Additional embodiments provide modified variants of SEQ ID NO: 1, as well as oligonucleotides and/or PNA-oligomers for analysis of cytosine methylation patterns within SEQ ID NO: 1.

An objective of the invention comprises analysis of the methylation state of one or more CpG dinucleotides within SEQ ID NO: 1 and sequences complementary thereto.

The disclosed invention provides treated nucleic acids, derived from genomic SEQ ID NO: 1, wherein the treatment is suitable to convert at least one unmethylated cytosine base of the genomic DNA sequence to uracil or another base that is detectably dissimilar to cytosine in terms of hybridization. The genomic sequences in question may comprise one, or more consecutive methylated CpG positions. Said treatment preferably comprises use of a reagent selected from the group consisting of bisulfite, hydrogen sulfite, disulfite, and combinations thereof. In a preferred embodiment of the invention, the invention provides a non-naturally occurring modified nucleic acid comprising a sequence of at least 16 contiguous nucleotide bases in length of a sequence selected from the group consisting of SEQ ID NOS: 6, 7, 16 AND 17. In further preferred embodiments of the invention said nucleic acid is at least 50, 100, 150, 200, 250 or 500 base pairs in length of a segment of the nucleic acid sequence disclosed in SEQ ID Nos: 6, 7, 16 and 17. Particularly preferred is a nucleic acid molecule that is not identical or complementary to all or a portion of the sequences SEQ ID Nos: 6, 7, 16 and 17 but not SEQ ID NO: 1 or other naturally occurring DNA.

It is preferred that said sequence comprises at least one CpG, TpA or CpA dinucleotide and sequences complementary thereto. The sequences of SEQ ID NOS: 6, 7, 16 AND 17 provide non-naturally occurring modified versions of the nucleic acid according to SEQ ID NO: 1, wherein the modification of each genomic sequence results in the synthesis of a nucleic acid having a sequence that is unique and distinct from said genomic sequence as follows. For each sense strand genomic DNA, e.g., SEQ ID NO: 1, four converted versions are disclosed. A first version wherein "C" is converted to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" is converted to "T," but "CpG" remains "CpG" (i.e., corresponds to case where, for all "C" residues of CpG dinucleotide sequences are methylated and are thus not converted). The 'upmethylated' converted sequences of SEQ ID NO: 1 correspond to SEQ ID NO: 6 and SEQ ID NO: 7. A third chemically converted version of each genomic sequences is provided, wherein "C" is converted to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" is converted to "T" for all "C" residues, including those of "CpG" dinucleotide sequences (i.e., corresponds to case where, for the complement (antisense strand) of each genomic sequence, all "C" residues of CpG dinucleotide sequences are unmethylated). The 'downmethylated' converted sequences of SEQ ID NO: 1 corresponds to SEQ ID NO: 4 and SEQ ID NO: 5.

Significantly, heretofore, the nucleic acid sequences and molecules according SEQ ID Nos: 6, 7, 16 and 17 were not implicated in or connected with the detection, classification or treatment of cancer.

In an alternative preferred embodiment, the invention further provides oligonucleotides or oligomers suitable for use in the methods of the invention for detecting the cytosine methylation state within genomic or treated (chemically modified) DNA, according to SEQ ID Nos: 1, 6, 7, 16 and 17. Said oligonucleotide or oligomer nucleic acids provide novel diagnostic means. Said oligonucleotide or oligomer comprising a nucleic acid sequence having a length of at least nine (9) nucleotides which is identical to, hybridizes, under moderately stringent or stringent conditions (as defined herein above), to a treated nucleic acid sequence according to SEQ ID Nos: 6, 7, 16 and 17 and/or sequences complementary thereto, or to a genomic sequence according to SEQ ID NO: 1 and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID Nos: 1, 6, 7, 16 and 17 or to the complements thereof. Particularly preferred is a nucleic acid molecule that hybridizes under moderately stringent and/or stringent hybridization conditions to all or a portion of the sequences SEQ ID Nos: 6, 7, 16 and 17 but not SEQ ID NO: 1 or other human genomic DNA.

The identical or hybridizing portion of the hybridizing nucleic acids is typically at least 9, 16, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID Nos: 1, 6, 7, 16 and 17, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NO: 1 (such as allelic variants and SNPs), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO: 1, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));
where n=1, 2, 3, . . . (Y−(X−1));
where Y equals the length (nucleotides or base pairs) of SEQ ID NO: 1 (1920);
where X equals the common length (in nucleotides) of each oligonucleotide in the set (e.g., X=20 for a set of consecutively overlapping 20-mers); and where the number (Z) of consecutively overlapping oligomers of length X for a given SEQ ID NO 1 of length Y is equal to Y−(X−1). For example Z=1920−19=1901 for either sense or antisense sets of SEQ ID NO: 1, where X=20.

Preferably, the set is limited to those oligomers that comprise at least one CpG, TpG or CpA dinucleotide.

Examples of inventive 20-mer oligonucleotides include the following set of 2,261 oligomers (and the antisense set complementary thereto), indicated by polynucleotide positions with reference to SEQ ID NO: 1:1-20, 2-21, 3-22, 4-23, 5-24, . . . and 1896-1920.

Preferably, the set is limited to those oligomers that comprise at least one CpG, TpG or CpA dinucleotide.

Likewise, examples of inventive 25-mer oligonucleotides include the following set of 2,256 oligomers (and the antisense set complementary thereto), indicated by polynucleotide positions with reference to SEQ ID NO: 1:1-25, 2-26, 3-27, 4-28, 5-29, . . . and 6072-6096.

Preferably, the set is limited to those oligomers that comprise at least one CpG, TpG or CpA dinucleotide.

The present invention encompasses, for each of SEQ ID Nos: 1, 6, 7, 16 and 17 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NO: 1. Preferred sets of such oligonucleotides or modified oligonucleotides of length X are those consecutively overlapping sets of oligomers corresponding to SEQ ID Nos: 1, 6, 7, 16 and 17 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinculeotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585, 481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., *BioTechniques* 6:958-976, 1988) or intercalating agents (Zon, *Pharm. Res.* 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets,' which contain at least one oligomer for analysis of each of the CpG dinucleotides of a genomic sequence selected from the group consisting SEQ ID NO: 1 and sequences complementary thereto, or to the corresponding CpG, TpG or CpA dinucleotide within a sequence of the treated nucleic acids according to SEQ ID Nos: 6, 7, 16 and 17 and sequences complementary thereto. However, it is anticipated that for economic or other factors it may be preferable to analyse a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in treated genomic DNA (SEQ ID Nos: 6, 7, 16 and 17), or in genomic DNA (SEQ ID NO: 1 and sequences complementary thereto). These probes enable diagnosis and detection of cell proliferative disorders, preferably cancerous or pre-cancerous disorders and more preferably a disorder selected from the group consisting of prostate cancer, colorectal cancer and pre-cancerous colorectal conditions. The set of oligomers may also be used for detecting single nucleotide polymorphisms (SNPs) in treated genomic DNA (SEQ ID Nos: 6, 7, 16 and 17), or in genomic DNA (SEQ ID NO: 1 and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID Nos: 1, 6, 7, 16, and 17 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminium, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (*Nature Genetics Supplement, Volume* 21, January 1999, and from the literature cited therein). Fluorescently labelled probes are often used for the scanning of immobilized DNA arrays. The simple attachment of Cy3 and Cy5 dyes to the 5'-OH of the specific probe are particularly suitable for fluorescence labels. The detection of the fluorescence of the hybridised probes may be carried out, for example, via a confocal microscope. Cy3 and Cy5 dyes, besides many others, are commercially available.

It is also anticipated that the oligonucleotides, or particular sequences thereof, may constitute all or part of an "virtual array" wherein the oligonucleotides, or particular sequences thereof, are used, for example, as 'specifiers' as part of, or in combination with a diverse population of unique labeled probes to analyze a complex mixture of analytes. Such a method, for example is described in US 2003/0013091 (U.S. Ser. No. 09/898,743, published 16 Jan. 2003). In such methods, enough labels are generated so that each nucleic acid in the complex mixture (i.e., each analyte) can be uniquely bound by a unique label and thus detected (each label is directly counted, resulting in a digital read-out of each molecular species in the mixture).

It is particularly preferred that the oligomers according to the invention are utilized for detecting, or for diagnosing cell proliferative disorders, preferably cancerous or pre-cancerous disorders and more preferably a disorder selected from the group consisting of prostate cancer, colorectal cancer and pre-cancerous colorectal conditions.

In the most preferred embodiment of the method, the presence or absence of prostate cancer or colorectal cancer is determined. This is achieved by analysis of the methylation status of at least one target sequence comprising at least one CpG position said sequence comprising, or hybridizing under stringent conditions to at least 16 contiguous nucleotides of a sequence selected from the group consisting SEQ ID NO: 1 and complements thereof. The present invention further provides a method for ascertaining genetic and/or epigenetic parameters of the genomic sequence according to SEQ ID NO: 1 within a subject by analysing cytosine methylation and single nucleotide polymorphisms. Said method comprising contacting a nucleic acid comprising SEQ ID NO: 1 in a biological sample obtained from said subject with at least one reagent or a series of reagents, wherein said reagent or series of reagents, distinguishes between methylated and non-methylated CpG dinucleotides within the target nucleic acid.

In a preferred embodiment, said method comprises the following steps: In the first step, a sample of the tissue to be analyzed is obtained. The source may be any suitable source, such as cell lines, histological slides, biopsies, paraffin-embedded tissue, body fluids, ejaculate, urine, blood plasma, blood serum, whole blood, isolated blood cells, cells isolated from the blood and all possible combinations thereof. It is preferred that said sources of DNA are ejaculate or body fluids selected from the group consisting ejaculate, urine, blood plasma, blood serum, whole blood, isolated blood cells, cells isolated from the blood.

The genomic DNA is then isolated from the sample. Genomic DNA may be isolated by any means standard in the art, including the use of commercially available kits. Briefly, wherein the DNA of interest is encapsulated in by a cellular membrane the biological sample must be disrupted and lyzed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Wherein the sample DNA is not enclosed in a membrane (e.g. circulating DNA from a blood sample) methods standard in the art for the isolation and/or purification of DNA may be employed. Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices e.g. ultrafiltration, silica surfaces or membranes, magnetic particles, polystyrene particles, polystyrene surfaces, positively charged surfaces, and positively charged membranes, charged membranes, charged surfaces, charged switch membranes, charged switched surfaces.

Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridization behavior. This will be understood as 'pre-treatment' or 'treatment' herein.

This is preferably achieved by means of treatment with a bisulfite reagent. The term "bisulfite reagent" refers to a reagent comprising bisulfite, disulfite, hydrogen sulfite or combinations thereof, useful as disclosed herein to distinguish between methylated and unmethylated CpG dinucleotide sequences. Methods of said treatment are known in the art (e.g. PCT/EP2004/011715, which is incorporated by reference in its entirety). It is preferred that the bisulfite treatment is conducted in the presence of denaturing solvents such as but not limited to n-alkylenglycol, particularly diethylene glycol dimethyl ether (DME), or in the presence of dioxane or dioxane derivatives. In a preferred embodiment the denaturing solvents are used in concentrations between 1% and 35% (v/v). It is also preferred that the bisulfite reaction is carried out in the presence of scavengers such as but not limited to chromane derivatives, e.g., 6-hydroxy-2,5,7,8, -tetramethylchromane 2-carboxylic acid or trihydroxybenzoe acid and derivates thereof, e.g. Gallic acid (see: PCT/EP2004/011715 which is incorporated by reference in its entirety). The bisulfite conversion is preferably carried out at a reaction temperature between 30° C. and 70° C., whereby the temperature is increased to over 85° C. for short periods of times during the reaction (see: PCT/EP2004/011715 which is incorporated by reference in its entirety). The bisulfite treated DNA is preferably purified priori to the quantification. This may be conducted by any means known in the art, such as but not limited to ultrafiltration, preferably carried out by means of Microcon™ columns (manufactured by Millipore™). The purification is carried out according to a modified manufacturer's protocol (see: PCT/EP2004/011715 which is incorporated by reference in its entirety).

In the third step of the method, fragments of the treated DNA are amplified, using sets of primer oligonucleotides according to the present invention, and an amplification enzyme. The amplification of several DNA segments can be carried out simultaneously in one and the same reaction vessel. Typically, the amplification is carried out using a polymerase chain reaction (PCR). Preferably said amplificates are 100 to 2,000 base pairs in length. The set of primer oligonucleotides includes at least two oligonucleotides whose sequences are each reverse complementary, identical, or hybridize under stringent or highly stringent conditions to an at least 16-base-pair long segment of the base sequences of one of SEQ ID Nos: 6, 7, 16, and 17 and sequences complementary thereto.

In an alternate embodiment of the method, the methylation status of pre-selected CpG positions within the nucleic acid sequences according to SEQ ID NO: 1, may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the position of the C position in the CpG. Preferably, therefore, the base sequence of said primers is required to comprise a sequence having a length of at least 9 nucleotides which hybridizes to a treated nucleic acid sequence according to one of SEQ ID Nos: 6, 7, 16, and 17 and sequences complementary thereto, wherein the base sequence of said oligomers comprises at least one CpG dinucleotide. A further preferred embodiment of the method comprises the use of blocker oligonucleotides (the HeavyMethyl™ assay). The use of such blocker oligonucleotides has been described by Yu et al., *BioTechniques* 23:714-720, 1997. Blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker-a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridizes to a treated nucleic acid sequence according to one of SEQ ID Nos: 6, 7, 16, and 17 and sequences complementary thereto, wherein the base sequence of said oligonucleotides comprises at least one CpG, TpG or CpA dinucleotide.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labeled amplificates have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas and Hillenkamp, *Anal Chem.*, 60:2299-301, 1988). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut and Beck, *Current Innovations and Future Trends,* 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrices have been found which produce a very fine crystallization. There are now several responsive matrices for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut and Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In the fourth step of the method, the amplificates obtained during the third step of the method are analyzed in order to ascertain the methylation status of the CpG dinucleotides prior to the treatment.

In embodiments where the amplificates were obtained by means of MSP amplification, the presence or absence of an amplificate is in itself indicative of the methylation state of the CpG positions covered by the primer, according to the base sequences of said primer.

Amplificates obtained by means of both standard and methylation specific PCR may be further analyzed by means of based-based methods such as, but not limited to, array technology and probe based technologies as well as by means of techniques such as sequencing and template directed extension.

In one embodiment of the method, the amplificates synthesized in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide. The hybridizing portion of the hybridizing nucleic acids is typically at least 9, 15, 20, 25, 30 or 35 nucleotides in length. However, longer molecules have inventive utility, and are thus within the scope of the present invention.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within a sequence selected from the group consisting SEQ ID NO: 1, and the equivalent positions within SEQ ID Nos: 6, 7, 16 and 17. Said oligonucleotides may also be present in the form of peptide nucleic acids. The non-hybridized amplificates are then removed. The hybridized amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes (as detailed above) that are hybridized to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393) employing a dual-labelled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a non-extendible interrogating oligonucleotide, called a TaqMan™ probe, which, in preferred embodiments, is designed to hybridize to a CpG-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the MethyLight™ assay. Variations on the TaqMann™ detection methodology that are also suitable for use with the described invention include the use of dual-probe technology (Lightcycler™) or fluorescent amplification primers (Sunrise™ technology). Both these techniques may be adapted in a manner suitable for use with bisulfite treated DNA, and moreover for methylation analysis within CpG dinucleotides.

In a further preferred embodiment of the method, the fourth step of the method comprises the use of template-directed oligonucleotide extension, such as MS-SNuPE as described by Gonzalgo and Jones, *Nucleic Acids Res.* 25:2529-2531, 1997.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

In the most preferred embodiment of the method the genomic nucleic acids are isolated and treated according to the first three steps of the method outlined above, namely:

a) obtaining, from a subject, a biological sample having subject genomic DNA;

b) extracting or otherwise isolating the genomic DNA;

c) treating the genomic DNA of b), or a fragment thereof, with one or more reagents to convert cytosine bases that are unmethylated in the 5-position thereof to uracil or to another base that is detectably dissimilar to cytosine in terms of hybridization properties; and wherein d) amplifying subsequent to treatment in c) is carried out in a methylation specific manner, namely by use of methylation specific primers or blocking oligonucleotides, and further wherein e) detecting of the amplificates is carried out by means of a real-time detection probe, as described above.

Preferably, where the subsequent amplification of d) is carried out by means of methylation specific primers, as described above, said methylation specific primers comprise a sequence having a length of at least 9 nucleotides which hybridizes to a treated nucleic acid sequence according to one of SEQ ID Nos: 6, 7, 16 and 17 and sequences complementary thereto, wherein the base sequence of said oligomers comprise at least one CpG dinucleotide.

Step e) of the method, namely the detection of the specific amplificates indicative of the methylation status of one or more CpG positions according to SEQ ID NO: 1 is carried out by means of real-time detection methods as described above.

Additional embodiments of the invention provide a method for the analysis of the methylation status of genomic DNA according to the invention (SEQ ID NO: 1, and complements thereof) without the need for bisulfite conversion. Methods are known in the art wherein a methylation sensitive restriction enzyme reagent, or a series of restriction enzyme reagents comprising methylation sensitive restriction enzyme reagents that distinguishes between methylated and non-methylated CpG dinucleotides within a target region are utilized in determining methylation, for example but not limited to DMH.

In the first step of such additional embodiments, the genomic DNA sample is isolated from tissue or cellular sources. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA. All clinical sample types comprising neoplastic or potentially neoplastic matter are suitable for use in the present method, preferred are cell lines, histological slides, biopsies, paraffin-embedded tissue, body fluids, ejaculate, urine, blood plasma, blood serum, whole blood, isolated blood cells, cells isolated from the blood and combinations thereof. Body fluids are the preferred source of the DNA; particularly preferred are blood plasma, blood serum, whole blood, isolated blood cells and cells isolated from the blood.

Once the nucleic acids have been extracted, the genomic double-stranded DNA is used in the analysis.

In a preferred embodiment, the DNA may be cleaved prior to treatment with methylation sensitive restriction enzymes. Such methods are known in the art and may include both physical and enzymatic means. Particularly preferred is the use of one or a plurality of restriction enzymes which are not methylation sensitive, and whose recognition sites are AT rich and do not comprise CG dinucleotides. The use of such enzymes enables the conservation of CpG islands and CpG rich regions in the fragmented DNA. The non-methylation-specific restriction enzymes are preferably selected from the group consisting of MseI, BfaI, Csp6I, Tru1I, Tvu1I, Tru9I, Tvu9I, MaeI and XspI. Particularly preferred is the use of two or three such enzymes. Particularly preferred is the use of a combination of MseI, BfaI and Csp6I.

The fragmented DNA may then be ligated to adaptor oligonucleotides in order to facilitate subsequent enzymatic amplification. The ligation of oligonucleotides to blunt and sticky ended DNA fragments is known in the art, and is carried out by means of dephosphorylation of the ends (e.g. using calf or shrimp alkaline phosphatase) and subsequent ligation using ligase enzymes (e.g. T4 DNA ligase) in the presence of dATPs. The adaptor oligonucleotides are typically at least 18 base pairs in length.

In the third step, the DNA (or fragments thereof) is then digested with one or more methylation sensitive restriction enzymes. The digestion is carried out such that hydrolysis of the DNA at the restriction site is informative of the methylation status of a specific CpG dinucleotide of the RASSF2 gene.

Preferably, the methylation-specific restriction enzyme is selected from the group consisting of Bsi EI, Hga I HinPI, Hpy99I, Ava I, Bce AI, Bsa HI, BisI, BstUI, BshI236I, AccII, BstFNI, McrBC, GlaI, MvnI, HpaII (HapII), HhaI, AciI, SmaI, HinP1I, HpyCH4IV, EagI and mixtures of two or more of the above enzymes. Preferred is a mixture containing the restriction enzymes BstUI, HpaII, HpyCH4IV and HinP1I.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels. Particularly preferred is amplification by means of an amplification enzyme and at least two primers comprising, in each case a contiguous sequence at least 16 nucleotides in length that is complementary to, or hybridizes under moderately stringent or stringent conditions to a sequence selected from the group consisting SEQ ID NO: 1, and complements thereof. Preferably said contiguous sequence is at least 16, 20 or 25 nucleotides in length. In an alternative embodiment said primers may be complementary to any adaptors linked to the fragments.

In the fifth step the amplificates are detected. The detection may be by any means standard in the art, for example, but not limited to, gel electrophoresis analysis, hybridization analysis, incorporation of detectable tags within the PCR products, DNA array analysis, MALDI or ESI analysis. Preferably said detection is carried out by hybridization to at least one nucleic acid or peptide nucleic acid comprising in each case a contiguous sequence at least 16 nucleotides in length that is complementary to, or hybridizes under moderately stringent or stringent conditions to a sequence selected from the group consisting SEQ ID NO: 1, and complements thereof. Preferably said contiguous sequence is at least 16, 20 or 25 nucleotides in length.

Subsequent to the determination of the methylation state or level of the genomic nucleic acids the presence, absence of cell proliferative disorders, preferably cancerous or pre-cancerous disorders (and more preferably a disorder selected from the group consisting of prostate cancer, colorectal cancer and pre-cancerous colorectal conditions), is deduced based upon the methylation state or level of at least one CpG dinucleotide sequence of SEQ ID NO: 1, or an average, or a value reflecting an average methylation state of a plurality of CpG dinucleotide sequences of SEQ ID NO: 1 wherein methylation is associated with the presence of prostate cancer, colorectal cancer and pre-cancerous colorectal conditions. Wherein said methylation is determined by quantitative means the cut-off point for determining said the presence of methylation is preferably zero (i.e. wherein a sample displays any degree of methylation it is determined as having a methylated status at the analysed CpG position). Nonetheless, it is foreseen that the person skilled in the art may wish to adjust said cut-off value in order to provide an assay of a particularly preferred sensitivity or specificity. Accordingly said cut-off value may be increased (thus increasing the specificity), said cut off value may be within a range selected form the group consisting of 0%-5%, 5%-10%, 10%-15%, 15%-20%, 20%-30% and 30%-50%. Particularly preferred are the cut-offs 10%, 15%, 25%, and 30%.

Kits

Moreover, an additional aspect of the present invention is a kit comprising: a means for determining RASSF2 methylation. The means for determining RASSF2 methylation comprise preferably a bisulfite-containing reagent; one or a plurality of oligonucleotides consisting whose sequences in each case are identical, are complementary, or hybridise under stringent or highly stringent conditions to a 9 or more preferably 18 base long segment of a sequence selected from SEQ ID Nos: 6, 7, 16 and 17; and optionally instructions for carrying out and evaluating the described method of methylation analysis. In one embodiment the base sequence of said oligonucleotides comprises at least one CpG, CpA or TpG dinucleotide.

In a further embodiment, said kit may further comprise standard reagents for performing a CpG position-specific methylation analysis, wherein said analysis comprises one or more of the following techniques: MS-SNuPE, MSP, MethyLight™, HeavyMethyl, COBRA, and nucleic acid sequencing. However, a kit along the lines of the present invention can also contain only part of the aforementioned components.

In a preferred embodiment the kit may comprise additional bisulfite conversion reagents selected from the group consisting: DNA denaturation buffer; sulfonation buffer; DNA recovery reagents or kits (e.g., precipitation, ultrafiltration, affinity column); desulfonation buffer; and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining a biological sample of the patient. Preferred is a kit, which further comprises a container suitable for containing the means for determining methylation of the gene RASSF2 in the biological sample of the patient, and most preferably further comprises instructions for use and interpretation of the kit results. In a preferred embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID Nos: 6, 7, 16 and 17; and optionally (d) instructions for use and interpretation of the kit results. In an alternative preferred embodiment the kit comprises: (a) a bisulfite reagent; (b) a container suitable for containing the said bisulfite reagent and the biological sample of the patient; (c) at least one oligonucleotides and/or PNA-oligomer having a length of at least 9 or 16 nucleotides which is identical to or hybridises to a pre-treated nucleic acid sequence according to one of SEQ ID Nos: 6, 7, 16 and 17 and sequences complementary thereto; and optionally (d) instructions for use and interpretation of the kit results.

In an alternative embodiment the kit comprises: (a) a bisulfite reagent; (b) a container suitable for containing the said bisulfite reagent and the biological sample of the patient; (c) at least one set of primer oligonucleotides containing two oligonucleotides whose sequences in each case are identical, are complementary, or hybridise under stringent or highly stringent conditions to a 9 or more preferably 18 base long segment of a sequence selected from SEQ ID Nos: 6, 7, 16 and 17; (d) at least one oligonucleotides and/or PNA-oligomer having a length of at least 9 or 16 nucleotides which is identical to or hybridises to a pre-treated nucleic acid sequence according to one of SEQ ID Nos: 6, 7, 16 and 17 and sequences complementary thereto; and optionally (e) instructions for use and interpretation of the kit results.

The kit may also contain other components such as buffers or solutions suitable for blocking, washing or coating, packaged in a separate container.

Another aspect of the invention relates to a kit for use in determining the presence of and/or diagnosing cell proliferative disorders, preferably cancerous or pre-cancerous disorders (and more preferably a disorder selected from the group consisting of prostate cancer, colorectal cancer and pre-cancerous colorectal conditions), said kit comprising: a means for measuring the level of transcription of the gene RASSF2 and a means for determining RASSF2 methylation.

Typical reagents (e.g., as might be found in a typical COBRA™-based kit) for COBRA™ analysis may include, but are not limited to: PCR primers for RASSF2; restriction enzyme and appropriate buffer; gene-hybridization oligo; control hybridization oligo; kinase labeling kit for oligo probe; and labeled nucleotides. Typical reagents (e.g., as might be found in a typical MethyLight™-based kit) for MethyLight™ analysis may include, but are not limited to: PCR primers for the bisulfite converted sequence of the RASSF2 gene; bisulfite specific probes (e.g. TaqMan™ or Lightcycler™; optimized PCR buffers and deoxynucleotides; and Taq polymerase.

Typical reagents (e.g., as might be found in a typical Ms-SNuPE™-based kit) for Ms-SNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for the bisulfite converted sequence of the RASSF2 gene; reaction buffer (for the Ms-SNuPE reaction); and labelled nucleotides.

Typical reagents (e.g., as might be found in a typical MSP-based kit) for MSP analysis may include, but are not limited to: methylated and unmethylated PCR primers for the bisulfite converted sequence of the RASSF2 gene, optimized PCR buffers and deoxynucleotides, and specific probes.

Moreover, an additional aspect of the present invention is an alternative kit comprising a means for determining RASSF2 methylation, wherein said means comprise preferably at least one methylation specific restriction enzyme; one or a plurality of primer oligonucleotides (preferably one or a plurality of primer pairs) suitable for the amplification of a sequence comprising at least one CpG dinucleotide of a sequence selected from SEQ ID NO: 1; and optionally instructions for carrying out and evaluating the described method of methylation analysis. In one embodiment the base sequence of said oligonucleotides are identical, are complementary, or hybridise under stringent or highly stringent conditions to an at least 18 base long segment of a sequence selected from SEQ ID NO: 1.

In a further embodiment said kit may comprise one or a plurality of oligonucleotide probes for the analysis of the digest fragments, preferably said oligonucleotides are identical, are complementary, or hybridise under stringent or highly stringent conditions to an at least 16 base long segment of a sequence selected from SEQ ID NO: 1.

In a preferred embodiment the kit may comprise additional reagents selected from the group consisting: buffer (e.g. restriction enzyme, PCR, storage or washing buffers); DNA recovery reagents or kits (e.g., precipitation, ultrafiltration, affinity column) and DNA recovery components.

In a further alternative embodiment, the kit may contain, packaged in separate containers, a polymerase and a reaction buffer optimized for primer extension mediated by the polymerase, such as PCR. In another embodiment of the invention the kit further comprising means for obtaining a biological sample of the patient. In a preferred embodiment the kit comprises: (a) a methylation sensitive restriction enzyme reagent; (b) a container suitable for containing the said reagent and the biological sample of the patient; (c) at least one set of oligonucleotides one or a plurality of nucleic acids or peptide nucleic acids which are identical, are complementary, or hybridize under stringent or highly stringent conditions to an at least 9 base long segment of a sequence selected from SEQ ID NO: 1; and optionally (d) instructions for use and interpretation of the kit results.

In an alternative preferred embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from SEQ ID NO: 1; and optionally (d) instructions for use and interpretation of the kit results.

In an alternative embodiment the kit comprises: (a) a methylation sensitive restriction enzyme reagent; (b) a container suitable for containing the said reagent and the biological sample of the patient; (c) at least one set of primer oligonucleotides suitable for the amplification of a sequence comprising at least one CpG dinucleotide of a sequence selected from SEQ ID NO: 1; (d) at least one set of oligonucleotides one or a plurality of nucleic acids or peptide nucleic acids which are identical, are complementary, or hybridize under stringent or highly stringent conditions to an at least 9 base long segment of a sequence selected from SEQ ID NO: 1 and optionally (e) instructions for use and interpretation of the kit results.

The kit may also contain other components such as buffers or solutions suitable for blocking, washing or coating, packaged in a separate container.

The invention further relates to a kit for use in providing a diagnosis of the presence of a cell proliferative disorders, preferably cancerous or pre-cancerous disorders (and more preferably a disorder selected from the group consisting of prostate cancer, colorectal cancer and pre-cancerous colorectal conditions), in a subject by means of methylation-sensitive restriction enzyme analysis. Said kit comprises a container and a DNA microarray component. Said DNA microarray component being a surface upon which a plurality of oligonucleotides are immobilized at designated positions and wherein the oligonucleotide comprises at least one CpG methylation site. At least one of said oligonucleotides is specific for the gene RASSF2 and comprises a sequence of at least 15 base pairs in length but no more than 200 bp of a sequence according to one of SEQ ID NO: 1. Preferably said sequence is at least 15 base pairs in length but no more than 80 bp of a sequence according to one of SEQ ID NO: 1. It is further preferred that said sequence is at least 20 base pairs in length but no more than 30 bp of a sequence according to one of SEQ ID NO: 1.

Said test kit preferably further comprises a restriction enzyme component comprising one or a plurality of methylation-sensitive restriction enzymes.

In a further embodiment said test kit is further characterized in that it comprises at least one methylation-specific restriction enzyme, and wherein the oligonucleotides comprise a restriction site of said at least one methylation specific restriction enzymes.

The kit may further comprise one or several of the following components, which are known in the art for DNA enrichment: a protein component, said protein binding selectively to methylated DNA; a triplex-forming nucleic acid component, one or a plurality of linkers, optionally in a suitable solution; substances or solutions for performing a ligation e.g. ligases, buffers; substances or solutions for performing a column chromatography; substances or solutions for performing an immunology based enrichment (e.g. immuno-precipitation); substances or solutions for performing a nucleic acid amplification e.g. PCR; a dye or several dyes, if applicable with a coupling reagent, if applicable in a solution; substances or solutions for performing a hybridization; and/or substances or solutions for performing a washing step.

The described invention further provides a composition of matter useful for detecting, or for diagnosing cell proliferative disorders, preferably cancerous or pre-cancerous disorders and more preferably a disorder selected from the group consisting of prostate cancer, colorectal cancer and pre-cancerous colorectal conditions. Said composition comprising at least one nucleic acid 18 base pairs in length of a segment of the nucleic acid sequence disclosed in SEQ ID Nos: 6, 7, 16, and 17, and one or more substances taken from the group comprising: 1-5 mM Magnesium Chloride, 100-500 µM dNTP, 0.5-5 units of taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridizes under moderately stringent or stringent conditions to a pretreated genomic DNA according to one of the SEQ ID Nos: 6, 7, 16, and 17 and sequences complementary thereto. It is preferred that said composition of matter comprises a buffer solution appropriate for the stabilization of said nucleic acid in an aqueous solution and enabling polymerase based reactions within said solution. Suitable buffers are known in the art and commercially available.

In further preferred embodiments of the invention said at least one nucleic acid is at least 50, 100, 150, 200, 250 or 500 base pairs in length of a segment of the nucleic acid sequence disclosed in SEQ ID Nos: 6, 7, 16, and 17.

EXAMPLES

Example 1

In the following example an MSP assay suitable for the methylation analysis of the gene RASSF2A according to was designed, in order to validate the suitability of said marker for the detection of colorectal carcinoma. The assay was designed to be run on the LightCycler platform (Roche Diagnostics), but other such instruments commonly used in the art are also suitable. The amplificate was designed to be detected by means of Taqman style fluorescent labelled detection probes.

Samples

In total 314 samples were analysed: 198 colorectal carcinoma of the following stages:

Stage 0: 4 samples
Stage 1: 19 samples
Stage 2: 84 samples

Stage 3: 57 samples
Stage 4: 20 samples
Stage unknown: 14 samples
22 normal or normal adjacent tissue
26 whole blood samples
40 other cancers (liver, breast and prostate)
28 other normal or normal adjacent tissues (liver, breast and prostate)

DNA Extraction and Bisulfite Treatment

The DNA was isolated from the all samples according to a modified protocol based on that disclosed in the Qiagen Genomic DNA Handbook (August 2001) (pg 28-31, 44-47). The eluate resulting from the purification was then converted according to the following bisulfite reaction. The eluate was mixed with 354 µl of bisulfite solution (5.89 mol/l) and 146 µl of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated at the following temperature program for a total of 7 h min 50° C.; one thermospike (99.9° C.) for 3 min; 1.5 h 50° C.; one thermospike (99° C.) for 3 min; 3 h 50° C. The reaction mixture was subsequently purified by ultrafiltration using a Millipore Microcon™ column. The purification was conducted essentially according to the manufacturer's instructions. For this purpose, the reaction mixture was mixed with 300 µl of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 75 µl of warm 1×TE buffer (50° C.). The membrane was turned over according to the manufacturer's instructions. Subsequently a repeated centrifugation was conducted, with which the DNA was removed from the membrane. 10 µl of the eluate was utilized for the Lightcycler Real Time PCR assay.

PCR Assay Component Sequences:

```
Primer:
gaagtagtcggggtcgtttacg           SEQ ID NO: 26

Primer:
Gcaaaatacgcgaaaaccgt             SEQ ID NO: 27

Detection oligonucleotide:
acgtcttctctcgccccgaacga          SEQ ID NO: 28
```

Thermal Cycling Conditions:

| degrees C. | time |
| --- | --- |
| Activation | |
| 95 | 10 min |
| Cycling (50x) | |
| 95 | 15 sec |
| 60 | 60 sec |

Control Assay

The GSTP1-C3 assay design makes it suitable for quantitating DNAs from different sources, including fresh/frozen samples, remote samples such as plasma or serum, and DNA obtained from archival specimen such as paraffin embedded material. The following oligonucleotides were used in the reaction to amplify the control amplificate:

```
Control Primer1:
                                 (SEQ ID NO: 29)
GGAGTGGAGGAAATTGAGAT Control Primer2:
                                 (SEQ ID NO: 30)
CCACACAACAAATACTCAAAAC Control Probe:
                                 (SEQ ID NO: 31)
FAM-TGGGTGTTTGTAATTTTTGTTTTGTGTTAGGTT-TAMRA
```

Cycle program (40 cycles): 95° C., 10 min
95° C., 15 sec
58° C., 1 min

Data Interpretation

Calculation of DNA concentration—The Cp (crossing point values) as calculated by the Lightcycler instrument software were used to determine DNA concentration. The DNA concentration was calculated by reference of the CP value of each well to a standard curve for both the methylation assays and the C3 assay.

Percentage methylation—For each sample the detected percentage methylation was calculated as the measured concentration of DNA quantified using the methylation assays over the concentration of DNA in the sample as quantified by the C3 assay.

Detection of methylation was determined at multiple different threshold levels, see tables) as well as at all methylation levels (i.e. any samples wherein methylation was detected were deemed positive).

The sensitivity of the assay was determined from the colorectal carcinoma sample positive detection rate, wherein sensitivity was determined as the % samples wherein methylation was positively detected (i.e. true positives).

The specificity of the assay was determined from the whole blood sample negative detection rate (i.e. true negative detection rate) wherein false positives were discounted from the total number of analysed samples.

Results

The term 'AUC' is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975).

At a cut-off 0% methylation (i.e. any detected methylation is considered "hypermethylated") the AUC was 0.86 for detection of colorectal carcinoma and 0.00 in blood. At a cut-off 10%, 20% and 30% methylation (i.e. any detected methylation is considered "hypermethylated") the AUCs were 0.73, 0.54 and 0.33 respectively for detection of colorectal carcinoma.

Example 2

In the following investigation, the performance of selected markers according to Table 2 were selected for further analysis by means of the HM (HeavyMethyl) assay. Target regions of each gene were bisulfite converted and amplified by means of non-MSP primers, in the presence of a blocker oligonucleotides designed to suppress amplificates that had not been methylated prior to bisulfite treatment. Amplificates were then detected by means of Lightcycler (dual) probes.

Plasma samples from the following patient classes were analyzed:

Colorectal carcinoma (131 total)
Stage 0=1
Stage I=13
Stage II=32
Stage III=27
Stage IV=8
Unclassified=50
Healthy colorectal (colonoscopy verified)=169
Non-cancerous diseases (NCD)=29
Cancers of non-colorectal origin (NCC)=31
In total 360 samples were analyzed.

DNA Extraction and Bisulfite Treatment

The DNA was isolated from the all samples by means of the Magna Pure method (Roche) according to the manufacturer's instructions. The eluate resulting from the purification was then converted according to the following bisulfite reaction.

The eluate was mixed with 354 µl of bisulfite solution (5.89 mol/l) and 146 µl of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated at the following temperature program for a total of 7 h min 50° C.; one thermospike (99.9° C.) for 3 min; 1.5 h 50° C.; one thermospike (99° C.) for 3 min; 3 h 50° C. The reaction mixture was subsequently purified by ultrafiltration using a Millipore Microcon™ column. The purification was conducted essentially according to the manufacturer's instructions. For this purpose, the reaction mixture was mixed with 300 µl of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 75 µl of warm 1×TE buffer (50° C.). The membrane was turned over according to the manufacturer's instructions. Subsequently a repeated centrifugation was conducted, with which the DNA was removed from the membrane. 10 µl of the eluate was utilized for the Lightcycler Real Time PCR assay.

Reaction Solutions and Thermal Cycling Conditions

PCR assay component sequences are provided in Table 3. Each assay was performed twice (independently) in each sample.

Thermal Cycling Conditions were:

| PCDHGC3 | | | | |
|---|---|---|---|---|
| activation: | 95° C. | 10 min | | |
| 50 cycles: | 95° C. | 10 sec | (20° C./s) | detection |
| | 56° C. | 30 sec | (20° C./s) | |
| | 60° C. | 3 sec | (20° C./s) | |
| | 72° C. | 10 sec | (20° C./s) | |

| -continued | | | | |
|---|---|---|---|---|
| melting curve: | 95° C. | 10 sec | (20° C./s) | Continuous |
| | 40° C. | 10 sec | (20° C./s) | |
| | 95° C. | 0 sec | (0.1° C./s) | |
| cooling: | 40° C. | 5 sec | | |
| All other assays: | | | | |
| activation: | 95° C. | 10 min | | |
| 55 cycles: | 95° C. | 10 sec | (20° C./s) | detection |
| | 56° C. | 30 sec | (20° C./s) | |
| | 72° C. | 10 sec | (20° C./s) | |
| melting curve: | 95° C. | 10 sec | (20° C./s) | Continuous |
| | 40° C. | 10 sec | (20° C./s) | |
| | 95° C. | 0 sec | (0.1° C./s) | |
| cooling: | 40° C. | 5 sec | | |

Results:

In order to predict the presence of CRC tumour DNA in the measured plasma samples we use a logistic regression model. The logistic regression model is build as follows. First the measurement data for each marker assay is encoded in a qualitative way by the following 3 levels:

Level 0—both replicate PCR reactions showed no amplification
Level 1—exactly one of the two PCR replicates showed an amplification curve
Level 2—both of the two PCR replicates showed amplification curves If any of the two PCR replicates could not be successfully measured the respective marker measurement was regarded as invalid. The five different DNA methylation markers were used as independent factors with 3 levels in a logistic regression model. An additional intercept factor but no factor interactions were included in the model. The logistic regression model was trained and optimal weights for all factor levels were determined by using the maximum likelihood procedure.

FIGS. 1 to 10 provide the plots of the measured log mean methylation of the individual assays. Each figures consists of three plots, the upper and lower left hand side plots provide the binary and multiclass analysis respectively, the right hand plot provides an ROC wherein sensitivity is shown on the Y-axis and 1-specificity is shown on the X-axis. Table 4 and FIGS. 1 to 5 provide an overview of marker performances in all sample groups. Table 5 and FIGS. 6 to 10 provide an overview of marker performances in the colorectal carcinoma and normal colorectal groups.

FIGS. 12 to 21 provide the plots of the measured log majority mean (analyzed sample is only counted as positive if both replicates are positive, the mean of the two measurements is taken as the quantitative methylation measurement) methylation of the individual assays. Each figures consists of three plots, the upper and lower left hand side plots provide the binary and multiclass analysis respectively, the right hand plot provides an ROC wherein sensitivity is shown on the Y-axis and 1-specificity is shown on the X-axis. Table 6 and FIGS. 12 to 16 provide an overview of marker performances in all sample groups. Table 7 and FIGS. 18 to 21 provide an overview of marker performances in the colorectal carcinoma and normal colorectal groups.

Table 8 provides an overview of the AUC and sensitivities of the single assays at 95% specificity (all p-values were less than 0.00001). Wherein said classes are:

All: Normal+NCD+NCC vs. CRC stages I to IV
I-IV: Normal vs. CRC stages I to IV
I-III: Normal vs. CRC stages I to III From the multiclass distribution of FIG. 6 (bottom left hand plot) and table 11 it can be determined that the gene RASSF2 is particularly effective at detecting Stage 1 and early colorectal carcinomas. Accordingly expression, most preferably CpG methylation, of said gene is in addition to being a preferred diagnostic marker is particularly preferred for the screening of general populations (individuals not displaying any indicators or symptoms of colorectal carcinoma) for the early detection of colorectal carcinomas.

Marker Combinations (Panels)

To identify the subset of DNA methylation markers that optimally predicts the presence of CRC the inventors use the backward elimination procedure. In each elimination step the DNA methylation marker with the lowest factor levels was removed from the model. The inventors compared the predictive power of the reduced model with the complete model by using the likelihood ratio test. To identify the subset of DNA methylation markers that optimally predicts the presence of CRC the inventors use the backward elimination procedure. In each elimination step the DNA methylation marker with the lowest factor levels was removed from the model. The inventors compared the predictive power of the reduced model with the complete model by using the likelihood ratio test. FIG. 11 shows that (in the Normal vs. CRC stages I to IV comparison) at each elimination step the predictive power of the logistic regression model was significantly reduced. The inventors conclude that all listed DNA methylation marker models give superior prediction performance as compared to the single marker or the respective simpler marker panels. The inventors conclude that the following DNA marker models give superior prediction performance as compared to the single marker or the respective simpler marker panels.

FIGS. 22 to 26 provide an overview of the performance of the following marker combinations:

Septin 9+TFAP2E+RASSF2+PCDHGC3+SND1 (FIG. 22)

| All | AUC | 80 |
|---|---|---|
|  | Sens/Spec | 57/95 |
| All CRC | AUC | 80 |
|  | Sens/Spec | 58/96 |
| CRC I-III | AUC | 76 |
|  | Sens/Spec | 50/96 |

Septin 9+TFAP2E+RASSF2+PCDHGC3 (FIG. 23)

| All | AUC | 80 |
|---|---|---|
|  | Sens/Spec | 53/95 |
| All CRC | AUC | 80 |
|  | Sens/Spec | 55/96 |
| CRC I-III | AUC | 77 |
|  | Sens/Spec | 48/96 |

Septin 9+TFAP2E+RASSF2 (FIG. 24)

| All | AUC | 77 |
|---|---|---|
|  | Sens/Spec | 48/96 |
| All CRC | AUC | 79 |
|  | Sens/Spec | 52/96 |
| CRC I-III | AUC | 75 |
|  | Sens/Spec | 42/96 |

Septin 9+TFAP2E (FIG. 25)

| All | AUC | 77 |
|---|---|---|
|  | Sens/Spec | 45/96 |
| All CRC | AUC | 79 |
|  | Sens/Spec | 51/96 |
| CRC I-III | AUC | 75 |
|  | Sens/Spec | 41/96 |

Septin 9+RASSF2 (FIG. 26)

| All | AUC | 77 |
|---|---|---|
|  | Sens/Spec | 43/96 |
| All CRC | AUC | 79 |
|  | Sens/Spec | 56/95 |
| CRC I-III | AUC | 74 |
|  | Sens/Spec | 46/95 |

In each case the upper plot shows all samples (Normals, Non Colorectal Disease, Non Colorectal Cancers and all CRC stages), the lower plot shows only Normal and CRC samples.

Example 3

Performance of Marker in Prostate Cancer Diagnosis

In the following investigation, the performance of selected markers in detecting prostate carcinoma was determined by means of the HM (Heavymethyl) assay. Target regions of each gene were bisulfite converted and amplified by means of non-MSP primers, in the presence of a blocker oligonucleotide designed to suppress amplificates that had not been methylated prior to bisulfite treatment. Amplificates were then detected by means of Lightcycler (dual) probes and the level of methylation was determined by reference to control assays.

Samples

For this experiment, we collected matched plasma and urine from a total of 191 men, including 91 males with biopsy-confirmed prostate cancer, 51 males with no cancer detected by biopsy (subsequently diagnosed with BPH), and 50 young healthy males. In all analyses, the positive class is comprised of the Prostate cancer samples.

In designing the present clinical study, the primary difficulty was in the definition of the negative class as there is no detection method that excludes presence of Prostate cancer with 100% certainty. Biopsy has a false negative diagnosis rate of at least 10% while PSA measurement is prone to both false negatives and false positives. Because the primary objective of the Present Study was to demonstrate the feasibility of measuring methylated markers of Prostate cancer in a remote body fluid, we focused on a negative class that minimized the probability of false positives. Consequently, young healthy males were chosen as the "true" negative class. We reasoned that young healthy males with no family history of prostate cancer should be truly negative for Prostate cancer.

In order to investigate the markers as a diagnostic follow-on to PSA, we also included a second negative class of biopsy negative, BPH samples. A potentially confounding factor in this class is the likely presence of false negative biopsies.

In five Prostate cancer cases, only a plasma sample was collected and in ten additional cases only a urine sample was collected. The samples were collected at multiple sites. The urine was collected after a prostatic massage. Both plasma and urine samples were obtained before any treatment for Prostate cancer. Inclusion and exclusion criteria were designed to ensure that the patients analyzed reflect the potential patients who would use Prostate cancer screening tests.

The following inclusion and exclusion criteria applied to the patients undergoing biopsy:

Inclusion Criteria:
- Indication for biopsy (elevated PSA and/or suspicious DRE)
- Biopsy scheduled within 1 week after sample collection
- Age 40-80

Exclusion Criteria:
Any prior treatment for prostate cancer
History of cancer or serious illness in the past 5 years
Symptoms of urinary tract infection The following criteria applied to the healthy men of the control group:

Inclusion Criteria:
- Male
- Age 18-30

Exclusion Criteria:
Any prior treatment for or symptoms of prostate cancer or prostate disease
History of cancer or serious illness in the past 5 years
Symptoms of urinary tract infection DNA Extraction DNA was extracted and isolated using standard protocols and commercially available kits.

Bisulfite Treatment

The eluate was mixed with 354 µl of bisulfite solution (5.89 mol/l) and 146 µl of dioxane containing a radical scavenger (6-hydroxy-2,5,7,8-tetramethylchromane 2-carboxylic acid, 98.6 mg in 2.5 ml of dioxane). The reaction mixture was denatured for 3 min at 99° C. and subsequently incubated at the following temperature program for a total of 7 h min 50° C.; one thermospike (99.9° C.) for 3 min; 1.5 h 50° C.; one thermospike (99° C.) for 3 min; 3 h 50° C. The reaction mixture was subsequently purified by ultrafiltration using a Millipore Microcon™ column. The purification was conducted essentially according to the manufacturer's instructions. For this purpose, the reaction mixture was mixed with 300 µl of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 75 µl of warm 1×TE buffer (50° C.). The membrane was turned over according to the manufacturer's instructions. Subsequently a repeated centrifugation was conducted, with which the DNA was removed from the membrane.

Real-time Lightcycler PCR Assay

For each assay, 1.5 ml analyte equivalent was run in duplicate, methylation was determined by means of the assay components according to Table 9. Control assays for the beta actin gene and "CFF" regions was used to determine total DNA concentration, in order to quantiate the amount of methylated DNA as determined by the Heavymethyl assay.

Results

One of the objectives was to develop markers targeted as a diagnostic follow-on to PSA tests of 4.0 ng/ml or more for men over 50 years of age to discriminate prostate cancer from non-cancerous conditions. We further focused on two indications: a screening application to identify men over 50 years with a high risk of prostate cancer and a diagnostic follow-on to PSA to inform the prostate re-biopsy decision in men with at least one negative prostate biopsy and persistently elevated PSA. We analyzed the data in two different ways: (i) we used prostate cancer and biopsy-negative samples to assess markers performance in the follow-on to PSA test (diagnostic application) and (ii) we used prostate cancer and all the non-cancer (biopsy-negative and healthy) samples to measure markers performance in screening test (screening application). We report marker performance for plasma and urine separately, we also provide data analysis for individual markers and marker panels. All data are reported as logmean raw methylation values.

Marker Performance in Screening Application

As a primary screening test, the marker would need to identify Prostate cancer in men over age 50 years with improved specificity relative to PSA. All screening application analyses use the Prostate cancer samples as the positive class. For the purposes of the Present clinical study, we analyzed data for our screening application with two alternative negative classes. The first negative class analyzed the 50 young healthy males with minimal likelihood of undetected Prostate cancer. While this negative class represents a "true" test negative, it is not age-matched to the target Prostate cancer screening population and does not include any likely false positive classes, e.g. BPH. Therefore, we performed a second analysis in which all 50 healthy young controls and all 51 biopsy negative controls were analyzed as a 101 sample size negative class.

On average, approximately 20,000,000 PSA tests are performed every year in the US with only approximately 1,000,000 cases moving forward to biopsy (of which approximately 750,000 biopsies are unnecessary). Therefore, less than 5% of individuals that are currently screened by PSA fall in the negative class that is represented by elevated-PSA-BPH-positive whereas as the vast majority of the target screening population fall into the PSA-low negative class. Whereas the negative class of only healthy young males may represent an overestimation of the discriminatory capacity of our markers, the combined negative class of healthy young males plus age-matched biopsy negative males may represent an underestimation of the discriminatory capacity of our markers.

Single Marker Performance in Urine

Figure 27:
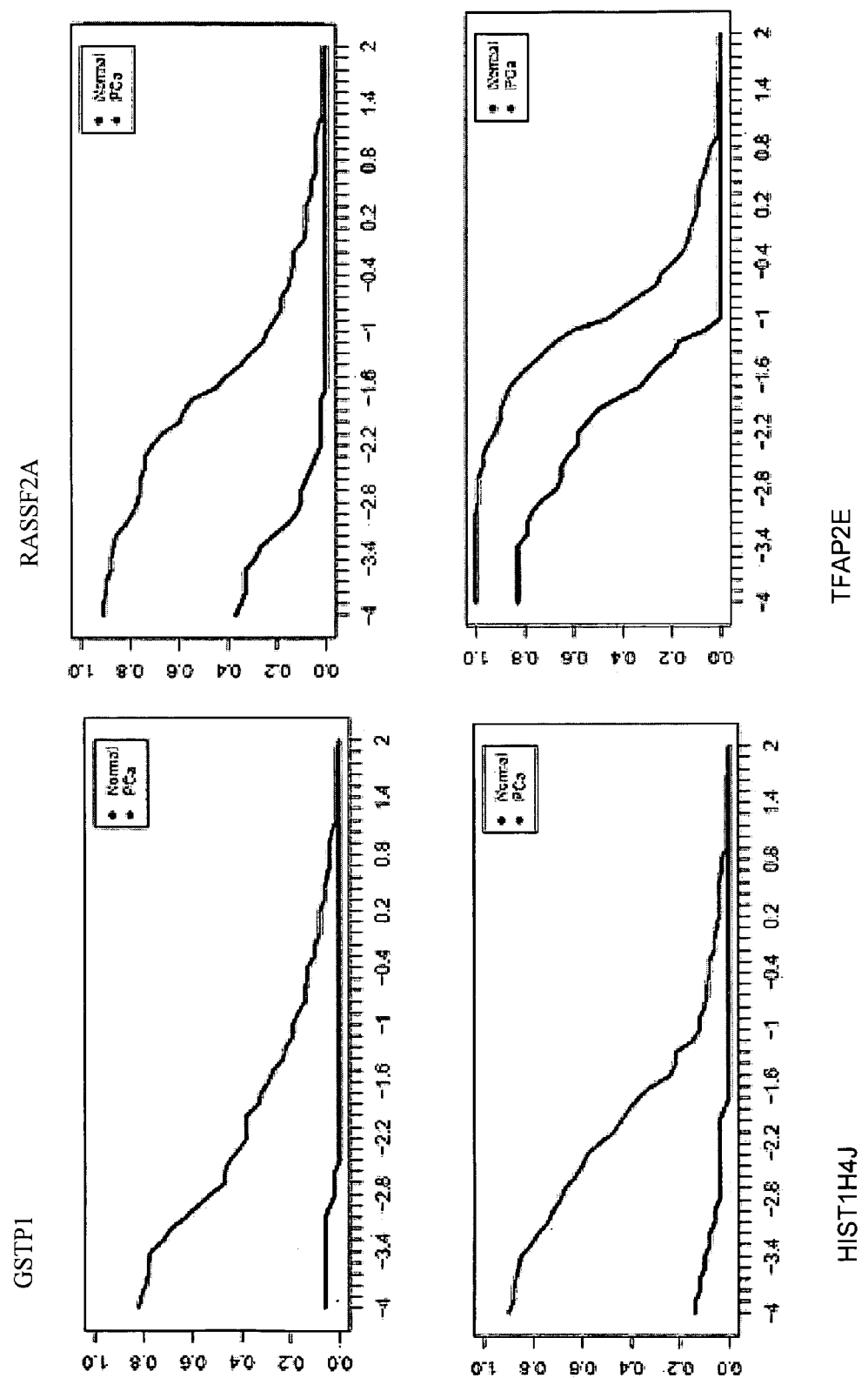
Figure 28:
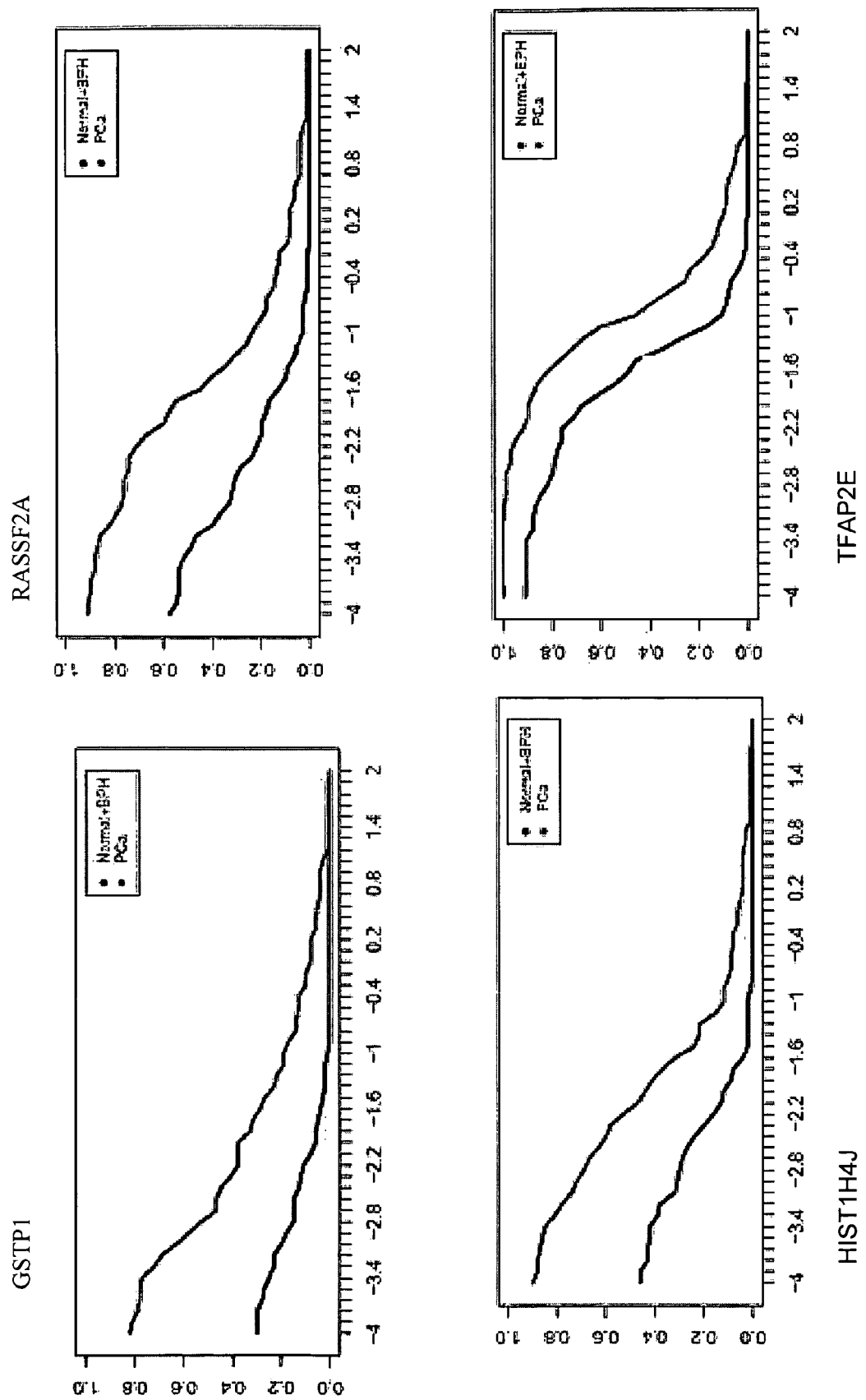

The sensitivity and specificity of markers tested by real-time PCR in post-prostatic massage urine from prostate cancer patients, biopsy negative patients and healthy control individuals is shown in Table 10, and the assay performance on post-prostatic massage urine as compared to with negative class I (healthy individuals) is shown in FIG. 27. The assay performance on post-prostatic massage urine as compared to with negative II (healthy plus biopsy negative individuals) is shown in FIG. 28.

Figure 29:
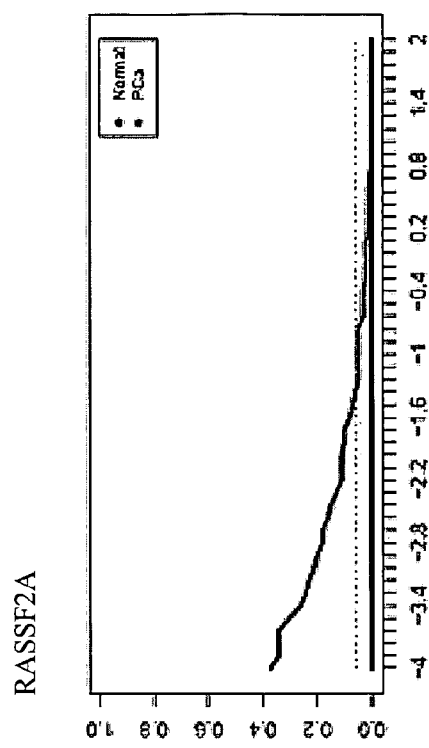
Figure 29:
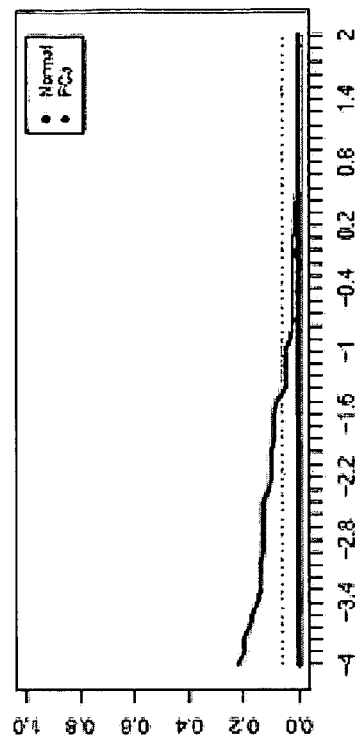
Figure 29:
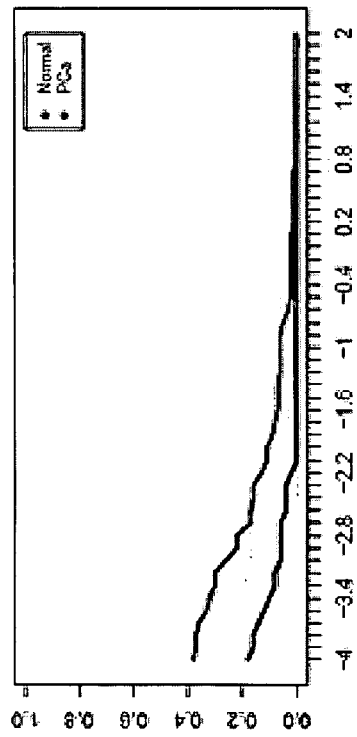
Figure 29:
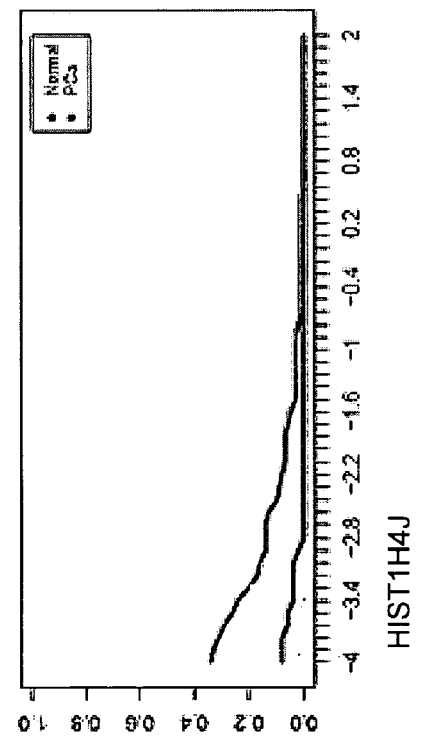
Figure 30:
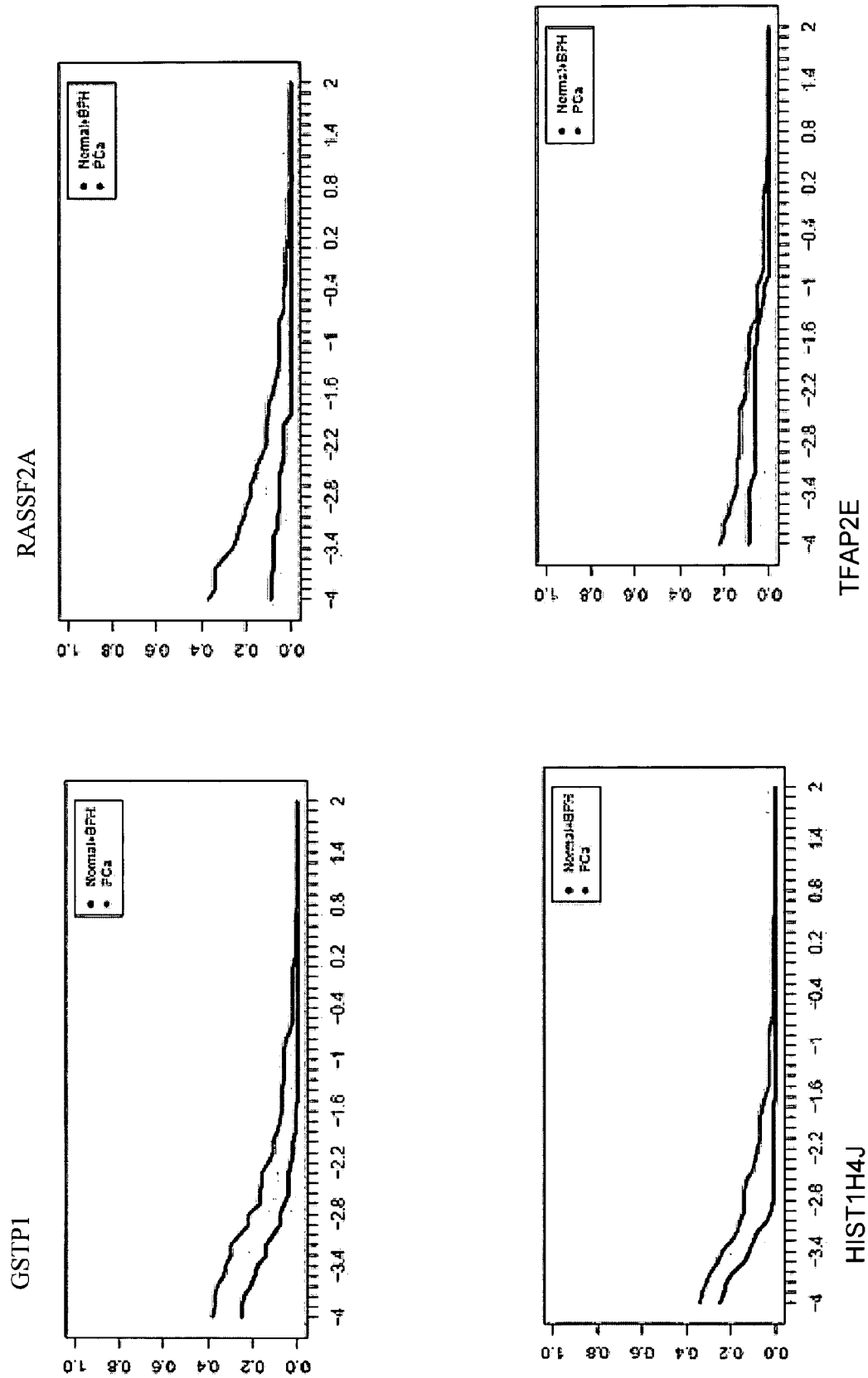

The sensitivity and specificity of markers tested by real-time PCR in plasma from prostate cancer patients, biopsy negative patients and healthy control individuals is shown in Table 11, and the assay performance on plasma as compared to with negative class I (healthy individuals) is shown in FIG. 29. The assay performance in plasma as compared to with negative II (healthy plus biopsy negative individuals) is shown in FIG. 30.

particularly preferred for the diagnosis of prostate cancer that the analyte is urine, either voided or post-prostatic massage.

Table 19 provides the performance of diagnostic marker panels to detect Prostate cancer in biopsy negative patients in urine.

TABLE 1

Sequences according to the present invention.

| Genomic SEQ ID NO: | Gene | Methylated bisulfite converted sequence (sense) | Methylated bisulfite converted sequence (antisense) | Unmethylated bisulfite converted sequence (sense) | Unmethylated bisulfite converted sequence (antisense) |
|---|---|---|---|---|---|
| 1 | RASSF2A | 6 | 7 | 16 | 17 |
| 2 | SCND1 | 8 | 9 | 18 | 19 |
| 3 | PCDHGC3 | 10 | 11 | 20 | 21 |
| 4 | TFAP2E | 12 | 13 | 22 | 23 |
| 5 | SEPTIN9 | 14 | 15 | 24 | 25 |
| 57 | GSTP1 | 59 | 60 | 63 | 64 |
| 58 | HIST1H4J | 61 | 62 | 65 | 66 |

In all negative class comparisons and for all markers urine was the more sensitive analyte as illustrated in Table 12. Increasing amounts of methylated marker DNA correlated with increasing Gleason score for all markers in plasma. This was true for samples with high amounts of methylated marker DNA in urine (especially markers TFAP2E and RASSF2A), this was especially so in DNA from plasma. PSA as a marker of Prostate cancer in patients with elevated PSA (>4 ng/ml) also correlated with increasing Gleason score.

Table 13 shows the performance of screening marker panels to distinguish Prostate cancer from negative class I (healthy males) in urine. Table 14 shows the performance of screening marker panels to distinguish Prostate cancer from negative class II (healthy males plus biopsy negative) in urine. Table 15 shows the performance of screening marker panels to distinguish Prostate cancer from negative class I (healthy males) in plasma. Table 16 shows the performance of screening marker panels to distinguish Prostate cancer from negative class II (healthy males plus biopsy negative) in plasma.

Marker Performance in Diagnostic Application: Follow-on to PSA

As a diagnostic application, the markers should identify Prostate cancer in men over age 50 years with persistently elevated PSA (>4.0 ng/ml) who have undergone at least one negative prostate biopsy. This is a distinct application and analysis and requires increased discrimination as compared to the screening test. False positives in this application arise from the elevated PSA, biopsy negative BPH class. Again, the Prostate cancer samples represent the positive class. For the purposes of a diagnostic application, we analyzed the data using a single negative class comprised of the 51 biopsy negative samples.

Single Marker Performance in Urine

Table 17 shows the sensitivity and specificity of markers tested by real-time PCR in post-prostatic massage urine from prostate cancer patients and biopsy negative patients.

Figure 31:
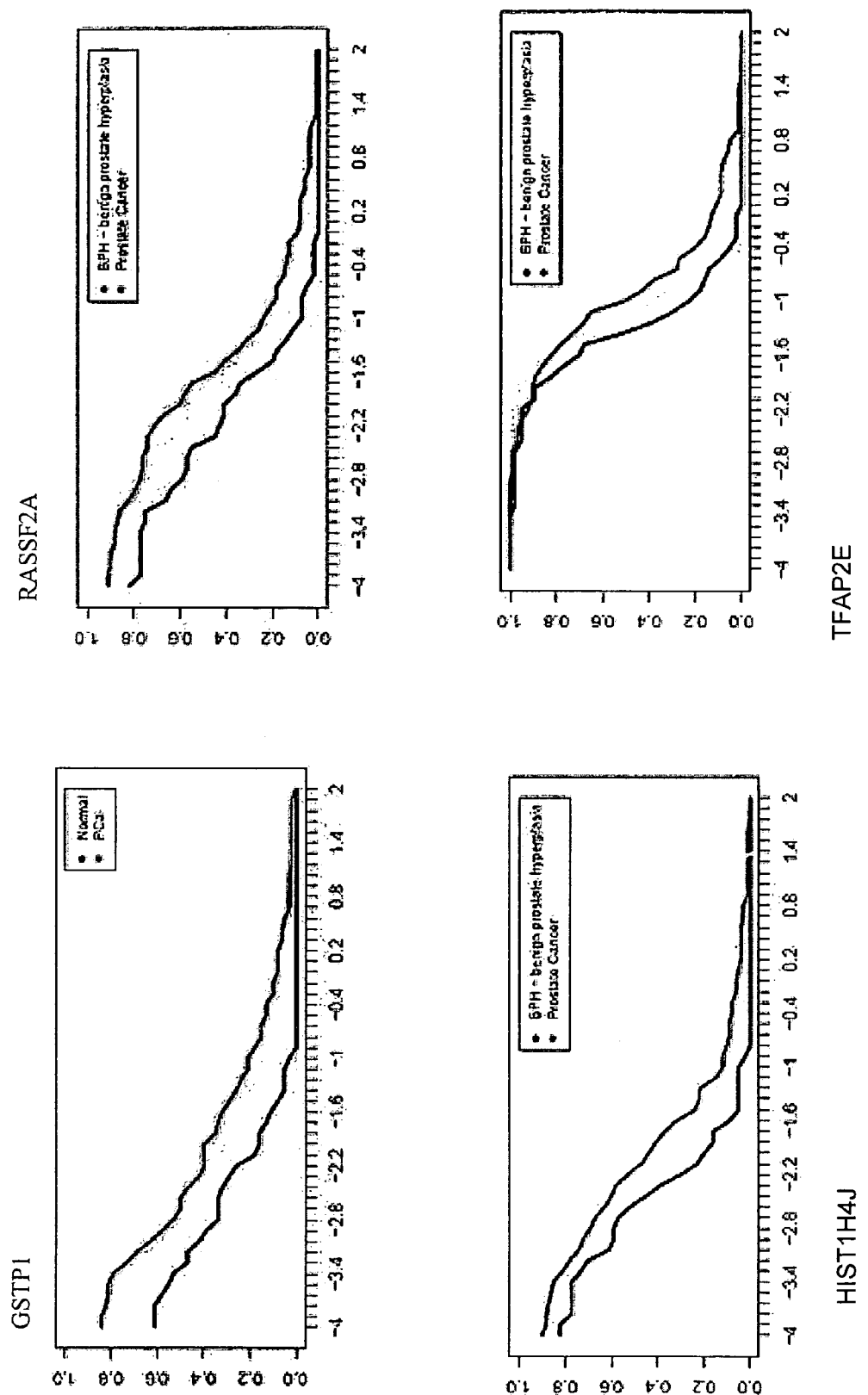

FIG. 31 shows the single assay performance for HM real-time PCR assays on post-prostatic massage urine.

As shown in Table 18, for all methylation markers analyzed urine was the more sensitive analyte. Accordingly it is

TABLE 2

Genes according to the present invention

| Genomic SEQ ID NO: | Gene | Abbreviation | Bisulfite converted sequences |
|---|---|---|---|
| | Staphylococcal nuclease domain-containing protein 1 (p100 co-activator) (100 kDa coactivator) (EBNA2 coactivator p100) | SND1 | |
| | Protocadherin gamma C5 precursor (PCDH-gamma-C5) | PCDHGC3 | |
| | transcription factor AP-2 epsilon (activating enhancer binding protein 2 epsilon) | TFAP2E | |
| | Septin-9 (MLL septin-like fusion protein) (MLL septin-like fusion protein MSF-A) (Ovarian/Breast septin) (Ov/Br septin) (Septin D1) | Septin 9 | |
| | Ras association domain family 2 | RASSF2 | |

*Unless otherwise stated all locations refer to Ensembl database v39 (June 2006)
**Ensembl database v31.35d (8 Jul. 2005)

TABLE 3

Primer, blocker and probe sequences according to Example 2.

| | Septin 9 | RASSF2 | SND1 | PCDHGC3 | TFAP2E |
|---|---|---|---|---|---|
| Forward primer SEQ ID NO: | 32 | 37 | 42 | 47 | 52 |
| Reverse primer SEQ ID NO: | 33 | 38 | 43 | 48 | 53 |
| Blocker SEQ ID NO: | 34 | 39 | 44 | 49 | 54 |
| Probe SEQ ID NO: | 35 | 40 | 45 | 50 | 55 |
| Probe SEQ ID NO: | 36 | 41 | 46 | 51 | 56 |

TABLE 4

HM assay (Example 2) performance in all tissue samples.

| | RASSF2 | Septin 9 | SND1 | PCDHGC3 | TFAP2E |
|---|---|---|---|---|---|
| AUC (95% confidence interval) | 0.72 (0.67, 0.77) | 0.75 (0.7, 0.79) | 0.66 (0.6, 0.71) | 0.66 (0.61, 0.72) | 0.69 (0.63, 0.74) |
| Sens/Spec | 0.4/0.95 | 0.47/0.95 | 0.25/0.95 | 0.32/0.95 | 0.29/0.95 |
| Sens/Spec cut off | −3.029 | −2.706 | −3.089 | −2.378 | −2.692 |
| Wilcoxon P | 0 | 0 | 0 | 0 | 0 |
| CRC + Adenoma-(pos) | 131 | 131 | 118 | 119 | 119 |
| Normal + non-cancerous diseases (NCD) + carcinoma other than colorectal (NCC)-(neg) | 228 | 228 | 205 | 206 | 206 |

TABLE 5

HM assay (Example 2) performance in colorectal carcinoma and normal colorectal tissue samples.

| | RASSF2 | Septin 9 | SND1 | PCDHGC3 | TFAP2E |
|---|---|---|---|---|---|
| AUC (95% confidence interval) | 0.73 (0.67, 0.78) | 0.76 (0.7, 0.8) | 0.67 (0.61, 0.73) | 0.68 (0.62, 0.73) | 0.71 (0.65, 0.76) |
| Sens/Spec | 0.47/0.95 | 0.48/0.95 | 0.39/0.95 | 0.32/0.95 | 0.39/0.95 |
| Sens/Spec cut off | −3.272 | −2.858 | −3.473 | −2.417 | −3.446 |
| Wilcoxon P | 0 | 0 | 0 | 0 | 0 |
| CRC + Adenoma (pos) | 131 | 131 | 118 | 119 | 119 |
| Normal (neg) | 168 | 169 | 148 | 148 | 148 |

TABLE 6

HM assay (Example 2) performance in all tissue samples.

| | RASSF2 | Septin 9 | SND1 | PCDHGC3 | TFAP2E |
|---|---|---|---|---|---|
| AUC (95% confidence interval) | 0.67 (0.62, 0.72) | 0.74 (0.69, 0.79) | 0.63 (0.57, 0.68) | 0.65 (0.6, 0.7) | 0.65 (0.6, 0.7) |
| Sens/Spec | 0.37 (0.96) | 0.51 | 0.28/0.95 | 0.34/0.95 | 0.34/0.96 |
| Sens/Spec cut off | −4 | −4 | −3.45 | −2.523 | −4 |
| Wilcoxon P | 0 | 0 | 0 | 0 | 0 |
| CRC + Adenoma-(pos) | 121 | 127 | 113 | 127 | 120 |
| Normal + non-cancerous diseases (NCD) + carcinoma other than colorectal (NCC)-(neg) | 206 | 220 | 194 | 224 | 203 |

TABLE 7

HM assay (Example 2) performance in colorectal carcinoma and normal colorectal tissue samples.

| | RASSF2 | Septin 9 | SND1 | PCDHGC3 | TFAP2E |
|---|---|---|---|---|---|
| AUC (95% confidence interval) | 0.67 (0.61, 0.73) | 0.74 (0.69, 0.79) | 0.64 (0.58, 0.7) | 0.66 (0.6, 0.71) | 0.66 (0.6, 0.72) |
| Sens/Spec | 0.37/0.97 | 0.51/0.97 | 0.3/0.97 | 0.35/0.95 | 0.34/0.98 |
| Sens/Spec cut off | −4 | −4 | −4 | −2.599 | −4 |
| Wilcoxon P | 0 | 0 | 0 | 0 | 0 |
| CRC + Adenoma (pos) | 121 | 121 | 113 | 127 | 120 |
| Normal (neg) | 154 | 164 | 146 | 167 | 154 |

TABLE 8

AUC and sensitivity (at 95% specificity) for single assays of markers according to class.*

| | AUC | | | Sensitivity | | |
|---|---|---|---|---|---|---|
| | All | I-IV | I-II | All | I-IV | I-II |
| Septin 9 (Majority mean) | 73 | 73 | 67 | 49 | 49 | 37 |
| RASSF2 (Log Mean) | 72 | 73 | 70 | 45 | 48 | 41 |
| TFAP2E (Log Mean) | 68 | 71 | 67 | 32 | 38 | 30 |
| SND1 (Log Mean) | 64 | 65 | 62 | 25 | 35 | 29 |
| PCDHGC3 (Log Mean) | 65 | 66 | 64 | 30 | 32 | 29 |

*all p-values were less than 0.00001

TABLE 9

Assays according to Example 2.

| Gene | Forward Primer SEQ ID NO: | Reverse Primer SEQ ID NO: | Blocker SEQ ID NO: | Probe SEQ ID NO: | Probe SEQ ID NO: |
|---|---|---|---|---|---|
| Actin B | 67 | 68 | | 69 | |
| Cytosine Free Fragment | 70 | 71 | | 72 | |
| GSTP | 73 | 74 | 75 | 76 | 77 |
| Histone H4 HIST1H4K | 78 | 79 | 80 | 81 | 82 |
| RASSF2 | 83 | 84 | 85 | 86 | 87 |
| TFAP2E | 88 | 89 | 90 | 91 | 92 |

TABLE 10

| | Negative Class I: Healthy | | | Negative Class II: Healthy + Biopsy (−) | | |
|---|---|---|---|---|---|---|
| Marker | AUC | Sens/Spec | Wilcoxon p value | AUC | Sens/Spec | Wilcoxon p value |
| GSTP1 | 0.89 | 0.63/0.96 | 0 | 0.79 | 0.31/0.96 | 0 |
| RASSF2A | 0.90 | 0.74/0.96 | 0 | 0.79 | 0.24/0.96 | 0 |
| HIST1H4J | 0.91 | 0.69/0.96 | 0 | 0.78 | 0.36/0.96 | 0 |
| TFAP2E | 0.86 | 0.47/0.96 | 0 | 0.76 | 0.27/0.96 | 0 |

TABLE 11

| | Negative Class I: Healthy | | | Negative Class II: Healthy + Biopsy (−) | | |
|---|---|---|---|---|---|---|
| Marker | AUC | Sens/Spec | Wilcoxon p value | AUC | Sens/Spec | Wilcoxon p value |
| GSTP1 | 0.61 | 0.17/0.96 | 0.0063 | 0.58 | 0.17/0.95 | 0.0183 |
| RASSF2A | 0.68 | 0.37/1.00 | 0 | 0.64 | 0.20/0.95 | 0 |
| HIST1H4J | 0.64 | 0.26/0.96 | 5e$^{-04}$ | 0.56 | 0.16/0.95 | 0.0572 |
| TFAP2E | 0.61 | 0.22/1.00 | 4e$^{-04}$ | 0.56 | 0.09/0.95 | 0.0128 |

TABLE 12

| | Negative Class I: Healthy | | Negative Class II: Healthy + Biopsy (—) | |
|---|---|---|---|---|
| Marker | Urine AUC | Plasma AUC | Urine AUC | Plasma AUC |
| GSTP1 | 0.89 | 0.61 | 0.79 | 0.58 |
| RASSF2A | 0.90 | 0.68 | 0.79 | 0.64 |
| HIST1H4J | 0.91 | 0.64 | 0.78 | 0.56 |
| TFAP2E | 0.86 | 0.61 | 0.76 | 0.56 |

TABLE 13

| Marker Panel | % Sens Prostate cancer | % Spec Healthy |
|---|---|---|
| Quantitative Single Markers: | | |
| RASSF2A | 74 | 96 |
| HIST1H4J | 69 | 96 |
| GSTP1 | 63 | 96 |
| TFAP2E | 46 | 100 |
| Qualitative Panels: | | |
| GSTP1 + HIST1H4J | 79 | 98 |
| RASSF2A + HIST1H4J | 94 | 88 |
| Quantitative Panels: | | |
| RASSF2A + HIST1H4J | 94 | 88 |
| quadSVM (all markers, no PSA) | 79 | 98 |

TABLE 14

| Marker Panel | % Sens Prostate cancer | % Spec Healthy + Biopsy (—) |
|---|---|---|
| Quantitative Single Markers: | | |
| RASSF2A | 74 | 76 |
| HIST1H4J | 69 | 68 |
| GSTP1 | 63 | 80 |
| TFAP2E | 46 | 88 |
| Qualitative Panels: | | |
| GSTP1 + HIST1H4J | 79 | 72 |
| RASSF2A + HIST1H4J | 94 | 54 |
| Quantitative Panels: | | |
| RASSF2A + HIST1H4J | 94 | 58 |
| quadSVM (all markers, no PSA) | 79 | 76 |

TABLE 15

| Marker Panel | % Sens Prostate cancer | % Spec Healthy |
|---|---|---|
| Quantitative Single Markers: | | |
| RASSF2A | 37 | 100 |
| HIST1H4J | 26 | 96 |
| GSTP1 | 17 | 94 |
| TFAP2E | 22 | 100 |
| Qualitative Panels: | | |
| RASSF2A + HIST1H4J | 41 | 98 |
| Quantitative Panels: | | |
| RASSF2A + TFAP2E (TFAP2E used to normalize) | 32 | 100 |
| quadSVM (all markers, no PSA) | 39 | 96 |

TABLE 16

| Marker Panel | % Sens Prostate cancer | % Spec Healthy + Biopsy (—) |
|---|---|---|
| Quantitative Single Markers: | | |
| RASSF2A | 37 | 91 |
| HIST1H4J | 26 | 88 |
| GSTP1 | 17 | 95 |
| TFAP2E | 22 | 92 |
| Qualitative Panels: | | |
| RASSF2A + HIST1H4J | 41 | 88 |
| Quantitative Panels: | | |
| RASSF2A + TFAP2E (TFAP2E used to normalize) | 32 | 92 |
| quadSVM (all markers, no PSA) | 39 | 94 |

TABLE 17

Prostate cancer vs. Biopsy (—)

| Marker | AUC | Sens/Spec | Wilcoxon p value |
|---|---|---|---|
| GSTP1 | 0.69 | 0.23/0.95 | 6e$^{-04}$ |
| RASSF2A | 0.66 | 0.18/0.95 | 0.0043 |
| HIST1H4J | 0.64 | 0.28/0.95 | 0.0126 |
| TFAP2E | 0.65 | 0.21/0.95 | 0.0062 |
| ***PSA | 0.56 | 0.22/0.95 | 0.3098 |

***Tests whether PSA contains further information beyond what was contributed by the >4 ng/ml cut-off indication for prostate biopsy.

TABLE 18

Prostate cancer vs. Biopsy (—)

| Marker | Urine AUC | Plasma AUC |
|---|---|---|
| GSTP1 | 0.69 | 0.55 |
| RASSF2A | 0.66 | 0.60 |
| HIST1H4J | 0.64 | 0.50 |
| TFAP2E | 0.65 | 0.52 |
| ***PSA | na | 0.56 |

***Tests whether PSA contains further information beyond what was contributed by the >4 ng/ml cut-off indication for prostate biopsy.

TABLE 19

| Marker Panel | % Sens Prostate cancer | % Spec Biopsy (—) |
|---|---|---|
| Quantitative Single Markers: | | |
| RASSF2A | 74 | 55 |
| HIST1H4J | 69 | 41 |
| GSTP1 | 63 | 64 |
| TFAP2E | 46 | 77 |
| Qualitative Panels: | | |
| GSTP1 + HIST1H4J | 79 | 46 |
| RASSF2A + HIST1H4J | 94 | 21 |
| Quantitative Panels: | | |
| RASSF2A + HIST1H4J | 94 | 27 |
| GSTP1 + PSA | 83 | 45 |
| quadSVM (all markers, no PSA) | 79 | 55 |

---

The invention claimed is:

1. A method for detecting CpG methylation in genomic DNA comprising a RASSF2 gene, comprising:
   a) isolating genomic DNA comprising a RASSF2 gene from a biological sample obtained from a subject, wherein the biological sample is selected from the group consisting of urine, blood plasma, blood serum, whole blood, blood, cells isolated from the blood and combinations thereof;
   b) treating the genomic DNA comprising the RASSF2 gene, or a fragment thereof comprising the RASSF2 gene, with bisulfite such that non-methylated cytosines are converted to uracil;
   c) contacting the bisulfite-treated genomic DNA comprising the RASSF2 gene, or the bisulfite-treated fragment thereof comprising the RASSF2 gene, with an amplification enzyme and:
      at least two methylation-specific primers comprising a contiguous sequence of at least 9 nucleotides, wherein each of the at least two methylation-specific primers is identical across its entire length or is fully complementary across its entire length to a sequence selected from the group consisting of SEQ ID NOs: 6, 7, 16, 17, or
      at least two primers comprising a contiguous sequence of at least 9 nucleotides wherein each of the at least two primers is identical across its entire length or is fully complementary across its entire length to a sequence selected from the group consisting of SEQ ID NOs: 6, 7, 16, 17, and at least one methylation-specific blocking nucleic acid molecule or peptide nucleic acid molecule comprising in each case a contiguous sequence at least 9 nucleotides in length that is identical across its entire length or is fully complementary across its entire length to a sequence selected from the group consisting of SEQ ID NO: 6, 7, 16, 17, wherein the nucleic acid molecule or peptide nucleic acid molecule suppresses amplification of a nucleic acid to which it is hybridized,
   wherein the bisulfite-treated genomic DNA or the bisulfite-treated fragment thereof is either amplified to produce at least one amplificate comprising a sequence selected from the group consisting of SEQ ID NOs: 6, 7, 16, 17 or a fragment thereof, or is not amplified; and
   d) determining a methylation state or level of the RASSF2 gene or a portion thereof, based on a presence or absence of the at least one amplificate, or on a property of the at least one amplificate, wherein increased methylation in the RASSF2 gene or portion thereof, compared to that of a normal control, indicates CpG methylation in the genomic DNA comprising the RASSF2 gene, thereby detecting CpG methylation in genomic DNA comprising a RASSF2 gene.

2. The method of claim 1, wherein contacting the bisulfite-treated genomic DNA comprising the RASSF2 gene, or the bisulfite-treated fragment thereof comprising the RASSF2 gene, comprises use of at least one method selected from the group consisting of use of a heat-resistant DNA polymerase as the amplification enzyme, use of a polymerase lacking 5'-3' exonuclease activity, use of a polymerase chain reaction (PCR), and generation of an amplificate nucleic acid molecule carrying a detectable label.

3. The method of claim 1, wherein determining the methylation state or level of the RASSF2 gene or portion thereof comprises hybridization of at least one nucleic acid molecule or peptide nucleic acid molecule in each case comprising a contiguous sequence at least 9 nucleotides in length that is identical across its entire length or is fully complementary across its entire length to a sequence selected from the group consisting of SEQ ID NO: 6, 7, 16, 17.

4. The method of claim 3, wherein at least one of the nucleic acid molecules or peptide nucleic acid molecules is bound to a solid phase.

5. The method of claim 3, further comprising extending at least one of the nucleic acid molecules by at least one nucleotide base.

6. The method of claim 1, wherein determining the methylation state or level of the RASSF2 gene or portion thereof comprises sequencing of the amplificate.

7. The method of claim 1, wherein the at least two primers comprise a first primer having the sequence of SEQ ID NO: 26 and a second primer having the sequence of SEQ ID NO: 27.

8. The method of claim 1, wherein contacting the bisulfite-treated genomic DNA comprising the RASSF2 gene, or the bisulfite-treated fragment thereof comprising the RASSF2 gene, comprises use of a blocking nucleic acid having the sequence of SEQ ID NO: 85 or a probe oligonucleotide having the sequence of SEQ ID NO: 86 or SEQ ID NO: 87.

9. The method of claim 1, wherein the subject has an increased risk of colorectal cancer.

10. The method of claim 1, wherein the subject has an increased risk of prostate cancer.

11. The method of claim 1, wherein the subject has colorectal cancer.

12. The method of claim 1, wherein the subject has prostate cancer.

* * * * *

SEQUENCE LISTING

<160> NUMBER OF SEQ ID NOS: 92

<210> SEQ ID NO 1
<211> LENGTH: 1920
<212> TYPE: DNA
<213> ORGANISM: Homo Sapiens

<400> SEQUENCE: 1

```
ccaggctgcc gtagacacag cctttgctct cccgaaaaac acgttctagg cgccgggatt    60
ccagatacct gggaaataga gtgcacgcag ctgttgagag gcctcgcgct tggcttctcc   120
tatcactgag gcgcagaggt gctgtggaca gcccagaccc acacggcgcc cgaggtgaaa   180
cagaaccctc agtctcccta tgaggccact ggcactctcg gctgtcccca gagctctccg   240
acttagagct gaatgcaaag taagcgctcg aaatgcagaa gtagccgggg ccgcccacgg   300
cacctgcctc gctcggggcg agagaagacg ccaggctgag gtcccagcga cctcaggcac   360
cagctccgaa ggagggcggg gagaccgcaa aggggaagtg cccggagggc caacggcccc   420
cgcgcaccct gcgcccctct gaagcgcgcc gcctcccgc gccggggact gggacctgcc   480
tctggggaat ccgcctagaa gacggcggcg gactggggtc gggcactctc cagggctgtc   540
aggccctccc cagccctgca cctgccgcgc gcccccacct cgccaggaag tctcagagac   600
cccggggatg gggtgggagc gccttcccat cgcgggctca aaaagaagga aggacgcccc   660 cagggtcgt agaaggagga ctagctccaa gccacaactt tcttcggacc caaggcaggc   720
cggctggggc tccgcgccta cacggcccct ggcggggtc cgcgcgcccc gggagcccgg   780
cggctcgggg aggaaagagg agacaagaga caggcgagga ttacggggct gacccagccg   840
```

-continued

```
gggtagggac catcgtggaa aaactttggc gaggtggggg gacgcggaaa gagagcggcc    900
cgcgccctgc accttgcgcc gggcatcccg cgccagtgcc tcgctcccag tgccccgcgc    960
cccgcgcccc gcgccttgcc ttcacccccgg gccagctgca tcgcgcccgc gccgcaggaa   1020
ccgtggagtt ggaaagtggg ggcgccgcgg ctgggggggct gcttcagctg cgcctcggcc   1080
agcgatcggc gggccgggct caaatccagc caggctgggc aggcggtggc cgcgcgactg    1140
gggaccgggc gccccgccct cctcgctccc ctcctccttc ctctccctcc ctccagcccc    1200
ttggcctttt tcagccccta ccggatctgc tcgtccgctg tcctctcttt tctctcgctc    1260
ttcatatcac tctccacccc ttcgccttgc cttcgccttt cttcctcccc ttgtctcctg    1320
cccctcctc ttctcccctc cctctaggg gcggagcttc tcccctccct cccagacaat      1380
gctgtggctg cgtccccttc cccgccagct cgtccaggct cccgccgcca gcgattcttc    1440
cgggctgggg gtggggaggt ggggggggag tgcagggttg gggaggatga gctggctccc    1500
ctcacctcct tgctgctgcc ctctccaaga gggatggaga cttggcccaa gctcctcggt    1560
tcacccggag ctgtgacagc cactcccagg gaacagtcac gctgccctac caagcccacc    1620
tccagcggcc tggattcccc aggcagaggt tgtgggattt tgttttttct aacatcccag    1680
cttattccca aaagggtttg agccggacag gggctaaaca ggcccccttcg acttggcggg   1740
ccggccagac gtgacagcaa tgccaaggag gccaagtttc tttgtccatt tctcacctcc    1800
ccctttttcca tccctggacc tcctggcgcc cccagtacac agaggcccttt gagcagcccg   1860
gctgcaggtt ccctatctac tcagagttct cccccctcacg tgcctatccc caaccctgca   1920
```

<210> SEQ ID NO 2
<211> LENGTH: 2519
<212> TYPE: DNA
<213> ORGANISM: Homo Sapiens

<400> SEQUENCE: 2

```
gatttatgag tgaatgacta aaagtgcagc tgagtcctgg cagagggcat ggggtcccac     60
ccagagacag gcagagaaag ttgaagtccc aggattggag gccgttcttc ctcacctccc    120
caccaggccc aggcagggct tgatctgaac ggaggcctgg gaacctgtgg ccagcccttta  180
cttgttggaa aagagcagtc cttaagctca attgctccag gttgatgctt ccctactttt    240
ttttatttat ttattttat tattattttt ttttattga gacggagtct tactctgttg     300
ccaggttgga gtgcagtggc gcgatctcgg ctcactgcca cctccgcctg ctgagttcaa    360
gcctcagcct cctgagtagc tcctgggta gctgggacta caggcgtgcg ccaccacgcc     420
aggctaattt tttgtatttt agtatagacg gagtttcacc actttggcca ggatggtctc    480
gatctcctga cctcgtgata ctcccgcctc ggtatcccaa agtgccggga ttacaggcat    540
gagccacagc gccggcccc tagttctttt taaaaaacgc tagatccgtc cgctgcgctg     600
agtggaggcg gggcaggcct ccgttctcca attggcctta tccaccgagc tcttcccttg    660
tgccgggctc tgtgccaagc acatcacacg ctgtatcctg cggccaggtt gctgtggtcc    720
agggtcgtac cctggtccaa ggtcgcaaac cgaggtggga ctccgatccg gcaaccacgc    780
ccgtggcccg gaaacggcgt cccctgaggc ccaggagagg ccgggcggtg agcggctgtg    840
gagccgagcg cggcagtgc ggatgctgcc tatggggag gcagccaagg acggagggcg      900
agaggcggtt cttccaaggt caccctcttc cgggttgcaa gcaaaggtca ggggatcccg    960
gaatggttag tgcaggagct tctctgtgcc ttccacgtcc tagatcctca gagcctcaga   1020
```

-continued

```
aacggagatc atcgtcccca cccccatttt acagatgaag aaactgagcc gaggaaagga      1080
agcgacttgg ccaaggtcgg agagctcatt ctttgcaggg cggggtttgg aacccggggt      1140
ctggctctcg gcaacgcgcc ctcggcccgc agcctcctgc ccctgtgcc ccgcttcggc       1200 ccccagcgca gctgcagagg ggccccctc gacgcataca ctcaagagcc cgaccgcgcg       1260
gctgaaatcg cggagctcgg agccgcggct ggctgagcga tcgcggttcc tgggctgcgt      1320
gcgcgcccct tggagctgaa aggagcgcca ggatcggggg cgctgcaccg ggctgggccc      1380
ctcaacgctc gcagaccggg ccgggctgca gctggagatg gcagcaatcc cgggaggtct      1440
ccgggcctct tcagggtgcg tccaggaggc gggttccgtg cgacgcggtg cagcccaccc      1500
ccccccccga daccgcttaa cttcgcgggg gcagcctcgg gcgctcggag acgcggaggc      1560
ccagactgca gcctccggat gctggaagcc cagactccct ggggtcaccg gctctcccgc      1620
caccccagct gcagagagtc ccattgcttc accgtccgga gcttagtctc cttgttcctc      1680
taccagtccc tccctccgca ggtctctggg gacttctgac cgcctgttct tactctcccc      1740 ctgccccat acttcccgcc cttgtctcag gaacggtgat acagtcaccg gattgctctc       1800
catctcctgt tagtctacac tgcacacaac tcaataatcc gcgccctcc atccgggtga       1860 cagagacaca gataatctga gctagtggtg ctcaaagtac cggtcccaga acagcagcat      1920
cagcatctct tgggaacttg ttaaaaatga gaattgggc cgggcgcggt ggctcacgcc       1980
tgtaatccca gcactttggg aggccgaggc gggcggatca cgaggtcagg agatcgagac      2040
catcccggct aaaacggtga aacccgtct ctactaaaaa tacaaaaaat tagccgggca       2100
tagtggcggg cgcctgtagt cccagctact tgggaggctg aggcaggaga atggcgtgaa      2160
cccgggaggc ggagcttgca gtgagccgag atcccgccac tgcactccag cctgggcgac      2220
agagcgagac tccgtctcaa aaaaaaaaa aatgcgaatt tgggggcccc accccagatc       2280
tactgaacag aaactctgtg gagcccagca gatgattccc atgcacacta aagtttgcga      2340
gccactgatc taaacattct ttcatccatt cattcttcac ctggcccacc cagcattgcc      2400
agtgggagag acaccgcaa agcaccaggc tgtgagcccc accgcgtgc actctgagac        2460 actgtccact agctttggga tggcaggcag aggtactcca gcttggtcta gtgcagacc      2519
```

<210> SEQ ID NO 3
<211> LENGTH: 2283
<212> TYPE: DNA
<213> ORGANISM: Homo Sapiens

<400> SEQUENCE: 3

```
aatgaagacg ctggagatcg ggcccctgcc cgtccccttt ctgcgccccg ggatgaggca        60
gagactgaac agccggcgag caaatcaacg gcatccagaa agccatgtcg gactcggcgc       120
ccagcgccca agcgctaacc cgctgaaagt ttctcagcga aatctcaggg acgatctgga       180
ccccgctgag aggaactgct tttgagtgag atggtcccag aggcctggag gagcggactg       240
gtaagcaccg ggagggtagt gggagttttg cttctgcttg gtgccttgaa caaggcttcc       300
acggtcattc actatgagat cccggaggaa agagagaagg gtttcgctgt gggcaacgtg       360
gtcgcgaacc ttggtttgga tctcggtagc ctctcagccc gcaggttccg ggtggtgtct       420
ggagctagcc gaagattctt tgaggtgaac cgggagaccg gagagatgtt tgtgaacgac       480
cgtctggatc gagaggagct gtgtgggaca ctgccctctt gcactgtaac tctggagttg       540
gtagtggaga acccgctgga gctgttcagc gtggaagtgg tgatccagga catcaacgac       600
aacaatcctg ctttccctac ccaggaaatg aaattggaga ttagcgaggc cgtggctccg       660
```

```
gggacgcgct ttccgctcga gagcgcgcac gatcccgatg tgggaagcaa ctctttacaa    720
acctatgagc tgagccgaaa tgaatacttt gcgcttcgcg tgcagacgcg ggaggacagc    780
accaagtacg cggagctggt gttggagcgc gccctggacc gagaacggga gcctagtctc    840
cagttagtgc tgacggcgtt ggacggaggg accccagctc tctccgccag cctgcctatt    900
cacatcaagg tgctggacgc gaatgacaat gcgcctgtct tcaaccagtc cttgtaccgg    960
gcgcgcgtcc tggaggatgc acctccggc acgcgcgtgg tacaagtcct tgcaacggat   1020
ctggatgaag ccccaacgg tgaaattatt tactccttcg gcagccacaa ccgcgccggc   1080
gtgcggcaac tattcgcctt agaccttgta accgggatgc tgacaatcaa gggtcggctg   1140
gacttcgagg acaccaaact ccatgagatt tacatccagg ccaaagacaa gggcgccaat   1200
cccgaaggag cacattgcaa agtgttggtg gaggttgtgg atgtgaatga caacgccccg   1260
gagatcacag tcacctccgt gtacagccca gtacccgagg atgcccctct ggggactgtc   1320
atcgctttgc tcagtgtgac tgacctggat gctggcgaga cgggctggt gacctgcgaa   1380 gttccaccgg gtctcccttt cagccttact tcttccctca agaattactt cactttgaaa   1440
accagtgcag acctggatcg ggagactgtg ccagaataca acctcagcat caccgcccga   1500
gacgccggaa ccccttccct ctcagccctt acaatagtgc gtgttcaagt gtccgacatc   1560
aatgacaacc ctccacaatc ttctcaatct tcctacgacg tttacattga agaaaacaac   1620
ctccccgggg ctccaatact aaacctaagt gtctgggacc ccgacgcccc gcagaatgct   1680
cggcttcctt tctttctctt ggagcaagga gctgaaaccg gctagtggg tcgctatttc   1740 acaataaatc gtgacaatgg catagtgtca tccttagtgc ccctagacta tgaggatcgg   1800
cgggaatttg aattaacagc tcatatcagc gatggggggca ccccggtcct agccaccaac   1860
atcagcgtga acatatttgt cactgatcgc aatgacaatg cccccaggt cctatatcct   1920 cggccaggtg ggagctcggt ggagatgctc cctcgaggta cctcagctgg ccacctagtg   1980
tcacgggtgg taggctggga cgcggatgca ggcacaatg cctggctctc ctacagtctc   2040
ttgggatccc ctaaccagag ccttttttgcc atagggctgc acactggtca aatcagtact   2100
gcccgtccag tccaagacac agattcaccc aggcagactc tcacggtctt gatcaaagac   2160
aatggggagc cttcgctctc caccactgct accctcactg tgtcagtaac cgaggactct   2220
cctgaagccc gagccgagtt cccctctggc tctgcccccc gggagcagaa aaaaatctc   2280 acc                                                                 2283
```

<210> SEQ ID NO 4
<211> LENGTH: 2001
<212> TYPE: DNA
<213> ORGANISM: Homo Sapiens
<400> SEQUENCE: 4

```
ggcaaaagcc tgcctggact tcctggccac cagaaatatg agcatggtgg tggtccccag     60
ttccctattc atgcttgggc tcaagagact gggagtctag gttcactgac tccctgagaa    120
agactaagac cctgcatttt agaaagaggt ttggggatct ctgccctgcg caagggtaga    180
aggatcagct gttcctctga gcaccttaac ccggaacccc ggtccgaagc cgagacagga    240
gactggatgc gaggccctcc cagagctggt ttctctcaaa caacttccaa aactcctaga    300
tcctaggggt acgccgaaat cccccaaagc agtccaaaga acacaacgag agtcctaaca    360
tcccaggtgg cggcgcgctg gctccctgga gcggggcggg acgcggccgc gcggactcac    420
```

-continued

| | |
|---|---|
| gtgcacaacc gcgcgggacg gggccacgcg gactcacgtg cacaaccgcg ggaccccagc | 480 |
| gccagcggga ccccagcgcc agcgggaccc cagcgccagc gggaccccag cgccagcggg | 540 |
| accccagcgc cagcgggacc ccagcgccag cgggacccca gcgccagcgg gtctgtggcc | 600 |
| cagtggagcg agtggagcgc tggcgacctg agcggagact gcgccctgga cgccccagcc | 660 |
| tagacgtcaa gttacagccc gcgcagcagc agcaaagggg aaggggcagg agccgggcac | 720 |
| agttggatcc ggaggtcgtg acccagggga aagcgtgggc ggtcgaccca gggcagctgc | 780 |
| ggcggcgagg caggtgggct ccttgctccc tggagccgcc cctccccaca cctgccctcg | 840 |
| gcgcccccag cagttttcac cttggccctc cgcggtcact gcgggattcg gcgttgccgc | 900 |
| cagcccagtg gggagtgaat tagcgccctc cttcgtcctc ggcccttccg acggcacgag | 960 |
| gaactcctgt cctgccccac agaccttcgg cctccgccga gtgcggtact ggagcctgcc | 1020 |
| ccgccagggc cctggaatca gagaaagtcg ctctttggcc acctgaagcg tcggatccct | 1080 |
| acagtgcctc ccagcctggg cgggagcggc ggctgcgtcg ctgaaggttg gggtccttgg | 1140 |
| tgcgaaaggg aggcagctgc agcctcagcc ccaccccaga agcggccttc gcatcgctgc | 1200 |
| ggtgggcgtt ctcgggcttc gacttcgcca gcgccgcggg gcagaggcac ctggagctcg | 1260 |
| cagggcccag acctggggtg gaaaagcttc gctgactgca gcaagcgtc cgggaggggc | 1320 |
| ggccaggcga agccccggcg ctttaccaca cacttccggg tcccatgcca gttgcatccg | 1380 |
| cggtattggg caggaaatgg cagggctgag gccgacccta ggagtataag ggagccctcc | 1440 |
| atttcctgcc cacatttgtc acctccagtt ttgcaaccta tcccagacac acagaaagca | 1500 |
| agcaggactg tggggagac ggagcttaac aggaatattt ccagcagtg agcaggggct | 1560 |
| gtatgggacg cggaggagc tcagaggagg cgcggagagt gcccgaggtt gggtgagtgc | 1620 |
| ctagagggga gatagttgaa ccgggttcaa gaggtgctta gtgggtgttt gttgaatgaa | 1680 |
| tgagtgatgg gctttgaagt ctgagtgcat tgaaagaggg ggtgtgtaaa aagggctcct | 1740 |
| ttcatcacac aggacacagc atatgcaaat cctctccctg tggaaaagcc agacaggtta | 1800 |
| aaaaggttac aaacaaatta gccgggcatg gtggtgcgcg tctgtagtcc cagctactag | 1860 |
| ggaggctgag ccaggggaat cgcttgaacc cgggaggcgg agattgcagt gagccaagat | 1920 |
| cgcgccactg cactccagcc tggaaacaga gcgagactcc gtctcggaaa aaaaaaaaa | 1980 |
| aagttacaaa ccgtgtgtgg g | 2001 |

<210> SEQ ID NO 5
<211> LENGTH: 2365
<212> TYPE: DNA
<213> ORGANISM: Homo Sapiens

<400> SEQUENCE: 5

| | |
|---|---|
| gtggtcgtgg tgggggtgtt agctgcaggg gtgccctcgg tgggtgggag ttggtggcct | 60 |
| ctcgctggtg ccatgggact cgcatgttcg ccctgcgccc ctcggctctt gagcccacag | 120 |
| gccgggatcc tgcctgccag ccgcgtgcgc tgccgtttaa cccttgcagg cgcagagcgc | 180 |
| gcggcggcgg tgacagagaa ctttgtttgg ctgcccaaat acagcctcct gcagaaggac | 240 |
| cctgcgcccg gggaagggga ggaatctctt cccctctggg cgcccgccct cctcgccatg | 300 |
| gcccggcctc cacatccgcc cacatctggc cgcagcgggg cgcccggggg gaggggctga | 360 |
| ggccgcgtct ctcgccgtcc cctgggcgcg ggccaggcgg ggaggagggg ggcgctccgg | 420 |
| tcgtgtgccc aggactgtcc cccagcgcc actcggccc cagccccca ggcctggcct | 480 |
| tgacaggcgg gcggagcagc cagtgcgaga cagggaggcc ggtgcgggtg cgggaacctg | 540 |

```
atccgcccgg gaggcggggg cggggcgggg gcgcagcgcg cggggagggg ccggcgcccg        600
ccttcctccc ccattcattc agctgagcca ggggcctag gggctcctcc ggcggctagc         660
tctgcactgc aggagcgcgg gcgcggcgcc ccagccagcg cgcagggccc ggccccgcc         720 gggggcgctt cctcgccgct gccctccgcg cgacccgctg ccaccagcc atcatgtcgg         780 accccgcggt caacgcgcag ctggatggga tcatttcgga cttcgaaggt gggtgctggg        840
ctggctgctg cggccgcgga cgtgctggag aggaccctgc gggtgggcct ggcgcgggac        900 ggggtgcgc tgaggggaga cgggagtgcg ctgaggggag acgggacccc taatccaggc        960
gccctcccgc tgagagcgcc gcgcgccccc ggccccgtgc ccgcgccgcc tacgtggggg       1020
accctgttag gggcacccgc gtagaccctg cgcgccctca caggaccctg tgctcgttct       1080
gcgcactgcc gcctgggttt ccttcctttt attgttgttt gtgtttgcca agcgacagcg       1140
acctcctcga gggctcgcga ggctgcctcg gaactctcca ggacgcacag tttcactctg       1200
ggaaatccat cggtcccctc cctttggctc tccccggcgg ctctcgggcc ccgcttggac       1260
ccggcaacgg gatagggagg tcgttcctca cctccgactg agtggacagc cgcgtcctgc       1320
tcgggtggac agccctcccc tcccccacgc cagtttcggg gccgcaagt tgtgcagccc       1380 gtgggccggg agcaccgaac ggacacagcc caggtcgtgg cagggtctag agtgggatgt       1440
cccatggccc ccatccaggc ctgggatat cctcatccgc ctcccagaat cgggccgtgg       1500
gggacagaag gggcctgcgt gcgggcaggg agagtatttt ggctctctcc tgtcttcggg       1560
gtttacaaag tgtgttggga cttgcggggc tgctctgtcc aagcctgggt ctggcgtccg       1620
cgtctctgag cctgtgagtg cgtgcgcttt cctgcgtcct cttgactgcc ggtgctgggg       1680
ctctgcgtcc tgcgtccgcg ggagtaaata cagcaggcga aggggaagct cacacaatgg       1740
tctccagcgc tctggggcag ggcttctgag gggcgggcct gcctctgccg ggacctggag       1800
cccccgcccc tcggagaggc tcctaggctg acttgggcag agccctctgg tgggccggga       1860
gggggaaagg ctgtgttgaa atgagcaaac tgtccaggtg tcaggccaag ctgggaggtg       1920
accagcctga ggtcctcccc gctccatggc cagaaccagg gctgacatct gggtgtcctg       1980
agcccagctg cccacacggc ccacctgggg tcagccctat ctgagtgggg gaggcggggc       2040
ctcctggggg accagaactt tggctggacg ccaagcagag tgccagtggc tgttcttcag       2100
ggctgggcct gaggagggtg tggggcggcg aagggacggg aggggttgt gatccagtgg       2160 ccactggcgc tgtgcagagt gtgagctgga acatcgtag ttactttgtc agcttagtgg       2220 tgaaagcccct ttttcaggct ctatcccttt gcatccctgc ttcccagagg gaggggaggt       2280
ctgggtctgc agagctggga gggcttgctg ttcccgcccc cctcccccac aacacctcct       2340
catctggaca tctttgggca catgc                                              2365
```

<210> SEQ ID NO 6
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6

```
ttaggttgtc gtagatatag tttttgtttt ttcgaaaaat acgttttagg cgtcgggatt         60
ttagatattt gggaaataga gtgtacgtag ttgttgagag gtttcgcgtt tggttttttt        120
tattattgag gcgtagaggt gttgtggata gtttagattt atacgcgtt cgaggtgaaa        180
```

-continued

| | |
|---|---|
| tagaattttt agttttttta tgaggttatt ggtattttcg gttgttttta gagtttttcg | 240 |
| atttagagtt gaatgtaaag taagcgttcg aaatgtagaa gtagtcgggg tcgtttacgg | 300 |
| tatttgtttc gttcggggcg agagaagacg ttaggttgag gttttagcga ttttaggtat | 360 |
| tagtttcgaa ggagggcggg gagatcgtaa aggggaagtg ttcggagggt taacggtttt | 420 |
| cgcgtatttt gcgttttttt gaagcgcgtc gttttttcgc gtcggggatt gggatttgtt | 480 |
| tttggggaat tcgtttagaa gacggcggcg gattgggtc gggtatttt tagggttgtt | 540 |
| aggtttttt tagttttgta tttgtcgcgt cgttttattt cgttaggaag ttttagagat | 600 |
| ttcggggatg gggtgggagc gttttttat cgcgggttta aaaagaagga aggacgtttt | 660 |
| tagggtcgt agaaggagga ttagttttaa gttataattt ttttcggatt taaggtaggt | 720 |
| cggttgggg ttcgcgttta tacgttttt ggcgggggtt cgcgcgtttc gggagtttcg | 780 |
| cggttcgggg aggaaagagg agataagaga taggcgagga ttacggggtt gatttagtcg | 840 |
| gggtagggat tatcgtggaa aaattttggc gaggtggggg gacgcggaaa gagagcggtt | 900 |
| cgcgttttgt attttgcgtc gggtatttcg cgttagtgtt tcgttttag tgtttcgcgt | 960 |
| ttcgcgtttc gcgttttgtt tttatttcgg gttagttgta tcgcgttcgc gtcgtaggaa | 1020 |
| tcgtggagtt ggaaagtggg ggcgtcgcgg ttgggggtt gttttagttg cgtttcggtt | 1080 |
| agcgatcggc gggtcgggtt taaatttagt taggttgggt aggcggtggt cgcgcgattg | 1140 |
| gggatcgggc gtttcgtttt tttcgttttt tttttttt tttttttt ttttagtttt | 1200 |
| ttggttttt ttagtttta tcggatttgt tcgttcgttg tttttttt ttttttcgttt | 1260 |
| tttatattat ttttatttt ttcgtttgt tttcgttttt tttttttt ttgtttttg | 1320 |
| tttttttt ttttttttt ttttttaggg gcggagtttt tttttttt tttagataat | 1380 |
| gttgtggttg cgtttttt ttcgttagtt cgtttaggtt ttcgtcgtta gcgattttt | 1440 |
| cgggttgggg gtggggaggt gggggggag tgtaggggttg gggaggatga gttggttttt | 1500 |
| tttattttt tgttgttgtt tttttaaga gggatggaga tttggtttaa gttttttcggt | 1560 |
| ttattcggag ttgtgatagt tatttttagg gaatagttac gttgttttat taagtttatt | 1620 |
| tttagcggtt tggattttt aggtagaggt tgtgggattt tgttttttt aatatttag | 1680 |
| tttatttta aaagggtttg agtcggatag gggttaaata ggttttttcg atttggcggg | 1740 |
| tcggttagac gtgatagtaa tgttaaggag gttaagtttt tttgtttatt ttttattttt | 1800 |
| tttttttta tttttggatt ttttggcgtt tttagtatat agaggtttt gagtagttcg | 1860 |
| gttgtaggtt tttatttat ttagagtttt ttttttacg tgtttatttt taattttgta | 1920 |

<210> SEQ ID NO 7
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7

| | |
|---|---|
| tgtagggttg gggataggta cgtgaggggg agaattttga gtagataggg aatttgtagt | 60 |
| cgggttgttt aagggttttt gtgtattggg ggcgttagga ggtttaggga tggaaaaggg | 120 |
| ggaggtgaga aatggataaa gaaatttggt ttttttggta ttgttgttac gtttggtcgg | 180 |
| ttcgttaagt cgaaggggtt tgtttagttt ttgttcggtt taaatttttt tgggaataag | 240 |
| ttgggatgtt agaaaaaata aaatttttata attttttgttt ggggaattta ggtcgttgga | 300 |
| ggtgggtttg gtagggtagc gtgattgttt tttgggagtg gttgttatag tttcgggtga | 360 |

```
atcgaggagt tgggttaagg tttttatttt ttttggagag ggtagtagta aggaggtgag    420
gggagttagt ttattttttt taattttgta tttttttttt attttttttat ttttagttcg    480 gaagaatcgt tggcggcggg agtttggacg agttggcggg aaggggacg tagttatagt     540 attgtttggg agggagggga aagtttcgt ttttagaggg gaggggagaa gaggaggggg     600
taggagataa gggaggaag aaaggcgaag gtaaggcgaa ggggtggaga gtgatatgaa     660
gagcgagaga aagagagga tagcggacga gtagattcgg tagggggttga aaaaggttaa    720 ggggttggag ggagggagag aaggaggag gggagcgagg agggcggggc gttcggtttt     780
tagtcgcgcg gttatcgttt gtttagtttg gttggatttg agttcggttc gtcgatcgtt    840
ggtcgaggcg tagttgaagt agttttttag tcgcggcgtt tttattttt aattttacgg    900 tttttgcggc gcgggcgcga tgtagttggt tcggggtgaa ggtaaggcgc ggggcgcggg    960
gcgcggggta ttgggagcga ggtattggcg cgggatgttc ggcgtaaggt gtagggcgcg    1020
ggtcgttttt ttttcgcgtt tttttatttc gttaaagttt tttacgatg gtttttattt     1080 cggttgggtt agtttcgtaa ttttcgtttg tttttttgttt tttttttttt tttcgagtcg    1140
cggggttttc gggcgcgcg gatttttcgtt aggggtcgtg taggcgcgga gttttagtcg    1200
gtttgttttg ggttcgaaga aagttgtggt ttggagttag ttttttttt acgattttttg    1260 ggggcgtttt tttttttttt tgagttcgcg atgggaaggc gtttttattt tattttcggg    1320 gttttttgaga tttttttggcg aggtgggggcg gcgcggtagg tgtagggttg gggagggttt    1380
gatagttttg gagagtgttc gatttttagtt cgtcgtcgtt ttttaggcgg atttttaga    1440 ggtaggtttt agttttcggc gcggggaggc ggcgcgtttt agaggggcgt agggtgcgcg    1500
ggggtcgttg gtttttcggg tatttttttt tgcggttttt ttcgtttttt ttcggagttg    1560
gtgtttgagg tcgttgggat tttagtttgg cgttttttt cgtttcgagc gaggtaggtg    1620
tcgtgggcgg tttcggttat ttttgtattt cgagcgttta ttttgtattt agttttaagt    1680
cggagagttt tgggggatagt cgagagtgtt agtggtttta tagggagatt gagggttttg    1740
ttttatttcg ggcgtcgtgt gggtttgggt tgtttatagt atttttgcgt tttagtgata    1800
ggagaagtta agcgcgaggt ttttttaatag ttgcgtgtat tttattttt aggtatttgg    1860 aatttcggcg tttagaacgt gtttttcggg agagtaaagg ttgtgtttac ggtagtttgg    1920
```

<210> SEQ ID NO 8  
<211> LENGTH: 2519  
<212> TYPE: DNA  
<213> ORGANISM: Artificial Sequence  
<220> FEATURE:  
<223> OTHER INFORMATION: chemically treated genomic DNA (Homo sapiens)

<400> SEQUENCE: 8

```
gatttatgag tgaatgatta aaagtgtagt tgagttttgg tagagggtat ggggttttat     60
ttagagatag gtagagaaag ttgaagtttt aggattggag gtcgtttttt tttattttt    120 tattaggttt aggtagggtt tgatttgaac ggaggtttgg gaatttgtgg ttagtttta    180 tttgttggaa aagagtagtt tttaagttta attgttttag gttgatgttt tttattttt    240 ttttattttat ttattttttat tattattttt ttttattga gacggagttt tattttgttg    300
ttaggttgga gtgtagtggc gcgatttcgg tttattgtta ttttcgtttg ttgagtttaa    360
gttttagttt tttgagtagt ttttgggta gttgggatta taggcgtgcg ttattacgtt    420
aggttaattt tttgtattt agtatagacg gagttttatt attttggtta ggatggtttc    480
```

```
gattttttga tttcgtgata ttttcgtttc ggtattttaa agtgtcggga ttataggtat     540
gagttatagc gttcggtttt tagttttttt taaaaaacgt tagattcgtt cgttgcgttg     600
agtggaggcg gggtaggttt tcgttttttta attggtttta tttatcgagt ttttttttg     660 tgtcgggttt tgtgttaagt atattatacg ttgtattttg cggttaggtt gttgtggttt     720
agggtcgtat tttggtttaa ggtcgtaaat cgaggtggga tttcgattcg gtaattacgt     780
tcgtggttcg gaaacggcgt ttttgaggt ttaggagagg tcgggcggtg agcggttgtg      840
gagtcgagcg cgggtagtgc ggatgttgtt tatggggag gtagttaagg acggagggcg      900
agaggcggtt tttttaaggt tatttttttt cgggttgtaa gtaaaggtta ggggatttcg     960
gaatggttag tgtaggagtt tttttgtgtt ttttacgttt tagattttta gagttttaga    1020
aacggagatt atcgttttta tttttatttt atagatgaag aaattgagtc gaggaaagga    1080
agcgatttgg ttaaggtcgg agagtttatt ttttgtaggg cggggtttgg aattcggggt    1140
ttggttttcg gtaacgcgtt ttcggttcgt agtttttgt tttttgtgtt tcgtttcggt     1200
ttttagcgta gttgtagagg ggtttttttc gacgtatata tttaagagtt cgatcgcgcg    1260
gttgaaatcg cggagttcgg agtcgcggtt ggttgagcga tcgcggtttt tgggttgcgt    1320
gcgcgttttt tggagttgaa aggagcgtta ggatcggggg cgttgtatcg ggttgggttt    1380
tttaacgttc gtagatcggg tcggttgta gttggagatg gtagtaattt cgggaggttt    1440
tcgggttttt ttagggtgcg tttaggaggc gggtttcgtg cgacgcggtg tagtttattt    1500 ttttttcga gatcgtttaa tttcgcgggg gtagtttcgg gcgttcggag acgcggaggt    1560
ttagattgta gttttcggat gttggaagtt tagattttt ggggtatcg gttttttcgt     1620 tattttagtt gtagagagtt ttattgtttt atcgttcgga gtttagtttt tttgtttttt    1680
tattagtttt tttttttcgta ggttttggg gattttgat cgtttgtttt tatttttttt    1740
ttgtttttat attttcgtt tttgttttag gaacggtgat atagttatcg gattgttttt    1800 tatttttgt tagtttatat tgtatataat ttaataattc gcgtttttttt attcgggtga   1860 tagagatata gataaatttga gttagtggtg tttaaagtat cggttttaga atagtagtat    1920
tagtattttt tgggaatttg ttaaaaatga gaatttgggt cgggcgcggt ggtttacgtt    1980 tgtaattttta gtattttggg aggtcgaggc gggcggatta cgaggttagg agatcgagat   2040
tatttcggtt aaaacggtga aatttcgttt ttattaaaaa tataaaaaat tagtcgggta    2100
tagtggcggg cgtttgtagt tttagttatt tgggaggttg aggtaggaga atggcgtgaa    2160
ttcgggaggc ggagtttgta gtgagtcgag atttcgttat tgtatttta tttgggcgat    2220 agagcgagat ttcgttttaa aaaaaaaaaa aatgcgaatt tgggggtttt attttagatt    2280
tattgaatag aaattttgtg gagtttagta gatgattttt atgtatatta aagtttgcga    2340
gttattgatt taaatatttt tttatttatt tatttttat ttggtttatt tagtatattgtt   2400 agtgggagag atattcgtaa agtattaggt tgtgagtttt atcgtcgtgt attttgagat    2460 attgttatt agtttgggga tggtaggtag aggtatttta gtttggttta gtgtagatt     2519
```

<210> SEQ ID NO 9
<211> LENGTH: 2519
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9

```
ggtttgtatt agattaagtt ggagtatttt tgtttgttat tttaaagtta gtggatagtg      60
```

```
ttttagagtg tacggcggtg gggtttatag tttggtgttt tgcgggtgtt ttttttattg    120
gtaatgttgg gtgggttagg tgaagaatga atggatgaaa gaatgtttag attagtggtt    180
cgtaaatttt agtgtgtatg ggaattattt gttgggtttt atagagtttt tgtttagtag    240
atttggggtg gggttttta a attcgtatt t ttttttttt tgagacggag tttcgttttg    300
tcgtttaggt tggagtgtag tggcgggatt tcggtttatt gtaagtttcg ttttcgggt    360 ttacgttatt tttttgtttt agttttttaa gtagttggga ttataggcgt tcgttattat    420
gttcggttaa tttttttgtat tttagtaga cgggtttt tatcgtttta gtcgggatgg    480
tttcgatttt tgatttcgt gattcgttcg tttcggtttt ttaaagtgtt gggattatag    540
gcgtgagtta tcgcgttcgg tttaaatttt tattttta at aagttttta a gagatgttga    600 tgttgttgtt tgggatcgg tattttgagt attattagtt tagattattt tgttttttgt    660
tattcggatg gaagggcgcg gattattgag ttgtgtgtag tgtagattaa taggagatgg    720
agagtaattc ggtgattgta ttatcgtttt tgagataagg gcgggaagta tgggggtagg    780
gggagagtaa gaataggcgg ttagaagttt ttagagattt gcggagggag ggattggtag    840
aggaataagg agattaagtt tcggacggtg aagtaatggg atttttttgta gttggggtgg    900 cgggagagtc ggtgatttta gggagtttgg gttttagta ttcggaggtt gtagtttggg    960
ttttcgcgtt ttcgagcgtt cgaggttgtt ttcgcgaagt taagcggttt cggggggggg    1020
ggtgggttgt atcgcgtcgt acggaattcg tttttggac gtattttgaa gaggttcgga    1080 gattttttcgg gattgttgtt attttttagtt gtagttcggt tcggtttgcg agcgttgagg    1140
ggtttagttc ggtgtagcgt tttcgatttt ggcgtttttt ttagttttaa ggggcgcgta    1200
cgtagtttag gaatcgcgat cgtttagtta gtcgcggttt cgagtttcgc gattttagtc    1260
gcgcggtcgg gttttttgagt gtatgcgtcg agggggtttt ttttgtagtt gcgttggggg    1320
tcgaagcggg gtatagggggg taggaggttg cgggtcgagg gcgcgttgtc gagagttaga    1380 tttcggggttt taaatttcgt tttgtaaaga atgagttttt cgattttggt taagtcgttt    1440 tttttttttcg gtttagtttt tttattttgta aaatggggggt ggggacgatg attttcgttt    1500
ttgaggtttt gaggatttag gacgtggaag gtatagagaa gttttttgtat taattatttc    1560 gggatttttt gattttttgtt tgtaattcgg aagagggtga ttttggaaga atcgtttttc    1620 gttttttcgtt tttggttgtt tttttatag gtagtattcg tattgttcgc gttcggtttt    1680
atagtcgttt atcgttcggt tttttttggg ttttagggga cgtcgttttc gggttacggg    1740
cgtggttgtc ggatcggagt tttatttcgg tttgcgattt tggattaggg tacgattttg    1800
gattatagta atttggtcgt aggatatagc gtgtgatgtg tttggtatag agttcggtat    1860
aagggaagag ttcggtggat aaggttaatt ggagaacgga ggtttgtttc gttttttattt    1920 agcgtagcgg acggatttag cgttttttaa aaagaattag gggtcgggcg ttgtggttta    1980
tgtttgtaat ttcggtattt tgggatatcg aggcggagt attacgaggt taggagatcg    2040
agattatttt ggttaaagtg gtgaaatttc gtttatatta aatataaaa aattagtttg    2100 gcgtggtggc gtacgtttgt agttttagtt atttaggagg ttatttagga ggttgaggtt    2160
tgaatttagt aggcggaggt ggtagtgagt cgagatcgcg ttattgtatt ttaatttggt    2220
aatagagtaa gatttcgttt taataaaaaa aaaataataa taaaaataaa taataaaaa    2280 aaagtagggga agtattaatt tggagtaatt gagtttaagg attgtttttt tttaataagt    2340
aaaggttggt tataggtttt taggttttcg tttagattaa gttttgtttg ggtttggtgg    2400
```

| | |
|---|---:|
| ggaggtgagg aagaacggtt tttaattttg ggattttaat ttttttttgtt tgtttttggg | 2460 |
| tgggatttta tgtttttttgt taggatttag ttgtatttttt agttatttat ttataaatt | 2519 |

```
<210> SEQ ID NO 10
<211> LENGTH: 2283
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10
```

| | |
|---|---:|
| aatgaagacg ttggagatcg ggttttttgtt cgtttttttt ttgcgtttcg ggatgaggta | 60 |
| gagattgaat agtcggcgag taaattaacg gtatttagaa agttatgtcg gattcggcgt | 120 |
| ttagcgttta agcgttaatt cgttgaaagt tttttagcga aattttaggg acgatttgga | 180 |
| tttcgttgag aggaattgtt tttgagtgag atggttttag aggtttggag gagcggattg | 240 |
| gtaagtatcg ggagggtagt gggagttttg ttttttgtttg gtgttttgaa taaggttttt | 300 |
| acggttatttt attatgagat ttcggaggaa agagagaagg gtttcgttgt gggtaacgtg | 360 |
| gtcgcgaatt ttggtttgga tttcggtagt ttttttagttc gtaggtttcg ggtggtgttt | 420 |
| ggagttagtc gaagattttt tgaggtgaat cgggagatcg gagagatgtt tgtgaacgat | 480 |
| cgtttggatc gagaggagtt gtgtgggata ttgtttttttt gtattgtaat tttggagttg | 540 |
| gtagtggaga attcgttgga gttgtttagc gtggaagtgg tgatttagga tattaacgat | 600 |
| aataattttg tttttttttat ttaggaaatg aaattggaga ttagcgaggt cgtggtttcg | 660 |
| gggacgcgtt tttcgttcga gagcgcgtac gattcgatg tgggaagtaa ttttttataa | 720 |
| atttatgagt tgagtcgaaa tgaatatttt gcgtttcgcg tgtagacgcg ggaggatagt | 780 |
| attaagtacg cggagttggt gttggagcgc gttttggatc gagaacggga gtttagtttt | 840 |
| tagttagtgt tgacggcgtt ggacggaggg attttagttt ttttcgttag tttgtttatt | 900 |
| tatattaagg tgttggacgc gaatgataat gcgtttgttt ttaattagtt tttgtatcgg | 960 |
| gcgcgcgttt tggaggatgt attttttcggt acgcgcgtgg tataagttttt tgtaacggat | 1020 |
| ttggatgaag gttttaacgg tgaaattatt tattttttcg gtagttataa tcgcgtcggc | 1080 |
| gtgcggtaat tattcgtttt agattttgta atcgggatgt tgataattaa gggtcggttg | 1140 |
| gatttcgagg atattaaatt ttatgagatt tatatttagg ttaaagataa gggcgttaat | 1200 |
| ttcgaaggag tatattgtaa agtgttggtg gaggttgtgg atgtgaatga taacgtttcg | 1260 |
| gagattatag ttatttttcgt gtatagttta gtattcgagg atgttttttt ggggattgtt | 1320 |
| atcgttttgt ttagtgtgat tgatttggat gttggcgaga acgggttggt gatttgcgaa | 1380 |
| gttttatcgg gttttttttt tagttttatt ttttttttta agaattattt tattttgaaa | 1440 |
| attagtgtag atttggatcg ggagattgtg ttagaatata attttagtat tatcgttcga | 1500 |
| gacgtcggaa tttttttttt tttagttttt ataatagtgc gtgtttaagt gttcgatatt | 1560 |
| aatgataatt ttttataatt ttttttaattt ttttacgacg tttatattga agaaaataat | 1620 |
| tttttcgggg tttaatatt aaatttaagt gtttgggatt tcgacgtttc gtagaatgtt | 1680 |
| cggtttttttt tttttttttt ggagtaagga gttgaaatcg ggttagtggg tcgttatttt | 1740 |
| ataataaatc gtgataatgg tatagtgtta tttttagtgt ttttagatta tgaggatcgg | 1800 |
| cgggaatttg aattaaatagt ttatattagc gatggggggta tttcggtttt agttattaat | 1860 |
| attagcgtga atatatttgt tattgatcgt aatgataatg ttttttaggt tttatatttt | 1920 |
| cggttaggtg ggagttcggt ggagatgttg tttcgaggta ttttagttgg ttatttagtg | 1980 |

-continued

```
ttacgggtgg taggttggga cgcggatgta gggtataatg tttggttttt ttatagtttt    2040
ttgggatttt ttaattagag ttttttttgtt atagggttgt atattggtta aattagtatt    2100
gttcgtttag tttaagatat agatttattt aggtagattt ttacggtttt gattaaagat    2160 aatgggagt  tttcgttttt tattattgtt atttttattg tgttagtaat cgaggatttt    2220
tttgaagttc gagtcgagtt ttttttggt  tttgttttc  gggagtagaa aaaaatttt     2280 att                                                                  2283
```

<210> SEQ ID NO 11
<211> LENGTH: 2283
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11

```
ggtgagattt ttttttttgtt ttcgggggt  agagttagag gggaattcgg ttcgggtttt      60
aggagagttt tcggttattg atatagtgag ggtagtagtg gtggagagcg aaggttttt      120 attgttttg  attaagatcg tgagagtttg tttgggtgaa tttgtgtttt ggattggacg     180
ggtagtattg atttgattag tgtgtagttt tatggtaaaa aggttttggt taggggattt     240
taagagatta taggagagtt aggtattgtg ttttgtattc cgttttagt  ttattattcg     300 tgatattagg tggttagttg aggtatttcg aggtagtatt tttatcgagt ttttatttgg     360
tcgaggatat aggatttggg gggtattgtt attgcgatta gtgataaata tgtttacgtt     420
gatgttggtg gttaggatcg gggtgttttt atcgttgata tgagttgtta atttaaattt     480
tcgtcgattt ttatagttta ggggtattaa ggatgatatt atgttattgt tacgatttat     540
tgtgaaatag cgatttatta gttcggtttt agttttttgt tttaagagaa agaaagaaag     600
tcgagtattt tgcggggcgt cggggtttta gatatttagg tttagtattg gagtttcggg     660
gaggttgttt tttttaatgt aaacgtcgta ggaagattga gaagattgtg gagggttgtt     720
attgatgtcg gatattttgaa tacgtattat tgtaagggtt gagagggaag gggtttcggc    780
gtttcgggcg gtgatgttga ggttgtattt tggtatagtt tttcgattta ggtttgtatt     840
ggtttttaaa gtgaagtaat ttttgaggga agaagtaagg ttgaaaggga gattcggtgg     900
aatttcgtag gttattagtt cgttttcgtt agtatttagg ttagttatat tgagtaaagc     960
gatgatagtt tttagagggg tattttcggg tattggggttg tatacggagg tgattgtgat    1020
tttcggggcg ttgttattta tatttataat ttttattaat attttgtaat gtgttttttc    1080
gggattggcg tttttgtttt tggtttggat gtaaatttta tggagtttgg tgttttcgaa    1140
gtttagtcga ttttgtgattg ttagtatttc ggttataagg tttaaggcga atagttgtcg    1200
tacgtcggcg cggttgtggt tgtcgaagga gtaaataatt ttatcgttgg ggttttttatt   1260 tagattcgtt gtaaggattt gtattacgcg cgtgtcggag ggtgtatttt ttaggacgcg    1320
cgttcggtat aaggattggt tgaagatagg cgtattgtta ttcgcgtttta gtattttgat   1380 gtgaataggt aggttggcgg agagagtttgg ggtttttcg tttaacgtcg ttagtattaa    1440
ttggagatta ggttttcgtt ttcggtttag ggcgcgtttt aatattagtt tcgcgtattt    1500
ggtgttgttt tttcgcgttt gtacgcgaag cgtaaagtat ttatttcggt ttagtttata    1560
ggtttgtaaa gagttgtttt ttatatcggg atcgtgcgcg ttttcgagcg gaaagcgcgt    1620
tttcggagtt acggtttcgt taattttaa  ttttatttttt tgggtaggga aagtaggatt    1680
```

| | | |
|---|---|---|
| gttgtcgttg atgttttgga ttattatttt tacgttgaat agttttagcg ggttttttat | 1740 | |
| tattaatttt agagttatag tgtaagaggg tagtgtttta tatagttttt ttcgatttag | 1800 | |
| acggtcgttt ataaatattt tttcggtttt tcggtttatt ttaaagaatt ttcggttagt | 1860 | |
| tttagatatt attcggaatt tgcgggttga gaggttatcg agatttaaat taaggttcgc | 1920 | |
| gattacgttg tttatagcga aattttttt tttttttttc gggattttat agtgaatgat | 1980 | |
| cgtggaagtt ttgtttaagg tattaagtag aagtaaaatt tttattattt tttcggtgtt | 2040 | |
| tattagttcg tttttttagg tttttgggat tatttttattt aaaagtagtt tttttttagcg | 2100 | |
| gggtttagat cgttttttgag atttcgttga gaaatttttta gcgggttagc gtttgggcgt | 2160 | |
| tgggcgtcga gttcgatatg gttttttgga tgtcgttgat ttgttcgtcg gttgtttagt | 2220 | |
| ttttgtttta tttcggggcg tagaaagggg acgggtaggg gttcgattttt tagcgttttt | 2280 | |
| att | 2283 | |

<210> SEQ ID NO 12
<211> LENGTH: 2001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12

| | | |
|---|---|---|
| ggtaaaagtt tgtttggatt ttttggttat tagaaatatg agtatggtgg tggtttttag | 60 | |
| tttttatttt atgtttgggt ttaagagatt gggagtttag gtttattgat tttttgagaa | 120 | |
| agattaagat tttgtatttt agaaagaggt ttggggattt ttgttttgcg taagggtaga | 180 | |
| aggattagtt gttttttttga gtattttaat tcggaatttc ggttcgaagt cgagatagga | 240 | |
| gattggatgc gaggttttt tagagttggt ttttttttaaa taattttaa aattttaga | 300 | |
| ttttaggggt acgtcgaaat ttttaaagt agtttaaaga atataacgag agttttaata | 360 | |
| ttttaggtgg cggcgcgttg gttttttgga gcggggcggg acgcggtcgc gcggatttac | 420 | |
| gtgtataatc gcgcgggacg gggttacgcg gatttacgtg tataatcgcg ggattttagc | 480 | |
| gttagcggga ttttagcgtt agcgggattt tagcgttagc gggattttag cgttagcggg | 540 | |
| attttagcgt tagcgggatt ttagcgttag cgggattttta gcgttagcgg gtttgtggtt | 600 | |
| tagtggagcg agtggagcgt tggcgatttg agcggagatt gcgttttgga cgttttagtt | 660 | |
| tagacgttaa gttatagttc gcgtagtagt agtaaagggg aaggggtagg agtcgggtat | 720 | |
| agttggattc ggaggtcgtg atttagggga aagcgtgggc ggtcgattta gggtagttgc | 780 | |
| ggcggcgagg taggtgggtt ttttgttttt tggagtcgtt tttttttata tttgttttcg | 840 | |
| gcgttttttag tagttttttat tttggttttt cgcggttatt gcgggattcg gcgttgtcgt | 900 | |
| tagtttagtg gggagtgaat tagcgttttt tttcgttttc ggtttttcg acggtacgag | 960 | |
| gaattttgt tttgttttat agattttcgg ttttcgtcga gtgcggtatt ggagtttgtt | 1020 | |
| tcgttagggt tttggaatta gagaaagtcg ttttttggtt atttgaagcg tcggattttt | 1080 | |
| atagtgtttt ttagtttggg cgggagcggc ggttgcgtcg ttgaaggttg gggttttttgg | 1140 | |
| tgcgaaaggg aggtagttgt agtttttagtt ttattttaga agcggttttc gtatcgttgc | 1200 | |
| ggtgggcgtt ttcgggtttc gatttcgtta gcgtcgcggg gtagaggtat ttggagttcg | 1260 | |
| tagggtttag atttggttg gaaaagttttc gttgattgta ggtaagcgtt cgggaggggc | 1320 | |
| ggttaggcga agtttcggcg ttttattata tattttcggg tttatgttta gttgtattcg | 1380 | |
| cggtattggg taggaaatgg tagggttgag gtcgatttta ggagtataag ggagttttt | 1440 | |

```
attttttgtt tatatttgtt atttttagtt ttgtaattta ttttagatat atagaaagta    1500
agtaggattg gtggggagac ggagtttaat aggaatattt tttagtagtg gtagggggtt    1560
gtatgggacg cgggaggagt ttagaggagg cgcggagagt gttcgaggtt gggtgagtgt    1620 ttagaggga gatagttgaa tcgggtttaa gaggtgttta gtgggtgttt gttgaatgaa     1680
tgagtgatgg gttttgaagt ttgagtgtat tgaaagaggg ggtgtgtaaa aagggttttt    1740
tttattatat aggatatagt atatgtaaat ttttttttttg tggaaaagtt agataggtta   1800
aaaaggttat aaataaatta gtcgggtatg gtggtgcgcg tttgtagttt tagttattag    1860
ggaggttgag ttaggggaat cgtttgaatt cgggaggcgg agattgtagt gagttaagat    1920
cgcgttattg tattttagtt tggaaataga gcgagatttc gtttcggaaa aaaaaaaaa    1980 aagttataaa tcgtgtgtgg g                                             2001

<210> SEQ ID NO 13
<211> LENGTH: 2001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
tttatatacg gtttgtaatt tttttttttt ttttcgaga cggagtttcg ttttgttttt     60
aggttggagt gtagtggcgc gattttggtt tattgtaatt ttcgttttc gggtttaagc    120 gattttttttg gttagttttt tttagtagtt gggattatag acgcgtatta ttatgttcgg   180
ttaatttgtt tgtaatttttt ttaatttgtt tggtttttttt atagggagag gatttgtata   240
tgttgtgttt tgtgtgatga aaggagtttt ttttatatat tttttttttt aatgtattta    300
gattttaaag tttattattt atttatttaa taaatattta ttaagtatt tttgaattcg     360 gtttaattat tttttttttta ggtatttatt taatttcggg tatttttcgc gtttttttttg  420 agtttttttc gcgttttata tagtttttgt ttattgttgg aaaatatttt tgttaagttt    480
cgttttttta ttagtttttgt ttgttttttg tgtgtttggg ataggttgta aaattggagg   540
tgataaatgt gggtaggaaa tggagggttt ttttatattt ttagggtcgg ttttagtttt   600
gttatttttt gtttaatatc gcggatgtaa ttggtatggg attcggaagt gtgtggtaaa   660
gcgtcggggt ttcgtttggt cgttttttttc ggacgtttgt ttgtagttag cgaagttttt   720
ttaatttagg tttgggtttt gcgagtttta ggtgttttttg tttcgcggcg ttggcgaagt  780
cgaagttcga gaacgtttat cgtagcgatg cgaaggtcgt ttttgggtg gggttgaggt    840 tgtagttgtt tttttttcgt attaaggatt ttaatttttta gcgacgtagt cgtcgttttc   900
gtttaggttg ggaggtattg tagggattcg acgtttttagg tggttaaaga gcgatttttt  960
ttgattttag ggtttttggcg gggtaggttt tagtatcgta ttcggcggag gtcgaaggtt   1020
tgtggggtag gataggagtt tttcgtgtcg tcggaagggt cgaggacgaa ggagggcgtt   1080
aatttatttt ttattgggtt ggcggtaacg tcgaatttcg tagtgatcgc ggagggtaa    1140 ggtgaaaatt gttgggggcg tcgagggtag gtgtggggag gggcggtttt agggagtaag   1200
gagtttattt gtttcgtcgt cgtagttgtt ttgggtcgat cgtttacgtt ttttttttggg  1260 ttacgatttt cggatttaat tgtgttcggt ttttgttttt ttttttttgt tgttgttgcg   1320
cgggttgtaa tttgacgttt aggttggggc gtttagggcg tagttttcgt ttaggtcgtt   1380
agcgttttat tcgtttttatt gggttatagaa ttcgttggcg ttggggtttc gttggcgttg  1440
```

```
gggtttcgtt ggcgttgggg tttcgttggc gttggggttt cgttggcgtt ggggtttcgt    1500
tggcgttggg gtttcgttgg cgttgggggtt tcgcggttgt gtacgtgagt tcgcgtggtt    1560
tcgtttcgcg cggttgtgta cgtgagttcg cgcggtcgcg tttcgtttcg ttttagggag    1620
ttagcgcgtc gttatttggg atgttaggat tttcgttgtg ttttttggat tgttttgggg    1680
gatttcggcg tattttttagg atttaggagt tttggaagtt gtttgagaga aattagttttt    1740 gggagggttt cgtatttagt ttttttgtttc ggtttcggat cggggtttcg ggttaaggtg    1800
tttagaggaa tagttgattt ttttatttttt gcgtagggta gagatttttta aattttttttt    1860 taaaatgtag ggttttagtt ttttttaggg agttagtgaa tttagatttt tagttttttg    1920
agtttaagta tgaataggga attggggatt attattatgt ttatattttt ggtggttagg    1980
aagtttaggt aggttttttgt t                                              2001

<210> SEQ ID NO 14
<211> LENGTH: 2365
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14
gtggtcgtgg tgggggtgtt agttgtaggg gtgttttcgg tgggtgggag ttggtggttt      60
ttcgttggtg ttatgggatt cgtatgttcg ttttgcgttt ttcggttttt gagtttatag     120
gtcgggattt tgtttgttag tcgcgtgcgt tgtcgtttaa ttttttgtagg cgtagagcgc     180 gcggcggcg tgatagagaa ttttgtttgg ttgtttaaat atagtttttt gtagaaggat      240
tttgcgttcg gggaagggga ggaattttttt ttttttgggg cgttcgtttt tttcgttatg     300
gttcggtttt tatattcgtt tatatttggt cgtagcgggg cgttcggggg gaggggttga     360
ggtcgcgttt ttcgtcgttt tttgggcgcg ggttaggcgg ggaggagggg ggcgtttcgg     420
tcgtgtgttt aggattgttt tttagcggtt attcggggttt tagtttttta ggtttggttt    480
tgataggcgg gcggagtagt tagtgcgaga taggaggtc ggtgcgggtg cgggaatttg     540
attcgttcgg gaggcggggg cggggcgggg gcgtagcgcg cggggagggg tcggcgttcg     600
tttttttttt ttatttattt agttgagtta gggggtttag gggtttttttc ggcggttagt     660 tttgtattgt aggagcgcgg gcgcggcgtt ttagttagcg cgtagggttc gggtttcgtc     720
gggggcgttt tttcgtcgtt gtttttcgcg cgattcgttg tttattagtt attatgtcgg     780
atttcgcggt taacgcgtag ttggatggga ttatttcgga tttcgaaggt gggtgttggg     840
ttggttgttg cggtcgcgga cgtgttggag aggattttgc gggtgggttt ggcgcgggac     900 ggggggtgcgt tgaggggaga cgggagtgcg ttgaggggag acgggatttt taatttaggc    960 gttttttttcgt tgagagcgtc gcgcgttttc ggtttcgtgt tcgcgtcgtt tacgtgggggg   1020 atttttgttag gggtattcgc gtagattttg cgcgttttta taggatttg tgttcgtttt    1080 gcgtattgtc gtttgggttt ttttttttttt attgttgttt gtgtttgtta agcgatagcg    1140
attttttcga gggttcgcga ggttgtttcg gaatttttta ggacgtatag ttttatttg     1200 ggaaatttat cggttttttt ttttttggttt tttcggcgg tttcgggttt tcgtttggat    1260
tcggtaacgg gatagggagg tcgtttttta ttttcgattg agtggatagt cgcgttttgt    1320
tcgggtggat agttttttttt tttttacgt tagtttcggg gtcgttaagt tgtgtagttc    1380
gtgggtcggg agtatcgaac ggatatagtt taggtcgtgg tagggtttag agtgggatgt    1440
tttatggttt ttatttaggt ttggggatat ttttattcgt tttttagaat cgggtcgtgg    1500
```

```
gggatagaag gggtttgcgt gcgggtaggg agagtatttt ggtttttttt tgttttcggg    1560
gtttataaag tgtgttggga tttgcggggt tgttttgttt aagtttgggt ttggcgttcg    1620 cgttttttgag tttgtgagtg cgtgcgtttt tttgcgtttt tttgattgtc ggtgttgggg   1680
ttttgcgttt tgcgttcgcg ggagtaaata tagtaggcga aggggaagtt tatataatgg    1740
tttttagcgt tttggggtag ggttttttgag gggcgggttt gttttttgtcg ggatttggag  1800 ttttcgtttt tcggagaggt tttaggttg atttgggtag agtttttttgg tgggtcggga    1860 ggggggaaagg ttgtgttgaa atgagtaaat tgtttaggtg ttaggttaag ttgggaggtg   1920
attagtttga ggttttttttc gttttatggt tagaattagg gttgatattt gggtgttttg   1980
agtttagttg tttatacggt ttatttgggg ttagttttat ttgagtgggg gaggcggggt    2040
tttttggggg attagaattt tggttggacg ttaagtagag tgttagtggt tgttttttag    2100
ggttgggttt gaggagggtg tggggcggcg aagggacggg aggggttgt gatttagtgg     2160 ttattggcgt tgtgtagagt gtgagttgga aatatcgtag ttattttgtt agtttagtgg    2220
tgaaagtttt tttttaggtt ttatttttttt gtattttttgt tttttagagg gaggggaggt  2280
ttgggtttgt agagttggga ggggtttgttg ttttcgtttt tttttttttat aatatttttt  2340 tatttggata tttttgggta tatgt                                          2365

<210> SEQ ID NO 15
<211> LENGTH: 2365
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15
gtatgtgttt aaagatgttt agatgaggag gtgttgtggg ggagggggggc gggaatagta     60 agtttttttta gttttgtaga tttagatttt tttttttttt gggaagtagg gatgtaaagg   120
gatagagttt gaaaaagggt ttttattatt aagttgataa agtaattacg atgtttttag    180
tttatatttt gtatagcgtt agtggttatt ggattataat ttttttttcgt tttttcgtcg   240 ttttatattt ttttttaggtt tagttttgaa gaatagttat tggtatttttg tttggcgttt  300 agttaaagtt ttggtttttt aggaggtttc gttttttttta tttagatagg ttgattttta   360
ggtgggtcgt gtgggtagtt gggtttagga tatttagatg ttagttttgg ttttggttat    420
ggagcgggga ggattttagg ttggttattt tttagtttgg tttgatattt ggatagtttg    480
tttattttaa tatagttttt ttttttttcg gttattagaa gggttttgtt taagttagtt    540
taggagtttt ttcgaggggc ggggtttta ggtttcggta gaggtaggtt cgttttttag    600 aagtttgtt ttagagcgtt ggagattatt gtgtgagttt ttttttcgtt tgttgtattt     660
attttcgcgg acgtaggacg tagagtttta gtatcggtag ttaagaggac gtaggaaagc    720
gtacgtattt ataggtttag agacgcggac gttagattta ggtttggata gagtagtttc    780
gtaagtttta atatatttg taaatttcga agataggaga gagttaaaat attttttttg    840
ttcgtacgta ggttttttttt gtttttttacg gttcgattt gggaggcgga tgaggatatt   900
tttaggtttg gatgggggtt atgggatatt ttatttaga ttttgttacg atttgggttg     960
tgttcgttcg gtgttttcgg tttacgggtt gtataatttg gcggtttcga aattggcgtg   1020
ggggagggga gggttgttta ttcgagtagg acgcggttgt ttatttagtc ggaggtgagg   1080
aacgattttt ttatttcgtt gtcgggttta agcggggttc gagagtcgtc ggggagagtt   1140
```

| | |
|---|---|
| aaagggaggg gatcgatgga tttttagag tgaaattgtg cgttttggag agtttcgagg | 1200 |
| tagtttcgcg agttttcgag gaggtcgttg tcgtttggta aatataaata ataataaaag | 1260 |
| gaaggaaatt taggcggtag tgcgtagaac gagtataggg ttttgtgagg gcgcgtaggg | 1320 |
| tttacgcggt tgtttttaat agggttttt acgtaggcgg cgcgggtacg gggtcggggg | 1380 |
| cgcgcggcgt tttagcggg agggcgtttg gattaggggt ttcgtttttt tttagcgtat | 1440 |
| tttcgttttt ttttagcgta ttttcgtttc gcgttaggtt tattcgtagg gttttttta | 1500 |
| gtacgttcgc ggtcgtagta gttagtttag tatttatttt cgaagttcga aatgattttta | 1560 |
| tttagttgcg cgttgatcgc ggggttcgat atgatggttg gtgggtagcg ggtcgcgcgg | 1620 |
| agggtagcgg cgaggaagcg ttttcggcgg ggttcgggtt ttgcgcgttg gttggggcgt | 1680 |
| cgcgttcgcg ttttttgtagt gtagagttag tcgtcggagg agttttttagg ttttttggtt | 1740 |
| tagttgaatg aatgggggag gaaggcgggc gtcggttttt tttcgcgcgt tgcgttttcg | 1800 |
| tttcgtttc gttttcgggg cggattaggt tttcgtattc gtatcggttt tttgtttcg | 1860 |
| tattggttgt ttcgttcgtt tgttaaggtt aggtttgggg ggttggggtt cgagtggtcg | 1920 |
| ttgggggata gttttgggta tacgatcgga gcgtttttt tttttcgtt tggttcgcgt | 1980 |
| ttaggggacg gcgagagacg cggttttagt ttttttttc gggcgtttcg ttgcggttag | 2040 |
| atgtgggcgg atgtggaggt cgggttatgg cgaggagggc gggcgtttag aggggaagag | 2100 |
| atttttttt tttttcgggc gtaggttttt tttgtaggag gttgtatttg ggtagttaaa | 2160 |
| taaagttttt tgttatcgtc gtcgcgcgtt ttgcgtttgt aagggttaaa cggtagcgta | 2220 |
| cgcggttggt aggtaggatt tcggtttgtg ggtttaagag tcgagggcg tagggcgaat | 2280 |
| atgcgagttt tatggtatta gcgagaggtt attaattttt atttatcgag ggtattttttg | 2340 |
| tagttaatat ttttattacg attat | 2365 |

<210> SEQ ID NO 16
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16

| | |
|---|---|
| ttaggttgtt gtagatatag ttttttgtttt tttgaaaaat atgttttagg tgttgggatt | 60 |
| ttagatattt gggaaataga gtgtatgtag ttgttgagag gttttgtgtt tggttttttt | 120 |
| tattattgag gtgtagaggt gttgtggata gtttagattt atatggtgtt tgaggtgaaa | 180 |
| tagaattttt agttttttta tgaggttatt ggtattttg gttgttttta gagttttttg | 240 |
| atttagagtt gaatgtaaag taagtgtttg aaatgtagaa gtagtggggg ttgtttatgg | 300 |
| tatttgtttt gtttggggtg agagaagatg ttaggttgag gtttagtga ttttaggtat | 360 |
| tagttttgaa ggagggtggg gagattgtaa aggggaagtg tttggagggt taatggtttt | 420 |
| tgtgtatttt gtgttttttt gaagtgtgtt gttttttgt gttggggatt gggatttgtt | 480 |
| tttggggaat ttgtttagaa gatggtggtg gattgggtt gggtatttt tagggttgtt | 540 |
| aggttttttt tagttttgta tttgttgtgt gtttttattt tgttaggaag ttttagagat | 600 |
| tttggggatg gggtgggagt gttttttat tgtgggttta aaagaagga aggatgtttt | 660 |
| taggggttgt agaaggagga ttagttttaa gttataattt tttttggatt taaggtaggt | 720 |
| tggttgggggt tttgtgttta tatggttttt ggtgggggtt tgtgtgtttt gggagttttg | 780 |
| tggtttgggg aggaaagagg agataagaga taggtgagga ttatgggggtt gatttagttg | 840 |

```
gggtagggat tattgtggaa aaattttggt gaggtggggg gatgtggaaa gagagtggtt      900
tgtgttttgt attttgtgtt gggtattttg tgttagtgtt ttgttttag tgttttgtgt      960 tttgtgtttt gtgttttgtt tttattttgg gttagttgta ttgtgtttgt gttgtaggaa    1020
ttgtggagtt ggaaagtggg ggtgttgtgg ttgggggggtt gttttagttg tgttttggtt   1080
agtgattggt gggttgggtt taaatttagt taggttgggt aggtggtggt tgtgtgattg    1140
gggattgggg gttttgtttt tttgttttt tttttttttt tttttttttt ttttagttt      1200 ttggtttttt ttagttttta ttggatttgt tgtttgttg tttttttttt tttttgttt      1260 tttatattat ttttattt ttgttttgt tttgttttt tttttttttt ttgttttttg        1320
tttttttttt tttttttttt tttttaggg gtggagttt tttttttttt tttagataat      1380
gttgtggttg tgttttttt ttgttagtt tgtttaggt tttgttgtta gtgattttt        1440 tgggttgggg gtgggaggt ggggggggag tgtaggtttg gggaggatga gttggttttt     1500 tttattttt tgttgttgtt tttttaaga gggatggaga tttggtttaa gttttttggt      1560
ttatttggag ttgtgatagt tattttagg gaatagttat gttgttttt taagtttatt      1620 tttagtggtt tggatttttt aggtagaggt tgtgggattt tgtttttttt aatattttag   1680 tttatttta aaagggtttg agttggatag gggttaaata ggttttttg atttggtggg      1740 ttggttagat gtgatagtaa tgttaaggag gttaagttt tttgttttt ttttatttt      1800 tttttttta ttttggatt ttttggtgtt tttagtatat agaggtttt gagtagtttg       1860 gttgtaggtt ttttatttat ttagagtttt ttttttatg tgtttatttt taattttgta    1920
```

<210> SEQ ID NO 17
<211> LENGTH: 1920
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17

```
tgtagggttg gggataggta tgtgaggggg agaattttga gtagataggg aatttgtagt      60
tgggttgttt aagggttttt gtgtattggg ggtgttagga ggtttaggga tggaaaaggg    120
ggaggtgaga aatggataaa gaaatttggt ttttttggta ttgttgttat gtttggttgg    180
tttgttaagt tgaaggggtt tgtttagttt tgtttggtt taaattttt tgggaataag     240 ttgggatgtt agaaaaaata aaattttata attttgttt ggggaattta ggttgttgga    300
ggtgggtttg gtagggtagt gtgattgttt tttgggagtg gttgttatag ttttgggtga   360
attgaggagt ttgggttaag tttttatttt ttttggagag ggtagtagta aggaggtgag   420
gggagttagt ttatttttt taattttgta tttttttttt attttttat ttttagtttg     480 gaagaattgt tggtggtggg agtttggatg agttggtggg gaagggatg tagttatagt    540 attgtttggg agggagggga gaagttttgt tttagaggg gaggggagaa gaggagggg     600 taggagataa gggaggaag aaaggtgaag gtaaggtgaa ggggtggaga gtgatatgaa    660
gagtgagaga aaagagagga tagtggatga gtagatttgg taggggttga aaaaggttaa   720
ggggttggag ggagggagag gaaggaggag gggagtgagg agggtggggt gtttggtttt    780
tagttgtgtg gttattgttt gtttagtttg ttggatttg agtttggttt gttgattgtt    840
ggttgaggtg tagttgaagt agtttttag ttgtggtgtt tttatttttt aatttatgg     900 ttttttgtggt gtgggtgtga tgtagttggt ttggggtgaa ggtaaggtgt gggtgtggg   960
```

```
gtgtgggta ttgggagtga ggtattggtg tgggatgttt ggtgtaaggt gtagggtgtg    1020
ggttgttttt tttttgtgtt tttttatttt gttaaagttt tttatgatg gtttttattt    1080 tggttgggtt agttttgtaa tttttgtttg tttttgttt ttttttttt ttttgagttg    1140 tggggttttt ggggtgtgtg gatttttgtt aggggttgtg taggtgtgga gttttagttg    1200
gtttgttttg ggtttgaaga aagttgtggt ttggagttag tttttttttt atgattttg    1260 ggggtgtttt tttttttttt tgagtttgtg atgggaaggt gtttttatttt tatttttggg    1320 gttttttgaga ttttttggtg aggtggggtg gtgtggtagg tgtagggttg gggagggttt    1380
gatagttttg gagagtgttt gattttagtt tgttgttgtt tttaggtgg attttttaga    1440 ggtaggtttt agttttggt gtggggaggt ggtgtgtttt agaggggtgt aggtgtgtg    1500 ggggttgttg gttttttggg tattttttttt tgtggtttt tttgttttttt tttggagttg    1560 gtgtttgagg ttgttgggat tttagtttgg tgttttttttt tgtttttgagt gaggtaggtg    1620 ttgtgggtgg ttttggttat ttttgtattt tgagtgttta ttttgtattt agttttaagt    1680
tggagagttt tggggatagt tgagagtgtt agtggttta tagggagatt gagggtttg    1740 ttttattttg ggtgttgtgt gggtttgggt tgtttatagt attttttgtgt tttagtgata    1800 ggagaagtta agtgtgaggt ttttttaatag ttgtgtgtat tttatttttt aggtatttgg    1860
aattttggtg tttagaatgt gtttttgggg agagtaaagg ttgtgtttat ggtagtttgg    1920

<210> SEQ ID NO 18
<211> LENGTH: 2519
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18
gatttatgag tgaatgatta aaagtgtagt tgagttttgg tagagggtat ggggttttat      60
ttagagatag gtagagaaag ttgaagtttt aggattggag gttgtttttt tttattttt     120 tattaggttt aggtagggtt tgatttgaat ggaggtttgg gaatttgtgg ttagttttta     180
tttgttggaa aagagtagtt tttaagttta attgttttag gttgatgttt ttttattttt     240
ttttatttat ttatttttat tattattttt ttttattga gatggagttt tattttgttg     300
ttaggttgga gtgtagtggt gtgatttgg tttattgtta tttttgtttg ttgagtttaa     360
gttttagttt tttgagtagt tttttgggta gttgggatta taggtgtgtg ttattatgtt     420
aggttaattt tttgtatttt agtatagatg gagtttttatt attttggtta ggatggttt      480 gatttttgta ttttgtgata tttttgtttt ggtattttaa agtgttggga ttataggtat     540
gagttatagt gtttggtttt tagtttttttt taaaaaatgt tagatttgtt tgttgtgttg     600
agtggaggtg gggtaggttt ttgttttttta attggttttta tttattgagt tttttttttg     660 tgttgggtttt tgtgttaagt atattatatg ttgtatttttg tggttaggtt gttgtggttt     720
agggttgtat tttggtttaa ggttgtaaat tgaggtggga ttttgatttg gtaattatgt     780
ttgtggtttg gaaatggtgt tttttgaggt ttaggagagg ttgggtggtg agtggttgtg     840
gagttgagtg tgggtagtgt ggatgttgtt tatggggag gtagttaagg atggagggtg     900
agaggtggtt tttttaaggt tatttttttt tgggttgtaa gtaaaggtta ggggattttg     960
gaatggttag tgtaggagtt ttttgtgtt tttatgttt tagatttta gagttttaga    1020 aatggagatt attgttttta ttttatttt atagatgaag aaattgagtt gaggaaagga    1080
agtgatttgg ttaaggttgg agagtttatt ttttgtaggg tggggtttgg aatttgggt    1140
```

-continued

```
ttggtttttg gtaatgtgtt tttggtttgt agttttttgt tttttgtgtt ttgttttggt    1200
ttttagtgta gttgtagagg ggttttttttt gatgtatata tttaagagtt tgattgtgtg    1260
gttgaaattg tggagtttgg agttgtggtt ggttgagtga ttgtggtttt tgggttgtgt    1320
gtgtgttttt tggagttgaa aggagtgtta ggattggggg tgttgtattg ggttgggttt    1380
tttaatgttt gtagattggg ttgggttgta gttggagatg gtagtaattt tgggaggttt    1440
ttgggttttt ttagggtgtg tttaggaggt gggttttgtg tgatgtggtg tagtttattt    1500
ttttttttga gattgtttaa ttttgtgggg gtagttttgg gtgtttggag atgtggaggt    1560
ttagattgta gttttttggat gttggaagtt tagatttttt ggggttattg gttttttttgt    1620 tattttagtt gtagagagtt ttattgtttt attgtttgga gtttagttttt tttgttttttt    1680 tattagtttt tttttttgta ggttttttggg gattttttgat tgtttgttttt tattttttttt    1740 ttgtttttat atttttttgtt tttgttttag gaatggtgat atagttattg gattgttttt    1800 tatttttttgt tagtttatat tgtatataat ttaataatttt gtgtttttttt atttgggtga    1860 tagagatata gataaatttga gttagtggtg tttaaagtat tggttttaga atagtagtat    1920
tagtattttt tgggaatttg ttaaaaatga gaatttgggt tgggtgtggt ggtttatgtt    1980 tgtaattttta gtattttggg aggttgaggt gggtggatta tgaggttagg agattgagat    2040
tattttggtt aaaatggtga aattttgttt ttattaaaaa tataaaaaat tagttgggta    2100
tagtggtggg tgtttgtagt tttagttatt tgggaggttg aggtaggaga atggtgtgaa    2160
tttgggaggt ggagtttgta gtgagttgag attttgttat tgtatttttag tttgggtgat    2220 agagtgagat tttgttttaa aaaaaaaaaa aatgtgaatt tgggggtttt attttagatt    2280
tattgaatag aaattttgtg gagtttagta gatgattttt atgtatatta aagtttgtga    2340
gttattgatt taaatatttt tttatttatt tattttttat ttggtttatt tagtattgtt    2400
agtgggagag atatttgtaa agtattaggt tgtgagtttt attgttgtgt attttgagat    2460
attgtttatt agttttggga tggtaggtag aggtatttta gtttggttta gtgtagatt    2519
```

<210> SEQ ID NO 19
<211> LENGTH: 2519
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19

```
ggtttgtatt agattaagtt ggagtatttt tgtttgttat tttaaagtta gtggatagtg     60
ttttagagtg tatggtggtg gggtttatag tttggtgttt tgtgggtgtt ttttttattg    120
gtaatgttgg gtgggttagg tgaagaatga atggatgaaa gaatgtttag attagtggtt    180 tgtaaattttt agtgtgtatg ggaattattt gttgggtttt atagagttttt gtttagtag    240 atttggggtg gggttttttaa atttgtattt ttttttttttt tgagatggag ttttgttttg    300
ttgtttaggt tggagtgtag tggtgggatt ttggtttatt gtaagttttg ttttttgggt    360
ttatgttatt ttttttgtttt agttttttaa gtagttggga ttataggtgt ttgttattat    420
gtttggttaa tttttttgtat tttttagtaga gatgggggtt tattgtttta gttgggatgg    480
ttttgatttt ttgattttgt gattgttttg ttttggtttt ttaaagtgtt gggattatag    540
gtgtgagtta ttgtgtttgg tttaaatttt tattttttaat aagtttttaa gagatgttga    600
tgttgttgtt ttgggattgg tatttgtagt attattagtt tagattattt gtgttttttgt    660
```

| | |
|---|---:|
| tatttggatg gaagggtgtg gattattgag ttgtgtgtag tgtagattaa taggagatgg | 720 |
| agagtaattt ggtgattgta ttattgtttt tgagataagg gtgggaagta tgggggtagg | 780 |
| gggagagtaa gaataggtgg ttagaagttt ttagagattt gtggagggag ggattggtag | 840 |
| aggaataagg agattaagtt ttggatggtg aagtaatggg attttttgta gttggggtgg | 900 |
| tgggagagtt ggtgattta gggagtttgg gttttagta tttggaggtt gtagtttggg | 960 |
| ttttgtgtt tttgagtgtt tgaggttgtt tttgtgaagt taagtggttt tggggggggg | 1020 |
| ggtgggttgt attgtgttgt atggaatttg ttttttggat gtattttgaa gaggtttgga | 1080 |
| gatttttgg gattgttgtt attttagtt gtagtttggt ttggtttgtg agtgttgagg | 1140 |
| ggtttagttt ggtgtagtgt ttttgatttt ggtgtttttt ttagttttaa ggggtgtgta | 1200 |
| tgtagtttag gaattgtgat tgtttagtta gttgtggttt tgagttttgt gattttagtt | 1260 |
| gtgtggttgg gttttttgagt gtatgtgttg agggggtttt ttttgtagtt gtgttggggg | 1320 |
| ttgaagtggg gtatagggg taggaggttg tgggttgagg gtgtgttgtt gagagttaga | 1380 |
| ttttgggttt taaattttgt tttgtaaaga atgagttttt tgattttggt taagttgttt | 1440 |
| tttttttttg gttagttttt tttatttgta aaatgggggt ggggatgatg atttttgttt | 1500 |
| ttgaggtttt gaggatttag gatgtggaag gtatagagaa gttttgtat taattatttt | 1560 |
| gggatttttt gattttgtt tgtaatttgg aagagggtga ttttggaaga attgttttt | 1620 |
| gttttttgtt tttggttgtt ttttttatag gtagtatttg tattgtttgt gtttggtttt | 1680 |
| atagttgttt attgtttggt ttttttggg tttaggga tgttgtttt gggttatggg | 1740 |
| tgtggttgtt ggattggagt tttatttgg tttgtgattt tggattaggg tatgattttg | 1800 |
| gattatagta atttggttgt aggatatagt gtgtgatgtg tttggtatag agtttggtat | 1860 |
| aagggaagag tttggtggat aaggttaatt ggagaatgga ggtttgtttt gttttattt | 1920 |
| agtgtagtgg atggatttag tgttttttaa aaagaattag gggttgggtg ttgtggttta | 1980 |
| tgtttgtaat tttggtatt tgggatattg aggtgggagt attatgaggt taggagattg | 2040 |
| agattatttt ggttaaagtg gtgaaatttt gtttatatta aaatataaaa aattagtttg | 2100 |
| gtgtggtggt gtatgtttgt agttttagtt atttaggagg ttatttagga ggttgaggtt | 2160 |
| tgaatttagt aggtggaggt ggtagtgagt tgagattgtg ttattgtatt ttaatttggt | 2220 |
| aatagagtaa gattttgttt taataaaaaa aaaataataa taaaaataaa taaataaaaa | 2280 |
| aaagtaggga agtattaatt tggagtaatt gagtttaagg attgtttttt tttaataagt | 2340 |
| aaaggttggt tataggtttt taggtttttg tttagattaa gttttgtttg ggtttggtgg | 2400 |
| ggaggtgagg aagaatggtt tttaattttg ggattttaat ttttttttgtt tgtttttggg | 2460 |
| tgggatttta tgttttttgt taggatttag ttgtattttt agttatttat ttataaaatt | 2519 |

<210> SEQ ID NO 20
<211> LENGTH: 2283
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20

| | |
|---|---:|
| aatgaagatg ttggagattg ggttttttgtt tgttttttttt ttgtgttttg ggatgaggta | 60 |
| gagattgaat agttggtgag taaattaatg gtatttagaa agttatgttg gatttggtgt | 120 |
| ttagtgttta agtgttaatt tgttgaaagt ttttttagtga aatttaggg atgatttgga | 180 |
| ttttgttgag aggaattgtt tttgagtgag atggttttag aggtttggag gagtggattg | 240 |

```
gtaagtattg ggagggtagt gggagttttg tttttgtttg gtgttttgaa taaggttttt        300 atggttatt attatgagat tttggaggaa agagagaagg gttttgttgt gggtaatgtg         360
gttgtgaatt ttggtttgga tttttggtagt tttttagttt gtaggttttg ggtggtgttt       420
ggagttagtt gaagattttt tgaggtgaat tgggagattg gagagatgtt tgtgaatgat        480
tgtttggatt gagaggagtt gtgtgggata ttgttttttt gtattgtaat tttggagttg        540
gtagtggaga atttgttgga gttgtttagt gtggaagtgg tgatttagga tattaatgat       600 aataatttg ttttttttat ttaggaaatg aaattggaga ttagtgaggt tgtggttttg         660
gggatgtgtt ttttgtttga gagtgtgtat gattttgatg tgggaagtaa tttttttataa      720 atttatgagt tgagttgaaa tgaatatttt gtgttttgtg tgtagatgtg ggaggatagt       780
attaagtatg tggagttggt gttggagtgt gttttggatt gagaatggga gtttagtttt       840
tagttagtgt tgatggtgtt ggatggaggg attttagttt tttttgttag tttgtttatt       900
tatattaagg tgttggatgt gaatgataat gtgtttgttt ttaattagtt tttgtattgg       960
gtgtgtgttt tggaggatgt attttttggt atgtgtgtgg tataagttttt tgtaatggat    1020 ttggatgaag gttttaatgg tgaaattatt tattttttg gtagttataa ttgtgttggt      1080
gtgtggtaat tatttgtttt agattttgta attgggatgt tgataattaa gggttggttg     1140
gattttgagg atattaaatt ttatgagatt tatatttagg ttaaagataa gggtgttaat      1200
tttgaaggag tatattgtaa agtgttggtg gaggttgtgg atgtgaatga taatgttttg     1260
gagattatag ttattttttgt gtatagttta gtatttgagg atgttttttt ggggattgtt    1320
attgttttgt ttagtgtgat tgatttggat gttggtgaga atgggttggt gatttgtgaa    1380
gttttattgg gttttttttt tagttttatt tttttttta agaattattt tattttgaaa     1440
attagtgtag atttggattg ggagattgtg ttagaatata attttagtat tattgtttga     1500
gatgttggaa tttttttttt tttagttttt ataatagtgt gtgtttaagt gtttgatatt     1560
aatgataatt tttataatt tttttaatt ttttatgatg tttatattga agaaaataat      1620 tttttttgggg tttaatatt aaatttaagt gtttgggatt ttgatgtttt gtagaatgtt     1680
tggttttttt tttttttttt gggagtaagga gttgaaattg ggttagtggg ttgttatttt    1740
ataataaatt gtgataatgg tatagtgtta tttttagtgt tttttagatta tgaggattgg    1800 tgggaatttg aattaatagt ttatattagt gatggggta ttttggtttt agttattaat       1860
attagtgtga atatatttgt tattgattgt aatgataatg tttttttaggt tttatatttt     1920 tggttaggtg ggagtttggt ggagatgttg ttttgaggta ttttagttgg ttatttagtg     1980
ttatgggtgg taggttggga tgtggatgta gggtataatg tttggttttt ttatagttt       2040 ttgggattt ttaattagag ttttttttgtt atagggttgt atattggtta aattagtatt      2100
gtttgtttag tttaagatat agatttattt aggtagattt ttatggtttt gattaaagat      2160
aatggggagt ttttgttttt tattattgtt attttttattg tgttagtaat tgaggatttt     2220
tttgaagttt gagttgagtt tttttttggt tttgttttt gggagtagaa aaaaattttt       2280
att                                                                   2283
```

<210> SEQ ID NO 21
<211> LENGTH: 2283
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21

```
ggtgagattt ttttttttgtt tttgggggt agagttagag gggaatttgg tttgggtttt      60
aggagagttt ttggttattg atatagtgag ggtagtagtg gtggagagtg aaggtttttt     120
attgttttg attaagattg tgagagtttg tttgggtgaa tttgtgtttt ggattggatg      180
ggtagtattg atttgattag tgtgtagttt tatggtaaaa aggttttggt taggggattt     240
taagagattg taggagagtt aggtattgtg ttttgtattt gtgttttagt ttattatttg     300
tgatattagg tggttagttg aggtattttg aggtagtatt tttattgagt ttttatttgg     360
ttgaggatat aggattgg gggtattgtt attgtgatta gtgataaata tgtttatgtt       420
gatgttggtg gttaggattg gggtgttttt attgttgata tgagttgtta atttaaattt    480
ttgttgatt ttatagttta ggggtattaa ggatgatatt atgttattgt tatgatttat     540
tgtgaaatag tgatttatta gtttggtttt agttttttgt tttaagagaa agaaagaaag     600
ttgagtattt tgtggggtgt tggggtttta gatatttagg tttagtattg gagttttggg     660
gaggttgttt ttttaatgt aaatgttgta ggaagattga gaagattgtg gagggttgtt    720
attgatgttg gatatttgaa tatgtattat tgtaagggtt gagagggaag gggttttggt    780
gttttgggtg gtgatgttga ggttgtattt tggtatagtt ttttgattta ggtttgtatt    840
ggttttaaaa gtgaagtaat ttttgaggga agaagtaagg ttgaaaggga gatttggtgg    900
aatttgtag gttattagtt tgttttgtt agtattagg ttagttatat tgagtaaagt      960
gatgatagtt tttagagggg tattttggg tattgggttg tatatggagg tgattgtgat   1020
ttttggggtg ttgttattta tatttataat ttttattaat atttgtaat gtgtttttt     1080
gggattggtg ttttgtttt tggtttggat gtaaattta tggagtttgg tgttttgaa      1140
gtttagttga ttttgattg ttagtatttt ggttataagg tttaaggtga atagttgttg   1200
tatgttggtg tggttgtggt tgttgaagga gtaaataatt ttattgttgg ggtttttatt   1260
tagatttgtt gtaaggattt gtattatgtg tgtgttggag ggtgtatttt ttaggatgtg   1320
tgtttggtat aaggattggt tgaagatagg tgtattgtta tttgtgttta gtatttgat    1380
gtgaataggg aggttggtgg agagagttgg ggtttttttg tttaatgttg ttagtattaa   1440
ttggagatta ggtttttgtt tttggtttag ggtgtgtttt aatattagtt ttgtgtattt   1500
ggtgttgttt ttttgtgttt gtatgtgaag tgtaaagtat ttattttggt ttagtttata   1560
ggtttgtaaa gagttgtttt ttatattggg attgtgtgtg ttttgagtg gaaagtgtgt   1620
ttttggagtt atggttttgt taatttttaa tttttatttt tgggtaggga aagtaggatt   1680
gttgttgttg atgttttgga ttattatttt tatgttgaat agttttagtg ggtttttat    1740
tattaatttt agagttatag tgtaagaggg tagtgttta tatagttttt tttgatttag   1800
atggttgttt ataaatattt ttttggtttt ttggtttatt ttaaagaatt tttggttagt   1860
tttagatatt atttggaatt tgtgggttga gaggttattg agatttaaat taaggtttgt   1920
gattatgttt tttatagtga aatttttttt ttttttttt gggattttat agtgaatgat   1980
tgtggaagtt ttgtttaagg tattaagtag aagtaaaatt tttattattt ttttggtgtt   2040
tattagtttg ttttttagg ttttgggat tattttattt aaaagtagtt ttttttagtg    2100
gggtttagat tgttttgag attttgttga gaaatttta gtgggttagt gtttgggtgt    2160
tgggtgttga gtttgatatg gtttttggga tgttgttgat ttgtttgttg gtgtttagt    2220
ttttgttta ttttggggtg tagaaagggg atgggtaggg gtttgatttt tagtgttttt   2280
att                                                                   2283
```

<210> SEQ ID NO 22
<211> LENGTH: 2001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22

```
ggtaaaagtt tgtttggatt ttttggttat tagaaatatg agtatggtgg tggttttttag    60
tttttttattt atgtttgggt ttaagagatt gggagtttag gtttattgat tttttgagaa   120
agattaagat tttgtatttt agaaagaggt ttggggattt ttgttttgtg taagggtaga   180
aggattagtt gttttttttga gtatttttaat ttggaatttt ggtttgaagt tgagatagga   240
gattggatgt gaggttttt tagagttggt ttttttttaaa taattttttaa aattttttaga   300
ttttaggggt atgttgaaat ttttttaaagt agtttaaaga atataatgag agttttaata   360
ttttaggtgg tggtgtgttg gttttttgga gtggggtggg atgtggttgt gtggattttat   420
gtgtataatt gtgtgggatg gggttatgtg gatttatgtg tataattgtg ggattttagt   480
gttagtggga ttttagtgtt agtgggattt tagtgttagt gggattttag tgttagtggg   540
atttagtgt tagtgggatt ttagtgttag tgggatttta gtgttagtgg gtttgtggtt   600
tagtggagtg agtggagtgt tggtgatttg agtggagatt gtgttttgga tgttttagtt   660
tagatgttaa gttatagttt gtgtagtagt agtaaagggg aagggtagg agttgggtat   720
agttggattt ggaggttgtg atttagggga aagtgtgggt ggttgattta gggtagttgt   780
ggtggtgagg taggtgggtt ttttgttttt tggagttgtt tttttttata tttgtttttg   840
gtgttttttag tagtttttat tttgttttt tgtggttatt gtgggatttg gtgttgttgt   900
tagtttagtg gggagtgaat tagtgttttt ttttgttttt ggttttttg atggtatgag   960
gaattttttgt tttgttttat agattttttgg ttttttgttga gtgtggtatt ggagtttgtt  1020
ttgttagggt tttggaatta gagaaagttg tttttttggtt atttgaagtg ttggattttt  1080
atagtgttttt ttagtttggg tgggagtggt ggttgtgttg ttgaaggttg gggttttttgg  1140
tgtgaaaggg aggtagttgt agttttagtt ttatttttaga agtggttttt gtattgttgt  1200
ggtgggtgtt tttgggtttt gattttgtta gtgttgtggg gtagaggtat ttggagtttg  1260
tagggtttag atttggggttg gaaaagtttt gttgattgta ggtaagtgtt tggagggggt  1320
ggttaggtga agtttttggtg ttttattata tattttttggg ttttatgtta gttgtatttg  1380
tggtattggg taggaaatgg tagggttgag gttgattttta ggagtataag ggagtttttt  1440
atttttttgtt tatatttgtt attttttagtt ttgtaattta ttttagatat atagaaagta  1500
agtaggattg gtggggagat ggagtttaat aggaatattt tttagtagtg agtaggggtt  1560
gtatgggatg tgggaggagt ttagaggagg tgtggagagt gtttgaggtt gggtgagtgt  1620
ttagagggga gatagttgaa ttgggtttaa gaggtgttta gtgggtgttt gttgaatgaa  1680
tgagtgatgg gttttgaagt ttgagtgtat tgaaagaggg ggtgtgtaaa aagggtttttt  1740
tttattatat aggatatagt atatgtaaat tttttttttg tggaaaagtt agataggtta  1800
aaaaggttat aaataaatta gttgggtatg gtggtgtgtg tttgtagttt tagttattag  1860
ggaggttgag ttaggggaat tgtttgaatt tgggaggtgg agattgtagt gagttaagat  1920
tgtgttattg tatttttagtt tggaaataga gtgagatttt gttttggaaa aaaaaaaaa  1980
aagttataaa ttgtgtgtgg g                                              2001
```

<210> SEQ ID NO 23
<211> LENGTH: 2001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 23

```
tttatatatg gtttgtaatt tttttttttt tttttttgaga tggagttttg ttttgttttt      60
aggttggagt gtagtggtgt gattttggtt tattgtaatt tttgtttttt gggtttaagt     120
gattttttg gtttagtttt tttagtagtt gggattatag atgtgtatta ttatgtttgg      180
ttaatttgtt tgtaattttt ttaatttgtt tggttttttt atagggagag gatttgtata     240
tgttgtgttt tgtgtgatga aaggagtttt ttttatatat tttttttttt aatgtattta     300
gattttaaag tttattattt atttatttaa taaatattta ttaagtattt tttgaatttg     360
gtttaattat tttttttttta ggtatttatt taattttggg tattttttgt gtttttttttg    420
agtttttttt gtgtttttata tagttttttgt ttattgttgg aaaatatttt tgttaagttt    480
tgtttttttta ttagttttgt ttgttttttg tgtgtttggg ataggttgta aaattggagg    540
tgataaatgt gggtaggaaa tggagggttt ttttatattt ttagggttgg ttttagtttt     600
gttattttttt gtttaatatt gtggatgtaa ttggtatggg atttggaagt gtgtggtaaa     660
gtgttggggt tttgtttggt tgttttttttt ggatgtttgt ttgtagttag tgaagttttt     720
ttaatttagg tttgggtttt gtgagtttta ggtgtttttg ttttgtggtg ttggtgaagt    780
tgaagtttga gaatgtttat tgtagtgatg tgaaggttgt ttttggggtg gggttgaggt     840
tgtagttgtt ttttttttgt attaaggatt ttaattttta gtgatgtagt tgttgttttt    900
gtttaggttg ggaggtattg tagggatttg atgttttagg tggttaaaga gtgattttttt   960
ttgattttag ggttttggtg gggtaggttt tagtattgta tttggtggag gttgaaggtt    1020
tgtggggtag gataggagtt ttttgtgttg ttggaagggt tgaggatgaa ggagggtgtt    1080
aattttatttt ttattgggtt ggtggtaatg ttgaattttg tagtgattgt ggagggttaa    1140
ggtgaaaatt gttgggggtg ttgagggtag gtgtggggag gggtggtttt agggagtaag    1200
gagtttatttt gttttgttgt tgtagttgtt ttgggttgat tgtttatgtt tttttttggg    1260
ttatgattttt tggatttaat tgtgtttggt ttttgttttt tttttttttgt tgttgttgtg    1320
tgggttgtaa tttgatgttt aggttggggt gtttagggtg tagttttttgt ttaggttgtt    1380
agtgttttat ttgttttatt gggttataga tttgttggtg ttggggtttt gttggtgttg    1440
gggttttgtt ggtgttgggg ttttgttggt gttgggtttt gttggtgtt ggggttttgt     1500
tggtgttggg gttttgttgg tgttgggggtt tgtggttgt gtatgtgagt ttgtgtggtt    1560
ttgttttgtg tggttgtgta tgtgagtttg tgtggttgtg ttttgttttg ttttagggag    1620
ttagtgtgtt gttatttggg atgttaggat ttttgttgtg ttttttggat tgttttgggg    1680
gattttggtg tattttttagg atttaggagt tttggaagtt gttgagaga aattagtttt    1740
gggagggttt tgtatttagt ttttttgtttt ggttttggat tggggttttg ggttaaggtg    1800
tttagaggaa tagttgattt tttttatttt gtgtagggta gagatttta aattttttt       1860
taaaatgtag ggttttagtt ttttttaggg agttagtgaa tttagatttt tagttttttg    1920
agtttaagta tgaatggga attgggggatt attattatgt ttatattttt ggtggttagg   1980
aagtttaggt aggttttttgt t                                                  2001
```

<210> SEQ ID NO 24
<211> LENGTH: 2365
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24

```
gtggttgtgg tggggtgtt agttgtaggg gtgtttttgg tgggtgggag ttggtggttt      60
tttgttggtg ttatgggatt tgtatgtttg ttttgtgttt tttggttttt gagtttatag     120
gttgggattt tgtttgttag ttgtgtgtgt tgttgtttaa tttttgtagg tgtagagtgt     180
gtggtggtgg tgatagagaa ttttgtttgg ttgtttaaat atagtttttt gtagaaggat     240
tttgtgtttg gggaagggga ggaattttt ttttttgggg tgtttgtttt ttttgttatg     300
gtttggtttt tatatttgtt tatatttggt tgtagtgggg tgtttggggg gaggggttga    360
ggttgtgttt tttgttgttt tttgggtgtg ggttaggtgg ggaggagggg ggtgttttgg    420
ttgtgtgttt aggattgttt tttagtggtt atttgggttt tagttttta  ggtttggttt    480
tgataggtgg gtggagtagt tagtgtgaga tagggaggtt ggtgtgggtg tgggaatttg    540
atttgtttgg gaggtggggg tggggtgggg gtgtagtgtg tggggagggg ttggtgtttg    600
tttttttttt ttatttattt agttgagtta ggggggtttag gggttttttt ggtggttagt    660
tttgtattgt aggagtgtgg gtgtggtgtt ttagttagtg tgtagggttt gggttttgtt    720
gggggtgttt ttttgttgtt gttttttgtg tgatttgttg tttattagtt attatgttgg    780
atttttgtgg taatgtgtag ttggatggga ttattttgga ttttgaaggt gggtgttggg    840
ttggttgttg tggttgtgga tgtgttggag aggattttgt gggtgggttt ggtgtgggat    900
ggggtgtgt tgaggggaga tgggagtgtg ttgaggggag atgggatttt taatttaggt    960
gtttttttgt tgagagtgtt gtgtgttttt ggttttgtgt ttgtgttgtt tatgtggggg   1020
attttgttag gggtatttgt gtagattttg tgtgttttta taggattttg tgtttgtttt   1080
gtgtattgtt gtttgggttt tttttttttt attgttgttt gtgtttgtta agtgatagtg   1140
attttttga gggtttgtga ggttgtttg gaatttttta ggatgtatag ttttattttg    1200
ggaaatttat tggtttttt ttttttggttt tttttggtgg ttttgggtt ttgtttggat   1260
ttggtaatgg gatagggagg ttgttttta tttttgattg agtggatagt gtgttttgt    1320
ttgggtggat agtttttttt ttttttatgt tagttttggg gttgttaagt tgtgtagttt   1380
gtgggttggg agtattgaat ggatatagtt taggttgtgg tagggtttag agtgggatgt   1440
tttatggttt ttattaggt ttggggatat tttatttgt tttttagaat tgggttgtgg    1500
gggatagaag gggtttgtgt gtgggtaggg agagtatttt ggttttttt  tgttttgg    1560
gtttataaag tgtgttggga tttgtggggt tgttttgttt aagttgggt ttggtgtttg    1620
tgttttgag tttgtgagtg tgtgtgtttt tttgtgtttt tttgattgtt ggtgttgggg    1680
ttttgtgttt tgtgtttgtg ggagtaaata tagtaggtga aggggaagtt tatataatgg   1740
tttttagtgt tttggggtag ggttttttgag gggtgggttt gttttttgttg ggatttggag   1800
tttttgtttt ttggagaggt tttaggttg atttgggtag agttttttgg tgggttggga   1860
ggggaaagg ttgtgttgaa atgagtaaat tgttaggtg ttaggttaag ttgggaggtg    1920
attagtttga ggtttttttt gttttatggt tagaattagg gttgatattt gggtgttttg   1980
agtttagttg tttatatggt ttatttgggg ttagttttat ttgagtgggg gaggtggggt   2040
tttttggggg attagaattt tggttggatg ttaagtagag tgttagtggt tgttttttag   2100
```

```
ggttgggttt gaggagggtg tgggtggtg aagggatggg aggggttgt gatttagtgg    2160 ttattggtgt tgtgtagagt gtgagttgga aatattgtag ttattttgtt agtttagtgg    2220
tgaaagtttt tttttaggtt ttattttttt gtattttgt tttttagagg gaggggaggt    2280
ttgggtttgt agagttggga gggtttgttg ttttgttt ttttttttat aatatttttt    2340
tatttggata tttttgggta tatgt                                          2365

<210> SEQ ID NO 25
<211> LENGTH: 2365
<212> TYPE: DNA
<213> ORGANISM: Artificial Sequence
<220> FEATURE:
<223> OTHER INFORMATION: chemically treated genomic DNA (Homo sapiens)

<400> SEQUENCE: 25
gtatgtgttt aaagatgttt agatgaggag gtgttgtggg ggaggggggt gggaatagta      60
agttttttta gttttgtaga tttagatttt tttttttttt gggaagtagg gatgtaaagg    120
gatagagttt gaaaaagggt ttttattatt aagttgataa agtaattatg atgttttag    180 tttatattt gtatagtgtt agtggttatt ggattataat ttttttttgt tttttgttg    240 ttttatattt ttttaggtt tagttttgaa gaatagttat tggtatttg tttggtgttt    300 agttaaagtt ttggttttt aggaggtttt gtttttttta tttagatagg gttgattta    360 ggtgggttgt gtgggtagtt gggtttagga tatttagatg ttagttttgg ttttggttat    420
ggagtgggga ggattttagg ttggttattt tttagtttgg tttgatattt ggatagttg    480 tttatttaa tatagttttt ttttttttg gtttattaga gggttttgtt taagttagtt    540
taggagtttt tttgaggggt gggggttta ggttttggta gaggtaggtt gtttttttag    600 aagtttgtt ttagagtgtt ggagattatt gtgtgagttt ttttttgtt tgttgtattt    660 atttttgtgg atgtaggatg tagagttta gtattggtag ttaagaggat gtaggaaagt    720
gtatgtattt ataggtttag agatgtggat gttagattta ggtttggata gagtagttt    780 gtaagtttta atatattttg taaattttga agataggaga gagttaaat atttttttg    840 tttgtatgta ggtttttttt gtttttatg gtttgatttt gggaggtgga tgaggatatt    900
tttaggtttg gatggggtt atgggatatt ttattttaga ttttgttatg atttgggttg    960
tgtttgtttg gtgtttttgg tttatgggtt gtataatttg gtggttttga aattggtgtg   1020
ggggagggga gggttgttta tttgagtagg atgtggttgt ttatttagtt ggaggtgagg   1080
aatgattttt ttattttgtt gttgggttta agtggggttt gagagttgtt ggggagagtt   1140
aaagggaggg gattgatgga tttttagag tgaaattgtg tgttttggag agttttgagg   1200
tagttttgtg agttttttgag gaggttgttg ttgttggta aatataaata ataataaaag   1260
gaaggaaatt taggtggtag tgtgtagaat gagtataggg ttttgtgagg gtgtgtaggg   1320
tttatgtggg tgttttttaat agggttttt atgtaggtgg tgtgggtatg gggttggggg   1380
tgtgtggtgt tttagtggg agggtgtttg gattagggt tttgttttttt tttagtgtat   1440 ttttgttttt tttagtgta tttttgtttt gtgttaggtt tatttgtagg gttttttta   1500 gtatgtttgt ggttgtagta gttagttag tattatttt tgaagtttga aatgattta    1560 tttagttgtg tgttgattgt ggggtttgat atgatggttg gtgggtagtg ggttgtgtgg   1620
agggtagtgg tgaggaagtg ttttggtgg ggtttgggtt ttgtgtgttg gtggggtgt   1680 tgtgttttgtg ttttttgtagt gtagagttag ttgtggagg agttttttagg ttttttggtt   1740 tagttgaatg aatgggggag gaaggtgggt gttggttttt ttttgtgtgt tgtgtttttg   1800
```

```
ttttgttttt gtttttggg tggattaggt ttttgtattt gtattggttt ttttgttttg    1860
tattggttgt tttgtttgtt tgttaaggtt aggtttgggg ggttggggtt tgagtggttg    1920
ttgggggata gttttgggta tatgattgga gtgttttttt ttttttgtt tggtttgtgt     1980 ttaggggatg gtgagagatg tggttttagt tttttttttt gggtgttttg ttgtggttag    2040
atgtgggtgg atgtggaggt tgggttatgg tgaggagggt gggtgtttag aggggaagag    2100 atttttttt ttttttgggt gtagggtttt tttgtaggag gttgtatttg ggtagttaaa     2160
taaagttttt tgttattgtt gttgtgtgtt ttgtgtttgt aagggttaaa tggtagtgta    2220
tgtggttggt aggtaggatt ttggtttgtg ggtttaagag ttgaggggtg tagggtgaat    2280
atgtgagttt tatggtatta gtgagaggtt attaattttt atttattgag ggtatttttg    2340
tagttaatat ttttattatg attat                                         2365

<210> SEQ ID NO 26
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26
gaagtagtcg gggtcgttta cg                                            22

<210> SEQ ID NO 27
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
gcaaaatacg cgaaaaccgt                                               20

<210> SEQ ID NO 28
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28
acgtcttctc tcgccccgaa cga                                           23

<210> SEQ ID NO 29
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
ggagtggagg aaattgagat                                               20

<210> SEQ ID NO 30
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30
```
ccacacaaca aatactcaaa ac                                                22

<210> SEQ ID NO 31
<211> LENGTH: 33
<212> TYPE: DNA
<213> ORGANISM: Artificial Sequence
<220> FEATURE:
<223> OTHER INFORMATION: chemically treated genomic DNA (Homo sapiens)

<400> SEQUENCE: 31
tgggtgtttg taatttttgt tttgtgttag gtt                                    33

<210> SEQ ID NO 32
<211> LENGTH: 26
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32
gtagtagtta gtttagtatt tatttt                                            26

<210> SEQ ID NO 33
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 33
gatttagagt tgaatgtaaa gtaa                                              24

<210> SEQ ID NO 34
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 34 tttttttggag ttgaaagg                                                    18

<210> SEQ ID NO 35
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35
ttaggaaatg aaattggaga                                                   20

<210> SEQ ID NO 36
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36
aaacccaaac ctaaattaaa                                                   20

<210> SEQ ID NO 37
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 37
cccaccaacc atcatat                                                    17

<210> SEQ ID NO 38
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 38
ctaaaacctc aacctaac                                                   18

<210> SEQ ID NO 39
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 39
aaattactac catctccaac tac                                             23

<210> SEQ ID NO 40
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 40 tataaaaat tacttcccac atc                                              23

<210> SEQ ID NO 41
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 41
ggaagtgtgt ggtaaag                                                    17

<210> SEQ ID NO 42
<211> LENGTH: 32
<212> TYPE: DNA
<213> ORGANISM: Artificial Sequence
<220> FEATURE:
<223> OTHER INFORMATION: chemically treated genomic DNA (Homo sapiens)

<400> SEQUENCE: 42
accatcatat caaaccccac aatcaacaca ca                                   32

<210> SEQ ID NO 43
<211> LENGTH: 31
<212> TYPE: DNA
<213> ORGANISM: Artificial Sequence
<220> FEATURE:
<223> OTHER INFORMATION: chemically treated genomic DNA (Homo sapiens)

<400> SEQUENCE: 43
cctaacatct tctctcaccc caaacaaaac a                                    31

<210> SEQ ID NO 44
<211> LENGTH: 31
<212> TYPE: DNA
<213> ORGANISM: Artificial Sequence
<220> FEATURE:
<223> OTHER INFORMATION: chemically treated genomic DNA (Homo sapiens)

<400> SEQUENCE: 44
caactacaac ccaacccaat ctacaaacat t                                31

<210> SEQ ID NO 45
<211> LENGTH: 37
<212> TYPE: DNA
<213> ORGANISM: Artificial Sequence
<220> FEATURE:
<223> OTHER INFORMATION: chemically treated genomic DNA (Homo sapiens)

<400> SEQUENCE: 45
ccacatcaaa atcatacaca ctctcaaaca aaaaaca                          37

<210> SEQ ID NO 46
<211> LENGTH: 28
<212> TYPE: DNA
<213> ORGANISM: Artificial Sequence
<220> FEATURE:
<223> OTHER INFORMATION: chemically treated genomic DNA (Homo sapiens)

<400> SEQUENCE: 46
taaagtgttg gggttttgtt tggttgtt                                    28

<210> SEQ ID NO 47
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 47
gttcgaaatg attttattta gttgc                                       25

<210> SEQ ID NO 48
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 48
aacgaaacaa ataccgtaaa cga                                         23

<210> SEQ ID NO 49
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 49
ggttgggttt tttaacgttc gt                                          22

<210> SEQ ID NO 50
<211> LENGTH: 16
<212> TYPE: DNA
<213> ORGANISM: Artificial Sequence
<220> FEATURE:
<223> OTHER INFORMATION: chemically treated genomic DNA (Homo sapiens)

-continued

<400> SEQUENCE: 50
ggtttcgggg acgcgt                                                   16

<210> SEQ ID NO 51
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 51
aaacaaacgt ccgaaaaaaa cga                                           23

<210> SEQ ID NO 52
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 52
cgttgatcgc ggggttc                                                  17

<210> SEQ ID NO 53
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 53
ccgactactt ctacatttcg aacg                                          24

<210> SEQ ID NO 54
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 54
atcgggtcgg gttgtagttg                                               20

<210> SEQ ID NO 55
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 55
ttcgttcgag agcgcgt                                                  17

<210> SEQ ID NO 56
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 56
caaacgaaac cccgacgc                                                 18

<210> SEQ ID NO 57

```
<211> LENGTH: 2501
<212> TYPE: DNA
<213> ORGANISM: Homo Sapiens

<400> SEQUENCE: 57
ttgttgtaca gaatatttca tcacccaggt attatgccga gtacccaata gttctctttt        60
ctgctcctct ccttcctccc atcctgcacc ctggagtcaa ccacagtgtc tgttgtttcc       120
ttgtttgtgt tataagttct catcatttag ctcccactta caagtgagaa catccagtat       180
ttggatttct gttcctgcat tagtttgcta aggataatag cctctagctc catccatgtt       240
cccacaaaag acatgatcta gttctttta atggctgcat taaatgaagt tttaaagata        300
caacataaac accaacctct tccccaccac aaaaatccct tgctgaattt gattacactt       360
aaattaacga gttttgtttc atgaaagact ccttggacaa acttgacagt tgatggaata       420
ggagaagctg tctgtcatgt ctaaagccaa caagagatca atatctagaa taaatggaga       480
tctgcaaatc aacagaaagt aggcagcaaa gccaaagaaa atagcctaag gcacagccac       540
taaaaggaac gtgatcatgt cctttgcagg gacatgggtg gagctggaag ccgttagcct       600
cagcaaactc acacaggaac agaaaaccag cgagaccgca tggtctcact tataagtggg       660
agctgaacaa tgagaacaca tggtcacatg gcggcgatca acacacactg gtgcctgttg       720
agcggggtgc tggggaggga gagtaccagg aagaatagct aagggatact gggcttaata       780
cctgggtgat gggatgatct gtacagcaaa ccatcatggc gcacacacct atgtaacaaa       840
cctgcacatc ctctacatgt accccagaac ttcaaataaa agttggacgg ccaggcgtgg       900
tggctcacgc ctgtaatccc agcactttgg gaagccgagg cgtgcagatc acctaaggtc       960
aggagttcga gaccagcccg gccaacatgg tgaaacccg tctctactaa aaatacaaaa       1020
atcagccaga tgtggcacgc acctataatt ccacctactc gggaggctga agcagaattg       1080
cttgaacccg agaggcggag gttgcagtga gccgccgaga tcgcgccact gcactccagc       1140
ctgggccaca gcgtgagact acgtcataaa ataaaataaa ataacacaaa ataaaataaa       1200
ataaaataaa ataaaataaa ataaaataaa ataaaataaa ataaaaaat aaaataaaat       1260 aaaataaaat aaagcaattt cctttcctct aagcggcctc caccctctc ccctgccctg        1320 tgaagcgggt gtgcaagctc cgggatcgca gcggtcttag ggaatttccc ccgcgatgt        1380 cccggcgcgc cagttcgctg cgcacacttc gctgcggtcc tcttcctgct gtctgtttac       1440
tccctaggcc ccgctgggga cctgggaaag agggaaaggc ttccccggcc agctgcgcgg       1500
cgactccggg gactccaggg cgcccctctg cggccgacgc ccggggtgca gcggccgccg       1560
gggctggggc cggcgggagt ccgcgggacc ctccagaaga gcggccggcg ccgtgactca       1620
gcactggggc ggagcggggc gggaccaccc ttataaggct cggaggccgc gaggccttcg       1680
ctggagtttc gccgccgcag tcttcgccac cagtgagtac gcgcggcccg cgtccccggg       1740 gatgggctc agagctccca gcatggggcc aacccgcagc atcaggcccg ggctcccggc       1800
agggctcctc gcccacctcg agacccggga cgggggccta ggggacccag gacgtcccca       1860
gtgccgttag cggctttcag ggggcccgga gcgcctcggg gagggatggg accccggggg       1920
cggggagggg gggcagactg cgctcaccgc gccttggcat cctccccgg gctccagcaa        1980 actttctttt gttcgctgca gtgccgccct acaccgtggt ctatttccca gttcgaggta       2040
ggagcatgtg tctggcaggg aagggaggca gggctgggg ctgcagccca cagcccctcg        2100
cccacccgga gagatccgaa ccccttatc cctccgtcgt gtggcttta ccccgggcct         2160 ccttcctgtt cccgcctct cccgccatgc ctgctccccg cccagtgtt gtgtgaaatc         2220
```

```
ttcggaggaa cctgtttccc tgttccctcc ctgcactcct gacccctccc cgggttgctg    2280
cgaggcggag tcggcccggt ccccacatct cgtacttctc cctccccgca ggccgctgcg    2340
cggccctgcg catgctgctg gcagatcagg gccagagctg aaggaggag gtggtgaccg     2400 tggagacgtg gcaggaggc tcactcaaag cctcctgcgt aagtgaccat gcccgggcaa    2460 ggggagggg tgctgggcct taggggctg tgactaggat c                         2501
```

<210> SEQ ID NO 58
<211> LENGTH: 3506
<212> TYPE: DNA
<213> ORGANISM: Homo Sapiens

<400> SEQUENCE: 58

```
cagcggtaaa gctctgccca cgttaagtaa caaaggataa gttagtcttt gttgtgatca      60
ctttgttgta ctgataagct acgtatttct actcaaggat tcaaattctc acctttctca     120
agaattgggc caaaaccgat aaactaaact tatttacggt ccactgatta aaggttgttg     180
cataataagt tcttgctatg ttcagcagtt ggattcacag cgccagaaac ctataactgc     240
ttgactttcc tccccactac actgcgaaaa ttgccccta aatgtaacta accctaaaac      300
ctcaacagta tcgtggccag gcgtggtggc tcactactgt aataccaaca ttaggcatag     360 gcgagggat tgaggccagg atatcgaaac tagcctggga acacacgga gacccggtct       420 ttggaaaaat aattagcctt gcgtggtggt gggcgcgagg ttccggctaa tcgggaggct     480
acagtgagcc atgatgacac tgcactacag tctgcgcgac ggcccatgtc agtaagctct     540
ggagcacctg aaacaagttg tgttgggtat tttatttact ggagagcgat tagtgactga    600
tgcctactta cagcgactag agacgcatgc tccgatagca gcacaaactc agcaggcgcg    660
aacaaatggt aaagagaaac tggcaaaca agcatcacgg ctcctcagct gagaaagtgg     720
gggccctaaa aagggccttt tgttgataga aagggacgct caaccaccga accgtagag      780 ggtgcggccc tggcgcttga gcgcgtagac cacatccatg gcggtgaccg tcttgcgctt    840
ggcgtgctct gtataggtca cggcgtcccg gatcacgttc tccaggaaca ccttcagcac    900
cccgcgagtc tcctcgtaga tgaggccgga gatgcgcttc acgccgccgc ggcgagcaag    960
gcgccggatg gccggcttgg tgatgccctg gatattgtcg cgcagtactt tacggtggcg    1020
cttagcgccg cctttgccaa gacccttccc gcctttgccg cggccagaca tgacgagcaa    1080
gaggagtctc acccaacgct ttgtgaggac tctggcctga ggcagcgcct ttatacgaca    1140
gttggcggac cgaactgaga acctgaaaga agtcggcggg aagtcccgcc ccggtggggg    1200 agggggaaatc taagggccaa accgaaata gggggaaaaa aaagcgagc ttcttgtttc     1260 cgtgttctga attttgtaac gtgcatagta ttttgttacc acgttatgag gctttaaaaa    1320
attgcttttg aacgcagaag atatacatca atactgtggg aaatacaaga aaggacaaga    1380
aattaagaaa ctacaatgtt atcccatcac acaggctagt taatcatgta ttttgcagag    1440
cagttgcaca tattttttcca agaaaatgta tacagtgttg tatatggagt tttgtaacct    1500
ccttatattg attataattt aaccaatttc tattaaagag ataaaagtga tgttttggtg    1560
tctatgtttc ttaggaatta tcaatagtta taatcagttc cccagcaatt ttttaatcgg    1620
ctgtatttta aaataatgt tttccacatt caacataaat gtacttttc tctatacttg      1680 ggaccaatat tgaaatttat gatttttatta caccaaaatt taaatttat tacattaata    1740 tttaaaattg tattagaggt ctcatgattt ggtactacgg gtctccgcat tatttccttt    1800
```

```
ccaaatttcc taatctgttt caccaaggtt tctggacaac tttagagacc ttttgtgaag    1860
tttgaataaa atctcttcga gatttttgata attgcattag ctttaggact taattggaat    1920
agaattaaaa tccttaaaac aagctcttat aactagaaaa ttggtgtttg taggttttgt    1980
gtgtggggtt ttttttttttt tttggaagga gtctcgctct gtcgtcaggc cggagggcag    2040
tggtgcaatc tcggctcact gcaacctcca cctcccgggt tcaagcgatt ctcatgcctc    2100
aacctccgga ttagcgcgga ctacaggcat gcgccaccac gcccagctaa ttttttgtat    2160
ttttagtaaa gaacaagttt caccatgttg gacaggatgc tcttgatctc ttgacatcgt    2220
gatccgcccg cctcagcctc ccaaagtgct gggattacag gcgtgagccg cttcgcttgg    2280
acgcttgtag gttttttaaaa agacactttt atatgaccca actaaagatt tgttatcaac    2340
cattatggag caactttgat tccgtatatt tgattttctt tcttattaat aaatacaggg    2400
ttatactctg aatttttttt ttttttttttt tttttgtgga gacggagtct cgcccttcg     2460 ctcaggctgg agtgcaatgg cccaatcttg gctcactgca acctccacct cccgggttca    2520
agcgattctc ccacctcagc ctcccctgag tagctgggat tacaggcact caccaccacg    2580
cccggctaat ttttttgtat ctttagtaga cgggggttt caccatgttg gccaggctag      2640
tctccaactc ccgacctcgt gatccatatg cctcggcctc ccaatgtgct gggattacag    2700
gcttgagcca ctgcgctcgg ccactctgaa attatttttaa catcaatgaa aattataaaa    2760
ctcctataac tattctaata taatctctta gtattcaatt ctttgtttag aaagtagtta    2820
agagttgaaa ctctggaaat agaaaacttt ggttttagat taaatgttta cctttcagac    2880
tcgagctgac ttgttaccga tcagacacga ggtgacttgt ttattctttt taaatctttg    2940
ctcatctaca aagttagaat aggatagtga cggtactgtt ggggtgcaga atgattcccc    3000
aaaatgtggt tcttgggcat gctgagcgct tttgaacatt gaaaggcctc agaaataagc    3060
ttcagaatca aagcccctct aacttcgtct tctttcccat acatgcgaag ggactctgac    3120
atttcctaat cggaccaaga aaatttctta ccagaagtaa caattgcctt ctatcccctc    3180
cctgttattt cattattgca gaaaagaata ctgaatatgg attttcaag  ataatgtctg     3240 cctctcggtc tcatttaaat taccaagaca tactaggtgc tgtggctcct cccactaatc    3300
ccagcactgt gggaggtcga ggcaggtgga tcccttgagc tcaggagttc gagaccagcc    3360
tggccaacat ggcgaatccc tgtctctaca aaatatacaa aaaattagcc aggtggtgtc    3420
acatgcctgt aatcccagct acttgggagg ctgaggcagg agaatcactt gaacctggga    3480
ggcggaggtt gcagtgagcc gagatt                                         3506
```

<210> SEQ ID NO 59
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 59

```
ttgttgtata gaatatttta ttatttaggt attatgtcga gtatttaata gttttttttt      60
ttgttttttt tttttttttt attttgtatt tggagttaa ttatagtgtt tgttgttttt      120
ttgtttgtgt tataagtttt tattatttag ttttatttta  aagtgagaa tatttagtat    180 tggatttttt gttttttgtat tagtttgtta aggataatag ttttagttt tatttatgtt    240 tttataaaag atatgattta gtttttttta atggttgtat taaatgaagt tttaaagata    300
taatataaat attaattttt tttttattat aaaaattttt tgttgaattt gattatattt    360
```

```
aaattaacga gttttgtttt atgaaagatt ttttggataa atttgatagt tgatggaata    420
ggagaagttg tttgttatgt ttaaagttaa taagagatta atatttagaa taaatggaga    480
tttgtaaatt aatagaaagt aggtagtaaa gttaaagaaa atagtttaag gtatagttat    540
taaaaggaac gtgattatgt tttttgtagg gatatgggtg gagttggaag tcgttagttt    600
tagtaaattt ataggaat agaaaattag cgagatcgta tggtttatt tataagtggg       660
agttgaataa tgagaatata tggttatatg gcggcgatta atatatattg gtgtttgttg    720
agcggggtgt tggggaggga gagtattagg aagaatagtt aagggatatt gggtttaata    780
tttgggtgat gggatgattt gtatagtaaa ttattatggc gtatatattt atgtaataaa    840
tttgtatatt ttttatatgt attttagaat tttaaataaa agttggacgg ttaggcgtgg    900
tggtttacgt ttgtaatttt agtattttgg gaagtcgagg cgtgtagatt atttaaggtt    960
aggagttcga gattagttcg gttaatatgg tgaaatttcg tttttattaa aaatataaaa   1020
attagttaga tgtggtacgt atttataatt ttatttattc gggaggttga agtagaattg   1080
tttgaattcg agaggcggag gttgtagtga gtcgtcgaga tcgcgttatt gtattttagt   1140
ttgggttata gcgtgagatt acgttataaa ataaaataaa ataatataaa ataaaataaa   1200
ataaaataaa ataaaataaa ataaaataaa ataaaataaa ataaaaaaat aaaataaaat   1260
aaaataaaat aaagtaattt tttttttttt aagcggtttt tatttttttt ttttgttttg   1320
tgaagcgggt gtgtaagttt cgggatcgta gcggttttag ggaattttt ttcgcgatgt    1380
ttcggcgcgt tagttcgttg cgtatatttc gttgcggttt tttttttgtt gtttgtttat   1440
tttttaggtt tcgttgggga tttgggaaag agggaaaggt tttttcggtt agttgcgcgg   1500
cgatttcggg gattttaggg cgttttttg cggtcgacgt tcggggtgta gcggtcgtcg    1560
gggttgggt cggcgggagt tcgcgggatt ttttagaaga gcggtcggcg tcgtgattta    1620
gtattgggc ggagcggggc gggattattt ttataaggtt cggaggtcgc gaggttttcg    1680
ttggagtttc gtcgtcgtag ttttcgttat tagtgagtac gcgcggttcg cgttttcggg   1740
gatgggtttt agagttttta gtatgggtt aattcgtagt attaggttcg ggttttcggt    1800
agggttttc gtttatttcg agattcggga cgggggttta ggggatttag gacgttttta   1860
gtgtcgttag cggtttttag ggggttcgga gcgtttcggg gagggatggg atttcggggg   1920
cggggagggg gggtagattg cgtttatcgc gttttggtat tttttttcgg gttttagtaa   1980
atttttttt gttcgttgta gtgtcgtttt atatcgtggt ttatttttta gttcgaggta   2040
ggagtatgtg tttggtaggg aagggaggta ggggttgggg ttgtagttta tagttttcg    2100
tttattcgga gagattcgaa ttttttatt ttttcgtcgt gtggttttta tttcgggttt    2160
tttttttgtt tttcgttttt ttcgttatgt ttgttttcg ttagtgtt gtgtgaaatt     2220
ttcggaggaa tttgtttttt tgtttttttt ttgtattttt gattttttt cgggttgttg   2280
cgaggcggag tcggttcggt ttttatattt cgtattttt ttttcgta ggtcgttgcg     2340
cggttttgcg tatgttgttg gtagattagg gttagagttg gaaggaggag gtggtgatcg   2400
tggagacgtg gtaggagggt ttatttaaag ttttttgcgt aagtgattat gttcgggtaa   2460
ggggagggg tgttgggttt taggggttg tgattaggat t                        2501
```

<210> SEQ ID NO 60
<211> LENGTH: 2501
<212> TYPE: DNA
<213> ORGANISM: Artificial Sequence
<220> FEATURE:

<223> OTHER INFORMATION: chemically treated genomic DNA (Homo sapiens)

<400> SEQUENCE: 60

```
gattttagtt atagttttt aaggtttagt atttttttt tttgttcggg tatggttatt      60
tacgtaggag gttttgagtg agttttttg ttacgttttt acggttatta tttttttttt    120
ttagttttgg ttttgatttg ttagtagtat gcgtagggtc gcgtagcggt ttgcggggag   180
ggagaagtac gagatgtggg gatcgggtcg atttcgtttc gtagtaattc ggggagggggt  240
taggagtgta gggagggaat agggaaatag gttttttcga agatttttata taatattggg  300
gcggggagta ggtatggcgg gagaggcggg gaataggaag gaggttcggg gtaaaagtta   360
tacgacggag ggataagggg gttcggatt ttcgggtgg gcgagggtt gtgggttgta      420
gttttagttt ttgttttttt ttttgttag atatatgttt ttatttcgaa ttgggaaata   480
gattacggtg tagggcggta ttgtagcgaa taaagaaaag tttgttggag ttcggggggag  540
gatgttaagg cgcggtgagc gtagtttgtt tttttttc gttttcgggg tttattttt      600
tttcgaggcg tttcggttt tttgaaagtc gttaacggta ttggggacgt tttgggtttt   660
ttaggttttc gtttcgggtt tcgaggtggg cgaggagttt tgtcgggagt tcgggtttga   720
tgttgcgggt tggttttatg ttgggagttt tgagttttat tttcggggac gcgggtcgcg   780
cgtatttatt ggtggcgaag attgcggcgg cgaaattta gcgaaggttt cgcggttttc    840
gagttttata agggtggttt cgtttcgttt cgttttagtg ttgagttacg gcgtcggtcg   900
tttttttgga gggtttcgcg gattttcgtc ggttttagtt tcggcggtcg ttgtatttcg   960
ggcgtcggtc gtagagggc gtttgggagt tttcggagtc gtcgcgtagt tggtcgggga  1020
agttttttt ttttttttag gttttagcg gggtttaggg agtaaataga tagtaggaag  1080
aggatcgtag cgaagtgtgc gtagcgaatt ggcgcgtcgg gatatcgcgg ggggaaattt  1140
tttaagatcg ttgcgattc ggagtttgta tattcgtttt atagggtagg ggagaggggt  1200
ggaggtcgtt tagaggaaag gaaattgttt tatttttattt tatttatttt tatttttta   1260
ttttatttta ttttattta ttttatttta ttttatttta ttttatttta ttttgtgtta  1320
ttttatttta ttttatgacg tagtttacg ttgtggttta ggttggagtg tagtggcgcg  1380
atttcggcgg tttattgtaa ttttcgtttt tcgggtttaa gtaattttgt tttagttttt  1440
cgagtaggtg gaattatagg tgcgtgttat atttggttga ttttgtatt tttagtagag  1500
acggggtttt attatgttgg tcgggttggt ttcgaattt tgattttagg tgatttgtac  1560
gtttcggttt tttaaagtgt tgggattata ggcgtgagtt attacgtttg gtcgtttaat  1620
ttttatttga agttttgggg tatatgtaga ggatgtgtag gtttgttata aggtgtgtg   1680
cgttatgatg gtttgttgta tagattattt tattatttag gtattaagtt tagtatttt   1740
tagttatttt ttttggtatt tttttttttt agtatttcgt ttaataggta ttagtgtgtg  1800
ttgatcgtcg ttatgtgatt atgtgttttt attgtttagt ttttatttat aagtgagatt  1860
atgcggtttc gttggttttt tgtttttgtg tgagtttgtt gaggttaacg gttttagtt   1920
ttatttatgt ttttgtaaag gatatgatta cgtttttttt agtggttgtg ttttaggtta  1980
tttttttgg ttttgttgtt tatttttgt tgatttgtag attttatttt attttagata  2040
ttgattttt gttggtttta gatatgatag atagttttt ttatttattt aattgttaag   2100
tttgtttaag gagtttttta tgaaataaaa ttcgttaatt taagtgtaat taaatttagt   2160
aagggatttt tgtggtgggg aagaggttgg tgttatgtt gtatttttaa aattttattt   2220
aatgtagtta ttaaaaagaa ttagattatg ttttttgtgg gaatatggat ggagttagag  2280
```

```
gttattattt ttagtaaatt aatgtaggaa tagaaattta aatattggat gtttttattt    2340
gtaagtggga gttaaatgat gagaatttat aatataaata aggaaataat agatattgtg    2400 gttgattta gggtgtagga tgggaggaag gagaggagta gaaagagaa ttattgggta      2460 ttcggtataa tatttgggtg atgaaatatt ttgtataata a                         2501
```

<210> SEQ ID NO 61
<211> LENGTH: 3506
<212> TYPE: DNA
<213> ORGANISM: Artificial Sequence
<220> FEATURE:
<223> OTHER INFORMATION: chemically treated genomic DNA (Homo sapiens)

<400> SEQUENCE: 61

```
tagcggtaaa gttttgttta cgttaagtaa taaaggataa gttagttttt gttgtgatta      60
ttttgttgta ttgataagtt acgtattttt atttaaggat ttaaattttt attttttta      120 agaattgggt taaaatcgat aaattaaatt tatttacggt ttattgatta aaggttgttg     180
tataataagt ttttgttatg tttagtagtt ggatttatag cgttagaaat ttataattgt     240
ttgatttttt tttttattat attgcgaaaa ttgtttttta aatgtaatta atttaaaat      300 tttaatagta tcgtggttag gcgtggtggt ttattattgt aatattaata ttaggtatag     360
gcgaggggat tgaggttagg atatcgaaat tagtttggga aatatacgga gattcggttt     420
ttggaaaaat aattagtttt gcgtggtggt gggcgcgagg tttcggttaa tcgggaggtt     480
atagtgagtt atgatgatat tgtattatag tttgcgcgac ggtttatgtt agtaagtttt     540
ggagtatttg aaataagttg tgttgggtat tttatttatt ggagagcgat tagtgattga     600
tgttatttta tagcgattag agacgtatgt ttcgatagta gtataaattt agtaggcgcg     660
aataaatggt aaagagaaat tgggtaaata agtattacgg ttttttagtt gagaaagtgg     720
gggttttaaa aagggttttt tgttgataga aagggacgtt taattatcga aatcgtagag     780
ggtgcggttt tggcgtttga gcgcgtagat tatatttatg gcggtgatcg ttttgcgttt     840
ggcgtgtttt gtataggtta cggcgtttcg gattacgttt ttaggaata ttttagtat      900 ttcgcgagtt ttttcgtaga tgaggtcgga gatgcgtttt acgtcgtcgc ggcgagtaag    960
gcgtcggatg gtcggtttgg tgatgttttg gatattgtcg cgtagtattt tacggtggcg    1020
tttagcgtcg ttttttgttaa gatttttttc gttttgtcg cggttagata tgacgagtaa    1080
gaggagtttt atttaacgtt ttgtgaggat tttggtttga ggtagcgttt ttatacgata    1140
gttggcggat cgaattgaga atttgaaaga agtcggcggg aagtttcgtt tcggtgggg    1200 aggggaaatt taaagggtta aatcgaaata ggggaaaaa aaagcgagt tttttgtttt       1260 cgtgttttga attttgtaac gtgtatagta ttttgttatt acgttatgag gttttaaaaa    1320
attgtttttg aacgtagaag atatatatta atattgtggg aaatataaga aaggataaga    1380
aattaagaaa ttataatgtt attttattat ataggttagt taattatgta ttttgtagag    1440
tagttgtata tattttttta agaaaatgta tatagtgttg tatatggagt tttgtaattt    1500
ttttatattg attataattt aattaatttt tattaaagag ataaaagtga tgttttggtg    1560
tttatgtttt ttaggaatta ttaatagtta aattagttt tttagtaatt ttttaatcgg     1620
ttgtatttta aaaataatgt tttttatatt taatataaat gtattttttt tttatatttg    1680
ggattaatat tgaaatttat gatttttatta ttaaaatt taaattttat tatattaata    1740
tttaaaattg tattagaggt tttatgattt ggtattacgg gttttcgtat tatttttttt    1800
```

| | |
|---|---|
| ttaaattttt taatttgttt tattaaggtt tttggataat tttagagatt ttttgtgaag | 1860 |
| tttgaataaa attttttcga gattttgata attgtattag tttaggatt taattggaat | 1920 |
| agaattaaaa ttttttaaaat aagttttat aattagaaaa ttggtgtttg taggttttgt | 1980 |
| gtgtggggtt tttttttttt tttggaagga gtttcgtttt gtcgttaggt cggagggtag | 2040 |
| tggtgtaatt tcggtttatt gtaattttta tttttcgggt ttaagcgatt tttatgtttt | 2100 |
| aattttcgga ttagcgcgga ttataggtat gcgttattac gttagttaa ttttttgtat | 2160 |
| ttttagtaaa gaataagttt tattatgttg gataggatgt ttttgatttt ttgatatcgt | 2220 |
| gattcgttcg ttttagtttt ttaaagtgtt gggattatag gcgtgagtcg tttcgtttgg | 2280 |
| acgtttgtag gttttttaaaa agatattttt atatgattta attaaagatt tgttattaat | 2340 |
| tattatggag taattttgat ttcgtatatt tgatttttt ttttattaat aaatataggg | 2400 |
| ttatattttg aattttttt ttttttttt tttttgtgga dacggagttt cgttttttcg | 2460 |
| tttaggttgg agtgtaatgg tttaattttg gttattgta atttttattt ttcgggttta | 2520 |
| agcgattttt ttatttagt ttttttgag tagttgggat tataggtatt tattattacg | 2580 |
| ttcggttaat tttttgtat tttagtaga acggggttt tattatgttg gttaggttag | 2640 |
| tttttaattt tcgatttcgt gatttatatg tttcggtttt ttaatgtgtt gggattatag | 2700 |
| gtttgagtta ttgcgttcgg ttattttgaa attatttttaa tattaatgaa aattataaaa | 2760 |
| tttttataat tattttaata taattttta gtatttaatt tttgtttag aaagtagtta | 2820 |
| agagttgaaa ttttggaaat agaaaatttt ggttttagat taaatgttta ttttttagat | 2880 |
| tcgagttgat ttgttatcga ttagatacga ggtgatttgt ttattttttt taaatttttg | 2940 |
| tttatttata aagttagaat aggatagtga cggtattgtt ggggtgtaga atgattttt | 3000 |
| aaaatgtggt ttttgggtat gttgagcgtt tttgaatatt gaaaggtttt agaaataagt | 3060 |
| tttagaatta aagtttttt aattcgtttt ttttttttat atatgcgaag ggattttgat | 3120 |
| attttttaat cggattaaga aaattttta ttagaagtaa taattgtttt ttattttttt | 3180 |
| tttgttattt tattattgta gaaaagaata ttgaatatgg attttttaag ataatgtttg | 3240 |
| tttttcggtt ttatttaaat tattaagata tattaggtgt tgtggttttt tttattaatt | 3300 |
| ttagtattgt gggaggtcga ggtaggtgga tttttttgagt ttaggagttc gagattagtt | 3360 |
| tggtaaatat ggcgaatttt tgttttata aatatataa aaaattagtt aggtggtgtt | 3420 |
| atatgtttgt aattttagtt atttgggagg ttgaggtagg agaattattt gaatttggga | 3480 |
| ggcggaggtt gtagtgagtc gagatt | 3506 |

<210> SEQ ID NO 62
<211> LENGTH: 3506
<212> TYPE: DNA
<213> ORGANISM: Artificial Sequence
<220> FEATURE:
<223> OTHER INFORMATION: chemically treated genomic DNA (Homo sapiens)

<400> SEQUENCE: 62

| | |
|---|---|
| aatttcggtt tattgtaatt ttcgtttttt aggtttaagt gattttttg ttttagtttt | 60 |
| ttaagtagtt gggattatag gtatgtgata ttatttggtt aattttttgt atattttgta | 120 |
| gagataggga ttcgttatgt tggttaggtt ggtttcgaat tttgagttt aagggattta | 180 |
| ttgttttcga ttttttatag tgtgggatt agtgggagga gttatagtat ttagtatgtt | 240 |
| ttggtaattt aaatgagatc gagaggtaga tattattttg aaaaatttat atttagtatt | 300 |
| tttttttgta ataatgaaat aataggggagg ggatagaagg taattgttat ttttggtaag | 360 |

```
aaattttttt ggttcgatta ggaaatgtta gagtttttc gtatgtatgg gaaagaagac      420
gaagttagag gggttttgat tttgaagttt atttttgagg ttttttaatg tttaaaagcg      480
tttagtatgt ttaagaatta tattttgggg aattattttg tattttaata gtatcgttat      540
tattttattt taattttgta gatgagtaaa gatttaaaaa gaataaataa gttatttcgt      600
gtttgatcgg taataagtta gttcgagttt gaaaggtaaa tatttaattt aaaattaaag      660 tttttattt ttagagtttt aatttttaat tatttttaa ataaagaatt gaatattaag       720
agattatatt agaatagtta taggagtttt ataattttta ttgatgttaa aataattta       780 gagtggtcga gcgtagtggt ttaagtttgt aattttagta tattgggagg tcgaggtata      840
tggattacga ggtcgggagt tggagattag tttggttaat atggtgaaat ttcgttttta      900
ttaaagatat aaaaaaatta gtcgggcgtg gtggtgagtg tttgtaattt tagttatta      960 ggggaggttg aggtgggaga atcgtttgaa ttcgggaggt ggaggttgta gtgagttaag     1020
attgggttat tgtatttag tttgagcgaa agggcgagat ttcgttttta taaaaaaaaa      1080 aaaaaaaaa aaaatttaga gtataatttt gtatttatta ataagaaaga aaattaaata     1140
tacgaaatta aagttgtttt ataatggttg ataataaatt tttagttggg ttatataaaa     1200
gtgttttttt aaaaatttat aagcgtttaa gcgaagcggt ttacgtttgt aattttagta     1260
ttttgggagg ttgaggcggg cggattacga tgttaagaga ttaagagtat tttgtttaat     1320
atggtgaaat ttgttttta ttaaaaatat aaaaaattag ttgggcgtgg tggcgtatgt     1380
ttgtagttcg cgttaattcg gaggttgagg tatgagaatc gtttgaattc gggaggtgga     1440
ggttgtagtg agtcgagatt gtattattgt ttttcggttt gacgatagag cgagattttt     1500
tttaaaaaaa aaaaaaaatt ttatatataa aatttataaa tattaattt ttagttataa    1560 gagtttgttt taaggatttt aatttttatt taattaagtt ttaaagttaa tgtaattatt     1620
aaaatttcga agagattta tttaaatttt ataaaaggtt tttaaagttg tttagaaatt      1680
ttggtgaaat agattaggaa atttggaaag gaaataatgc ggagattcgt agtattaaat     1740
tatgagattt ttaatataat tttaaatatt aatgtaataa aatttaaatt ttggtgtaat     1800
aaaattataa attttaatat tggttttaag tatagagaaa aagtatattt atgttgaatg     1860
tggaaaatat tattttttaaa atatagtcga ttaaaaaatt gttggggaat tgattataat    1920
tattgataat tttaagaaa tatagatatt aaaatattat ttttattttt ttaatagaaa      1980
ttggttaaat tataattaat ataaggaggt tataaaattt tatatataat attgtatata     2040 ttttttgga aaaatatgtg taattgtttt gtaaatatat tgattaatta gtttgtgtga     2100
tgggataata ttgtagtttt ttaattttt gtttttttt gtatttttta tagtattgat      2160
gtatattttt tgcgtttaaa agtaattttt taaagttta taacgtggta ataaaatatt     2220
atgtacgtta taaaatttag aatacggaaa taagaagttc gtttttttt tttttttatt     2280 tcggtttggt ttttagatt tttttttt tatcggggcg ggattttcg tcgatttttt       2340 ttaggtttt agttcggttc gttaattgtc gtataaaggc gttgttttag gttagagttt     2400
ttataaagcg ttgggtgaga ttttttttgt tcgttatgtt tggtcgcggt aaaggcggga     2460
agggttttgg taaaggcggc gttaagcgtt atcgtaaagt attgcgcgat aatatttagg     2520
gtattattaa gtcggttatt cggcgttttg ttcgtcgcgg cggcgtgaag cgtattttcg     2580
gttttattta cgaggagatt cgcggggtgt tgaaggtgtt tttggagaac gtgattcggg     2640
acgtcgtgat ttatatagag tacgttaagc gtaagacggt tatcgttatg gatgtggttt     2700
```

```
acgcgtttaa gcgttagggt cgtatttttt acggtttcgg tggttgagcg ttttttttta     2760
ttaataaaag gttttttta gggttttat ttttttagtt gaggagtcgt gatgtttgtt       2820
tgtttagttt ttttttatta tttgttcgcg tttgttgagt ttgtgttgtt atcggagtat     2880 gcgttttag tcgttgtaag taggtattag ttattaatcg ttttttagta aataaaatat      2940
ttaatataat ttgttttagg tgttttagag tttattgata tgggtcgtcg cgtagattgt     3000
agtgtagtgt tattatggtt tattgtagtt tttcgattag tcggaatttc gcgtttatta    3060
ttacgtaagg ttaattattt ttttaaagat cgggttttcg tgtgtttttt aggttagttt    3120
cgatattttg gttttaattt tttcgtttat gtttaatgtt ggtattatag tagtgagtta    3180
ttacgtttgg ttacgatatt gttgaggttt tagggttagt tatatttaag gggtaatttt    3240
cgtagtgtag tggggaggaa agttaagtag ttataggttt ttggcgttgt gaatttaatt    3300
gttgaatata gtaagaattt attatgtaat aatttttaat tagtggatcg taaataagtt    3360
tagtttatcg gttttggttt aattttgag aaaggtgaga atttgaattt ttgagtagaa     3420
atacgtagtt tattagtata ataaagtgat tataataaag attaatttat tttttgttat    3480
ttaacgtggg tagagtttta tcgttg                                          3506
```

<210> SEQ ID NO 63
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 63

```
ttgttgtata gaatatttta ttatttaggt attatgttga gtatttaata gtttttttt       60 ttgttttttt tttttttttt attttgtatt ttggagttaa ttatagtgtt tgttgttttt     120
ttgtttgtgt tataagtttt tattatttag tttttattta aagtgagaa tatttagtat      180 ttggattttt gttttgtat tagtttgtta aggataatag ttttagttt tatttatgtt       240 tttataaaag atatgattta gttttttta atggttgtat taaatgaagt tttaaagata     300 taatataat attaattttt tttttattat aaaaatttt tgttgaattt gattatattt      360
aaattaatga gttttgttt atgaaagatt ttttggataa atttgatagt tgatggaata    420
ggagaagttg tttgttatgt ttaaagttaa taagagatta atatttagaa taaatggaga    480
tttgtaaatt aatagaaagt aggtagtaaa gttaaagaaa atagttttaag gtatagttat    540 taaaaggaat gtgattatgt ttttttgtagg gatatgggtg gagttggaag ttgttagttt    600
tagtaaattt atataggaat agaaaattag tgagattgta tggttttatt tataagtggg    660
agttgaataa tgagaatata tggttatatg gtggtgatta atatatattg gtgtttgttg     720
agtggggtgt tgggaggga gagtattagg aagaatagtt aagggatatt gggtttaata    780
tttgggtgat gggatgattt gtatagtaaa ttattatggt gtatatttt atgtaataaa    840 tttgtatatt ttttatatgt atttagaat tttaaataaa agttggatgg ttaggtgtgg    900
tggtttatgt ttgtaatttt agtattttgg gaagttgagg tgtgtagatt atttaaggtt    960
aggagtttga gattagtttg gttaatatgg tgaatttttg ttttattaa aaatataaaa    1020 attagttaga tgtggtatgt atttataatt ttatttattt gggaggttga agtagaattg    1080 tttgaattg agaggtggag gttgtagtga gttgttgaga ttgtgttatt gtattttagt    1140
ttgggttata gtgtgagatt atgttataaa ataaaataaa ataatataa ataaaataaa     1200 ataaaataaa ataaaataaa ataaaataaa ataaaataaa ataaaaaat aaaataaaat    1260
```

```
aaaataaaat aaagtaattt tttttttttt aagtggtttt tattttttttt ttttgttttg    1320 tgaagtgggt gtgtaagttt tgggattgta gtggttttag ggaattttttt tttgtgatgt    1380 tttggtgtgt tagtttgttg tgtatatttt gttgtggttt ttttttttgtt gtttgtttat    1440 tttttaggtt ttgttgggga tttgggaaag agggaaaggt tttttttggtt agttgtgtgg    1500 tgattttggg gattttaggg tgttttttttg tggttgatgt ttggggtgta gtggttgttg    1560
gggttggggt tggtgggagt ttgtgggatt tttttagaaga gtggttggtg ttgtgattta    1620 gtattgggggt ggagtggggt gggattattt ttataaggtt tggaggttgt gaggttttttg    1680 ttggagtttt gttgttgtag ttttttgttat tagtgagtat gtgtggtttg tgttttttggg    1740 gatgggggttt agagttttta gtatgggggtt aatttgtagt attaggtttg gttttttggt    1800
agggtttttt gtttattttg agatttggga tgggggttta gggggatttag gatgttttta    1860 gtgttgttag tggttttttag ggggtttgga gtgttttggg gagggatggg attttggggg    1920
tggggagggg gggtagattg tgtttattgt gttttggtat ttttttttggg gttttagtaa    1980 attttttttt gtttgttgta gtgttgtttt atattgtggt ttattttttta gtttgaggta    2040 ggagtatgtg tttggtaggg aagggaggta ggggttgggg ttgtagtttta tagttttttg    2100 tttatttgga gagatttgaa ttttttttatt ttttttgttgt gtggttttta ttttgggttt    2160 ttttttttgtt ttttgttttt tttgttatgt ttgttttttg tttagtgtt gtgtgaaatt    2220 tttggaggaa tttgttttttt tgtttttttt ttgtatttttt gatttttttt tggggttgttg    2280 tgaggtggag ttggttttggt ttttatattt tgtattttt tttttttttgta ggttgttgtg    2340 tggttttgtg tatgttgttg gtagattagg gttagagttg gaaggaggag gtggtgattg    2400
tggagatgtg gtaggagggt ttatttaaag tttttttgtgt aagtgattat gtttgggtaa    2460 ggggagggggg tgttgggttt taggggggttg tgattaggat t                       2501
```

<210> SEQ ID NO 64
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 64

```
gattttagtt atagttttttt aaggtttagt atttttttttt tttgtttggg tatggttatt      60
tatgtaggag ttttgagtg agtttttttg ttatgttttt atggttatta tttttttttt     120
ttagttttgg ttttgatttg ttagtagtat gtgtaggggt gtgtagtggt ttgtggggag     180
ggagaagtat gagatgtggg gattgggttg attttgtttt gtagtaattt ggggaggggt     240
taggagtgta gggagggaat agggaaatag ggttttttga agattttata taatattggg     300
gtggggagta ggtatggtgg gagaggtggg gaataggaag gaggtttggg gtaaaagtta     360
tatgatggag ggataagggg gtttggattt tttgggtgg gtgaggggtt gtgggttgta     420
gttttagttt ttgtttttttt tttttgttag atatatgttt ttattttgaa ttgggaaata     480
gattatggtg tagggtggta ttgtagtgaa taaagaaaag tttgttggag tttgggggag     540
gatgttaagg tgtggtgagt gtagtttgtt ttttttttttt gttttttgggg ttttattttt     600 ttttgaggtg ttttgggttt ttgaaagtt gttaatggta ttgggggatgt tttgggtttt     660 ttaggttttt gttttgggtt ttgaggtggg tgaggagttg tgttgggagt ttgggtttga     720
tgttgtgggt tggttttatg ttgggagttt tgagtttttat ttttgggggat gtgggttgtg     780
```

```
tgtatttatt ggtggtgaag attgtggtgg tgaaattttta gtgaaggttt tgtggttttt     840
gagttttata agggtggttt tgttttgttt tgttttagtg ttgagttatg tgttggttg       900
ttttttttgga gggttttgtg gattttttgtt ggttttagtt ttggtggttg ttgtatttttg    960
ggtgttggtt gtagagggt gttttggagt ttttggagtt gttgtgtagt tggttgggga      1020
agttttttttt ttttttttag gttttttagtg gggtttaggg agtaaataga tagtaggaag    1080
aggattgtag tgaagtgtgt gtagtgaatt ggtgtgttgg gatattgtgg ggggaaattt     1140
tttaagattg ttgtgatttt ggagtttgta tatttgtttt atagggtagg ggagagggggt    1200
ggaggttgtt tagaggaaag gaaattgttt tatttttattt tatttttattt tattttttta    1260
ttttatttta tttttattta tttttattta tttttattta tttttattta tttgtgtta      1320
ttttatttta ttttatgatg tagttttatg tgtggttta ggttggagtg tagtggtgtg     1380
attttggtgg tttattgtaa ttttttgttttt tgggtttaa gtaattttgt tttagttttt    1440
tgagtaggtg gaattatagg tgtgtgttat atttggttga ttttttgtatt tttagtagag    1500
atggggtttt attatgttgg ttgggttggt tttgaattttt tgatttttagg tgatttgtat    1560
gttttggttt tttaaagtgt tgggattata ggtgtgagtt attatgtttg gttgtttaat    1620
ttttatttga agttttgggg tatatgtaga ggatgtgtag gtttgttata taggtgtgtg    1680
tgttatgatg gtttgttgta tagattattt tattatttag gtattaagtt tagtattttt    1740
tagttatttt ttttggtatt ttttttttttt agtattttgt ttaataggta ttagtgtgtg   1800
ttgattgttg ttatgtgatt atgtgttttt attgtttagt ttttatttat aagtgagatt    1860
atgtggtttt gttggttttt tgtttttgtg tgagtttgtt gaggtaatg gtttttagtt     1920
ttatttatgt ttttgtaaag gatatgatta tgtttttttt agtggttgtg ttttaggtta   1980
ttttttttgg ttttgttgtt tatttttttgt tgatttgtag atttttatttt attttagata   2040
ttgattttttt gttggttttta gatatgatag atagtttttt ttattttatt aattgttaag   2100
tttgtttaag gagttttttta tgaaataaaa tttgttaatt taagtgtaat taaatttagt   2160
aagggatttt tgtggtgggg aagaggttgg tgtttatgtt gtatttttaa aatttttattt   2220
aatgtagtta ttaaaaagaa ttagattatg tttttttgtgg gaatatggat ggagttagag   2280
gttattattt ttagtaaatt aatgtaggaa tagaaattta aatattggat gttttttattt   2340
gtaagtggga gttaaatgat gagaatttat aatataaata aggaaataat agatattgtg    2400
gttgattta gggtgtagga tgggaggaag gagaggagta gaaaagagaa ttattgggta   2460
tttggtataa tatttgggtg atgaaatatt ttgtataata a                         2501
```

<210> SEQ ID NO 65
<211> LENGTH: 3506
<212> TYPE: DNA
<213> ORGANISM: Artificial Sequence
<220> FEATURE:
<223> OTHER INFORMATION: chemically treated genomic DNA (Homo sapiens)

<400> SEQUENCE: 65

```
tagtggtaaa gttttgttta tgttaagtaa taaaggataa gttagttttt gttgtgatta      60
ttttgttgta ttgataagtt atgtattttt atttaaggat ttaaattttt attttttta     120
agaattgggt taaaattgat aaattaaatt tatttatggt ttattgatta aaggttgttg    180
tataataagt ttttgttatg tttagtagtt ggatttatag tgttagaaat ttataattgt    240
ttgatttttt ttttattat attgtgaaaa ttgtttttta aatgtaatta atttttaaaat    300
tttaatagta ttgtggttag gtgtggtggt ttattattgt aatattaata ttaggtatag    360
```

```
gtgaggggat tgaggttagg atattgaaat tagtttggga aatatatgga gatttggttt    420
ttggaaaaat aattagtttt gtgtggtggt gggtgtgagg ttttggttaa ttgggaggtt    480
atagtgagtt atgatgatat tgtattatag tttgtgtgat ggtttatgtt agtaagtttt    540
ggagtatttg aaataagttg tgtttgggtat tttatttatt ggagagtgat tagtgattga    600
tgtttatttta tagtgattag agatgtatgt tttgatagta gtataaattt agtaggtgtg    660
aataaatggt aaagagaaat tgggtaaata agtattatgg tttttttagtt gagaaagtgg    720
gggttttaaa aagggttttt tgttgataga aagggatgtt taattattga aattgtagag    780
ggtgtggttt tggtgtttga gtgtgtagat tatatttatg gtggtgattg ttttgtgttt    840
ggtgtgtttt gtataggtta tggtgttttg gattatgttt tttaggaata tttttagtat    900
tttgtgagtt ttttttgtaga tgaggttgga gatgtgtttt atgttgttgt ggtgagtaag    960
gtgttggatg gttggtttgg tgatgttttg gatattgttg tgtagtattt tatggtggtg   1020
tttagtgttg tttttgttaa gatttttttt gttttttgttg tggttagata tgatgagtaa   1080
gaggagtttt atttaatgtt ttgtgaggat tttggtttga ggtagtgttt ttatatgata   1140
gttggtggat tgaattgaga atttgaaaga agttggtggg aagttttgtt ttggtggggg   1200
agggggaaatt taagggttta aattgaaata gggggaaaaa aaagtgagt tttttgtttt   1260
tgtgttttga attttgtaat gtgtatagta ttttgttatt atgttatgag gttttaaaaa   1320
attgttttttg aatgtagaag atatatatta atattgtggg aaatataaga aaggataaga   1380
aattaagaaa ttataatgtt atttttattat ataggttagt taattatgta ttttgtagag   1440
tagttgtata tatttttttta agaaaatgta tatagtgttg tatatggagt tttgtaattt   1500
ttttatattg attataattt aattaatttt tattaaagag ataaaagtga tgttttggtg   1560
tttatgtttt ttaggaatta ttaatagtta taattagttt tttagtaatt tttttaattgg   1620
ttgtatttta aaaataatgt tttttatatt taatataaat gtattttttt tttatatttg   1680
ggattaatat tgaaatttat gattttatta tattaaaatt taaattttat tatattaata   1740
tttaaaattg tattagaggt tttatgattt ggtattatgg gttttttgtat tattttttttt   1800
ttaaatttttt taatttgttt tattaaggtt tttggataat tttagagatt ttttgtgaag   1860
tttgaataaa attttttttga gattttgata attgtattag ttttaggatt taattggaat   1920
agaattaaaa ttttttaaaat aagttttttat aattagaaaa ttggtgtttg taggttttgt   1980
gtgtggggtt tttttttttt tttggaagga gttttgtttt gttgttaggt tggagggtag   2040
tggtgtaatt ttggtttatt gtaattttta tttttttgggt ttaagtgatt tttatgtttt   2100
aattttttgga ttagtgtgga ttataggtat gtgttattat gtttagttaa tttttttgtat   2160
ttttagtaaa gaataagttt tattatgttg gataggatgt ttttgatttt ttgatattgt   2220
gatttgtttg tttttagtttt ttaaagtgtt gggattatag gtgtgagttg ttttgtttgg   2280
atgtttgtag gtttttaaaa agatatttt atatgattta attaaagatt tgttattaat   2340
tattatggag taattttgat tttgtatatt tgatttttttt ttttattaat aaatataggg   2400
ttatattttg aatttttttt tttttttttt ttttgtggaa gatggagttt tgttttttttg   2460
tttaggttgg agtgtaatgg tttaattttg gtttattgta attttttattt tttgggttta   2520
agtgattttt ttattttagt ttttttttgag tagttgggat tatagggtatt tattattatg   2580
tttggttaat ttttttgttat ttttagtaga gatgggggtt tattatgttg gttaggttag   2640
tttttaattt ttgatttttgt gatttatatg tttttggtttt ttaatgtgtt gggattatag   2700
```

| | |
|---|---:|
| gtttgagtta ttgtgtttgg ttattttgaa attattttaa tattaatgaa aattataaaa | 2760 |
| tttttataat tatttttaata taatttttta gtatttaatt ttttgtttag aaagtagtta | 2820 |
| agagttgaaa ttttggaaat agaaaatttt ggttttagat taaatgttta tttttttagat | 2880 |
| ttgagttgat ttgttattga ttagatatga ggtgatttgt ttattttttt taaattttg | 2940 |
| tttatttata aagttagaat aggatagtga tggtattgtt ggggtgtaga atgattttt | 3000 |
| aaaatgtggt ttttgggtat gttgagtgtt tttgaatatt gaaaggtttt agaaataagt | 3060 |
| tttagaatta aagtttttt aattttgttt tttttttat atatgtgaag ggattttgat | 3120 |
| attttttaat tggattaaga aaattttta ttagaagtaa taattgtttt ttatttttt | 3180 |
| tttgttatt tattattgta gaaaagaata ttgaatatgg attttttaag ataatgtttg | 3240 |
| tttttttggtt ttatttaaat tattaagata tattaggtgt tgtggttttt tttattaatt | 3300 |
| ttagtattgt gggaggttga ggtaggtgga tttttttgagt ttaggagttt gagattagtt | 3360 |
| tggttaaatat ggtgaatttt tgttttata aatatataa aaaattagtt aggtggtgtt | 3420 |
| atatgttgt aattttagtt atttggggagg ttgaggtagg agaattattt gaatttggga | 3480 |
| ggtggaggtt gtagtgagtt gagatt | 3506 |

<210> SEQ ID NO 66
<211> LENGTH: 3506
<212> TYPE: DNA
<213> ORGANISM: Artificial Sequence
<220> FEATURE:
<223> OTHER INFORMATION: chemically treated genomic DNA (Homo sapiens)

<400> SEQUENCE: 66

| | |
|---|---:|
| aattttggtt tattgtaatt tttgtttttt aggtttaagt gatttttttg ttttagtttt | 60 |
| ttaagtagtt gggattatag gtatgtgata ttatttggtt aatttttgt atattttgta | 120 |
| gagataggga tttgttatgt tggttaggtt ggttttgaat ttttgagttt aagggattta | 180 |
| tttgttttga tttttttatag tgtttgggatt agtgggagga gttatagtat ttagtatgtt | 240 |
| ttggtaattt aaatgagatt gagaggtaga tattattttg aaaaatttat atttagtatt | 300 |
| ttttttgta ataatgaaat aatagggagg ggatagaagg taattgttat ttttggtaag | 360 |
| aaatttttt ggtttgatta ggaaatgtta gagttttttt gtatgtatgg gaaagaagat | 420 |
| gaagttagag ggggttttgat tttgaagttt attttgagg tttttttaatg tttaaaagtg | 480 |
| tttagtatgt ttaagaatta tattttgggg aattattttg tattttaata gtattgttat | 540 |
| tatttattt taatttgta gatgagtaaa gatttaaaaa gaataaataa gttattttgt | 600 |
| gtttgattgg taataagtta gtttgagttt gaaaggtaaa tatttaattt aaaattaaag | 660 |
| tttttttattt ttagagtttt aattttttaat tattttttaa ataaagaatt gaatattaag | 720 |
| agattatatt agaatagtta taggagttttt ataattttta ttgatgttaa ataattttta | 780 |
| gagtggttga gtgtagtggt ttaagtttgt aattttagta tattgggagg ttgaggtata | 840 |
| tggattatga ggttgggagt tggagattag tttggttaat atggtgaaat tttgttttta | 900 |
| ttaaagatat aaaaaaatta gttgggtgtg gtggtgagtg tttgtaattt tagttatttta | 960 |
| ggggaggttg aggtgggaga attgtttgaa tttgggaggt ggaggttgta gtgagttaag | 1020 |
| attgggttat tgtatttttag tttgagtgaa agggtgagat tttgttttta taaaaaaaaa | 1080 |
| aaaaaaaaaa aaaatttaga gtataatttt gtatttatta ataagaaaga aaattaaata | 1140 |
| tatgaatta agttgtttt ataatggttg ataataaatt tttagttggg ttatataaaa | 1200 |
| gtgttttttt aaaatttat aagtgtttaa gtgaagtggt ttatgtttgt aattttagta | 1260 |

```
ttttgggagg ttgaggtggg tggattatga tgttaagaga ttaagagtat tttgtttaat    1320
atggtgaaat ttgttttttta ttaaaaatat aaaaaattag ttgggtgtgg tggtgtatgt    1380
ttgtagtttg tgttaatttg gaggttgagg tatgagaatt gtttgaattt gggaggtgga    1440
ggttgtagtg agttgagatt gtattattgt tttttggttt gatgatagag tgagattttt    1500
tttaaaaaaa aaaaaaaatt ttatatataa aatttataaa tattaattt ttagttataa    1560 gagtttgttt taaggatttt aatttttattt taattaagtt ttaaagttaa tgtaattatt    1620
aaaattttga agagatttta tttaaattt ataaaggtt tttaaagttg tttagaaatt    1680
ttggtgaaat agattaggaa atttggaaag gaaataatgt ggagatttgt agtattaaat    1740
tatgagattt ttaatataat tttaaatatt aatgtaataa aatttaaatt ttggtgtaat    1800
aaaattataa attttaatat tggttttaag tatagagaaa aagtatattt atgttgaatg    1860
tggaaaatat tattttttaaa atatagttga ttaaaaaatt gttggggaat tgattataat    1920
tattgataat ttttaagaaa tatagatatt aaaatattat ttttattttt ttaatagaaa    1980
ttggttaaat tataattaat ataaggaggt tataaaattt tatatataat attgtatata    2040
tttttttgga aaaatatgtg taattgtttt gtaaaatata tgattaatta gtttgtgtga    2100
tgggataata ttgtagtttt ttaatttttt gttttttttt gtattttta tagtattgat    2160 gtatatttt tgtgtttaaa agtaattttt taaagtttta taatgtggta ataaaatatt    2220
atgtatgtta taaaatttag aatatggaaa taagaagttt gttttttttt tttttttatt    2280
ttggtttggt tttttagatt tttttttttt tattggggtg ggatttttg ttgattttt    2340 ttaggttttt agtttggttt gttaattgtt gtataaaggt gttgttttag gttagagttt    2400
ttataaagtg ttgggtgaga tttttttttgt ttgttatgtt tggttgtggt aaaggtggga    2460
agggttttgg taaggtggt gttaagtgtt attgtaaagt attgtgtgat aatatttagg    2520
gtattattaa gttggttatt tggtgttttg tttgttgtgg tggtgtgaag tgtattttg    2580 gttttattta tgaggagatt tgtggggtgt tgaaggtgtt tttggagaat gtgatttggg    2640
atgttgtgat ttatatagag tatgttaagt gtaagatggt tattgttatg gatgtggttt    2700
atgtgtttaa gtgttagggt tgtattttt atggttttgg tggttgagtg ttttttttta    2760
ttaataaaag ttttttttta gggttttat ttttttagtt gaggagttgt gatgtttgtt    2820
tgtttagttt ttttttatta tttgtttgtg tttgttgagt ttgtgttgtt attggagtat    2880 gtgttttag ttgttgtaag taggtattag ttattaattg ttttttagta aataaaatat    2940
ttaatataat ttgttttagg tgttttagag tttattgata tgggttgttg tgtagattgt    3000
agtgtagtgt tattatggtt tattgtagtt ttttgattag ttggaattttt gtgtttatta    3060 ttatgtaagg ttaattattt ttttaaagat tgggttttttg tgtgttttt aggttagttt    3120 tgatattttg gttttaattt ttttgtttat gtttaatgtt ggtattatag tagtgagtta    3180
ttatgtttgg ttatgatatt gttgaggttt tagggttagt tatatttaag gggtaatttt    3240
tgtagtgtag tggggaggaa agttaagtag ttataggttt ttggtgttgt gaatttaatt    3300
gttgaatata gtaagaattt attatgtaat aatttttaat tagtggattg taaataagtt    3360
tagtttattg gttttggttt aattttttgag aaaggtgaga atttgaattt ttgagtagaa    3420
atatgtagtt tattagtata ataaagtgat tataataaag attaatttat tttttgttat    3480
ttaatgtggg tagagtttta ttgttg                                          3506
```

<210> SEQ ID NO 67

```
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 67
tggtgatgga ggaggtttag taagt                                          25

<210> SEQ ID NO 68
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 68
aaccaataaa acctactcct cccttaa                                        27

<210> SEQ ID NO 69
<211> LENGTH: 30
<212> TYPE: DNA
<213> ORGANISM: Artificial Sequence
<220> FEATURE:
<223> OTHER INFORMATION: chemically treated genomic DNA (Homo sapiens)

<400> SEQUENCE: 69
accaccaccc aacacacaat aacaaacaca                                     30

<210> SEQ ID NO 70
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 70
taagagtaat aatggatgga tgatg                                          25

<210> SEQ ID NO 71
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 71
cctcccatct cccttcc                                                   17

<210> SEQ ID NO 72
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 72
atggatgaag aaagaaagga tgagt                                          25

<210> SEQ ID NO 73
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 73
```

```
gggattattt ttataaggtt                                                   20

<210> SEQ ID NO 74
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 74
cccatactaa aaactctaaa c                                                 21

<210> SEQ ID NO 75
<211> LENGTH: 33
<212> TYPE: DNA
<213> ORGANISM: Artificial Sequence
<220> FEATURE:
<223> OTHER INFORMATION: chemically treated genomic DNA (Homo sapiens)

<400> SEQUENCE: 75
ctaaacccca tccccaaaaa cacaaaccac aca                                    33

<210> SEQ ID NO 76
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 76
agtttcgtcg tcgtagtttt cgtt                                              24

<210> SEQ ID NO 77
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 77
tagtgagtac gcgcggttcg                                                   20

<210> SEQ ID NO 78
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 78 tttttagga atatttttag tattt                                              25

<210> SEQ ID NO 79
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 79
ccaaaacatc accaaac                                                      17

<210> SEQ ID NO 80
<211> LENGTH: 33
<212> TYPE: DNA
```

```
<213> ORGANISM: Artificial Sequence
<220> FEATURE:
<223> OTHER INFORMATION: chemically treated genomic DNA (Homo sapiens)

<400> SEQUENCE: 80
caaaccaacc atccaacacc ttactcacca caa                                    33

<210> SEQ ID NO 81
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 81
cgtagatgag gtcggagatg cgt                                               23

<210> SEQ ID NO 82
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 82
ttacgtcgtc gcggcgag                                                     18

<210> SEQ ID NO 83
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 83
ctaaaacctc aacctaac                                                     18

<210> SEQ ID NO 84
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 84
gatttagagt tgaatgtaaa gtaa                                              24

<210> SEQ ID NO 85
<211> LENGTH: 31
<212> TYPE: DNA
<213> ORGANISM: Artificial Sequence
<220> FEATURE:
<223> OTHER INFORMATION: chemically treated genomic DNA (Homo sapiens)

<400> SEQUENCE: 85
cctaacatct tctctcaccc caaacaaaac a                                      31

<210> SEQ ID NO 86
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 86
aacgaaacaa ataccgtaaa cga                                               23
```

<210> SEQ ID NO 87
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 87
ccgactactt ctacatttcg aacg          24

<210> SEQ ID NO 88
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 88
aaacccaaac ctaaattaaa          20

<210> SEQ ID NO 89
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 89
ggaagtgtgt ggtaaag          17

<210> SEQ ID NO 90
<211> LENGTH: 28
<212> TYPE: DNA
<213> ORGANISM: Artificial Sequence
<220> FEATURE:
<223> OTHER INFORMATION: chemically treated genomic DNA (Homo sapiens)

<400> SEQUENCE: 90
taaagtgttg gggttttgtt tggttgtt          28

<210> SEQ ID NO 91
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 91
aaacaaacgt ccgaaaaaaa cga          23

<210> SEQ ID NO 92
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 92
caaacgaaac cccgacgc          18